(12) United States Patent
Balog et al.

(10) Patent No.: US 11,447,449 B2
(45) Date of Patent: Sep. 20, 2022

(54) INHIBITORS OF INDOLEAMINE 2,3-DIOXYGENASE AND METHODS OF THEIR USE

(71) Applicant: BRISTOL-MYERS SQUIBB COMPANY, Princeton, NJ (US)

(72) Inventors: James Aaron Balog, Lambertville, NJ (US); Steven P. Seitz, Swarthmore, PA (US); David K. Williams, Delran, NJ (US); Murugaiah Andappan Murugaiah Subbaiah, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 127 days.

(21) Appl. No.: 16/959,487

(22) PCT Filed: Jan. 3, 2019

(86) PCT No.: PCT/US2019/012118
§ 371 (c)(1),
(2) Date: Jul. 1, 2020

(87) PCT Pub. No.: WO2019/136112
PCT Pub. Date: Jul. 11, 2019

(65) Prior Publication Data
US 2021/0070698 A1    Mar. 11, 2021

Related U.S. Application Data

(60) Provisional application No. 62/613,783, filed on Jan. 5, 2018.

(51) Int. Cl.
*C07C 275/42* (2006.01)
*C07K 16/28* (2006.01)

(52) U.S. Cl.
CPC ........ *C07C 275/42* (2013.01); *C07C 2601/16* (2017.05); *C07K 16/2818* (2013.01)

(58) Field of Classification Search
CPC .......................... C07C 275/42; C07C 2601/16
See application file for complete search history.

(56) References Cited

U.S. PATENT DOCUMENTS

| | | | |
|---|---|---|---|
| 9,624,188 B2 * | 4/2017 | Balog | A61P 31/12 |
| 2010/0233166 A1 | 9/2010 | Prendergast et al. | |
| 2016/0060237 A1 * | 3/2016 | Balog | A61K 31/41 |
| | | | 514/249 |

FOREIGN PATENT DOCUMENTS

| | | |
|---|---|---|
| WO | 99/29310 A2 | 6/1999 |
| WO | 2004/094409 A1 | 11/2004 |
| WO | 2006/029879 | 3/2006 |
| WO | 2006/105021 A2 | 10/2006 |
| WO | 2006/122150 A1 | 11/2006 |
| WO | 2007/005874 A2 | 1/2007 |
| WO | 2007/075598 A2 | 7/2007 |
| WO | 2008/036642 A2 | 3/2008 |
| WO | 2008/036653 A2 | 3/2008 |
| WO | 2008/132601 A1 | 11/2008 |
| WO | 2009/009116 | 1/2009 |
| WO | 2009/044273 A2 | 4/2009 |
| WO | 2009/073620 A2 | 6/2009 |
| WO | 2010/019570 A2 | 2/2010 |
| WO | 2010/077634 A1 | 7/2010 |
| WO | 2011/028683 | 3/2011 |
| WO | 2011/056652 A1 | 5/2011 |
| WO | 2011/070024 A1 | 6/2011 |
| WO | 2011/107553 A1 | 9/2011 |
| WO | 2011/109400 A2 | 9/2011 |
| WO | 2011/131407 A1 | 10/2011 |
| WO | 2011/140249 A2 | 11/2011 |
| WO | 2012/032433 A1 | 3/2012 |
| WO | 2012/142237 A1 | 10/2012 |
| WO | 2012/145493 A1 | 10/2012 |
| WO | 2013/079174 A1 | 6/2013 |

(Continued)

OTHER PUBLICATIONS

Luo et al. Cell, 2009, 136, pp. 823-837 (Year: 2009).*
Inaba et al. Gynecologic Oncology 2009, 115, 185-192 (Year: 2009).*
Speeckaert et al. European Journal of Cancer, 2012, 48, 2004-2011 (Year: 2012).*
Feder-Mengus et al. European Journal of Cancer, 2008, 44, 2266-2275 (Year: 2008).*
Holmgaard et al. J. Exp. Med. 2013, 210, 1389-1402 (Year: 2013).*
Ball, H.J. et al, Characterization of an indoleamine 2,3-dioxygenase-like protein found in humans and mice, , Gene, 396(1):203-213 (Jul. 2007).

(Continued)

*Primary Examiner* — Matthew P Coughlin
(74) *Attorney, Agent, or Firm* — BakerHostetler

(57) ABSTRACT

The present invention provides a compound of formula (II): an inhibitor of indoleamine 2,3-dioxygenase (IDO), which may be used as medicaments for the treatment of proliferative disorders, such as cancer, viral infections and/or autoimmune diseases. Its prodrugs are disclosed.

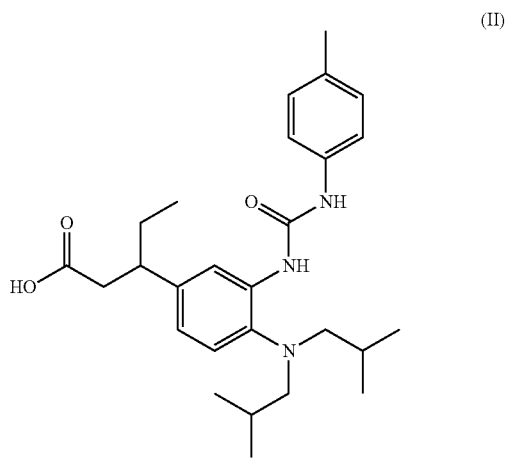

(II)

9 Claims, No Drawings

(56) References Cited

FOREIGN PATENT DOCUMENTS

| WO | 2013/087699 A1 | 6/2013 |
| --- | --- | --- |
| WO | 2013/119716 A1 | 8/2013 |
| WO | 2013/132044 A1 | 9/2013 |
| WO | 2013/169264 A1 | 11/2013 |
| WO | 2014/008218 | 1/2014 |
| WO | 2014/036357 A1 | 3/2014 |
| WO | 2014/150646 A1 | 9/2014 |
| WO | 2015/031295 A1 | 3/2015 |
| WO | 2016/073738 A2 | 5/2016 |
| WO | 2016/073770 A1 | 5/2016 |
| WO | 2016/073774 A2 | 5/2016 |
| WO | 2016/161279 A1 | 10/2016 |
| WO | 2017/051353 A1 | 3/2017 |
| WO | 2017/051354 A1 | 3/2017 |
| WO | 2017/139414 A1 | 8/2017 |

OTHER PUBLICATIONS

Brandacher, G. et al., Prognostic value of indoleamine 2,3-Dioxygenase expression in colorectal cancer: effect on tumor-infiltrating T-cells, Clin. Cancer Res., 12(4):1144-1151 (Feb. 15, 2006).
Bundgaard, H., (C) Means to Enhance Penetration, (1) Prodrugs as a means to improve the delivery of peptide drugs, Adv. DrugDeliv. Rev., 8:1-38 (1992).
Bundgaard, H., Chapter 5: "Design and Application of Prodrugs", A Textbook of Drug Design and Development, pp. 113-191, Krogsgaard-Larsen, P. et al., eds., Harwood Academic Publishers (1991).
Bundgaard, H., ed., Design of Prodrugs, Chapter 1, Elsevier (1985).
Goldstein et al., Biological Efficacy of a Chimeric Antibody to the Epidermal Growth Factor Receptor in a Human Tumor Xenograft Model, Clin. Cancer Res., 1:1311-1318 (1995).
International Search Report, dated Feb. 5, 2019, dated Sep. 17, 2020.
Kakeya, N. et al., Studies on Prodrugs of Cephalosporins, Chem. Pharm. Bull., 32:692-698 (1984).
Kohl et al, Inhibition of Farnesyltransferase Induces Regression of Mammary and Silavary Carcinomas in ras Transgenic Mice, Nat. Med., I(8):792-797 (1995).
Littlejohn, T.K. et al., Expression and Purification of Recombinant Human Indoleamine 2,3-Dioxygenase, Protein Expression and Purification, 19:22-29 (2000).
Nielsen, N.M. et al., Glycolamide Esters as Biolabile Prodrugs of Carboxylic Acid Agents: Synthesis, Stability, Bioconversion, and Physicochemical Properties, J. Pharm. Sci., 77:285-298 (1988).
PCT, PCT/US2019/012118 International Search Report dated May 2, 2019, dated May 2, 2019.
Sarkar, S.A. et al., Induction of Indoleamine 2,3-Dioxygenase by Interferon-y in Human Islets, Diabetes, 56:72-79 (2007).
Sausville, Cyclin-Dependent Kinase Modulators Studied at the NCI: Pre-Clinical and Clinical Studies, Curr. Med. Chem. Anti-Canc. Agents, 3:47-56 (2003).
Scheller et al., Paclitaxel Balloon Coating, a Novel Method for Prevention and Therapy of Restenosis, Circulation, 110:810-814 (2004).
Sekulic, A direct linkage between the phosphoinositide 3-kinase-AKT signaling pathway and the mammalian target of rapamycin in mitogen-stimulated and transformed cells, Cancer research, Jul. 1, 2000;60(13):3504-3513.
Serafini P, et ah, Semin. Cancer Biology, Myeloid suppressor cells in cancer: Recruitment, phenotype, properties, and mechanisms of immune suppression, 16(I):53-65 (Feb. 2006).
Vlahos et al., A Specifi Inhibitor of Phosphatidylinositol 3-Kinase, 2-(4-Morpholinyl)-8-phenyl-4H-1-benzopyran-4-one (LY294002), J. Biol. Chem., 269:5241-5248 (1994).
Widder, K. et al., eds., Methods in Enzymology, 112:309-396, Academic Press (1985).

* cited by examiner

INHIBITORS OF INDOLEAMINE 2,3-DIOXYGENASE AND METHODS OF THEIR USE

CROSS-REFERENCE TO RELATED APPLICATIONS

This application is the National Stage Application of International Patent Application No. PCT/US2019/012118, filed Jan. 3, 2019, which claims the priority benefit of U.S. Provisional Application No. 62/613,783, filed Jan. 5, 2018; the entire content of which is herein incorporated by reference.

FIELD OF THE INVENTION

The invention relates generally to compounds that modulate or inhibit the enzymatic activity of indoleamine 2,3-dioxygenase (IDO), prodrugs, pharmaceutical compositions containing said compounds or prodrugs and methods of treating proliferative disorders, such as cancer, viral infections and/or autoimmune diseases utilizing the compounds of the invention.

BACKGROUND OF THE INVENTION

Indoleamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formyl-kynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini P, et al., *Semin. Cancer Biol.*, 16(1):53-65 (February 2006) and Ball, H. J. et al., *Gene*, 396(1):203-213 (July 2007)).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in, for example, WO 2004/094409, WO2014/150646, WO2016/073770, WO2016/073738, and WO2016/073774.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

SUMMARY OF THE INVENTION

The invention is directed to compounds of formula (I):

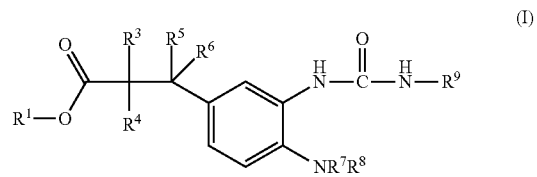

(I)

wherein all of the variables are as defined herein below.

Also within the scope of the invention are salts, stereoisomers, tautomers, and solvates of the compounds of formula (I).

The invention is also directed to a compound of formula (II):

(II)

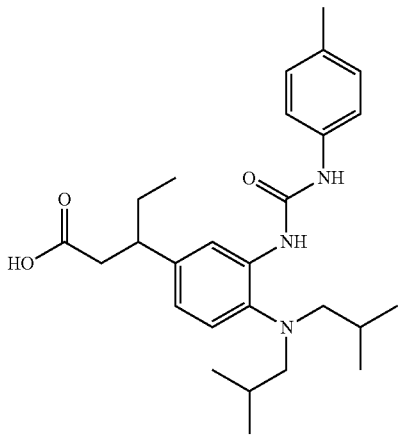

or a pharmaceutically acceptable salt, a stereoisomer, a tautomer, or a solvate thereof.

The invention is also directed to pharmaceutical compositions comprising the compound of formula (II) or. The invention is also directed to methods of treating cancer using one or more compounds of the invention.

The invention also provides processes and intermediates for making the compounds of formula (I) or salts, or formula (II) or pharmaceutically acceptable salts, stereoisomers, tautomers, and solvates thereof.

The compounds of the invention may be used in therapy.

The compounds of the invention may be used for the manufacture of a medicament for the treatment of cancer.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

Compounds of the Invention

In a first aspect, the present invention provides, inter alia, a compound of formula (I):

(I)

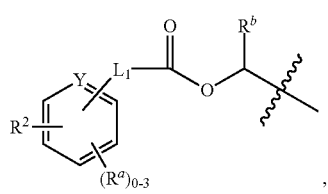

wherein:

$R^1$ is a straight or branched $C_1$-$C_8$ alkyl substituted with $R^2$,

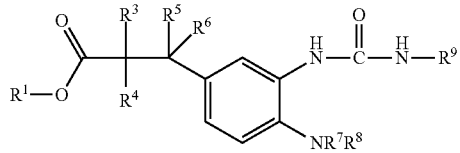

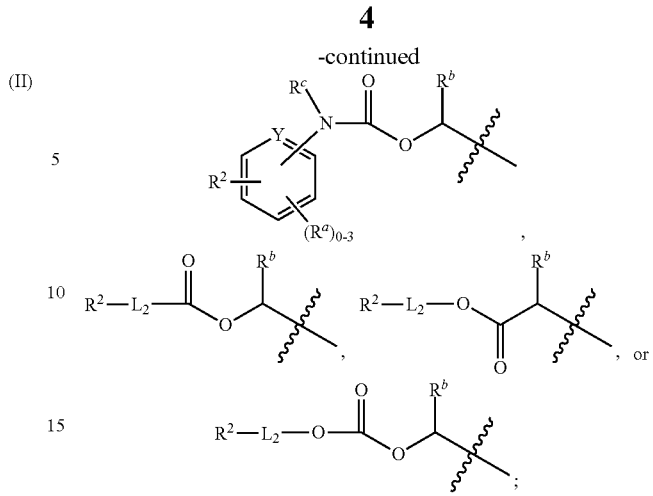

$Y$ is CH or N;

$L_1$ is independently a bond or a straight or branched $C_1$-$C_8$ alkylene;

$L_2$ is independently a bond, a straight or branched $C_1$-$C_8$ alkylene, —OC(O)N($R^c$)CH($R^b$)—, —C(O)N($R^c$)$L_3$-, $C_3$-$C_6$ cycloalkyl,

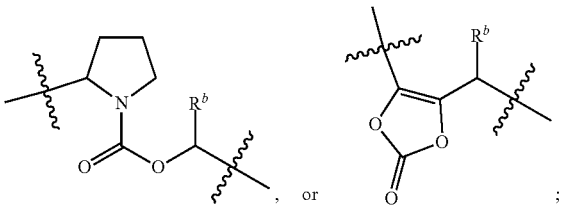

$R^2$ is independently $NH_2$,

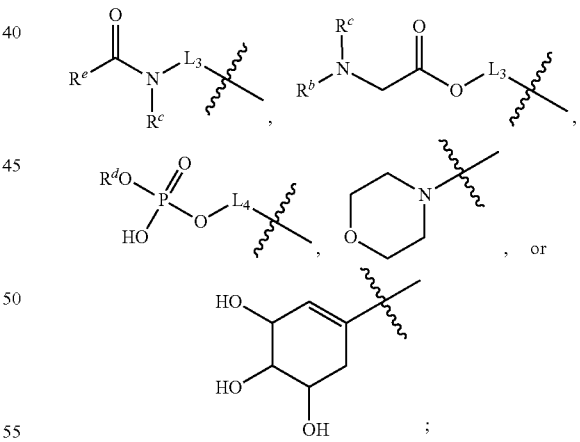

$L_3$ is independently a straight or branched $C_1$-$C_6$ alkylene;

$L_4$ is independently a bond, a straight or branched $C_1$-$C_6$ alkylene wherein two carbon atoms of said alkylene are optionally replaced by —C(O)N($R^c$)— or —N($R^c$)C(O)—;

$R^3$, $R^4$, $R^5$ and $R^6$ are independently H or $C_1$-$C_4$ alkyl;

$R^7$ and $R^8$ are independently H or $C_1$-$C_6$ alkyl;

$R^9$ is aryl optionally substituted with one to three substituents selected from: halo, OH, CN, $C_1$-$C_6$ alkyl, —O$C_1$-$C_6$ alkyl, $C_1$-$C_6$ haloalkyl, benzyl, and phenoxy;

$R^a$ is independently halo, OH, CN, $C_1$-$C_6$ alkyl, —O$C_1$-$C_6$ alkyl, or $C_1$-$C_6$ haloalkyl;

$R^b$ and $R^c$ are independently H, or $C_1$-$C_6$ alkyl;

$R^d$ is independently H, $C_1$-$C_6$ alkyl, —$CH_2OC(O)(C_1$-$C_6$ alkyl), —$CH_2OC(O)O(C_1$-$C_6$ alkyl), or Bn; and $R^e$ is independently $C_1$-$C_6$ alkyl optionally substituted with a substituent selected from halo, OH, CN, $C_1$-$C_4$ alkyl, —$OC_1$-$C_6$ alkyl, and $C_1$-$C_4$ haloalkyl;

or a salt, a stereoisomer, a tautomer, or a solvate thereof.

In a second aspect, the present invention provides a compound of formula (I), within the scope of the first aspect, wherein:

$R^1$ is a straight or branched $C_1$-$C_6$ alkyl substituted with $R^2$,

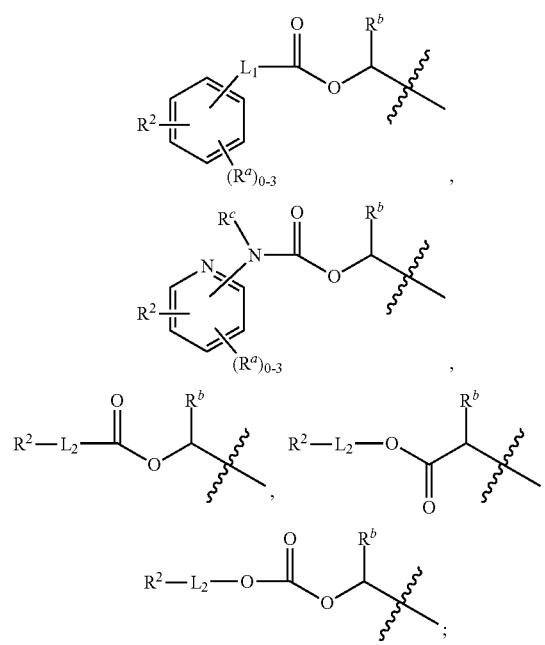

$L_1$ is independently a bond or a straight or branched $C_1$-$C_6$ alkylene;

$L_2$ is independently a bond, a straight or branched $C_1$-$C_6$ alkylene, —OC(O)N($R^c$)CH($R^b$)—, —C(O)N($R^c$)$L_3$-, $C_3$-$C_6$ cycloalkyl,

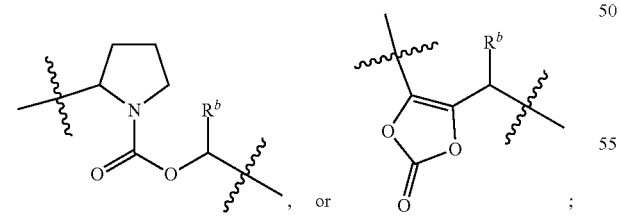

and $R^9$ is phenyl optionally substituted with one to three substituents selected from: halo, OH, CN, $C_1$-$C_6$ alkyl, —$OC_1$-$C_6$ alkyl, and $C_1$-$C_6$ haloalkyl.

In a third aspect, the present invention provides a compound of formula (I), within the scope of the first or second aspect, wherein:

$R^2$ is independently $NH_2$,

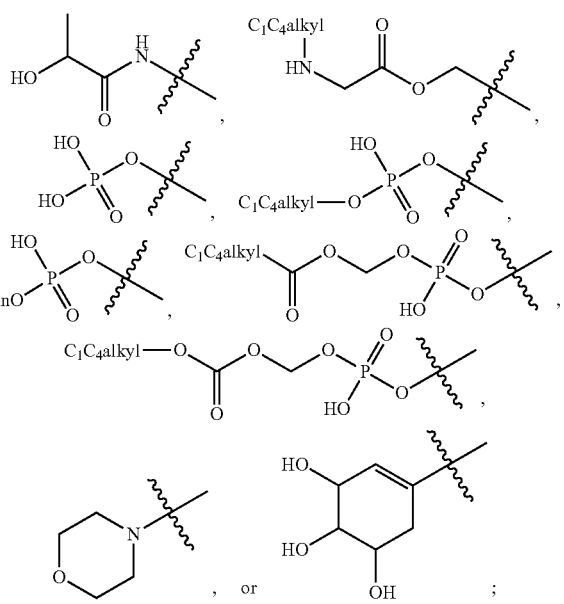

$R^a$ is independently $C_1$-$C_4$ alkyl or —$OC_1$-$C_4$ alkyl;
$R^b$ is independently H or $C_1$-$C_4$ alkyl;
$R^c$ is independently H or $C_1$-$C_2$ alkyl;
$R^d$ is independently H, $C_1$-$C_4$ alkyl, —$CH_2OC(O)(C_1$-$C_4$ alkyl), —$CH_2OC(O)O(C_1$-$C_4$ alkyl), or Bn; and
$R^e$ is independently $C_1$-$C_4$ alkyl optionally substituted OH.

In a fourth aspect, the present invention provides a compound of formula (I), within the scope of any of the above aspects, wherein:

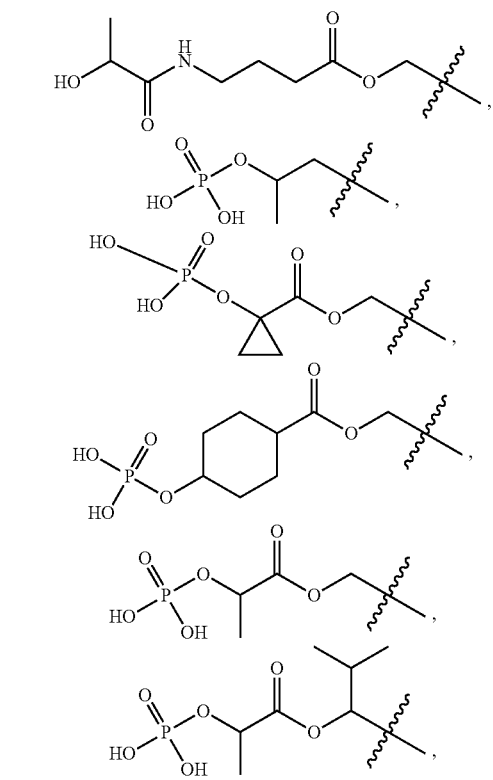

-continued
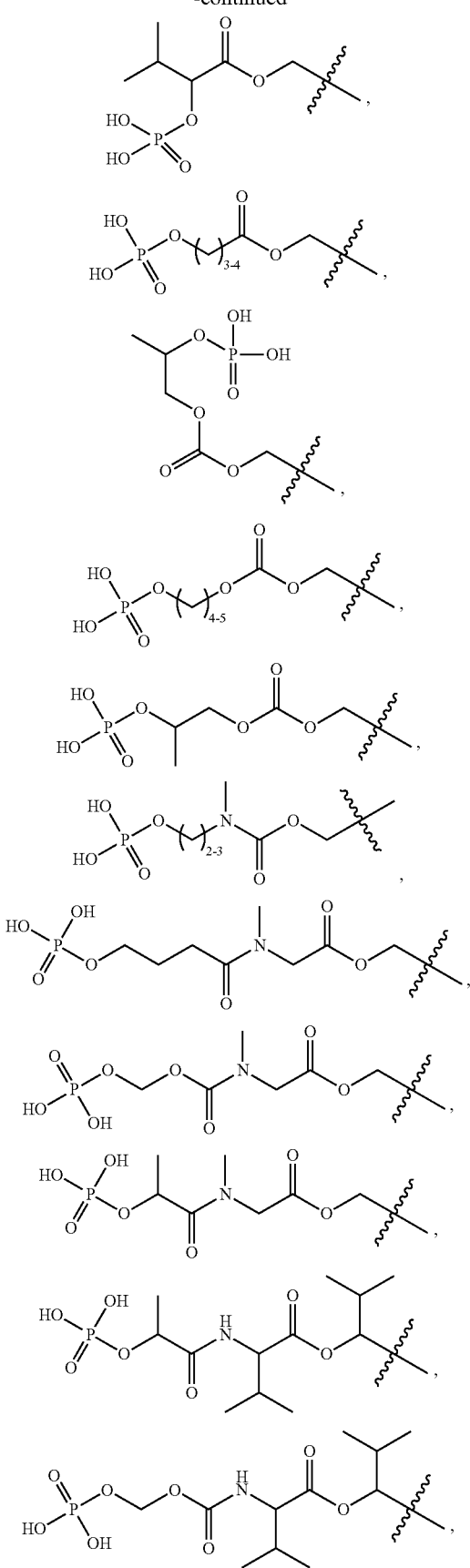
-continued
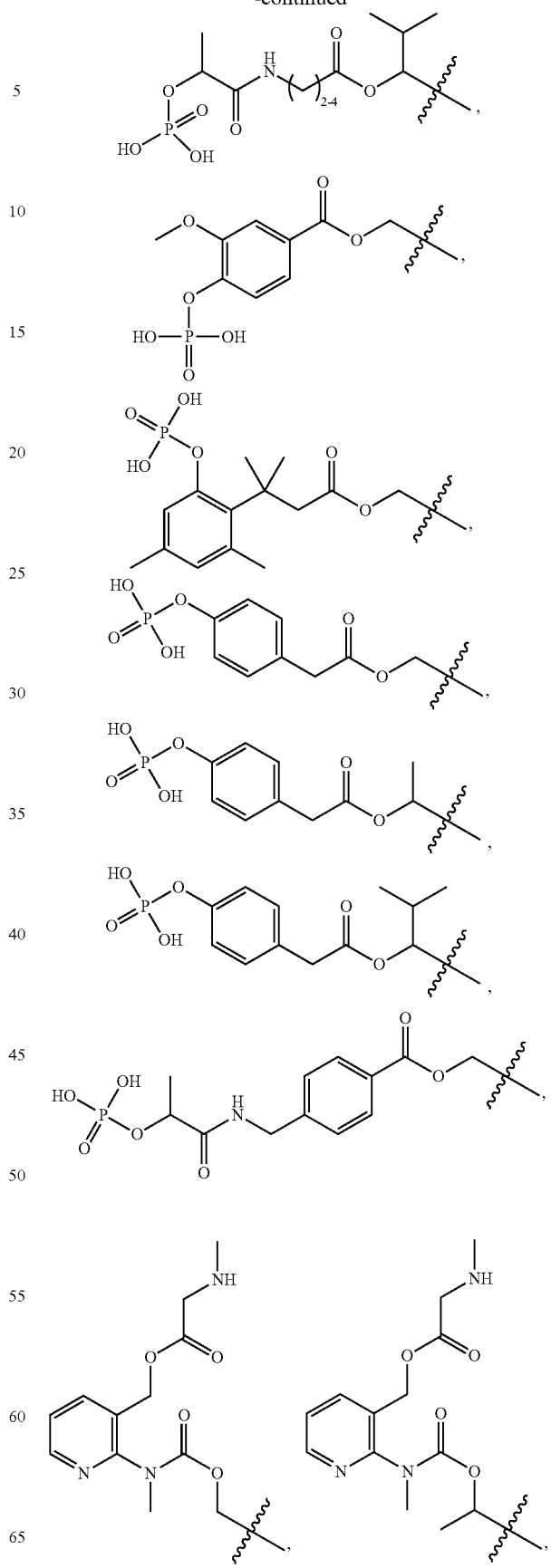

-continued
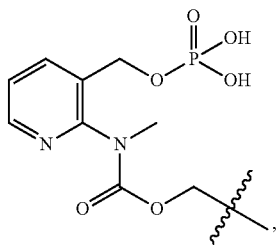
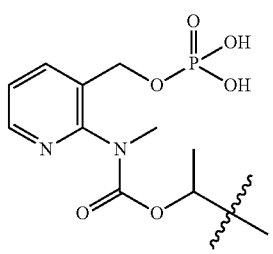
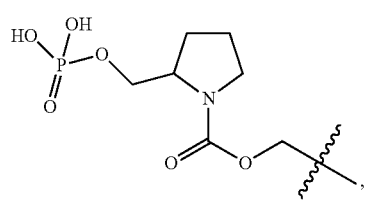
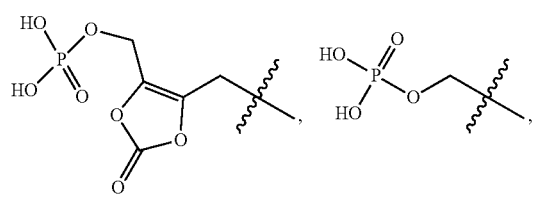
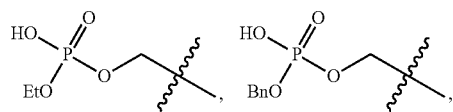
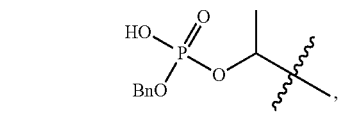
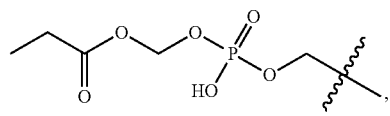
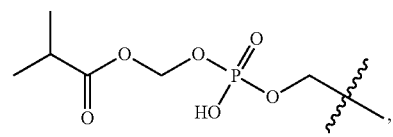
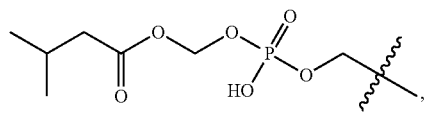
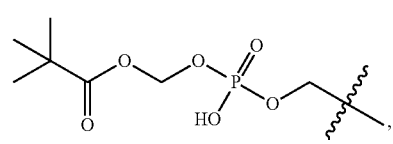
-continued
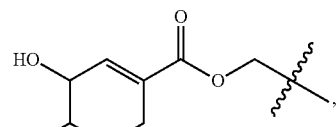
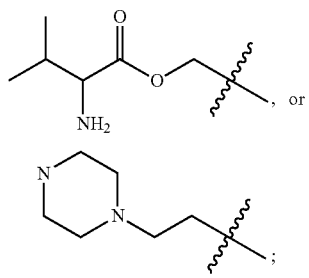
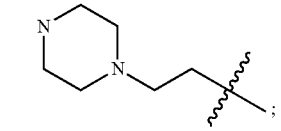
$R^3$, $R^4$, and $R^5$ are H;
$R^6$ is $CH_2CH_3$;
$R^7$ and $R^8$ are i-Bu; and
$R^9$ is 4-methoxy-phenyl.
In a fifth aspect, the present invention provides a compound of formula (I), within the scope of any of the above aspects, wherein:
$R^1$ is
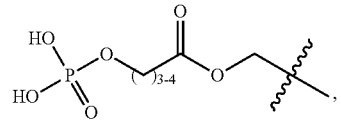
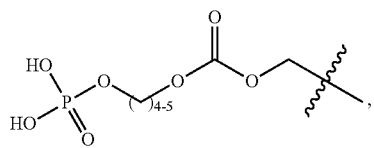
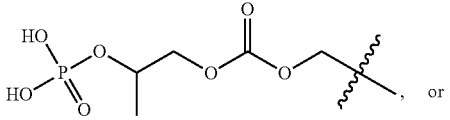
, or
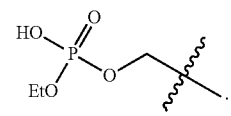
.
In a sixth aspect, the present invention provides a compound of formula (II):

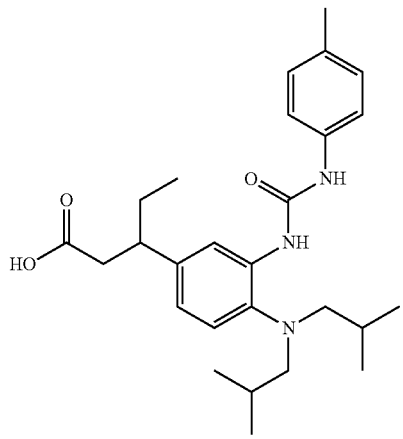

(II)

or a pharmaceutically acceptable salt, a stereoisomer, or a solvate thereof.

In a seventh aspect, the invention provides a compound selected from the exemplified examples or a salt, a stereoisomer, a tautomer, or a solvate thereof.

In another aspect, the present invention provides a compound selected from any subset list of compounds or a single compound from the exemplified examples within the scope of any of the above aspects.

In some aspects, $R^1$ is a straight or branched $C_1$-$C_6$ alkyl substituted with $R^2$,

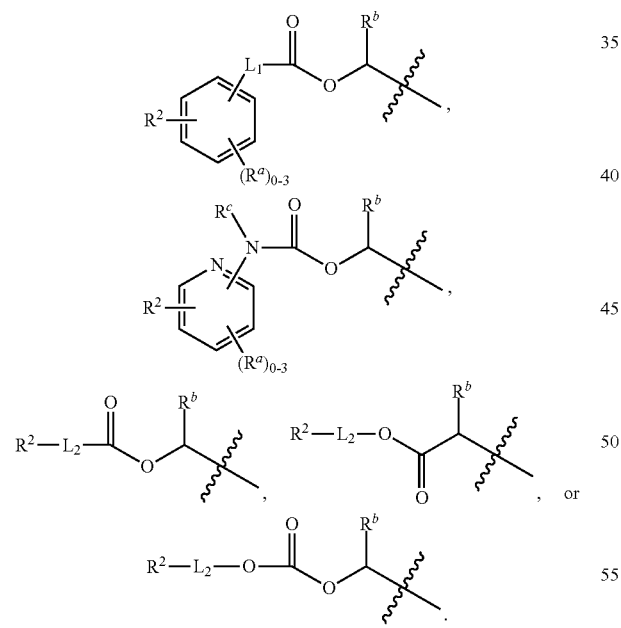

In other aspects, $R^1$ is

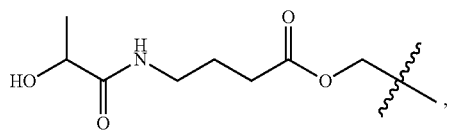

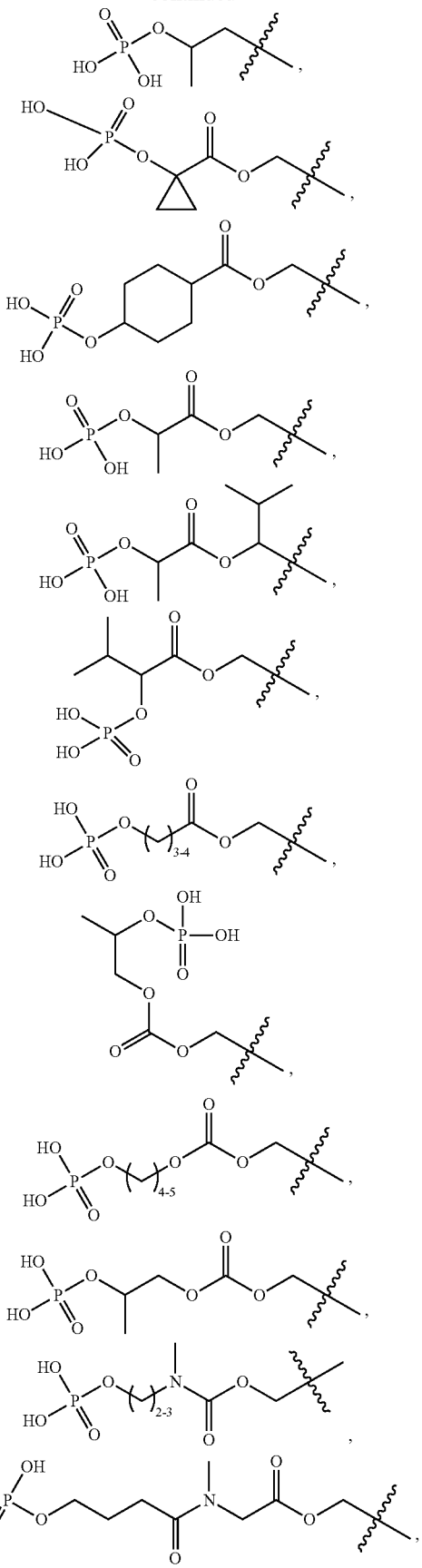

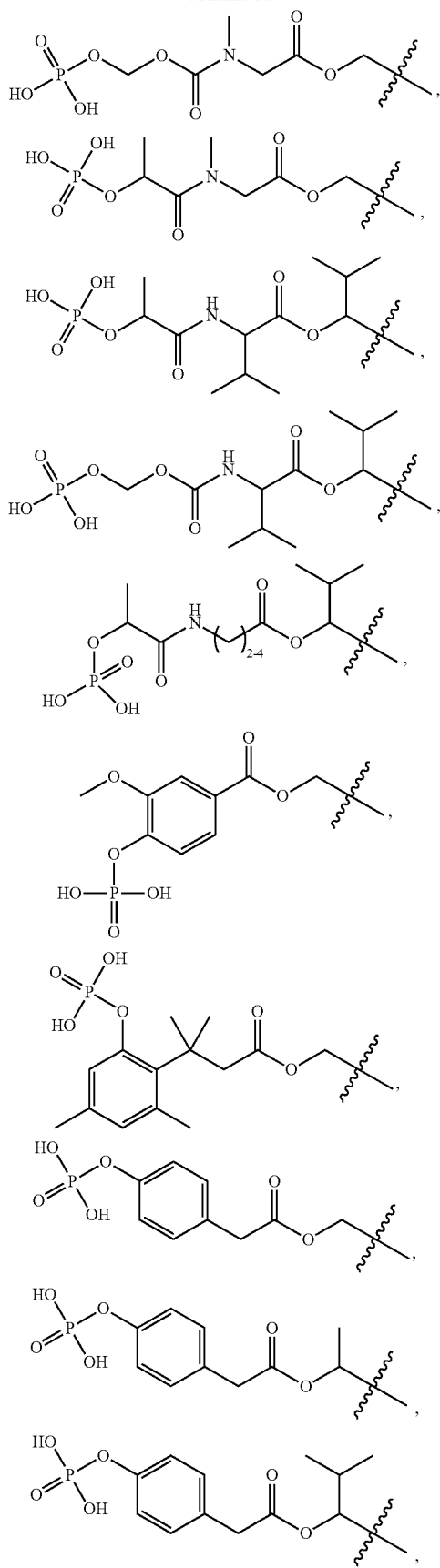
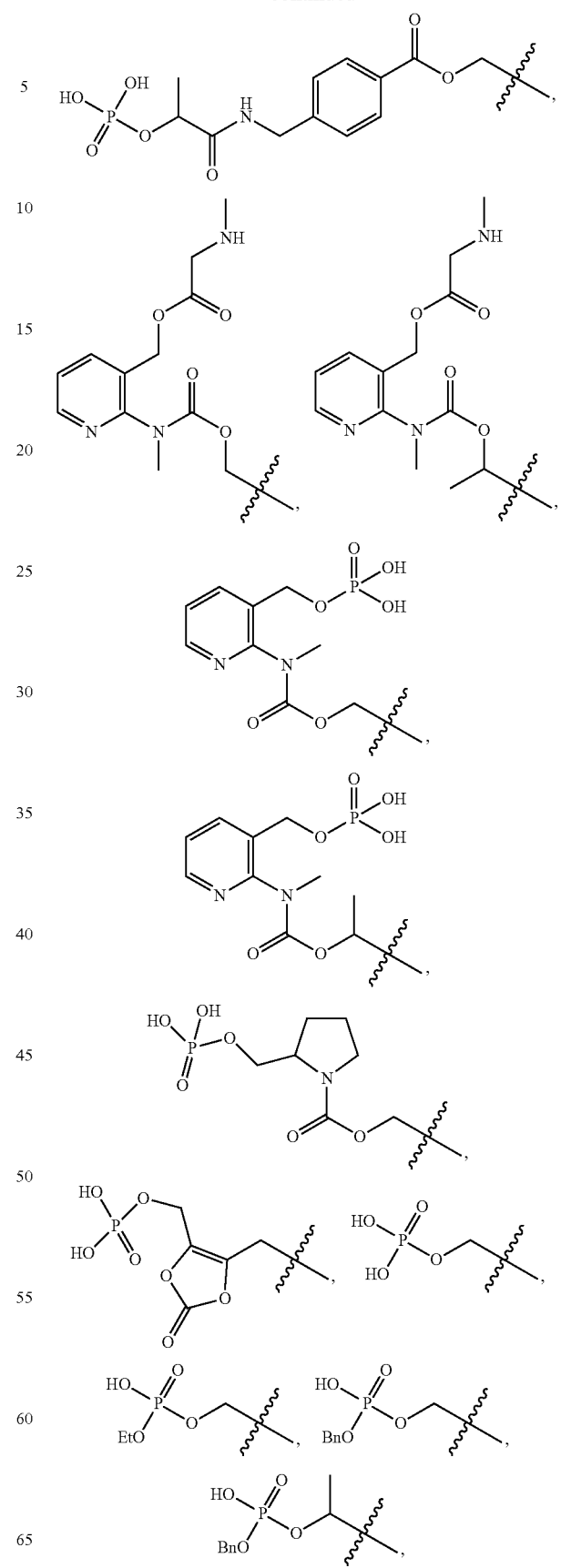

-continued

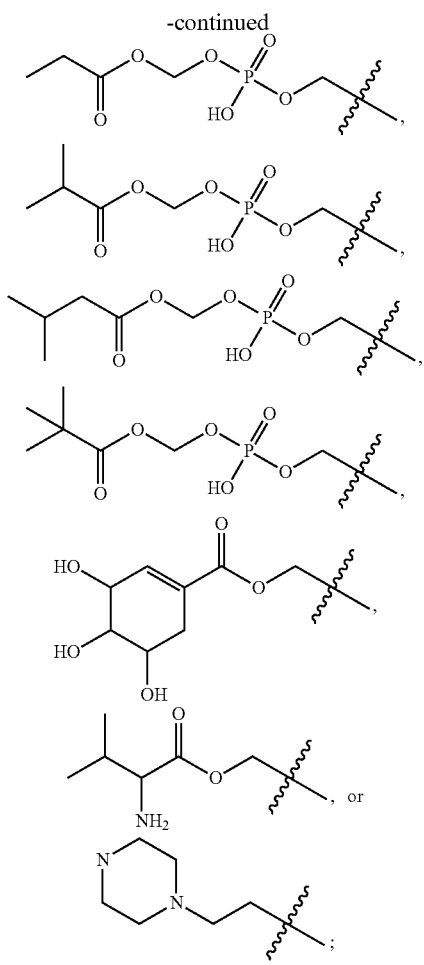

In other aspects, $R^1$ is

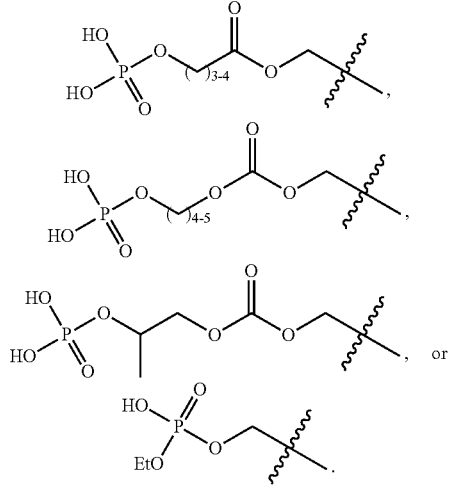

In some aspects, Y is CH. In other aspects, Y is N.

In some aspects, $L_1$ is independently a bond or a straight or branched $C_1$-$C_6$ alkylene.

In some aspects, $L_2$ is independently a bond, a straight or branched $C_1$-$C_6$ alkylene, —OC(O)N(R)CH(R)—, —C(O)N(R^c)L_3$-, $C_3$-$C_6$ cycloalkyl,

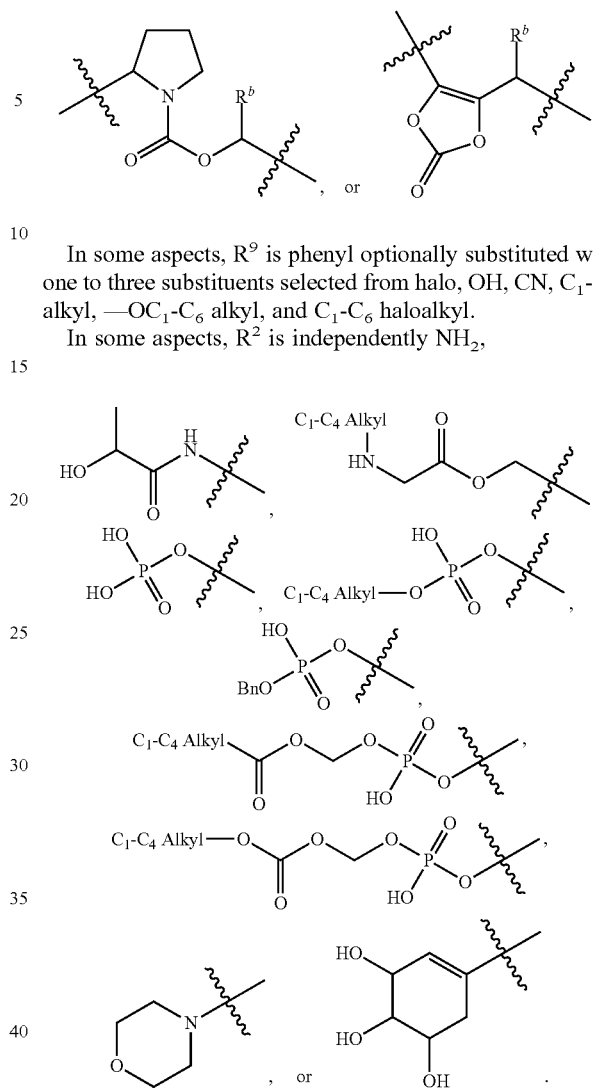

In some aspects, $R^9$ is phenyl optionally substituted with one to three substituents selected from halo, OH, CN, $C_1$-$C_6$ alkyl, —OC_1$-$C_6$ alkyl, and $C_1$-$C_6$ haloalkyl.

In some aspects, $R^2$ is independently $NH_2$,

In some aspects, $R^a$ is independently $C_1$-$C_4$ alkyl or —OC_1$-$C_4$ alkyl.

In some aspects, $R^b$ is independently H or $C_1$-$C_4$ alkyl.

In some aspects, $R^c$ is independently H or $C_1$-$C_2$ alkyl.

In some aspects, $R^d$ is independently H, $C_1$-$C_4$ alkyl, —CH_2OC(O)(C_1$-$C_4$ alkyl), —CH_2OC(O)O(C_1$-$C_4$ alkyl), or Bn.

In some aspects, $R^e$ is independently $C_1$-$C_4$ alkyl optionally substituted OH.

OTHER EMBODIMENTS OF THE INVENTION

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another embodiment, the additional therapeutic agent(s) are YERVOY, OPDIVO, or KEYTRUDA, or a combination thereof.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

THERAPEUTIC APPLICATIONS

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barré syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anticancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-O1 (see, for example, Sausville, *Curr. Med. Chem.* *Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas I and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see, e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil

[bis(POM)-PMEA]; lobucavir (BMS-180194); BCH-I0652; emtricitabine [(−)-FTC]; beta-L-FD4 (also called beta-L-D4C and named beta-L-2′,3′-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a compound of the present invention is administered with one or more immuno-oncology agents. The immuno-oncology agents used herein, also known as cancer immunotherapies, are effective to enhance, stimulate, and/or upregulate immune responses in a subject.

In one aspect, the Compound of the present invention is sequentially administered prior to administration of the immuno-oncology agent. In another aspect, the Compound of the present invention is administered concurrently with the immunology-oncology agent. In yet another aspect, the Compound of the present invention is sequentially administered after administration of the immuno-oncology agent.

In another aspect, the Compound of the present invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1B), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In another aspect, the immuno-oncology agent is a cytokine that inhibits T cell activation (e.g., IL-6, IL-10, TGF-ß, VEGF, and other immunosuppressive cytokines) or a cytokine that stimulates T cell activation, for stimulating an immune response.

In one aspect, T cell responses can be stimulated by a combination of the Compound of the present invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with the Compound of the present invention for the treatment of cancer include antagonists of inhibitory receptors on NK cells or agonists of activating receptors on NK cells. For example, the Compound of the present invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the Compound of the present invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MEDI4736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO 08/132601, WO 09/44273).

In another aspect, the immuno-oncology agent is a CD137 (4-1B) agonist, such as an agonistic CD137 antibody. Suitable CD137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of the present invention, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol

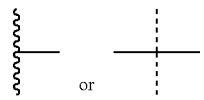

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" is intended to include both branched and straight-chain saturated aliphatic hydrocarbon groups having the specified number of carbon atoms. For example, "C$_1$-C$_6$ alkyl" or "C$_{1-6}$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). The term "alkenyl" refers to an alkyl group having one or more double bonds.

As used herein, "alkylene" (also referred to as "alk") denotes an alkylene having the specified number of carbon atoms. For example, "C$_1$-C$_6$alkylene" denotes an alkylene having 1 to 6 carbon atoms. Example alkylene groups include, but are not limited to, methylene (—CH$_2$—), ethylene (—CH$_2$CH$_2$—), and the like.

As used herein, "aryl" refers to an aromatic ring system which includes, but not limited to phenyl, biphenyl, indanyl, 1-naphthyl, 2-naphthyl and terahydronaphthyl.

"Halo" or "halogen" includes fluoro, chloro, bromo, and iodo.

"Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "cycloalkyl" refers to cyclized alkyl groups. C$_{3-6}$ cycloalkyl is intended to include C$_3$, C$_4$, C$_5$, and C$_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. C$_{4-6}$ cycloalkenyl is intended to include C$_4$, C$_5$, and C$_6$ cycloalkenyl groups. Example cycloalkenyl groups include, but are not limited to, cyclobutenyl, cyclopentenyl, and cyclohexenyl.

As used herein, the term "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

As referred to herein, the term "substituted" means that at least one hydrogen atom is replaced with a non-hydrogen group, provided that normal valencies are maintained and that the substitution results in a stable compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., Remington: The Science and Practice of Pharmacy, 22nd Edition, Pharmaceutical Press, London, UK (2012). The disclosure of which is hereby incorporated by reference.

In addition, compounds of the present invention may have prodrug forms. Any compound that will be converted in vivo to provide the bioactive agent (i.e., a compound of the present invention) is a prodrug within the scope and spirit of the invention. Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5: "Design and Application of Prodrugs", *A Textbook of Drug Design and Development*, pp. 113-191, Krogsgaard-Larsen, P. et al., eds., Harwood Academic Publishers (1991);
c) Bundgaard, H., *Adv. Drug Deliv. Rev.*, 8:1-38 (1992);
d) Nielsen, N. M. et al., *J. Pharm. Sci.*, 77:285 (1988);
e) Kakeya, N. et al., *Chem. Pharm. Bull.*, 32:692 (1984); and
g) Rautio, J., ed., *Prodrugs and Targeted Delivery* (*Methods and Principles in Medicinal Chemistry*), Vol. 47, Wiley-VCH (2011).

Compounds containing a carboxy group can form physiologically hydrolyzable esters that serve as prodrugs by being hydrolyzed in the body to yield Formula (I) or Formula (II) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl(e.g., acetoxymethyl, pivaloyloxymethyl or propionyloxymethyl), $C_{1-6}$alkoxycarbonyloxy-$C_{1-6}$alkyl (e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared by methods such as those illustrated in the following Schemes utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

Reference can also be made to International Publication Nos. WO2016/073738, WO2016/073770, and WO2016/073774.

References to many of these chemical transformations employed herein can be found in Smith, M. B. et al., *March's Advanced Organic Chemistry Reactions, Mecha-* nisms, and Structure, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

Schemes 1-6 depict methods for preparing compounds of Formula (I).

Scheme 1 below shows a general route to prepare compounds of Formula (I). Starting with commercially available reagents such as the chlroalkylchloroformate and reacting with chlorosulfonic acid in a solvent, such as dichloromethane, will afford a chlrorsulfate of the general structure II, which can be in racemic or enantiomerically pure state. The chlorosulfate II can be treated with a dialkyl hydrogen phosphate, such as dibenzyl hydrogen phosphate, and a tetra-alkylammonium hydrogen sulfate, such as tetrabutylammonium hydrogen sulfate, to afford compounds of the general structure III. Chloroalkyl phosphates of general structure III can be treated with a carboxylic acid, such as compound IV, in the presence of sodium iodide and a base such as potassium carbonate followed by deprotection of the phosphate by treatment with hydrogen gas in the presence of Pd/C, to afford a compound of Formula (I).

Scheme 1

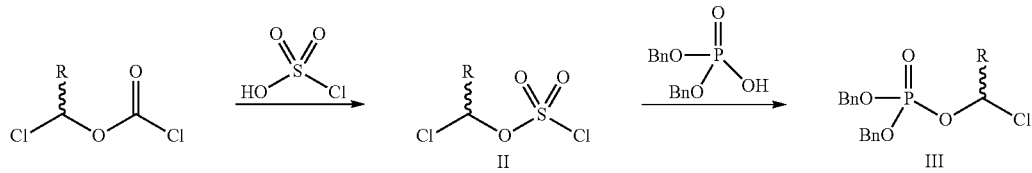

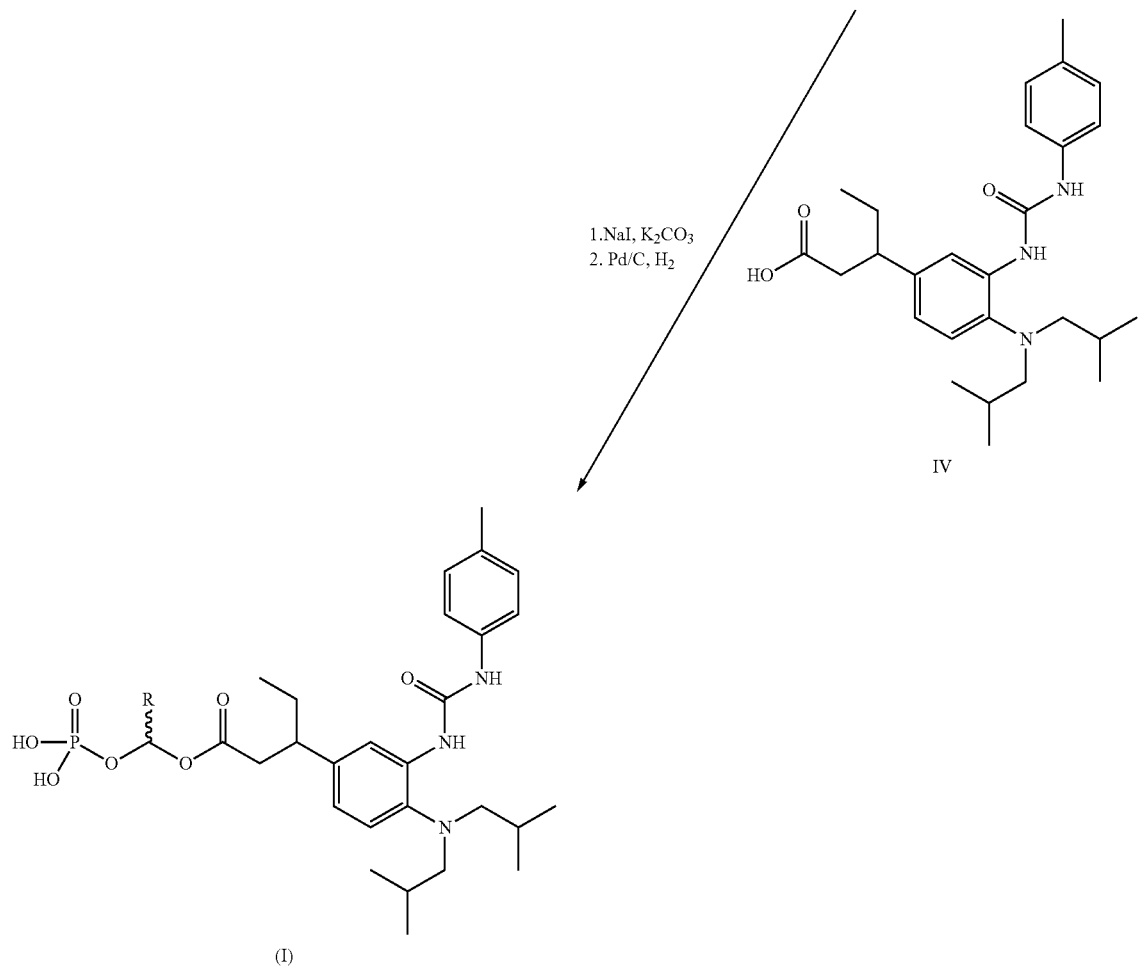

Scheme 2 depicts another synthetic route to prepare compounds of Formula (I). An acid of general structure V, can be treated with a chlorosulfate of general structure II in the presence of a base, such as cesium carbonate, to afford the chloroalkyl ester of general structure VI. Compounds of general structure VI can be treated with a carboxylic acid IV in the presence of sodium iodide and a base such as cesium carbonate to afford a prodrug VII, which is a compound of Formula (I).

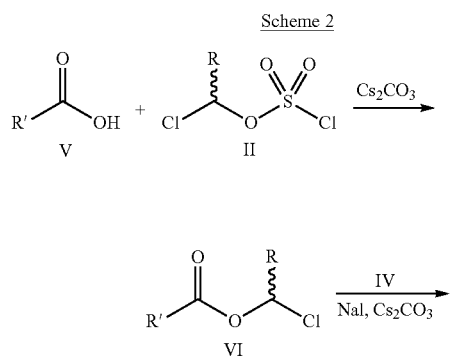

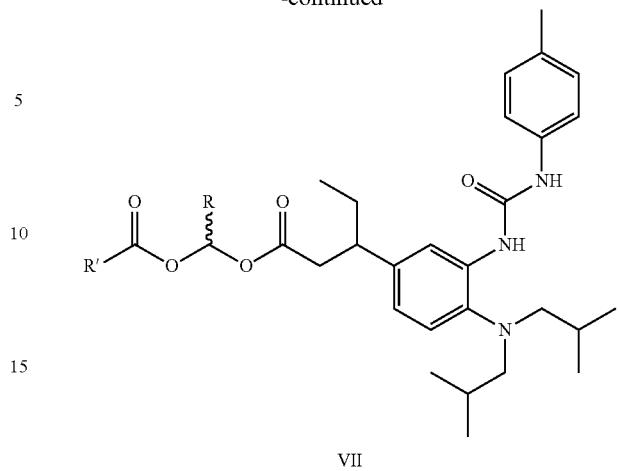

One skilled in the art can further elaborate compounds of general structure VII, which is a compound of Formula (I), as shown in Scheme 3. Treatment of the phosphate VII with a chloromethyl ester of general structure VIII in the presence of sodium iodide and a base, such as cesium carbonate, will afford a dialkyl phosphate of general structure IX, which is a compound of Formula (I).

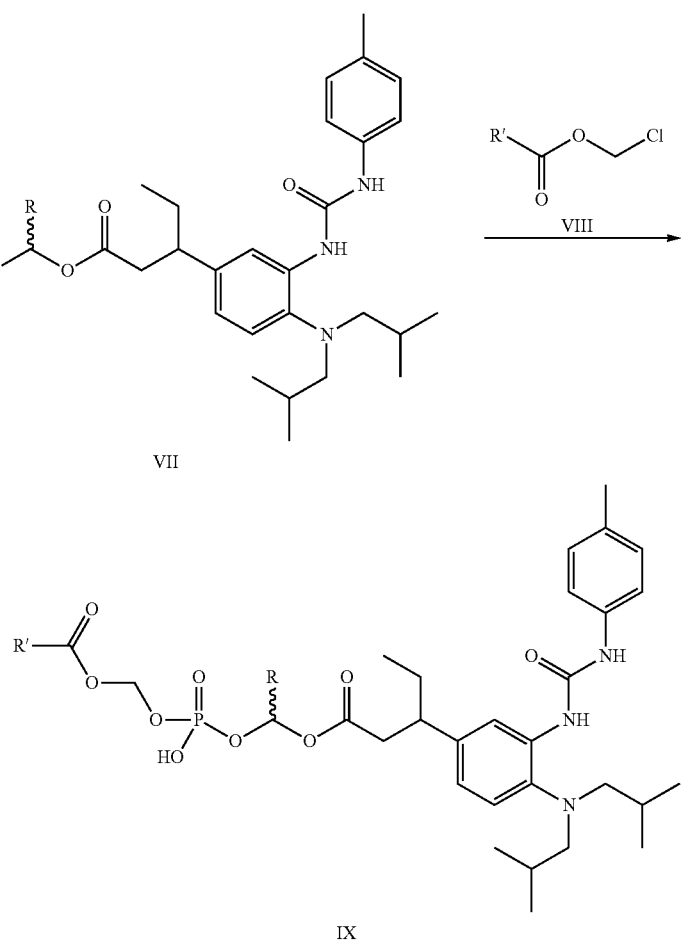

In another embodiment, amines of structure X in Scheme 4 can be treated with a chloroalkylchloroformate of general structure XI in the presence of an organic base, such as diisopropylethylamine, to afford the chloroalkyl carbamate of general structure XI. Treatment of IX with a carboxylic acid, such as IV, in the presence of sodium iodide and a base such as potassium carbonate, will give compounds of the general structure XII, which is also a compound of Formula (I).

Scheme 4

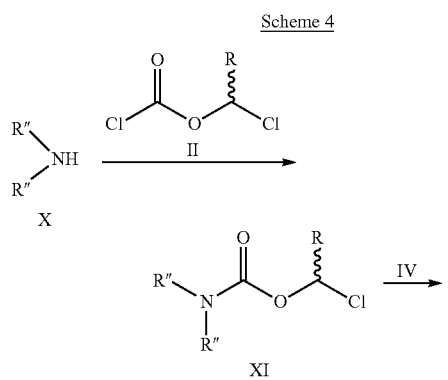

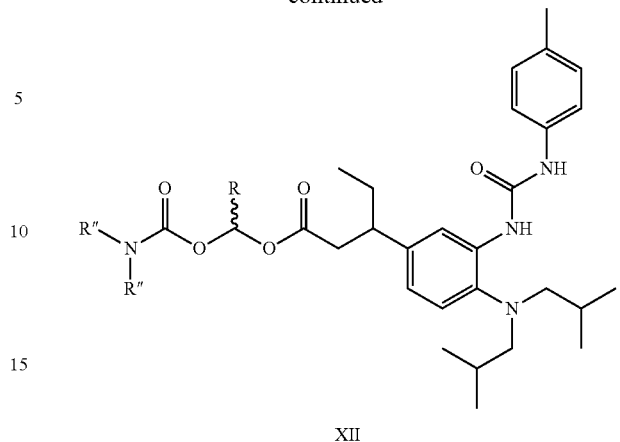

XII

Compounds of general structure XIII can be further elaborated by one skilled in the art, as shown in Scheme 5. Sequential treatment with of XIII with chloromethylchloroformate followed by di-tert-butyl hydrogen phosphate and subsequent treatment with a strong acid, such as TFA, will afford compounds of general structure XIV, which is a compound of Formula (I).

Scheme 5

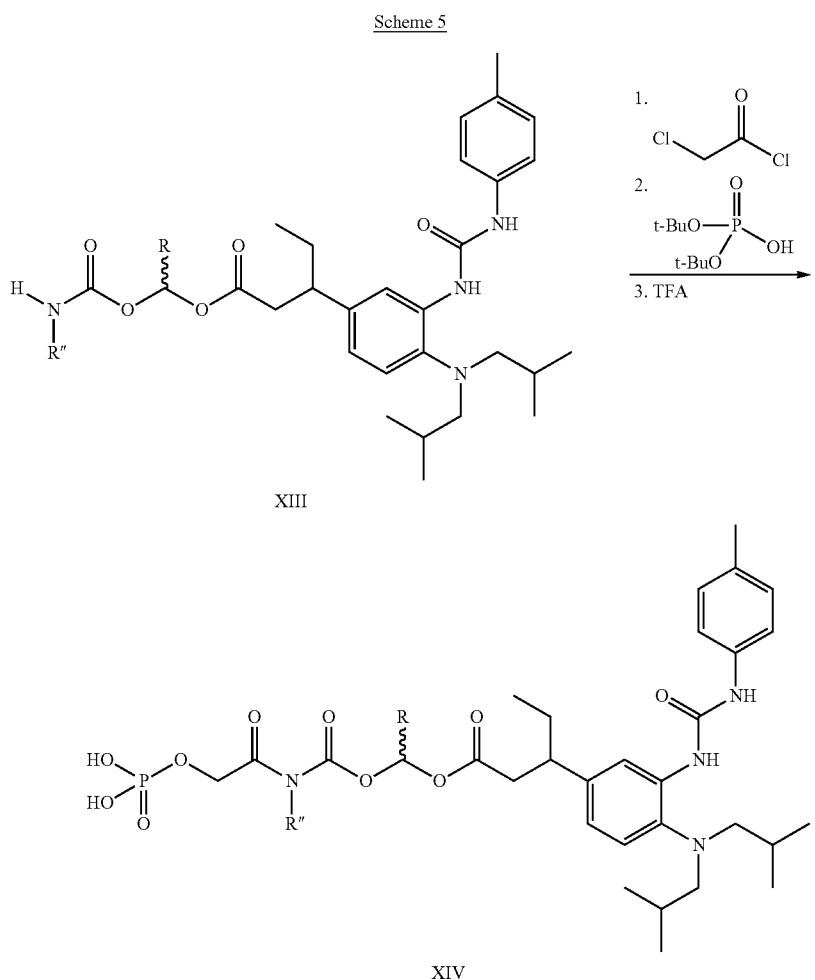

In another embodiment, an alpha-hydroxyester of general structure XV can be treated sequentially with a phosphoramidite, such as dibenzyl N,N-diisopropylphosphoramidite and 1H-tetrazole followed by hydrogen peroxide to afford a phosphate of general structure XVI. The chloroalkyl ester of general structure XVII can be prepared by hydrolysis of an ester of general structure XVI by treatment with a strong aqueous base such as LiOH to afford the corresponding acid which can be treated with a chlorosulfate of general structure II under basic conditions. The chloroalkyl ester of general structure XVII can then be treated with a carboxylic acid such as IV in the presence of sodium iodide and a base, such as cesium carbonate, to afford the trialkyl phosphonate XVIII, which can be treated under catalytic hydrogenation conditions, well known to one skilled in the art, to afford the phosphonic acid XIX, a compound of Formula (I).

ing the following: rt or RT room temperature; $T_r$=retention time; wt=wildtype; bp=base pair(s); kb=kilobase(s); nt=nucleotides(s); aa=amino acid(s); s or sec=second(s); min=minute(s); h or hr=hour(s); ng=nanogram; g=microgram; mg=milligram; g=gram; kg=kilogram; dl or dL=deciliter; or L=microliter; ml or mL=milliliter; l or L=liter; M=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; BW=body weight; U=unit; ns=not statistically significant; PBS=phosphate-buffered saline; IHC=immunohistochemistry; DMEM=Dulbecco's Modification of Eagle's Medium; LG=leaving group; conc.=concentrate or concentrated; aq=aqueous; sat or sat'd=saturated; MW=molecular weight; mp=melting point; MS or Mass Spec=mass spectrometry; ESI=electrospray ionization mass spectroscopy; HR=high Scheme 6

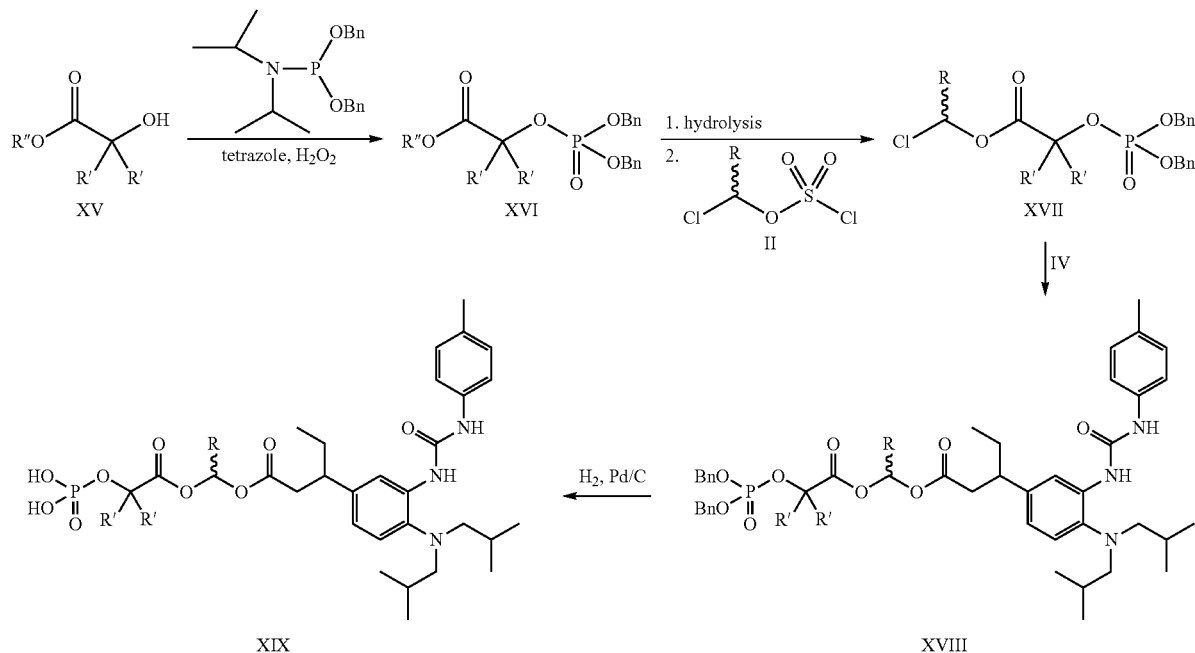

EXAMPLES

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following:

resolution; HRMS=high resolution mass spectrometry; LCMS liquid chromatography mass spectrometry; HPLC=high performance liquid chromatography; RP HPLC=reverse phase HPLC; SFC=Supercritical Fluid Chromatography; TLC or tlc=thin layer chromatography; NMR=nuclear magnetic resonance spectroscopy; "$^1$H" for proton, "δ" for delta, "s" for singlet, "d" for doublet, "t" for triplet, "q" for quartet, "m" for multiplet, "br" for broad, "Hz" for hertz; and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes MeOH methanol
EtOH ethanol
i-PrOH or IPA isopropanol
AcOH or HOAc acetic acid
BOP (Benzotriazol-1-yloxy)tris(dimethylamino)phosphonium hexafluorophosphate
CDCl₃ deutero-chloroform
CHCl₃ chloroform
cDNA complimentary DNA
DMF dimethyl formamide
DMSO dimethyl sulfoxide
DIAD Diisopropyl azodicarboxylate
EDTA ethylenediaminetetraacetic acid
EtOAc ethyl acetate
Et₂O diethyl ether
AlCl₃ aluminum chloride
Boc tert-butyloxycarbonyl
CH₂Cl₂ dichloromethane
CH₃CN or ACN acetonitrile
Cs₂CO₃ cesium carbonate
HCl hydrochloric acid
H₂SO₄ sulfuric acid
Hunig's base diisopropylethylamine
K₂CO₃ potassium carbonate
mCPBA or m-CPBA meta-chloroperbenzoic acid
Pd/C palladium on carbon
PS polystyrene
SiO₂ silica oxide
SnCl₂ tin(II) chloride
TEA triethylamine
TFA trifluoroacetic acid
TFAA trifluoroacetic anhydride
THF tetrahydrofuran
TMSCHN₂ trimethylsilyldiazomethane
KOAc potassium acetate
LHMDS Lithium hexamethyldisilazide
MgSO₄ magnesium sulfate
NMP N-Methylpyrrolidone
MsOH or MSA methylsulfonic acid
NaCl sodium chloride
NaH sodium hydride
NaHCO₃ sodium bicarbonate
NaOH sodium hydroxide
Na₂SO₃ sodium sulfite
Na₂SO₄ sodium sulfate
NH₃ ammonia
NH₄Cl ammonium chloride
NH₄OH ammonium hydroxide Analytical HPLC/MS was performed using the following methods:
Method A: SUNFIRE C18 [150×4.6 mm] column; 0.05% trifluoroacetic acid in water with pH 2.5 as buffer; mobile phase A=buffer: MeCN [95:5]; mobile phase B: MeCN:buffer [95:5]; 10% B to 100% B; 23 min; Flow rate: 1.0 mL/min).
Method B: XBridge Phenyl C18 [150×4.6 mm] column; 0.05% trifluoroacetic acid in water pH 2.5 as buffer; mobile phase A=buffer: MeCN [95:5]; mobile phase B: MeCN:buffer [95:5]; 10% B to 100% B; 23 min; Flow rate: 1.0 mL/min).
Method C: Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA.

NMR Employed in Characterization of Examples
¹H NMR spectra (unless otherwise noted) were obtained with JEOL or Bruker FOURIER® transform spectrometers operating at 400 MHz or 500 MHz.
Spectral data are reported as chemical shift (multiplicity, number of hydrogens, coupling constants in Hz) and are reported in ppm (S units) relative to either an internal standard (tetramethyl silane=0 ppm) for ¹H NMR spectra, or are referenced to the residual solvent peak (2.49 ppm for CD₃SOCD₂H, 3.30 ppm for CD₂HOD, 1.94 for CHD₂CN, 7.26 ppm for CHCl₃, 5.32 ppm for CDHCl₂). Abbreviations used in the description of NMR peaks: "a"=apparent, "br. s."=broad singlet Example 1

3S)-1-(((Benzyloxy)(hydroxy)phosphoryl)oxy)ethyl-3-(4-(diisobutylamino)-3-(3-(p-tolyl)ureido)phenyl)pentanoate

1A: 1-Chloroethyl Chlorosulfate

To a stirred solution of 1-chloroethyl chloroformate (3.02 mL, 28.0 mmol) in dry dichloromethane (40 mL) at 0° C., chlorosulfonic acid (3.72 mL, 56.0 mmol) was added slowly for 10 min. The reaction mixture was stirred at 0° C. for 4 h under nitrogen atmosphere. The reaction mixture was quenched with ice water and extracted with dichloromethane (200 mL). The organic layer was washed with 10% sodium bicarbonate solution and brine solution, dried over anhydrous sodium sulphate and concentrated under vacuum at ~30° C. to give 1-chloroethyl chlorosulfate (4.500 g, 25.1 mmol, 90%) as a light yellowish liquid. $^1$H NMR (300 MHz, chloroform-d) δ ppm=6.54-6.42 (m, 1H), 2.00 (d, J=6.0 Hz, 3H).

1B: Dibenzyl(1-chloroethyl) Phosphate

To a biphasic mixture of dibenzyl hydrogen phosphate (2.000 g, 7.19 mmol), sodium bicarbonate (2.415 g, 28.8 mmol), tetrabutylammonium hydrogen sulfate (0.244 g, 0.719 mmol) in dichloromethane (20 mL) and water (20 mL) at 0° C., 1-chloroethyl chlorosulfate (2.57 g, 14.38 mmol) was added slowly. After being stirred at room temperature for 16 h, the reaction mixture was extracted with dichloromethane (3×100 mL). The organic layer was washed with 10% sodium bicarbonate solution, water and brine solution, dried over anhydrous sodium sulphate and concentrated under vacuum at ~30° C. to give colorless liquid. The crude product was purified by ISCO [silica gel 60-120 mesh; 19% ethyl acetate in hexane as eluent] to give dibenzyl(1-chloroethyl) phosphate (0.900 g, 2.377 mmol, 33.1%) as a colorless semi-solid. $^1$H NMR (400 MHz, chloroform-d) δ ppm=7.42-7.30 (m, 10H), 6.22-6.19 (m, 1H), 5.09 (dd, J=18.8, 8.0 Hz, 4H), 1.75 (d, J=5.6, 0.9 Hz, 3H).

1C: (S)-Methyl 3-(4-(diisobutylamino)-3-nitrophenyl)pentanoate

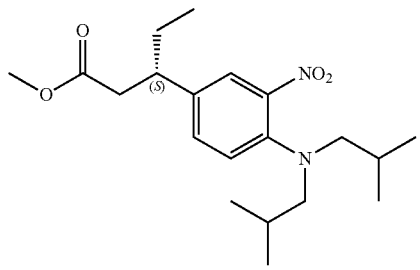

To a $N_2$ flushed, four necked, 2 L RBF equipped with a mechanical stirrer was added Dioxane (771 ml). The solvent was bubbled with $N_2$ for 15 min. To the solvent was added [Rh($C_2H_4$)]$Cl_2$ (0.899 g, 2.312 mmol) and R-Binap (2.111 g, 3.39 mmol). After the mixture was bubbled with $N_2$ and stirring for 30 min at RT, 4-(5,5-dimethyl-1,3,2-dioxaborinan-2-yl)-N,N-diisobutyl-2-nitroaniline (prepared by procedures in WO14150677; 55.8 g, 154 mmol), (E)-methyl pent-2-enoate (17.58 g, 154 mmol) and NaOH (13.86 ml, 13.86 mmol) were added respectively. After bubbled for another 10 min, the reaction mixture was heated to 47-50° C. for 1 h, and then quenched with acetic acid. The reaction mixture was concentrated in vacuum to remove dioxane. The residue was diluted with AcOEt and washed with water (1 L), brine (1 L), dried over $Na_2SO_4$, filtered and concentrated in vacuum to give a brown oil (~69 g). The oil was purified on an Isco CombiFlash System: RediSep normal phase silica flash column (80 g), detection wavelength=254 nm, run time=40 min, flow rate=60 mL/min. Mobile phase: (5 min at 100% hexane then 20 min gradient from 0-25% EtOAc in hexane) to give (S)-methyl 3-(4-(diisobutylamino)-3-nitrophenyl)pentanoate (43 g, 118 mmol, 77% yield). $^1$H NMR (400 MHz, CHLOROFORM-d) δ 7.50 (d, J=2.2 Hz, 1H), 7.20 (dd, J=8.7, 2.3 Hz, 1H), 7.05 (d, J=8.7 Hz, 1H), 3.59 (s, 3H), 3.01-2.92 (m, 1H), 2.88 (d, J=7.2 Hz, 4H), 2.66-2.48 (m, 2H), 1.92-1.82 (m, 2H), 1.73-1.51 (m, 2H), 0.84-0.78 (m, 15H). MS (ES): m/z=365 [M+H]$^+$, $T_r$=1.23 min (Method A).

1D: (S)-Methyl 3-(4-(diisobutylamino)-3-(3-(p-tolyl)ureido)phenyl)pentanoic Acid

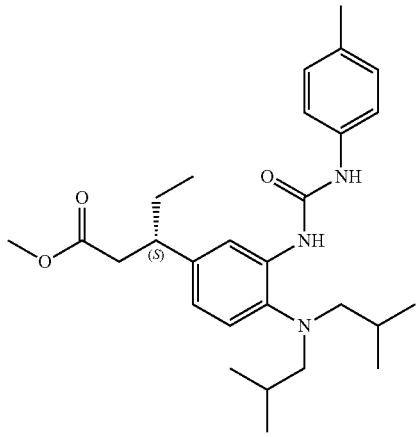

To a solution of (S)-methyl 3-(4-(diisobutylamino)-3-nitrophenyl)pentanoate (83.1 g, 228 mmol) in Ethyl acetate (912 ml) was added 10% wet Pd/C (4 g, 3.38 mmol) and the bottle was equipped with a hydrogen balloon. The reaction solution was stirred for 3 h at RT, than isocyanato-4-methylbenzene (33.4 g, 251 mmol) was added to the solution and stirred for 2 h. The reaction mixture was filtered through Celite and the solution was washed with water then brine, dried, and stripped to afford an oil, which was submitted for iPAC purification to give (S)-methyl 3-(4-(diisobutylamino)-3-(3-(p-tolyl)ureido)phenyl)pentanoate (100.22 g, 214 mmol, 94% yield) as an off-white solid. $^1$H NMR (400 MHz, CHLOROFORM-D) δ 6.96 (d, J=7.9 Hz, 1H), 6.54-6.48 (m, 2H), 4.08 (br. s., 2H), 3.59 (s, 3H), 2.90-2.82 (m, 1H), 2.58-2.53 (m, 6H), 1.79-1.61 (m, 4H), 0.89 (d, J=6.6 Hz, 12H), 0.78 (t, J=7.3 Hz, 3H). MS (ES): m/z=335 [M+H]$^+$, $T_r$=0.91 min (Method A).

1E: (S)-3-(4-(diisobutylamino)-3-(3-(p-tolyl)ureido)phenyl)pentanoic Acid

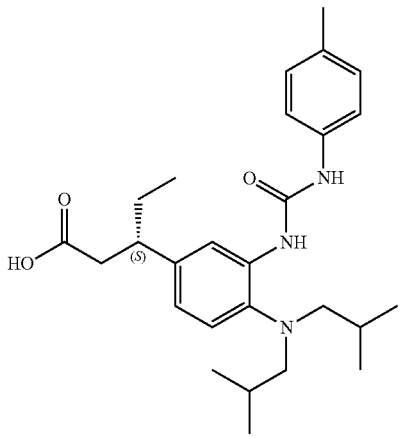

To a solution of (S)-methyl 3-(4-(diisobutylamino)-3-(3-(p-tolyl)ureido)phenyl) pentanoate (159.2 g, 323 mmol) in THF (1000 mL)/methanol (1000 mL) was added 1N NaOH solution (969 ml, 969 mmol). The reaction mixture was stirred overnight at RT, then quenched with 12 N hydrochloric acid to pH=4.5, concentrated to remove THF, extracted with ethyl acetate. The combined extracts were washed with water and dried over $Na_2SO_4$. After removing ethyl acetate, the residue was purified by recrystallization from ethanol to give (S)-3-(4-(diisobutylamino)-3-(3-(p-tolyl)ureido)phenyl)pentanoic acid (140.5 g, 308 mmol, 95% yield) (S:R=99.90/0.10, chemical purity: 99.64%) as a white solid.

Example 1

To a solution of (S)-3-(4-(diisobutylamino)-3-(3-(p-tolyl)ureido)phenyl)pentanoic acid (0.200 g, 0.441 mmol) in dry acetonitrile (5 mL), was added potassium carbonate (0.183 g, 1.323 mmol). After being stirred at room temperature for 15 min, dibenzyl(1-chloroethyl) phosphate (0.300 g, 0.882 mmol), sodium iodide (0.066 g, 0.441 mmol) were added. After being stirred at 70° C. for 16 h, the reaction mixture was diluted with water and extracted with ethyl acetate (3×50 mL). The organic layer was washed with brine, dried over anhydrous sodium sulphate and concentrated under vacuum at ~30° C. The crude product was purified by RP HPLC (X Bridge phenyl [250×19 mm]; mobile phase A: 10 mM ammonium acetate in water; mobile phase B: acetonitrile; flow rate: 18 mL/min.) to afford (3S)-1-(((benzyloxy)(hydroxy)phosphoryl)oxy)ethyl-3-(4-(diisobutylamino)-3-(3-(p-tolyl)ureido)phenyl)pentanoate (0.100 g, 0.142 mmol, 32.1%) as an off-white solid. $^1$H NMR (400 MHz, methanol-$d_4$) δ ppm=7.79 (br. s., 1H), 7.42-7.36 (m, 2H), 7.35-7.19 (m, 5H), 7.13 (d, J=8.0 Hz, 3H), 6.82 (br. s., 1H), 6.44-6.32 (m, 1H), 4.96-4.89 (m, 2H), 2.96-2.78 (m, 1H), 2.65 (d, J=5.5 Hz, 4H), 2.57-2.39 (m, 2H), 2.32 (s, 3H), 1.78-1.48 (m, 3H), 1.34-1.27 (m, 1H), 1.20 (d, J=4.0 Hz, 3H), 0.93-0.83 (m, 12H), 0.78 (t, J=7.3 Hz, 3H); LC-MS (ES): m/z 668 [M+H]$^+$; HPLC T$_r$: 18.0 min (Method A) and 18.3 min (Method B).

Example 2

(S)-((3-(4-(Diisobutylamino)-3-(3-(p-tolyl)ureido)phenyl)pentanoyl)oxy)methyl 3-methoxy-4-(phosphonooxy) Benzoate

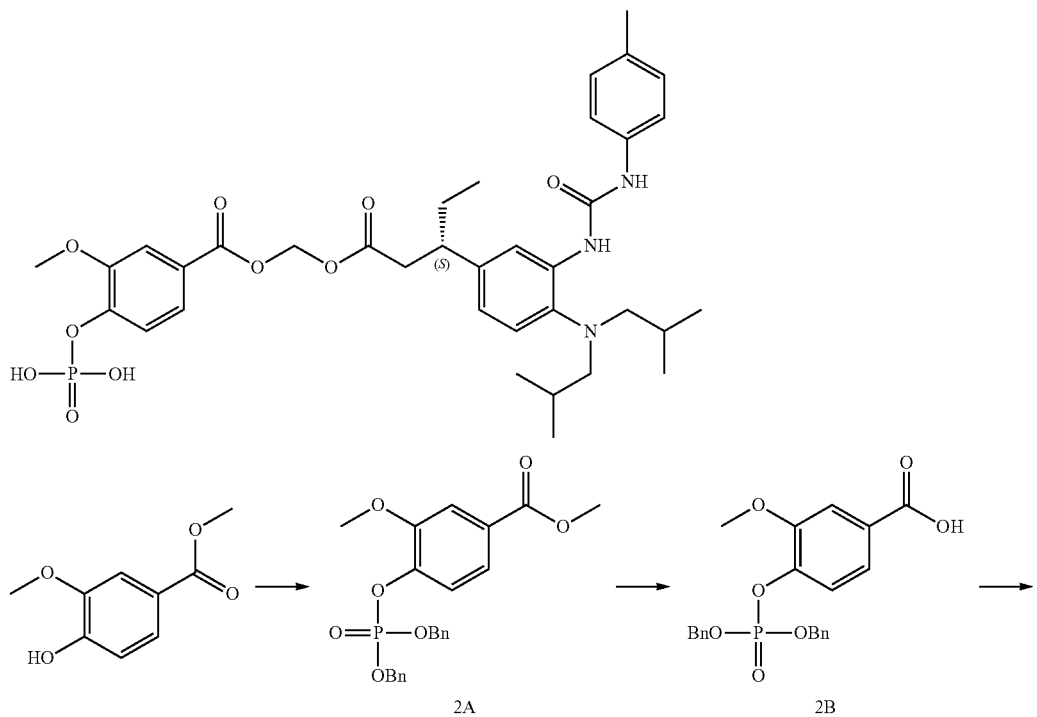

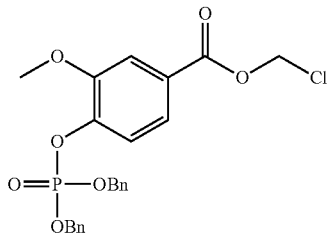

2C

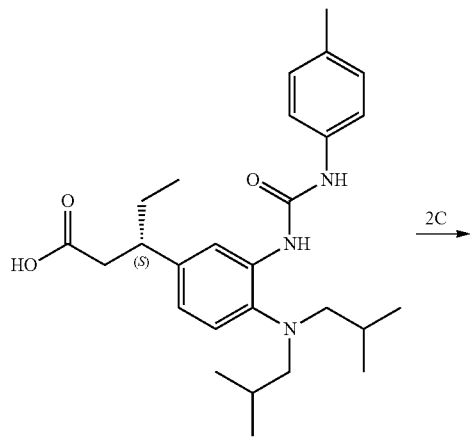

2C →

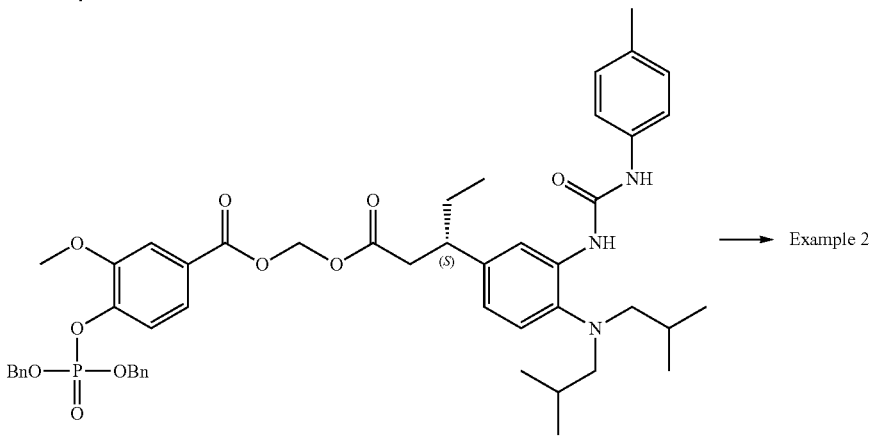

2D

→ Example 2

2A: Methyl 4-((bis(benzyloxy)phosphoryl)oxy)-3-methoxybenzoate

To a stirred solution of methyl 4-hydroxy-3-methoxybenzoate (3.000 g, 16.47 mmol) in dry dichloromethane (30 mL), was added dibenzyl N,N-diisopropylphosphoramidite (8.30 mL, 24.70 mmol), and 1H tetrazole (0.4 M in acetonitrile, 73.0 mL, 24.70 mmol). The mixture was stirred at room temperature for 8 h and cooled to 0° C. $H_2O_2$ (5.05 mL, 165 mmol) was added. The mixture was stirred at room temperature for 2 h, diluted with water and extracted with dichloromethane (3×100 mL). The organic layer was washed with brine, dried over anhydrous sodium sulfate, filtered and concentrated under vacuum at ~30° C. to give colorless oil. The crude product was purified by ISCO (silica gel 60-120 mesh; 30% ethyl acetate in hexane as eluent) to give methyl 4-((bis(benzyloxy)phosphoryl)oxy)-3-methoxybenzoate (8.200 g, 15.94 mmol, 97%) as a colorless oil. $^1$H NMR (400 MHz, chloroform-d) δ ppm=7.59-7.56 (m, 2H), 7.37-7.33 (m, 10H), 7.27 (dd, J=8.3, 1.1 Hz, 1H), 5.17 (d, J=8.3 Hz, 4H), 3.91 (s, 3H), 3.84 (s, 3H). LC-MS (ES): m/z=443 [M+H]$^+$.

2B: 4-((bis(Benzyloxy)phosphoryl)oxy)-3-methoxybenzoic Acid

To a biphasic mixture of methyl 4-((bis(benzyloxy)phosphoryl)oxy)-3-methoxybenzoate (3.000 g, 5.83 mmol) in dry tetrahydrofuran (30 mL) and water (15 mL) at 0° C., was added lithium hydroxide (0.279 g, 11.66 mmol). After being stirred for 1 h at 0° C., organic solvent was removed under vacuum at ~30° C. The aqueous layer was extracted with ethyl acetate (2×100 mL). The aqueous layer was acidified with 1.5 N HCl solution (adjusted to pH-1) and extracted with ethyl acetate (3×100 mL). The organic layer was washed with brine solution, dried over anhydrous sodium sulphate and concentrated under vacuum at ~30° C. to give 4-((bis(benzyloxy)phosphoryl)oxy)-3-methoxybenzoic acid (2.700 g, 2.017 mmol, 34.6%) as a colorless oil. $^1$H NMR (300 MHz, DMSO-d$_6$) δ ppm=7.58-7.49 (m, 2H), 7.42-7.31 (m, 10H), 7.27 (dd, J=8.3, 1.1 Hz, 1H), 5.16 (d, J=8.3 Hz, 4H), 3.82 (s, 3H). LC-MS (ES): m/z=429 [M+H]$^+$.

2C: Chloromethyl 4-((bis (benzyloxy)phosphoryl)oxy)-3-methoxybenzoate

To a biphasic solution of 4-((bis(benzyloxy)phosphoryl) oxy)-3-methoxybenzoic acid (0.800 g, 1.868 mmol), sodium bicarbonate (0.628 g, 7.47 mmol) and tetrabutylammonium hydrogen sulfate (0.063 g, 0.187 mmol) in dichloromethane (10 mL) and water (5 mL) at 0° C., chloromethyl chlorosulfate (0.378 mL, 3.74 mmol) was added slowly. The mixture was stirred at room temperature for 16 h. The mixture was diluted with water and extracted with dichloromethane (3×50 mL). The organic layer was washed with 10% sodium bicarbonate solution and brine solution, dried over anhydrous sodium sulphate and concentrated under vacuum at ~30° C. to give chloromethyl 4-((bis(benzyloxy) phosphoryl)oxy)-3-methoxybenzoate (0.850 g, 1.783 mmol, 95%) as a colorless oil. $^1$H NMR (300 MHz, DMSO-d$_6$) δ ppm=7.64-7.56 (m, 2H), 7.41-7.30 (m, 10H), 7.27 (dd, J=8.3, 1.1 Hz, 1H), 6.07 (s, 2H), 5.17 (d, J=8.7 Hz, 4H), 3.84 (s, 3H); LC-MS (ES): m/z=477 [M+H].

2D: (((S)-3-(4-(Diisobutylamino)-3-(3-(p-tolyl) ureido)phenyl)pentanoyl)oxy)methyl 4-(((benzyloxy)(hydroxy)phosphoryl)oxy)-3-methoxybenzoate To a stirred solution of (S)-3-(4-(diisobutylamino)-3-(3-(p-tolyl)ureido)phenyl)pentanoic acid (0.300 g, 0.661 mmol) in dry DMF (10 mL), was added cesium carbonate (0.431 g, 1.323 mmol) and the mixture was stirred at room temperature for 30 min. (S)-3-(4-(diisobutylamino)-3-(3-(p-tolyl)ureido)phenyl)pentanoic acid (0.300 g, 0.661 mmol), and sodium iodide (0.099 g, 0.661 mmol) were added. After being stirred at room temperature for 16 h, the reaction mixture was diluted with water and extracted with ethyl acetate (3×50 mL). The organic layer was washed with brine solution, dried over anhydrous sodium sulphate and concentrated under vacuum at ~30° C. to give light yellowish oil. The crude product was purified by RP HPLC (Symmetry C18 [250×19 mm]; mobile phase A: 10 mM ammonium acetate in water; mobile phase B: acetonitrile; flow rate: 17 mL/min) to afford (((S)-3-(4-(diisobutylamino)-3-(3-(p-tolyl)ureido)phenyl)pentanoyl)oxy)methyl 4-(((benzyloxy)(hydroxy)phosphoryl)oxy)-3-methoxybenzoate (0.260 g, 0.310 mmol, 46.9%) as an off-white solid. $^1$H NMR (400 MHz, DMSO-d$_6$) δ ppm=9.57 (s, 1H), 7.82-7.73 (m, 2H), 7.60 (d, J=8.5 Hz, 1H), 7.42-7.32 (m, 4H), 7.31-7.26 (m, 5H), 7.25-7.21 (m, 1H), 7.06 (d, J=8.5 Hz, 3H), 6.79 (dd, J=8.3, 2.3 Hz, 1H), 5.89-5.81 (m, 2H), 4.80 (d, J=6.5 Hz, 2H), 3.74 (s, 3H), 2.89-2.80 (m, 1H), 2.77-2.66 (m, 1H), 2.65-2.54 (m, 5H), 2.24 (s, 3H), 1.67-1.44 (m, 4H), 0.81 (dd, J=6.5, 2.0 Hz, 12H), 0.71 (t, J=7.3 Hz, 3H); LC-MS (ES): m/z=804 [M+H].

Example 2

A stirred solution of (((S)-3-(4-(diisobutylamino)-3-(3-(p-tolyl)ureido)phenyl) pentanoyl)oxy)methyl(((benzyloxy)(hydroxy)phosphoryl)oxy)-3-methoxybenzoate (0.230 g, 0.286 mmol) in dry ethyl acetate (10 mL), was added Pd/C (10%, 0.061 g, 0.572 mmol). The mixture was degassed and then flushed with H$_2$ gas and stirred at room temperature for 0.5 h under H$_2$ atmosphere. The reaction mixture was filtered through celite bed, which was washed with ethyl acetate. The filtrate was concentrated under vacuum at ~30° C. The crude product was purified by RP HPLC (Luna C18 [250×30 mm]; mobile phase A: 10 mM ammonium acetate in water; mobile phase B: acetonitrile; flow rate: 18 mL/min.) to afford (S)-((3-(4-(diisobutylamino)-3-(3-(p-tolyl)ureido) phenyl)pentanoyl)oxy)methyl 3-methoxy-4-phosphonooxy) benzoate (0.115 g, 0.160 mmol, 55.8%) as an off-white solid. $^1$H NMR (400 MHz, DMSO-d$_6$) δ ppm=9.58 (s, 1H), 7.80 (s, 1H), 7.74 (d, J=2.0 Hz, 1H), 7.64 (d, J=8.5 Hz, 1H), 7.42-7.31 (m, 4H), 7.06 (d, J=8.0 Hz, 3H), 6.79 (dd, J=8.0, 2.0 Hz, 1H), 5.88-5.80 (m, 2H), 3.71 (s, 3H), 2.90-2.78 (m, 1H), 2.76-2.65 (m, 2H), 2.64-2.55 (m, 5H), 2.24 (s, 3H), 1.68-1.42 (m, 4H), 0.81 (dd, J=6.5, 1.5 Hz, 12H), 0.71 (t, J=7.3 Hz, 3H); LC-MS (ES): m/z=714 [M+H]$^+$; HPLC T$_r$: 18.1 min (Method A) and 15.8 min (Method B).

Example 3

(S)-((3-(2,4-Dimethyl-6-(phosphonooxy)phenyl)-3-methylbutanoyl)oxy)methyl-3-(4-(diisobutylamino)-3-(3-(p-tolyl)ureido)phenyl)pentanoate

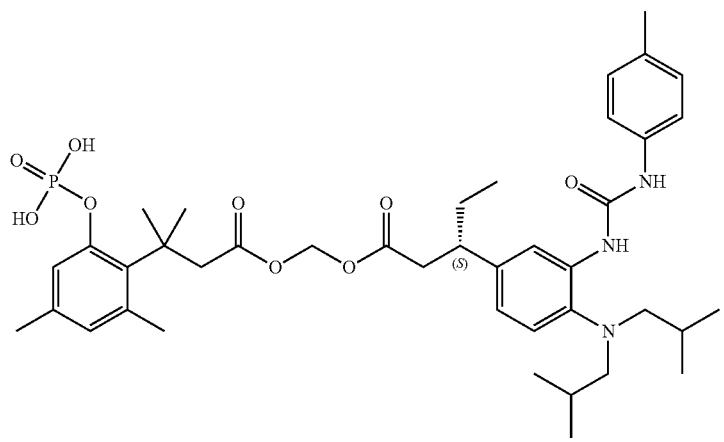

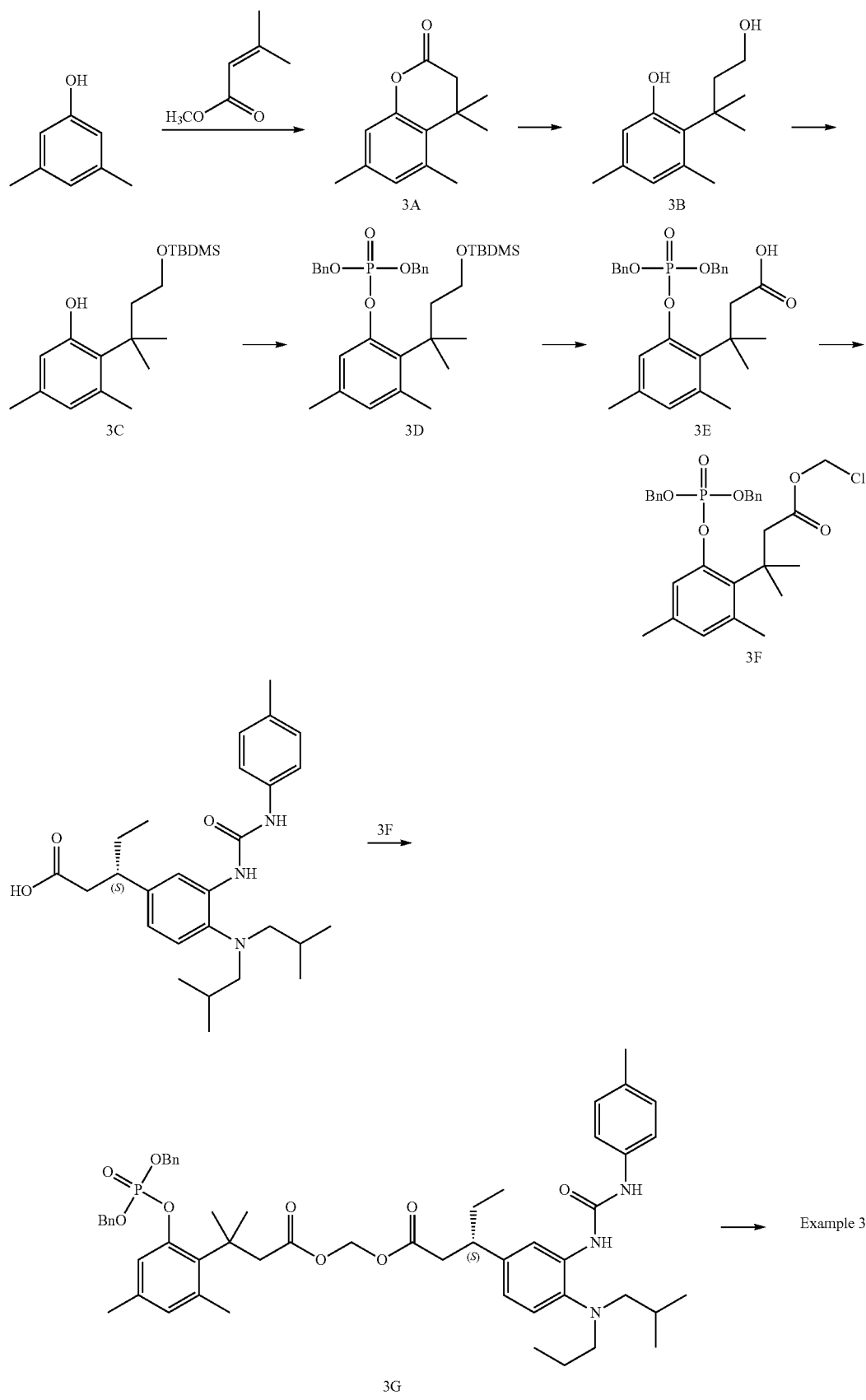

3A: 4,4,5,7-Tetramethylchroman-2-one

To a stirred solution of 3,5-dimethylphenol (5.00 g, 40.9 mmol) in methanesulfonic acid (5.32 ml, 82 mmol), was added methyl 3-methylbut-2-enoate (5.14 g, 45.0 mmol). The mixture was stirred at 70° C. for 16 h under nitrogen. The reaction mixture was diluted with water and extracted with ethyl acetate (3×100 mL). The organic layer was washed with brine, dried over anhydrous sodium sulphate and concentrated under vacuum to give 4,4,5,7-tetramethylchroman-2-one (8.000 g, 34.5 mmol, 84%) as a light yellow solid. $^1$H NMR (400 MHz, DMSO-$d_6$) δ ppm=6.83-6.69 (m, 2H), 2.71-2.62 (m, 2H), 2.42 (s, 3H), 2.22 (s, 3H), 1.40-1.30 (m, 6H); LC-MS (ES): m/z=205 [M+H]$^+$.

3B: 2-(4-Hydroxy-2-methylbutan-2-yl)-3,5-dimethylphenol

To a stirred solution of 4,4,5,7-tetramethylchroman-2-one (1.000 g, 4.90 mmol) in dry tetrahydrofuran (10 mL) at 0° C., a solution of 2.4 M LiAlH$_4$ in THF (4.08 mL, 9.79 mmol) was added slowly. After being stirred at room temperature for 12 h, the reaction mixture was quenched with ice water at 0° C., and filtered through celite bed, which was washed with ethyl acetate (100 mL). The filtrate was dried over anhydrous sodium sulphate and concentrated under vacuum to give 2-(4-hydroxy-2-methylbutan-2-yl)-3,5-dimethylphenol (0.950 g, 4.01 mmol, 82%) as a light yellow oil. $^1$H NMR (300 MHz, chloroform-d) δ ppm=6.52 (s, 1H), 6.37 (s, 1H), 4.20-4.08 (m, 1H), 3.63 (t, J=7.0 Hz, 2H), 2.49 (s, 3H), 2.20 (s, 3H), 1.58 (s, 6H), 1.33-1.21 (m, 2H); LC-MS (ES): m/z=209 [M+H]$^+$.

3C: 2-(4-((tert-Butyldimethylsilyl)oxy)-2-methylbutan-2-yl)-3,5-dimethylphenol To a stirred solution of 2-(4-hydroxy-2-methylbutan-2-yl)-3,5-dimethylphenol (0.950 g, 4.56 mmol) in dry dichloromethane (10 mL), were added TEA (1.907 mL, 13.68 mmol), TBDMS-Cl (1.031 g, 6.84 mmol). The mixture was stirred at room temperature for 16 h, diluted with water and extracted with ethyl acetate (3×50 mL). The organic layer was washed with brine, dried over anhydrous sodium sulphate and concentrated under vacuum at ~30° C. to give light yellowish oil. The crude product was purified by ISCO (silica gel 60-120 mesh; 9% ethyl acetate in hexane as eluent) to give 2-(4-((tert-butyldimethylsilyl)oxy)-2-methylbutan-2-yl)-3,5-dimethylphenol (1.000 g, 3.10 mmol, 68.0%) as an off-white solid. $^1$H NMR (400 MHz, DMSO-$d_6$) δ ppm=8.99 (s, 1H), 6.44 (s, 1H), 6.31 (s, 1H), 3.46 (t, J=7.4 Hz, 2H), 2.37 (s, 3H), 2.11 (t, J=7.4 Hz, 2H), 2.09 (s, 3H), 1.46 (s, 6H), 0.81 (s, 9H), 0.86 (s, 6H); LC-MS (ES): m/z=323 [M+H]$^+$.

3D: Dibenzyl (2-(4-((tert-butyldimethylsilyl)oxy)-2-methylbutan-2-yl)-3,5-dimethylphenyl) Phosphate To a solution of 2-(4-((tert-butyldimethylsilyl)oxy)-2-methylbutan-2-yl)-3,5-dimethylphenol (4.500 g, 13.95 mmol) in dry dichloromethane (5 mL), was added dibenzyl N,N-diisopropylphosphoramidite (7.03 mL, 20.93 mmol) followed by 1H-tetrazole (0.4 M in acetonitrile) (46.5 mL, 20.93 mmol). After being stirred at room temperature for 8 h, the reaction was cooled at 0° C. H$_2$O$_2$ (2.138 mL, 69.8 mmol) was added. After being stirred at room temperature for 2 h, the reaction mixture was diluted with water and extracted with dichloromethane (3×100 mL). The organic layer was washed with brine, dried over anhydrous sodium sulfate, filtered and concentrated under vacuum at ~30° C. to give colorless oil. The crude product was purified by ISCO (silica gel 60-120 mesh; 30% ethyl acetate in hexane as eluent) to give dibenzyl (2-(4-((tert-butyldimethylsilyl)oxy)-2-methylbutan-2-yl)-3,5-dimethylphenyl) phosphate (7.000 g, 11.89 mmol, 85%) as a colorless oil. $^1$H NMR (300 MHz, DMSO-$d_6$) δ ppm=7.44-7.28 (m, 10H), 6.95 (s, 1H), 6.76 (s, 1H), 5.13 (d, J=7.9 Hz, 4H), 3.40 (t, J=7.4 Hz, 2H), 2.45 (s, 3H), 2.11 (s, 3H), 2.00 (t, J=7.4 Hz, 2H), 1.45 (s, 6H), 0.77 (s, 9H), 0.86 (s, 6H); LC-MS (ES): m/z=583 [M+H]$^+$.

3E: 3-(2-((bis(Benzyloxy)phosphoryl)oxy)-4,6-dimethylphenyl)-3-methylbutanoic Acid To a stirred mixture of dibenzyl (2-(4-((tert-butyldimethylsilyl)oxy)-2-methylbutan-2-yl)-3,5-dimethylphenyl) phosphate (3.000 g, 5.15 mmol) and potassium fluoride (1.196 g, 20.59 mmol) in dry acetone (30 mL) at 0° C., Jones reagent (4.59 mL, 23.16 mmol) was added slowly. After being stirred at room temperature for 2 h, the reaction mixture was quenched with 2-propanol (5 mL), stirred at room temperature for 20 min and concentrated under reduced temperature. The crude mass was diluted with ice water and extracted with ethyl acetate (3×100 mL). The combined organic layer was dried over anhydrous sodium sulphate and concentrated under vacuum at ~30° C. The crude product was recrystallized in a mixture of diethyl ether and hexane to give 3-(2-((bis(benzyloxy)phosphoryl)oxy)-4,6-dimethylphenyl)-3-methylbutanoic acid (2.500 g, 3.42 mmol, 66.4%) as an off-white solid. $^1$H NMR (300 MHz, DMSO-$d_6$) δ ppm=7.68-7.18 (m, 10H), 6.93 (s, 1H), 6.73 (s, 1H), 5.14 (d, J=7.9 Hz, 4H), 2.79 (s, 2H), 2.10 (s, 3H), 1.99 (s, 3H), 1.51 (s, 6H); LC-MS (ES): m/z=483 [M+H]$^+$.

3F: Chloromethyl 3-(2-((bis(benzyloxy)phosphoryl)oxy)-4,6-dimethylphenyl)-3-methylbutanoate To a biphasic solution of 3-(2-((bis (benzyloxy)phosphoryl)oxy)-4, 6-dimethylphenyl)-3-methylbutanoic acid (2.000 g, 4.15 mmol), sodium bicarbonate (1.393 g, 16.58 mmol) and tetrabutylammonium hydrogen sulfate (0.141 g, 0.415 mmol) in dichloromethane (20 mL) and water (10 mL) at 0° C., chloromethyl chlorosulfate (0.839 mL, 8.29 mmol) was added slowly. After being stirred at room temperature for 16 h, the reaction mixture was diluted with water, and extracted with DCM (3×100 mL). The organic layer was washed with 10% sodium bicarbonate solution and brine solution, dried over anhydrous sodium sulphate and concentrated under vacuum at ~30° C. to give colorless oil. The crude product was purified by ISCO (using silica gel 60-120 mesh; 19% ethyl acetate in hexane as eluent) to give chloromethyl 3-(2-((bis(benzyloxy)phosphoryl)oxy)-4,6-dimethylphenyl)-3-methylbutanoate (0.800 g, 1.326 mmol, 32.0%) as a colorless oil. $^1$H NMR (400 MHz, DMSO-$d_6$) δ ppm=7.44-7.31 (m, 10H), 6.95 (s, 1H), 6.76 (s, 1H), 5.68 (s, 2H), 5.15 (d, J=8.5 Hz, 4H), 2.96 (s, 2H), 2.48 (s, 3H), 2.12 (s, 3H), 1.51 (s, 6H); LC-MS (ES): m/z=531 [M+H]$^+$.

3G: (S)-((3-(2-((bis(Benzyloxy)phosphoryl)oxy)-4,6-dimethylphenyl)-3-methylbutanoyl)oxy)methyl 3-(4-(diisobutylamino)-3-(3-(p-tolyl)ureido)phenyl) pentanoate A mixture of (S)-3-(4-(diisobutylamino)-3-(3-(p-tolyl) ureido)phenyl)pentanoic acid (0.130 g, 0.287 mmol) and cesium carbonate (0.187 g, 0.573 mmol) in dry DMF (3 mL) was stirred at room temperature for 30 min. (S)-3-(4-(Diisobutylamino)-3-(3-(p-tolyl)ureido)phenyl)pentanoic acid (0.130 g, 0.287 mmol), and sodium iodide (0.043 g, 0.287 mmol) were added. The mixture was stirred at room temperature for 16 h and diluted with water and extracted with ethyl acetate (3×25 mL). The organic layer was washed with brine, dried over anhydrous sodium sulphate and concentrated under vacuum at ~30° C. to give light yellowish oil. The crude product was purified by ISCO (silica gel 60-120 mesh; 23% ethyl acetate in hexane as eluent) to give (S)-((3-(2-((bis(benzyloxy)phosphoryl)oxy)-4,6-dimethylphenyl)-3-methylbutanoyl)oxy)methyl 3-(4-(diisobutylamino)-3-(3-(p-tolyl)ureido)phenyl)pentanoate (0.180 g, 0.175 mmol, 60.9%) as a colorless oil. $^1$H NMR (400 MHz, DMSO-$d_6$) δ ppm=9.33 (s, 1H), 7.90-7.81 (m, 2H), 7.41-7.28 (m, 12H), 7.10 (t, J=8.8 Hz, 3H), 6.92 (s, 1H), 6.75 (d, J=10.5 Hz, 2H), 5.53-5.41 (m, 2H), 5.12 (d, J=8.5 Hz, 4H), 2.91-2.83 (m, 3H), 2.70-2.59 (m, 4H), 2.44 (s, 3H), 2.25 (s, 3H), 2.07 (s, 3H), 1.69-1.53 (m, 4H), 1.48 (s, 6H), 0.83 (d, J=6.5 Hz, 12H), 0.68 (t, J=7.3 Hz, 3H); LC-MS (ES): m/z 949 [M+H]$^+$.

Example 3

To a solution of (S)-((3-(2-((bis(benzyloxy)phosphoryl)oxy)-4,6-dimethylphenyl)-3-methylbutanoyl)oxy)methyl 3-(4-(diisobutylamino)-3-(3-(p-tolyl)ureido)phenyl)pentanoate (0.130 g, 0.137 mmol) in dry ethyl acetate (3 mL), was added 10% Pd/C (0.029 g, 0.274 mmol). The mixture was degassed, then flushed with H2 gas and stirred at room temperature for 0.5 h under H$_2$ atmosphere. The reaction mixture was filtered through celite bed, washed with ethyl acetate and concentrated under vacuum at ~30° C. The crude product was purified by RP HPLC (Luna C18 [250×30 mm]; mobile phase A: 10 mM ammonium acetate in water; mobile phase B: acetonitrile; flow rate: 27 mL/min) to afford (S)-((3-(2,4-dimethyl-6-(phosphonooxy)phenyl)-3-methylbutanoyl)oxy)methyl 3-(4-(diisobutylamino)-3-(3-(p-tolyl)ureido)phenyl)pentanoate (0.045 g, 0.057 mmol, 41.5%) as an off-white solid. $^1$H NMR (400 MHz, DMSO-$d_6$) δ ppm=9.44 (s, 1H), 7.90 (s, 1H), 7.77 (d, J=2.0 Hz, 1H), 7.37 (d, J=8.5 Hz, 2H), 7.22 (s, 2H), 7.09 (dd, J=13.3, 8.3 Hz, 4H), 6.78 (dd, J=8.5, 2.0 Hz, 1H), 6.42 (s, 1H), 5.50-5.39 (m, 2H), 3.02 (s, 2H), 2.86-2.75 (m, 2H), 2.70-2.58 (m, 5H), 2.39 (s, 3H), 2.24 (s, 3H), 2.08 (s, 3H), 1.71-1.53 (m, 4H), 1.47 (s, 6H), 0.83 (d, J=6.5 Hz, 12H), 0.71 (t, J=7.3 Hz, 3H); LC-MS (ES): m/z=768.2 [M+H]$^+$; HPLC T$_r$: 20.1 min (Method A) and 18.7 min (Method B).

Example 4

(S)-((4-(Phosphonooxy)butanoyl)oxy)methyl 3-(4-(diisobutylamino)-3-(3-(p-tolyl)ureido) Phenyl) Pentanoate

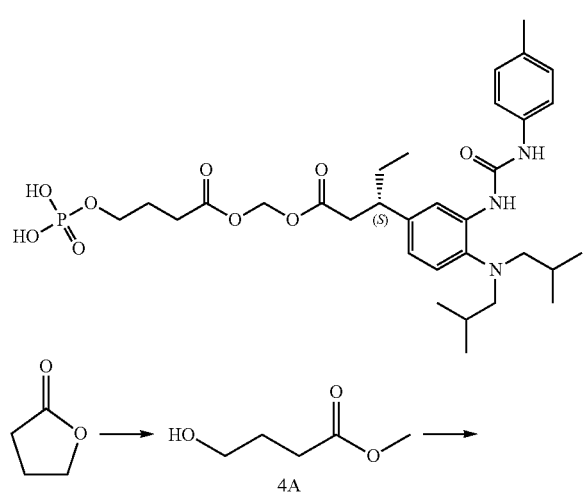

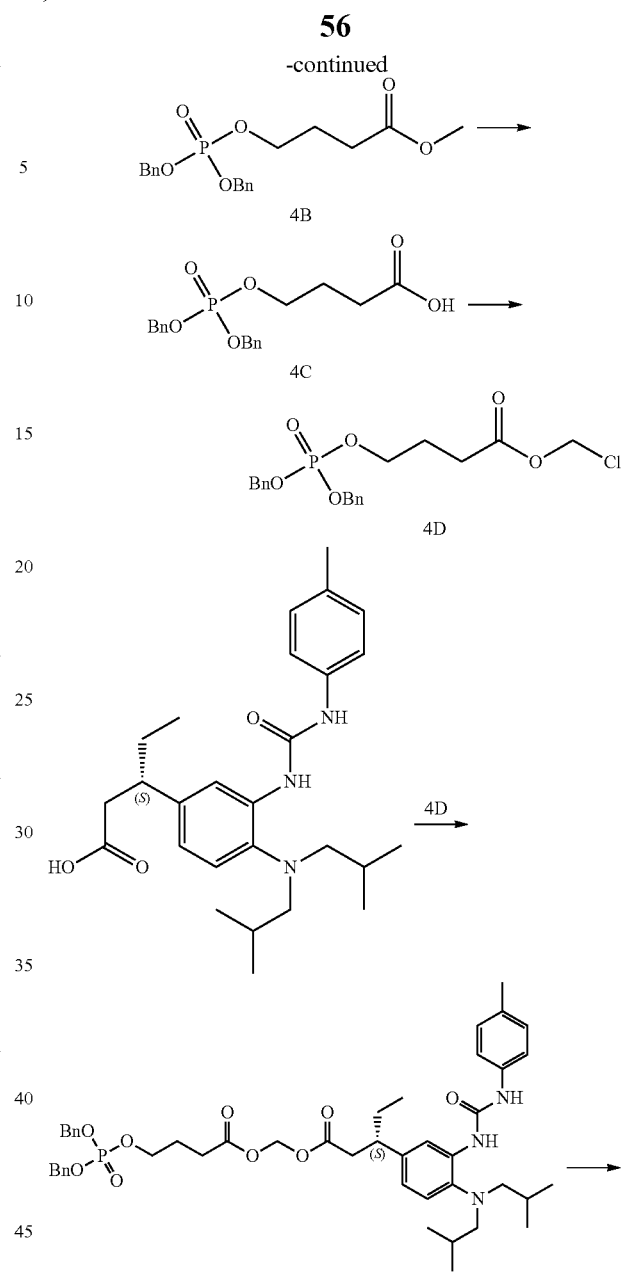

Example 4

4A: Methyl 4-hydroxybutanoate

To a stirred solution of dihydrofuran-2(3H)-one (10.00 mL, 131 mmol) in dry methanol (650 mL), was added triethylamine (110 mL, 789 mmol) and heated at 60° C. for 16 h. The reaction mixture was diluted with hexane (2×200 mL) and concentrated under high vacuum to give methyl 4-hydroxybutanoate (14.00 g, 119 mmol, 90%) as a light yellowish oil. $^1$H NMR (400 MHz, DMSO-$d_6$) δ ppm=4.47 (t, J=5.0 Hz, 1H), 3.58 (s, 3H), 3.42-3.36 (m, 2H), 2.35-2.30 (m, 2H), 1.70-1.62 (m, 2H).

4B: Methyl 4-((bis(benzyloxy)phosphoryl)oxy)butanoate

To a stirred solution of methyl 4-hydroxybutanoate (13.00 g, 110 mmol) in dry dichloromethane (100 mL), was added dibenzyl N, N-diisopropylphosphoramidite (55.5 mL, 165 mmol) followed by a solution of 1H tetrazole (0.4 M in acetonitrile; 418 mL, 165 mmol). The mixture was stirred at room temperature for 8 h. After cooling the reaction mixture to 0° C., $H_2O_2$ (2.138 mL, 69.8 mmol) was added and the mixture was stirred at room temperature for 2 h. The reaction mixture was diluted with water, extracted with dichloromethane (3×200 mL). The combined organic layer was washed with brine, dried over anhydrous sodium sulfate, filtered and concentrated under vacuum at ~30° C. to give colorless oil. The crude product was purified by ISCO (silica gel 60-120 mesh; 40% ethyl acetate in hexane as eluent) to give methyl 4-((bis(benzyloxy)phosphoryl)oxy)butanoate (27.00 g, 68.2 mmol, 61.9%) as a colorless oil. $^1$H NMR (400 MHz, DMSO-$d_6$) δ ppm=7.44-7.32 (m, 10H), 5.03 (d, J=8.0 Hz, 4H), 3.56 (s, 3H), 3.99 (q, J=6.5 Hz, 2H), 2.36 (t, J=7.3 Hz, 2H), 1.83 (quin, J=6.9 Hz, 2H); LC-MS (ES): m/z=379 [M+H]$^+$.

4C: 4-((bis (Benzyloxy)phosphoryl)oxy)butanoic Acid

To a biphasic solution of methyl 4-((bis(benzyloxy)phosphoryl)oxy)butanoate (27.000 g, 71.4 mmol) in tetrahydrofuran (270 mL) and water (180 mL) at 0° C., was added LiOH (3.42 g, 143 mmol). The mixture was stirred at 0° C. for 1 h. The organic solvent was removed under vacuum at ~30° C. The aqueous layer was extracted with ethyl acetate (2×50 mL). The aqueous layer was acidified with 1.5 N HCl solution (adjusted to pH-1) and extracted with ethyl acetate (3×200 mL). The combined organic layer was washed with brine, dried over anhydrous sodium sulphate and concentrated under vacuum at ~30° C. to give 4-((bis(benzyloxy)phosphoryl)oxy)butanoic acid (25.00 g, 63.1 mmol, 88%) as a colorless oil. $^1$H NMR (400 MHz, DMSO-$d_6$) δ ppm=7.45-7.28 (m, 10H), 5.03 (d, J=8.5 Hz, 4H), 4.15 (q, J=6.5 Hz, 2H), 2.27 (t, J=7.3 Hz, 2H), 1.80 (quin, J=6.9 Hz, 2H); LC-MS (ES): m/z=365 [M+H]$^+$.

4D: Chloromethyl 4-((bis (benzyloxy)phosphoryl)oxy)butanoate

To a biphasic solution of 4-((bis(benzyloxy)phosphoryl) oxy)butanoic acid (25.000 g, 68.6 mmol), sodium bicarbonate (23.06 g, 274 mmol) and tetrabutylammonium hydrogen sulfate (2.330 g, 6.86 mmol) in DCM (250 mL) and water (100 ml) at 0° C., chloromethyl chlorosulfate (13.88 mL, 137 mmol) was added slowly. After being stirred for 16 h, the reaction mixture was diluted with water and extracted with DCM (3×200 mL). The organic layer was washed with 10% sodium bicarbonate solution and brine solution, dried over anhydrous sodium sulphate and concentrated under vacuum at ~30° C. to give chloromethyl 4-((bis(benzyloxy) phosphoryl)oxy)butanoate (26 g, 63.0 mmol, 92%) as a colorless oil. $^1$H NMR (300 MHz, DMSO-$d_6$) δ ppm=7.46-7.31 (m, 10H), 5.84 (s, 2H), 5.03 (d, J=8.3 Hz, 4H), 3.99 (q, J=6.4 Hz, 2H), 2.47-2. (t, J=7.3 Hz, 2H), 1.90-1.78 (quin, J=6.9 Hz, 2H); LC-MS (ES): m/z=413 [M+H]$^+$.

4E: (S)-((4-((bis(Benzyloxy)phosphoryl)oxy)butanoyl)oxy)methyl 3-(4-(diisobutylamino)-3-(3-(p-tolyl)ureido)phenyl)pentanoate A mixture of (S)-3-(4-(diisobutylamino)-3-(3-(p-tolyl) ureido)phenyl)pentanoic acid (23.00 g, 50.7 mmol), and cesium carbonate (33.0 g, 101 mmol) in dry DMF (230 mL) was stirred at room temperature for 30 min. (S)-3-(4-(Diisobutylamino)-3-(3-(p-tolyl)ureido)phenyl)pentanoic acid (23.00 g, 50.7 mmol), and sodium iodide (7.60 g, 50.7 mmol) were added. After being stirred for 16 h, the reaction mixture was diluted with water (200 mL) and extracted with ethyl acetate (3×250 mL). The organic layer was washed with brine, dried over anhydrous sodium sulphate and concentrated under vacuum at ~30° C. to give light yellowish oil. The crude product was purified by ISCO (silica gel 60-120 mesh; 38% ethyl acetate in hexane as eluent) to give (S)-((4-((bis(benzyloxy)phosphoryl)oxy)butanoyl)oxy) methyl 3-(4-(diisobutylamino)-3-(3-(p-tolyl)ureido)phenyl) pentanoate as a colorless oil. $^1$H NMR (400 MHz, DMSO-$d_6$) δ ppm=9.31 (s, 1H), 7.89-7.81 (m, 2H), 7.42-7.29 (m, 12H), 7.10 (dd, J=13.6, 8.0 Hz, 3H), 6.78 (dd, J=8.5, 2.0 Hz, 1H), 5.65-5.58 (m, 2H), 5.02 (d, J=8.0 Hz, 4H), 4.07 (q, J=6.4 Hz, 2H), 2.87-2.76 (m, 1H), 2.72-2.61 (m, 4H), 2.60-2.55 (m, 1H), 2.48-2.42 (m, 1H), 2.37 (t, J=7.3 Hz, 2H), 2.25 (s, 3H), 1.81 (quin, J=6.8 Hz, 2H), 1.62 (dd, J=12.9, 6.1 Hz, 3H), 1.54-1.42 (m, 1H), 0.83 (d, J=6.5 Hz, 12H), 0.71 (t, J=7.3 Hz, 3H); LC-MS (ES): m/z=830 [M+H]$^+$.

Example 4

To a solution of (S)-((4-((bis(benzyloxy)phosphoryl)oxy) butanoyl)oxy)methyl 3-(4-(diisobutylamino)-3-(3-(p-tolyl) ureido)phenyl)pentanoate (24.00 g, 28.9 mmol) in dry ethyl acetate (250 mL), was added Pd/C (10%, 15.39 g, 14.46 mmol). The mixture was degassed, then flushed with H2 and stirred at room temperature in autoclave for 1 h under $H_2$ atmosphere. The reaction mixture was filtered through celite bed, which was washed with ethyl acetate. The filtrate was concentrated under vacuum at ~30° C. The crude product was purified by RP HPLC (HSS Cyano [250×19 mm]; mobile phase A: 10 mM ammonium acetate in water; mobile phase B: acetonitrile; flow rate: 17 mL/min) to afford (S)-((4-(phosphonooxy)butanoyl)oxy)methyl 3-(4-(diisobutylamino)-3-(3-(p-tolyl)ureido)phenyl) pentanoate (9.800 g, 14.59 mmol, 50.4%) as an off-white solid. $^1$H NMR (400 MHz, methanol-$d_4$) δ ppm=7.85-7.78 (m, 1H), 7.35-7.29 (m, 2H), 7.20-7.10 (m, 3H), 6.87 (dd, J=8.0, 2.0 Hz, 1H), 5.75-5.60 (m, 2H), 3.91 (q, J=6.4 Hz, 2H), 3.03-2.90 (m, 1H), 2.78-2.59 (m, 6H), 2.45 (t, J=7.3 Hz, 2H), 1.87 (quin, J=6.8 Hz, 2H), 1.80-1.57 (m, 4H), 0.89 (d, J=6.5 Hz, 12H), 0.83 (t, J=7.5 Hz, 3H); LC-MS (ES): m/z=650 [M+H]$^+$; HPLC $T_r$: 10.0 min (Method A) and 8.5 min (Method B).

Example 5

(3S)-2-Methyl-1-(2-(4-(phosphonooxy)phenyl)ac-
etoxy)propyl 3-(4-(diisobutylamino)-3-(3-(p-tolyl)
ureido)phenyl) Pentanoate

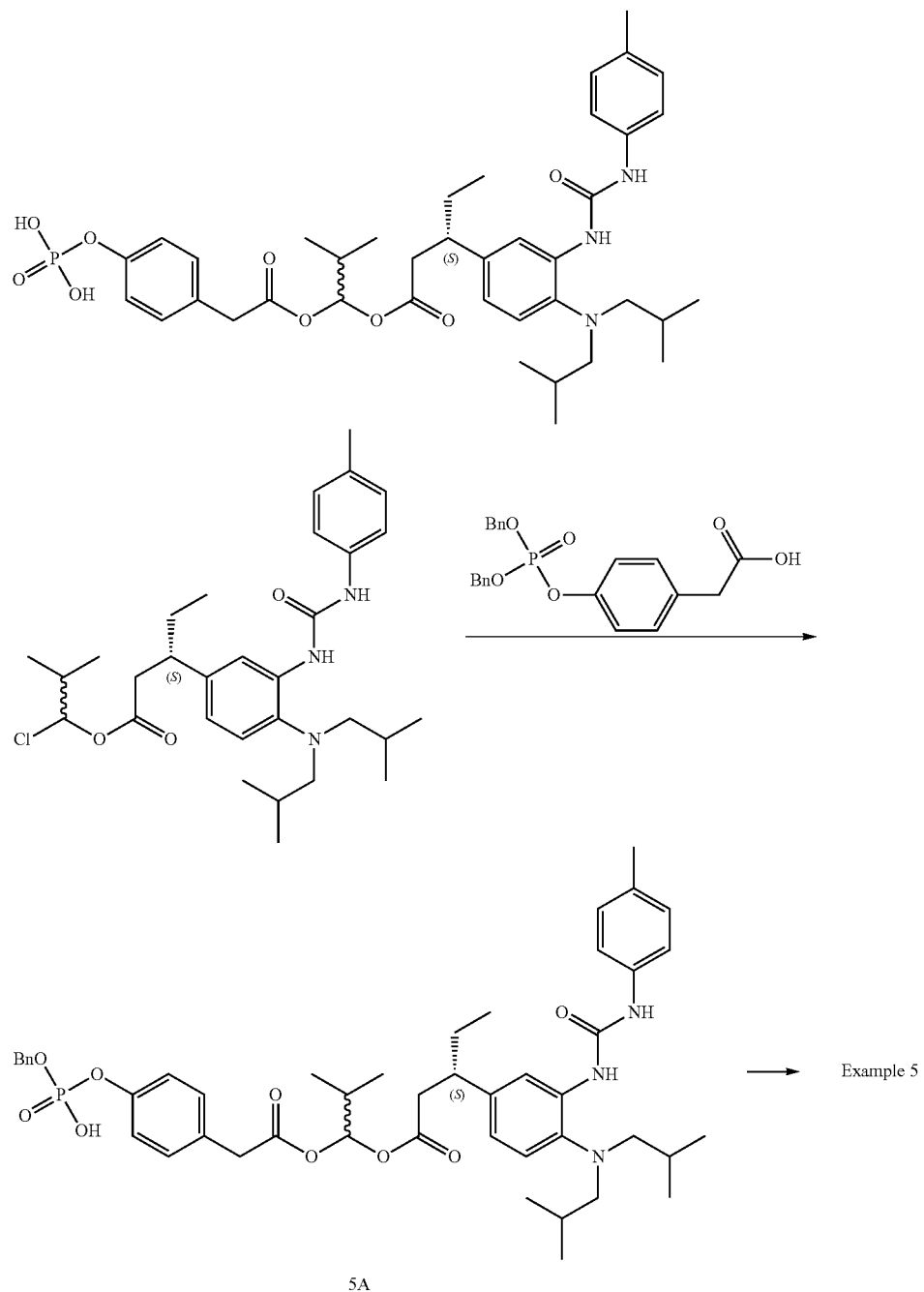

5A: (3S)-1-(2-(4-(((Benzyloxy)(hydroxy)phospho-
ryl)oxy)phenyl)acetoxy)-2-methylpropyl 3-(4-(di-
isobutylamino)-3-(3-(p-tolyl)ureido)phenyl)pentano-
ate To a stirred solution of 2-(4-((bis(benzyloxy)phosphoryl)
oxy)phenyl)acetic acid (0.568 g, 1.378 mmol), cesium car-
bonate (0.599 g, 1.838 mmol) in dry DMF (5 mL) and stirred
at room temperature for 30 min. (3S)-1-chloro-2-methylpro-
pyl 3-(4-(diisobutylamino)-3-(3-(p-tolyl)ureido)phenyl)
pentanoate (0.500 g, 0.919 mmol) was added and stirred at
70° C. for 16 h. The reaction mixture was diluted with water
and extracted with ethyl acetate (3×50 mL). The organic
layer was dried over anhydrous sodium sulphate and concentrated under vacuum at ~30° C. to give light yellowish oil. The crude product was purified by RP HPLC (Kinetex C18 [250×21.2 mm]; mobile phase A: 10 mM ammonium acetate in water; mobile phase B: acetonitrile; flow rate: 17 mL/min) to afford (3S)-1-(2-(4-(((benzyloxy)(hydroxy)phosphoryl)oxy)phenyl)acetoxy)-2-methylpropyl 3-(4-(diisobutylamino)-3-(3-(p-tolyl)ureido)phenyl)pentanoate (0.080 g, 0.055 mmol, 5.98%) as an off-white solid. LC-MS (ES): m/z=830 [M+H]+.

Example 5

To a stirred solution of (3S)-1-(2-(4-(((benzyloxy)(hydroxy)phosphoryl)oxy) phenyl)acetoxy)-2-methylpropyl 3-(4-(diisobutylamino)-3-(3-(p-tolyl)ureido)phenyl)pentanoate (0.070 g, 0.048 mmol) in dry ethyl acetate (2.0 mL), was added Pd/C (10%, 10.23 mg, 0.096 mmol). The mixture was degassed and then flushed with H2 and stirred at room temperature for 0.5 h under H₂ atmosphere. The reaction mixture was filtered through celite bed, which was washed with ethyl acetate and concentrated under vacuum at ~30° C. The crude product was purified by RP HPLC (X Bridge phenyl [250×19 mm]; mobile phase A: 10 mM ammonium acetate in water; mobile phase B: acetonitrile; flow rate: 18 mL/min) to afford (3S)-2-methyl-1-(2-(4-(phosphonooxy)phenyl)acetoxy)propyl 3-(4-(diisobutylamino)-3-(3-(p-tolyl)ureido)phenyl)pentanoate (0.012 g, 0.016 mmol, 32.7%) as an off-white solid. ¹H NMR (400 MHz, DMSO-d₆) δ ppm=9.37 (s, 1H), 7.92-7.76 (m, 2H), 7.43-7.30 (m, 2H), 7.22-6.92 (m, 7H), 6.80 (dd, J=8.0, 2.5 Hz, 1H), 6.44 (dd, J=7.0, 5.0 Hz, 1H), 3.62-3.46 (m, 2H), 2.90-2.74 (m, 2H), 2.73-2.55 (m, 6H), 2.25 (s, 3H), 1.95-1.42 (m, 4H), 0.85 (d, J=6.5 Hz, 12H), 0.78-0.71 (m, 6H), 0.68 (t, J=7.3 Hz, 3H); LC-MS (ES): m/z=740 [M+H]+; HPLC T_r: 20.3 min (Method A) and 17.7 min (Method B).

Example 6

(3S)-1-(2-(4-(Phosphonooxy)phenyl)acetoxy)ethyl-3-(4-(diisobutylamino)-3-(3-(p-tolyl)ureido)phenyl) Pentanoate

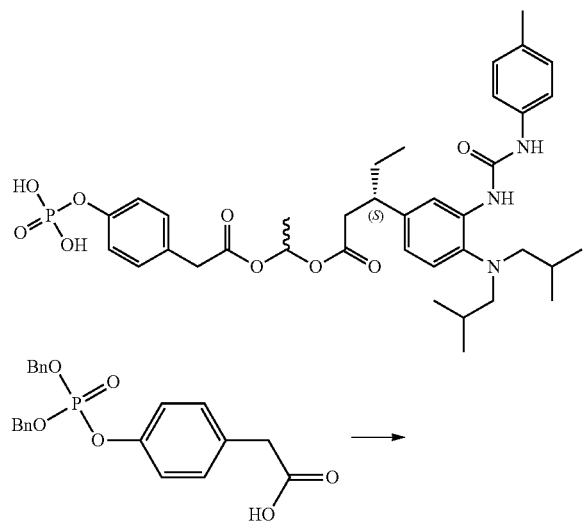

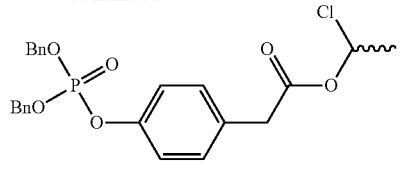

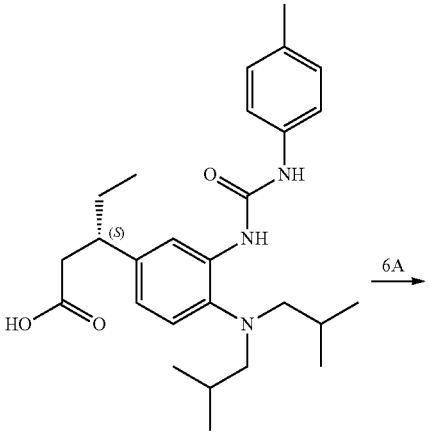

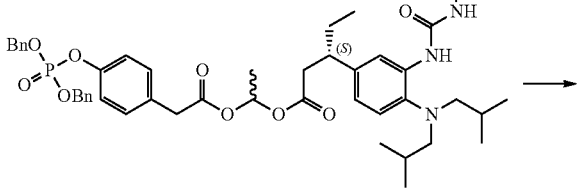

Example 6

6A: 1-Chloroethyl 2-(4-((bis(benzyloxy)phosphoryl)oxy)phenyl)acetate

To a stirred solution of 2-(4-((bis(benzyloxy)phosphoryl)oxy)phenyl)acetic acid (0.500 g, 1.212 mmol) in dry dichloromethane (5 mL), 1-chloro-N,N,2-trimethylprop-1-en-1-amine (0.192 mL, 1.455 mmol) was added. After being stirred at room temperature for 2 h, the mixture was cooled to 0° C. Zinc chloride (0.418 g, 3.06 mmol), and acetaldehyde (0.337 g, 7.66 mmol) were added slowly. After being stirred at 0° C. for 2 h, the reaction mixture was neutralized with sodium bicarbonate solution at 0° C., and extracted with DCM (3×50 mL). The organic layer was washed with brine solution, dried over anhydrous sodium sulphate and concentrated under vacuum at ~30° C. to give light yellowish oil. The crude product was purified by ISCO (using silica gel 60-120 mesh; 38% ethyl acetate in hexane as eluent) to give diastereomeric mixture of 1-chloroethyl 2-(4-((bis(benzyloxy)phosphoryl)oxy)phenyl)acetate (0.540 g, 0.864 mmol, 56.4%) as a light yellowish oil. ¹H NMR (300 MHz, DMSO-d₆) δ ppm=7.48-7.32 (m, 10H), 7.29 (d, J=8.7 Hz, 2H), 7.15 (d, J=7.6 Hz, 2H), 6.59 (q, J=5.7 Hz, 1H), 5.15 (d, J=8.3 Hz, 4H), 3.78 (s, 2H), 1.75 (d, J=5.7 Hz, 3H); LC-MS (ES): m/z=475 [M+H]+.

6B: (3S)-1-(2-(4-(((Benzyloxy)(hydroxy)phosphoryl)oxy)phenyl)acetoxy)ethyl 3-(4-(diisobutylamino)-3-(3-(p-tolyl)ureido)phenyl)pentanoate A mixture of 1-chloroethyl 2-(4-((bis(benzyloxy)phosphoryl)oxy)phenyl)acetate (0.576 g, 1.212 mmol), and potassium carbonate (0.305 g, 2.205 mmol) in acetonitrile (5 mL) was stirred at room temperature for 30 min. (S)-3-(4-(Diisobutylamino)-3-(3-(p-tolyl)ureido)phenyl)pentanoic acid (0.500 g, 1.102 mmol) and sodium iodide (0.165 g, 1.102 mmol) were added. After being stirred at 70° C. for 16 h, the reaction mixture was cooled to room temperature, diluted with water and extracted with ethyl acetate (3×25 mL). The organic layer was dried over anhydrous sodium sulphate and concentrated under vacuum at ~30° C. to give light yellowish oil. The crude product was purified by RP HPLC (Kinetex C18 [250×21.5 mm]; mobile phase A: 10 mM ammonium acetate in water; mobile phase B: acetonitrile; flow rate: 20 mL/min) to afford (3S)-1-(2-(4-(((benzyloxy)(hydroxy)phosphoryl)oxy)phenyl)acetoxy)ethyl 3-(4-(diisobutylamino)-3-(3-(p-tolyl)ureido)phenyl)pentanoate (0.040 g, 0.033 mmol, 3.03%) as an off-white solid. $^1$H NMR (400 MHz, DMSO-d$_6$) δ ppm=9.39 (s, 1H), 7.87 (d, J=13.1 Hz, 1H), 7.80 (d, J=2.0 Hz, 1H), 7.38 (dd, J=8.5, 2.5 Hz, 2H), 7.30 (d, J=8.7 Hz, 2H), 7.15 (d, J=7.6 Hz, 2H), 7.13-6.99 (m, 10H), 6.83-6.78 (m, 1H), 6.63 (q, J=5.7 Hz, 1H), 3.55 (dd, J=11.5, 2.5 Hz, 2H), 2.89-2.74 (m, 1H), 2.71-2.58 (m, 6H), 2.25 (s, 3H), 1.69-1.46 (m, 4H), 1.31 (d, J=5.5 Hz, 2H), 1.22 (d, J=5.5 Hz, 2H), 0.88 (d, J=6.5 Hz, 12H), 0.74 (t, J=6.8 Hz, 3H); LC-MS (ES): m/z=802 [M+H]$^+$.

Example 6

To a stirred solution of (3S)-1-(2-(4-(((benzyloxy)(hydroxy)phosphoryl)oxy) phenyl)acetoxy)ethyl 3-(4-(diisobutylamino)-3-(3-(p-tolyl)ureido)phenyl)pentanoate (0.040 g, 0.050 mmol) in dry ethyl acetate (2.0 mL), was added Pd/C (10%, 10.62 mg, 0.100 mmol). The mixture was degassed and then flushed with H2 and stirred at room temperature for 0.5 h under H$_2$ atmosphere. The reaction mixture was filtered through celite bed, which was washed with ethyl acetate. The filtrate was concentrated under vacuum at ~30° C. The crude product was purified by RP HPLC (Kinetex Biphenyl [250×21.2 mm]; mobile phase A: 10 mM ammonium acetate in water; mobile phase B: acetonitrile; flow rate: 18 mL/min) to afford (3S)-1-(2-(4-(phosphonooxy)phenyl)acetoxy)ethyl 3-(4-(diisobutylamino)-3-(3-(p-tolyl)ureido)phenyl)pentanoate (0.010 g, 0.013 mmol, 26.8%) as an off-white solid. $^1$H NMR (400 MHz, DMSO-d$_6$) δ ppm=9.40 (s, 1H), 7.89 (d, J=13.1 Hz, 1H), 7.82 (d, J=2.0 Hz, 1H), 7.38 (dd, J=8.5, 2.5 Hz, 2H), 7.15-6.99 (m, 5H), 6.83-6.77 (m, 1H), 6.61 (q, J=5.7 Hz, 1H), 3.54 (dd, J=11.5, 2.5 Hz, 2H), 2.88-2.73 (m, 2H), 2.71-2.58 (m, 5H), 2.25 (s, 3H), 1.69-1.46 (m, 4H), 1.31 (d, J=5.5 Hz, 2H), 1.22 (d, J=5.5 Hz, 2H), 0.88 7 (d, J=6.5 Hz, 12H), 0.74 (t, J=6.8 Hz, 3H); LC-MS (ES): m/z=712 [M+H]$^+$; HPLC T$_r$: 9.9 min (Method A) and 16.3 min (Method B).

Example 7

(3S)-((Hydroxy((pivaloyloxy)methoxy)phosphoryl)oxy)methyl 3-(4-(diisobutylamino)-3-(3-(p-tolyl)ureido)phenyl)pentanoate

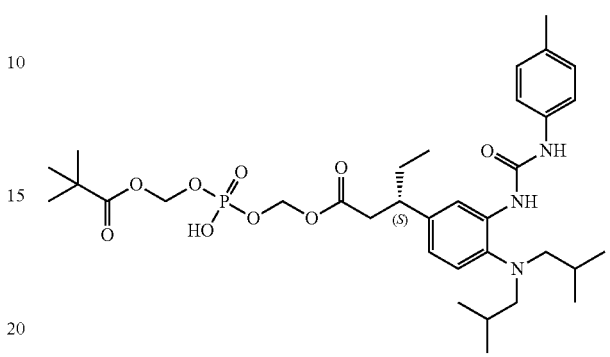

To a stirred solution of (S)-(phosphonooxy)methyl 3-(4-(diisobutylamino)-3-(3-(p-tolyl)ureido)phenyl)pentanoate (0.500 g, 0.887 mmol), chloromethyl pivalate (0.256 mL, 1.774 mmol), DIPEA (0.465 mL, 2.66 mmol) and sodium iodide (0.133 g, 0.887 mmol) in dry DMF (5 mL). The reaction mixture was stirred at room temperature for 12 h. The solvent was concentrated under high vacuum at ~30° C. The crude product was purified by RP HPLC (X Bridge phenyl [250×19 mm]; mobile phase A: 10 mM ammonium acetate in water; mobile phase B: acetonitrile; flow rate: 17 mL/min) to afford (3S)-((hydroxy((pivaloyloxy)methoxy)phosphoryl)oxy)methyl 3-(4-(diisobutylamino)-3-(3-(p-tolyl)ureido)phenyl)pentanoate (0.070 g, 0.102 mmol, 11.46%) as an off-white solid. $^1$H NMR (400 MHz, DMSO-d$_6$) δ ppm=9.31 (s, 1H), 7.86 (d, J=10.0 Hz, 2H), 7.40-7.34 (m, 2H), 7.10 (dd, J=13.6, 8.5 Hz, 4H), 6.80 (dd, J=8.5, 2.0 Hz, 1H), 5.37-5.20 (m, 4H), 2.91-2.77 (m, 1H), 2.70-2.55 (m, 6H), 2.25 (s, 3H), 1.71-1.31 (m, 4H), 1.13 (s, 9H), 0.84 (d, J=6.5 Hz, 12H), 0.72 (t, J=7.3 Hz, 3H); LC-MS (ES): m/z=678 [M+H]$^+$; HPLC T$_r$: 21.4 min (Method A) and 18.0 min (Method B).

Example 8

(3S)-(((Benzyloxy)(hydroxy)phosphoryl)oxy)methyl 3-(4-(diisobutylamino)-3-(3-(p-tolyl)ureido)phenyl)pentanoate

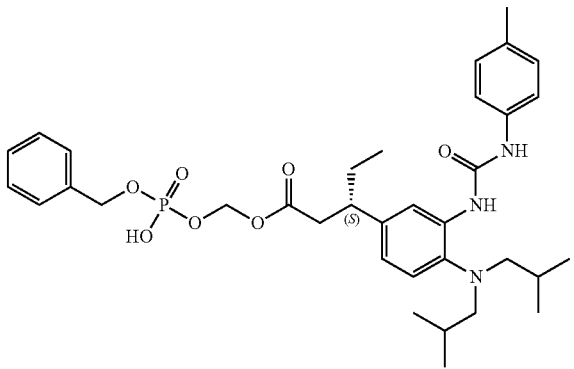

A mixture of (S)-3-(4-(diisobutylamino)-3-(3-(p-tolyl)ureido)phenyl)pentanoic acid (2.000 g, 4.41 mmol) and potassium carbonate (1.219 g, 8.82 mmol) in dry acetonitrile (20 mL) was stirred at room temperature for 30 min. Then (S)-3-(4-(diisobutylamino)-3-(3-(p-tolyl)ureido)phenyl) pentanoic acid (2.000 g, 4.41 mmol) and sodium iodide (0.661 g, 4.41 mmol) were added. The mixture was stirred at 60° C. for 12 h. The reaction mixture was diluted with water (100 mL) and extracted with ethyl acetate (3×50 mL). The organic layer was washed with brine, dried over anhydrous sodium sulphate and concentrated under vacuum at ~30° C. The crude product was purified by RP HPLC (X-Select Cyano [250×19 mm]; mobile phase A: 10 mM ammonium acetate in water; mobile phase B: acetonitrile; flow rate: 18 mL/min) to afford (3S)-(((benzyloxy)(hydroxy)phosphoryl)oxy)methyl 3-(4-(diisobutylamino)-3-(3-(p-tolyl)ureido)phenyl)pentanoate (1.700 g, 2.470 mmol, 56.0%) as an off-white solid. $^1$H NMR (400 MHz, DMSO-$d_6$) δ ppm=9.34 (s, 1H), 7.88 (s, 1H), 7.82 (d, J=2.5 Hz, 1H), 7.42-7.28 (m, 6H), 7.27-7.18 (m, 2H), 7.09 (dd, J=8.0, 4.5 Hz, 3H), 6.75 (dd, J=8.0, 2.0 Hz, 1H), 5.41-5.29 (m, 2H), 4.72 (d, J=6.5 Hz, 2H), 2.87-2.77 (m, 1H), 2.70-2.60 (m, 4H), 2.57-2.53 (m, 1H), 2.48-2.40 (m, 1H), 2.25 (s, 3H), 1.69-1.54 (m, 3H), 1.51-1.39 (m, 1H), 0.83 (d, J=6.5 Hz, 12H), 0.68 (t, J=7.3 Hz, 3H); LC-MS (ES): m/z=654 [M+H]$^+$; HPLC T$_r$: 20.2 min (Method A) and 12.5 min (Method B).

Example 9

(3S)-((Ethoxy(hydroxy)phosphoryl)oxy)methyl 3-(4-(diisobutylamino)-3-(3-(p-tolyl)ureido)phenyl)pentanoate

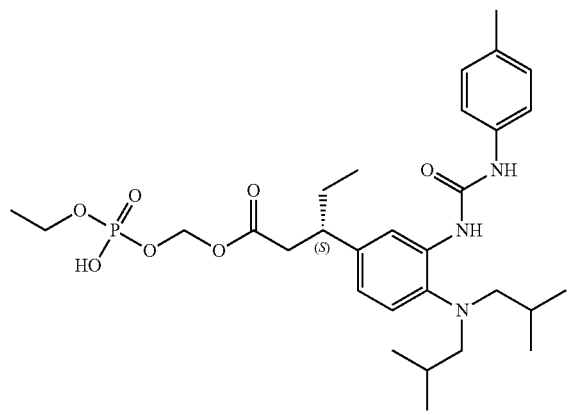

A mixture of (S)-(phosphonooxy) methyl 3-(4-(diisobutylamino)-3-(3-(p-tolyl)ureido)phenyl)pentanoate (0.500 g, 0.887 mmol), iodoethane (0.142 mL, 1.774 mmol), DIPEA (0.465 mL, 2.66 mmol) and sodium iodide (0.133 g, 0.887 mmol) in dry DMF (5 mL). The reaction mixture was stirred at room temperature for 12 h. The solvent was concentrated under high vacuum at ~30° C. The crude product was purified by RP HPLC (Kinetex C18 [250×21.2 mm]; mobile phase A: 10 mM ammonium acetate in water; mobile phase B: acetonitrile; flow rate: 17 mL/min) to afford (3S)-((ethoxy(hydroxy)phosphoryl)oxy)methyl 3-(4-(diisobutylamino)-3-(3-(p-tolyl)ureido)phenyl)pentanoate (0.095 g, 0.156 mmol, 17.63%) as an off-white solid. $^1$H NMR (400 MHz, DMSO-$d_6$) δ ppm=9.32 (s, 1H), 7.87 (s, 1H), 7.83 (d, J=2.0 Hz, 1H), 7.36 (d, J=8.5 Hz, 2H), 7.13-7.05 (m, 4H), 6.80 (dd, J=8.5, 2.0 Hz, 1H), 5.37-5.25 (m, 2H), 3.69 (q, J=7.2 Hz, 2H), 2.90-2.80 (m, 1H), 2.70-2.59 (m, 5H), 2.57-2.52 (m, 1H), 2.25 (s, 3H), 1.69-1.57 (m, 3H), 1.56-1.43 (m, 1H), 1.10 (t, J=7.0 Hz, 3H), 0.83 (d, J=7.0 Hz, 12H), 0.72 (t, J=7.3 Hz, 3H); LC-MS (ES): m/z=592 [M+H]$^+$; HPLC T$_r$: 16.4 min (Method A) and 15.5 min (Method B).

Example 10

(3S)-((Hydroxy(((isopropoxycarbonyl)oxy)methoxy)phosphoryl)oxy)methyl 3-(4-(diisobutylamino)-3-(3-(p-tolyl)ureido)phenyl)pentanoate

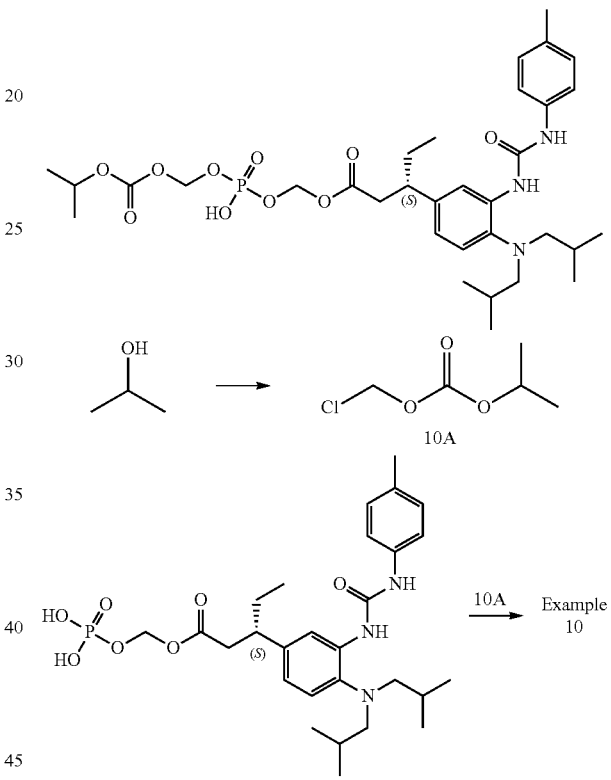

10A: Chloromethyl Isopropyl Carbonate

To a stirred solution of chloromethyl chloroformate (14.80 mL, 166 mmol) and propan-2-ol (6.36 mL, 83 mmol) in dry diethyl ether (150 mL) at 0° C., was added pyridine (20.19 mL, 250 mmol) slowly. The reaction mixture was stirred at room temperature for 16 h. The mixture was filtered through celite bed. The filtrate was washed with 1% citric acid solution (100 mL), water (100 mL), 10% sodium bicarbonate solution (100 mL) and brine solution. The organic layer was dried over anhydrous sodium sulphate and concentrated under vacuum at ~30° C. to give chloromethyl isopropyl carbonate (11.5 g, 75 mmol, 91%) as a colorless liquid. $^1$H NMR (300 MHz, chloroform-d) δ ppm=5.74 (s, 2H), 5.04-4.88 (m, 1H), 1.35 (d, J=6.0 Hz, 6H).

Example 10

A mixture of (S)-(phosphonooxy)methyl 3-(4-(diisobutylamino)-3-(3-(p-tolyl)ureido)phenyl)pentanoate (0.500 g, 0.887 mmol), chloromethyl isopropyl carbonate (0.271 g, 1.774 mmol), DIPEA (0.465 mL, 2.66 mmol) and sodium iodide (0.133 g, 0.887 mmol) in DMF (5 mL) was stirred at room temperature for 12 h. The solvent was concentrated under high vacuum at ~30° C. The crude product was purified by RP HPLC (X-Bridge phenyl [250×19 mm]; mobile phase A: 10 mM ammonium acetate in water; mobile phase B: acetonitrile; flow rate: 17 mL/min) to afford (3S)-((hydroxy(((isopropoxycarbonyl)oxy)methoxy)phosphoryl)oxy)methyl 3-(4-(diisobutylamino)-3-(3-(p-tolyl)ureido)phenyl)pentanoate (0.040 g, 0.055 mmol, 6.19%) as an off-white solid. $^1$H NMR (400 MHz, DMSO-d$_6$) δ ppm=9.29 (s, 1H), 7.86 (s, 1H), 7.83 (d, J=1.5 Hz, 1H), 7.36 (d, J=8.5 Hz, 2H), 7.24 (s, 1H), 7.15-7.05 (m, 2H), 6.98 (s, 1H), 6.80 (dd, J=8.3, 1.8 Hz, 1H), 5.34-5.22 (m, 4H), 4.76-4.73 (m, 1H), 2.90-2.80 (m, 1H), 2.69-2.58 (m, 5H), 2.57-2.52 (m, 1H), 2.24 (s, 3H), 1.71-1.56 (m, 3H), 1.55-1.44 (m, 1H), 1.20 (d, J=6.0 Hz, 6H), 0.83 (d, J=6.5 Hz, 12H), 0.72 (t, J=7.3 Hz, 3H); LC-MS (ES): m/z=670 [M+H]$^+$; HPLC T$_r$: 20.4 min (Method A) and 16.8 min (Method B).

Example 11

(S)-(2-(Methyl(((phosphonooxy)methoxy)carbonyl)amino)acetoxy)methyl 3-(4-(diisobutylamino)-3-(3-(p-tolyl)ureido)phenyl)pentanoate

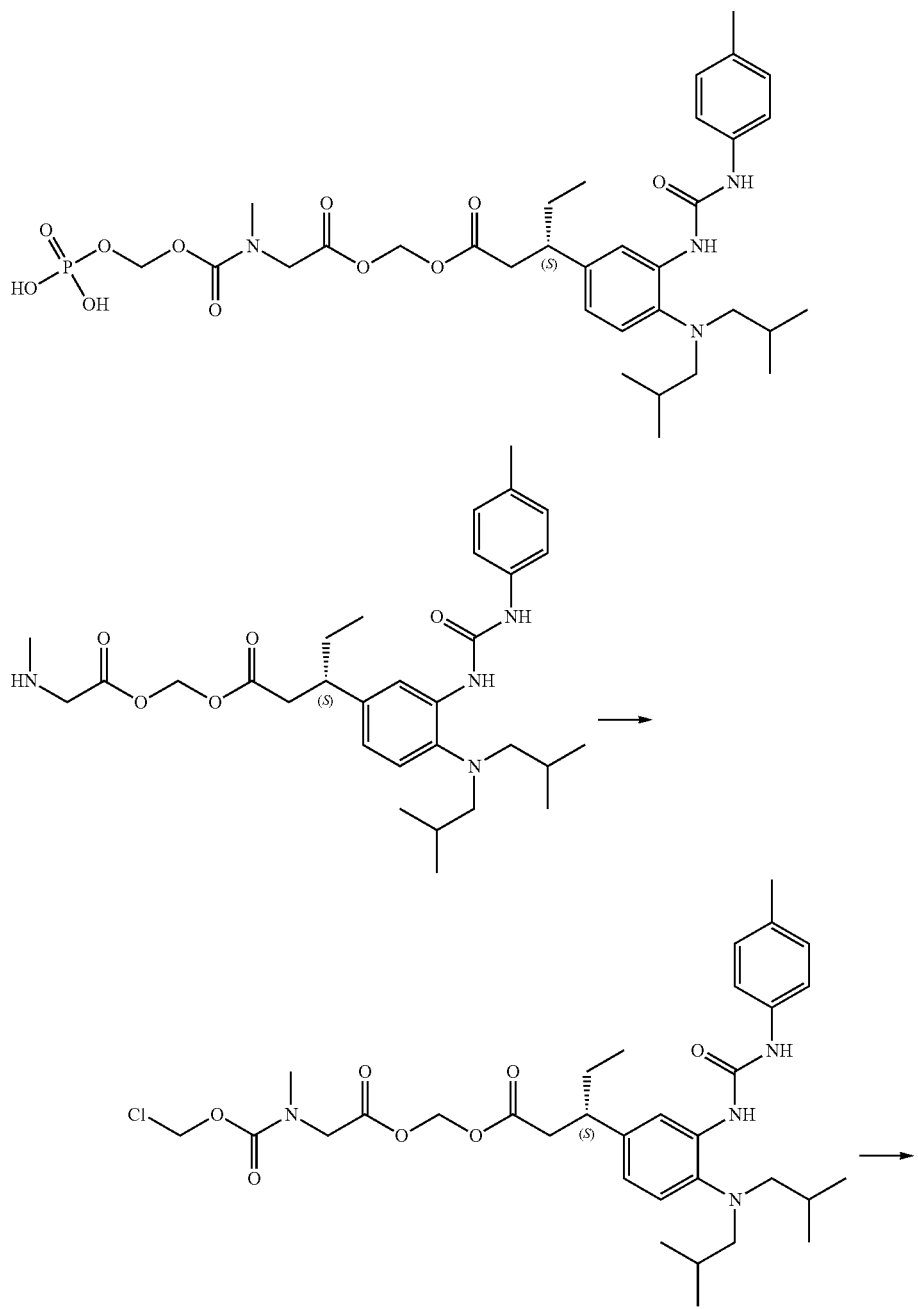

11A

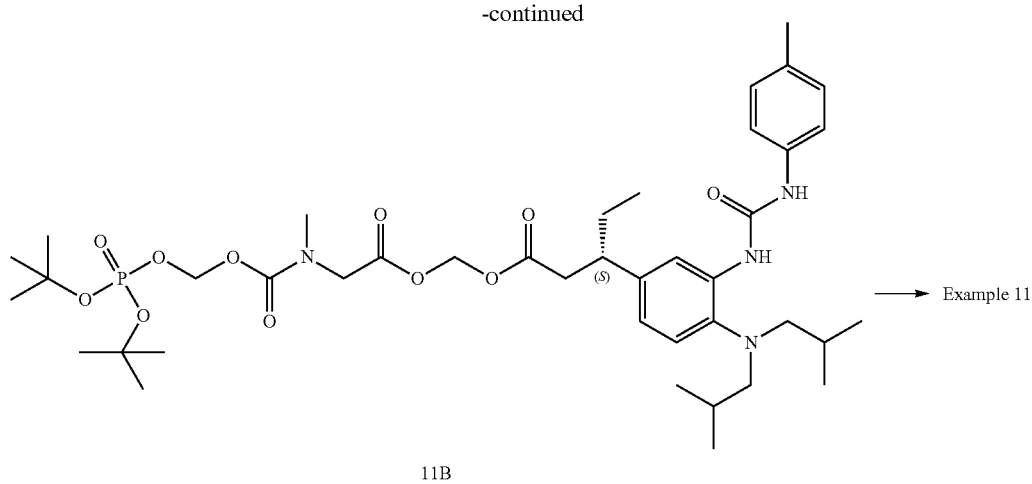

→ Example 11

11B

11A: (S)-(2-(((Chloromethoxy)carbonyl)(methyl)amino)acetoxy)methyl 3-(4-(diisobutylamino)-3-(3-(p-tolyl)ureido)phenyl)pentanoate To a stirred solution of (S)-(2-(methylamino)acetoxy)methyl 3-(4-(diisobutylamino)-3-(3-(p-tolyl)ureido)phenyl)pentanoate (0.750 g, 1.352 mmol) in dry dichloromethane (5 mL) at 0° C., pyridine (0.328 mL, 4.06 mmol) and chloromethyl chloroformate (0.180 mL, 2.028 mmol) were added slowly. After being stirred at 0° C. for 1 h, the reaction mixture was diluted with water and extracted with DCM (3×50 mL). The organic layer was washed with brine solution, dried over anhydrous sodium sulphate and concentrated under vacuum at ~30° C. to give light yellowish oil. The crude product was purified by ISCO (silica gel 60-120 mesh; 39% ethyl acetate in hexane as eluent) to give (S)-(2-(((chloromethoxy)carbonyl)(methyl)amino)acetoxy)methyl 3-(4-(diisobutylamino)-3-(3-(p-tolyl)ureido)phenyl)pentanoate (0.540 g, 0.834 mmol, 61.7%) as a colorless oil. $^1$H NMR (400 MHz, DMSO-$d_6$) δ ppm=9.32 (s, 1H), 7.87 (s, 1H), 7.85 (d, J=1.5 Hz, 1H), 7.39-7.34 (m, 2H), 7.14 (dd, J=8.3, 2.3 Hz, 1H), 7.09 (d, J=8.0 Hz, 2H), 6.81 (dd, J=8.0, 2.0 Hz, 1H), 5.91-5.81 (m, 2H), 5.72-5.66 (m, 2H), 4.12 (d, J=2.0 Hz, 2H), 2.90 (s, 3H), 2.87-2.80 (m, 1H), 2.76-2.67 (m, 1H), 2.64 (d, J=6.5 Hz, 4H), 2.61-2.54 (m, 1H), 2.26 (s, 3H), 1.64 (dd, J=13.4, 6.6 Hz, 3H), 1.57-1.48 (m, 1H), 0.84 (d, J=6.5 Hz, 12H), 0.73 (t, J=7.3 Hz, 3H); LC-MS (ES): m/z=647 [M+H]$^+$.

11B: (S)-(2-(((((Di-tert-butoxyphosphoryl)oxy)methoxy)carbonyl)(methyl)amino)acetoxy)methyl 3-(4-(diisobutylamino)-3-(3-(p-tolyl)ureido)phenyl)pentanoate A mixture of (S)-(2-(((chloromethoxy)carbonyl)(methyl)amino)acetoxy)methyl 3-(4-(diisobutylamino)-3-(3-(p-tolyl)ureido)phenyl)pentanoate (0.540 g, 0.834 mmol), tetra-n-butylammonium di-tert-butylphosphate (1.131 g, 2.503 mmol) and sodium iodide (0.375 g, 2.503 mmol) in dry tetrahydrofuran (5 mL) was stirred at room temperature for 24 h. The mixture was diluted with water and extracted with DCM (3×50 mL). The organic layer was dried over anhydrous sodium sulphate and concentrated under vacuum at ~30° C. to give light yellowish oil. The crude product was purified by ISCO (silica gel 60-120 mesh; 24% ethyl acetate in hexane as eluent) to give (S)-(2-(((((di-tert-butoxyphosphoryl)oxy)methoxy)carbonyl)(methyl)amino)acetoxy)methyl 3-(4-(diisobutylamino)-3-(3-(p-tolyl)ureido)phenyl)pentanoate (0.150 g, 0.150 mmol, 17.96%) as an off-white solid. $^1$H NMR (300 MHz, DMSO-$d_6$) δ ppm=9.34 (s, 1H), 7.90 (s, 1H), 7.43-7.32 (m, 2H), 7.16-7.02 (m, 4H), 6.83-6.72 (m, 1H), 5.76-5.59 (m, 2H), 5.46 (dd, J=19.1, 13.0 Hz, 2H), 4.11 (d, J=12.1 Hz, 2H), 2.91 (s, 3H), 2.88-2.70 (m, 3H), 2.63 (d, J=6.8 Hz, 4H), 2.24 (s, 3H), 1.63 (dd, J=13.3, 6.4 Hz, 3H), 1.56-1.45 (m, 1H), 1.43-1.37 (m, 18H), 0.83 (d, J=6.8 Hz, 12H), 0.71 (t, J=7.2 Hz, 3H); LC-MS (ES): m/z=821 [M+H]$^+$

Example 11

To a stirred solution of (S)-(2-(((((di-tert-butoxyphosphoryl)oxy)methoxy) carbonyl)(methyl)amino)acetoxy)methyl 3-(4-(diisobutylamino)-3-(3-(p-tolyl)ureido)phenyl)pentanoate (0.140 g, 0.171 mmol) in dichloromethane (2 mL) at 0° C., was added TFA (1.314 mL, 17.05 mmol). After being stirred at 0° C. for 1 h, the solvent was concentrated under high vacuum at ~30° C. The crude product was purified by RP HPLC (Sunfire C18 [250×19 mm]; mobile phase A: 0.1% TFA in water; mobile phase B: acetonitrile; flow rate: 18 mL/min) to afford (S)-(2-(methyl(((phosphonooxy)methoxy)carbonyl)amino)acetoxy)methyl 3-(4-(diisobutylamino)-3-(3-(p-tolyl)ureido) phenyl)pentanoate (0.035 g, 0.049 mmol, 28.6%) as an off-white solid. $^1$H NMR (400 MHz, DMSO-$d_6$) δ ppm=9.31 (s, 1H), 7.90-7.80 (m, 1H), 7.38-7.33 (m, 2H), 7.14 (d, J=8.0 Hz, 3H), 7.09 (d, J=8.0 Hz, 1H), 6.80 (d, J=7.5 Hz, 1H), 5.72-5.65 (m, 2H), 5.50 (dd, J=19.1, 13.0 Hz, 2H), 4.16-4.07 (m, 2H), 2.91 (s, 3H), 2.88-2.79 (m, 2H), 2.75-2.54 (m, 5H), 2.25 (s, 3H), 1.62-1.58 (m, 3H), 1.54-1.43 (m, 1H), 0.84 (d, J=6.5 Hz, 12H), 0.72 (t, J=7.3 Hz, 3H); LC-MS (ES): m/z=709 [M+H]$^+$; HPLC T$_r$: 17.5 min (Method A) and 9.2 min (Method B).

Example 12
(3S)-2-Methyl-1-(((S)-3-methyl-2-((((phosphonooxy)methoxy)carbonyl)amino) Butanoyl)oxy) propyl 3-(4-(diisobutylamino)-3-(3-(p-tolyl)ureido)phenyl)pentanoate
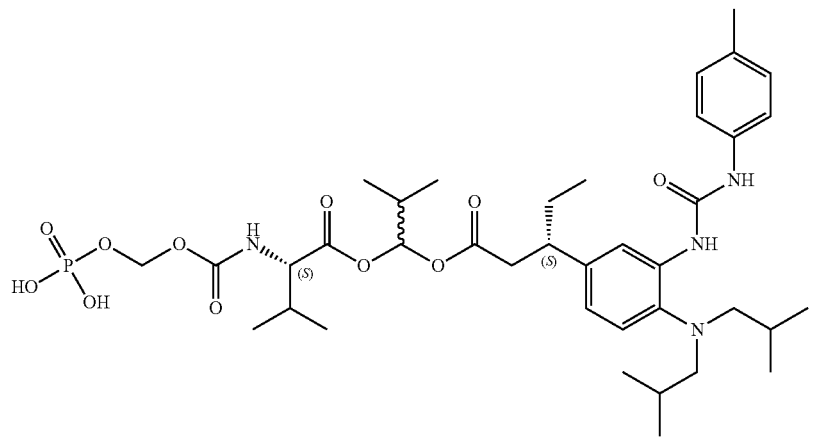
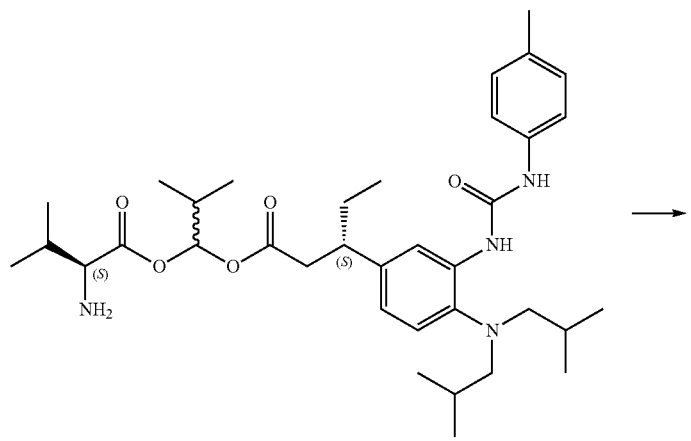
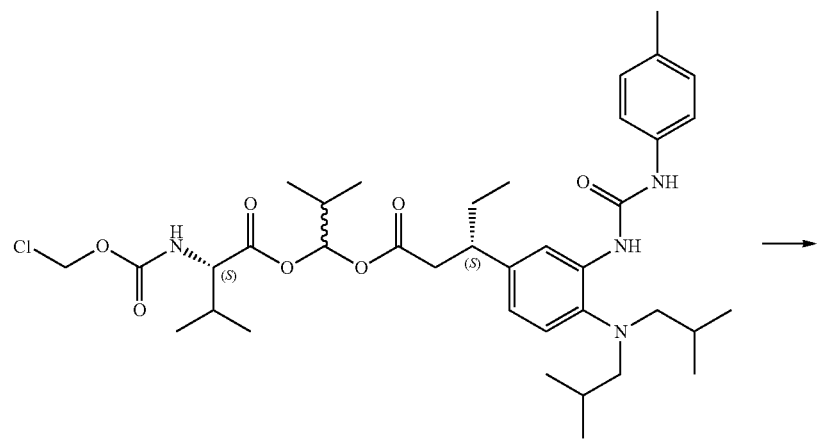
12A

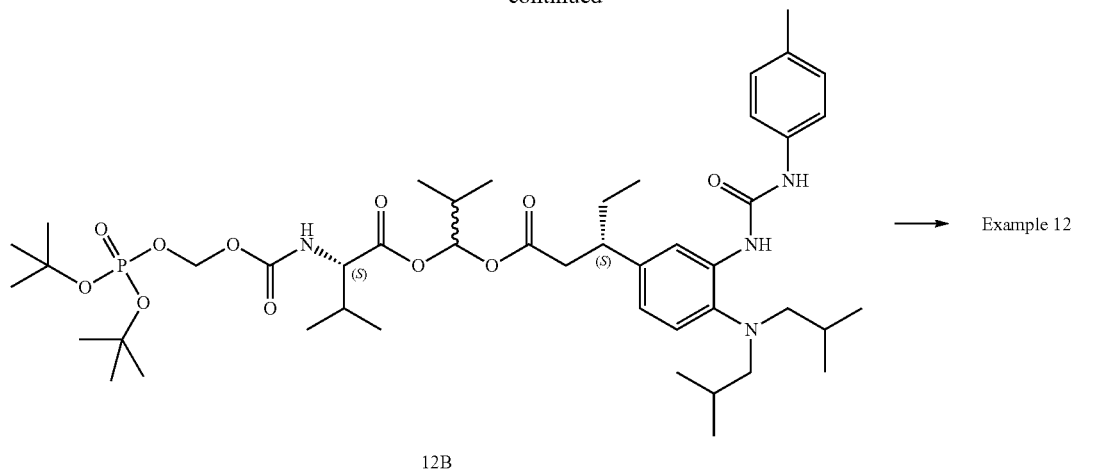

12B

12A: (3S)-1-(((S)-2-(((Chloromethoxy)carbonyl) amino)-3-methylbutanoyl)oxy)-2-methylpropyl 3-(4-(diisobutylamino)-3-(3-(p-tolyl)ureido)phenyl)pentanoate To a stirred solution of (3S)-1-(((S)-2-amino-3-methylbutanoyl)oxy)-2-methylpropyl 3-(4-(diisobutylamino)-3-(3-(p-tolyl)ureido)phenyl)pentanoate (1.400 g, 1.501 mmol) in dry dichloromethane (10 mL) at 0° C., pyridine (0.364 mL, 4.50 mmol) and chloromethyl chloroformate (0.290 g, 2.252 mmol) were added slowly. After being stirred at 0° C. for 1 h, the reaction mixture was diluted with water and extracted with DCM (3×50 mL). The organic layer was washed with brine solution, dried over anhydrous sodium sulphate and concentrated under vacuum at ~30° C. to give light yellowish oil. The crude product was purified by ISCO (silica gel 60-120 mesh; 29% ethyl acetate in hexane as eluent) to give (3S)-1-(((S)-2-(((chloromethoxy)carbonyl) amino)-3-methylbutanoyl)oxy)-2-methylpropyl 3-(4-(diisobutylamino)-3-(3-(p-tolyl)ureido)phenyl)pentanoate (0.550 g, 0.629 mmol, 41.9%) as a colorless oil. $^1$H NMR (400 MHz, DMSO-$d_6$) δ ppm=9.30 (s, 1H), 8.07-8.02 (m, 1H), 7.86 (dd, J=4.3, 2.4 Hz, 2H), 7.35 (d, J=8.0 Hz, 2H), 7.17-7.04 (m, 3H), 6.78 (d, J=8.0 Hz, 1H), 6.52-6.44 (m, 1H), 5.50-5.38 (m, 2H), 4.00-3.89 (m, 1H), 2.95-2.73 (m, 1H), 2.75-2.56 (m, 6H), 2.28 (s, 3H), 2.11-1.96 (m, 1H), 1.95-1.77 (m, 1H), 1.70-1.46 (m, 4H), 0.88 (d, J=7.0 Hz, 6H), 0.84 (d, J=6.5 Hz, 12H), 0.81 (t, J=7.3 Hz, 3H), 0.77-0.69 (m, 6H); LC-MS (ES): m/z=717 [M+H]$^+$.

12B: (3S)-1-(((S)-2-(((((Di-tert-butoxyphosphoryl) oxy)methoxy)carbonyl)amino)-3-methylbutanoyl) oxy)-2-methylpropyl-3-(4-(diisobutylamino)-3-(3-(p-tolyl)ureido)phenyl) Pentanoate A mixture of (3S)-1-(((S)-2-(((chloromethoxy)carbonyl) amino)-3-methylbutanoyl)oxy)-2-methylpropyl-3-(4-(diisobutylamino)-3-(3-(p-tolyl)ureido)phenyl)pentanoate (0.550 g, 0.767 mmol), tetra-n-butylammonium di-tert-butylphosphate (1.039 g, 2.300 mmol) and sodium iodide (0.345 g, 2.300 mmol) in dry tetrahydrofuran (5 mL) was stirred at room temperature for 24 h. The mixture was diluted with water and extracted with DCM (3×50 mL). The organic layer was dried over anhydrous sodium sulphate and concentrated under vacuum at ~30° C. to give light yellowish oil. The crude product was purified by RP HPLC (Kinetex C18 [250×21.2 mm]; mobile phase A: 10 mM ammonium acetate in water; mobile phase B: acetonitrile; flow rate: 18 mL/min) gave (3S)-1-(((S)-2-(((((di-tert-butoxyphosphoryl)oxy) methoxy)carbonyl)amino)-3-methylbutanoyl)oxy)-2-methylpropyl 3-(4-(diisobutylamino)-3-(3-(p-tolyl)ureido)phenyl)pentanoate (0.160 g, 0.177 mmol, 23.07%) as an off-white solid. $^1$H NMR (400 MHz, DMSO-$d_6$) δ ppm=9.31 (s, 1H), 8.07-8.01 (m, 1H), 7.87 (dd, J=4.3, 2.4 Hz, 2H), 7.37 (d, J=8.0 Hz, 2H), 7.16-7.04 (m, 3H), 6.79 (d, J=8.0 Hz, 1H), 6.52-6.44 (m, 1H), 5.51-5.39 (m, 2H), 4.00-3.88 (m, 1H), 2.94-2.75 (m, 1H), 2.72-2.54 (m, 6H), 2.26 (s, 3H), 2.11-1.96 (m, 1H), 1.94-1.76 (m, 1H), 1.70-1.44 (m, 4H), 1.40 (s, 18H), 0.88 (d, J=7.0 Hz, 6H), 0.84 (d, J=6.5 Hz, 12H), 0.80 (t, J=7.3 Hz, 3H), 0.77-0.69 (m, 6H); LC-MS (ES): m/z=892.4 [M+H]$^+$.

Example 12

To a stirred solution of (3S)-1-(((S)-2-(((((di-tert-butoxyphosphoryl)oxy)methoxy) carbonyl)amino)-3-methylbutanoyl)oxy)-2-methylpropyl 3-(4-(diisobutylamino)-3-(3-(p-tolyl)ureido)phenyl)pentanoate (0.160 g, 0.180 mmol) in dry dichloromethane (2 mL) at 0° C., was added TFA (1.383 mL, 17.96 mmol). After being stirred at 0° C. for 1 h, the solvent was concentrated under high vacuum at ~30° C. The crude product was purified by RP HPLC (Kinetex Biphenyl [250×30 mm]; mobile phase A: 10 mM ammonium acetate in water; mobile phase B: acetonitrile; flow rate: 18 mL/min) to afford (3S)-2-methyl-1-(((S)-3-methyl-2-(((phosphonooxy)methoxy)carbonyl)amino)butanoyl) oxy)propyl 3-(4-(diisobutylamino)-3-(3-(p-tolyl)ureido)phenyl)pentanoate (0.085 g, 0.106 mmol, 59.0%) as an off-white solid. $^1$H NMR (400 MHz, DMSO-$d_6$) (ppm=9.35 (s, 1H), 7.90-7.81 (m, 1H), 7.73 (m, 3H), 7.36 (dd, J=8.5, 2.5 Hz, 2H), 7.10 (dd, J=12.0, 8.5 Hz, 2H), 6.82-6.76 (m, 1H), 6.47 (dd, J=6.8, 4.8 Hz, 1H), 5.40-5.19 (m, 2H), 3.94-3.87 (m, 1H), 2.87-2.76 (m, 1H), 2.73-2.53 (m, 6H), 2.25 (s, 3H), 2.06-1.96 (m, 1H), 1.92-1.74 (m, 1H), 1.68-1.43 (m, 4H), 0.87 (d, J=6.5 Hz, 6H), 0.83 (d, J=6.5 Hz, 12H), 0.78 (t, J=7.3 Hz, 3H), 0.75-0.69 (m, 6H); LC-MS (ES): m/z=779 [M+H]$^+$; HPLC $T_r$: 17.9 min (Method A) and 17.3 min (Method B).

Example 13

(3S,4S,5S)—(((S)-3-(4-(Diisobutylamino)-3-(3-(p-tolyl)ureido)phenyl)pentanoyl)oxy)methyl 3,4,5-trihydroxycyclohex-1-enecarboxylate

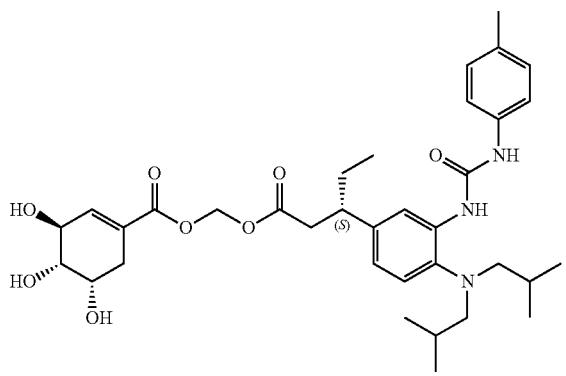

A mixture of (S)-chloromethyl 3-(4-(diisobutylamino)-3-(3-(p-tolyl)ureido) phenyl)pentanoate (0.500 g, 0.996 mmol), (3R,4S,5R)-3,4,5-trihydroxycyclohex-1-enecarboxylic acid (0.347 g, 1.992 mmol), potassium carbonate (0.275 g, 1.992 mmol) and sodium iodide (0.149 g, 0.996 mmol) in acetonitrile (5 mL) was stirred at room temperature for 12 h. The mixture was filtered through celite bed, which was washed with ethyl acetate and concentrated under vacuum at ~30° C. The crude product was purified by RP HPLC (Kinetex C18 [250×21.2 mm]; mobile phase: 10 mM ammonium acetate in water; mobile phase B: acetonitrile; flow rate: 18 mL/min) to afford (3S,4S,5S)—(((S)-3-(4-(diisobutylamino)-3-(3-(p-tolyl)ureido)phenyl)pentanoyl)oxy) methyl 3,4,5-trihydroxycyclohex-1-enecarboxylate (0.030 g, 0.045 mmol, 4.47%) as an off-white solid. $^1$H NMR (400 MHz, methanol-$d_4$) δ ppm=7.80 (d, J=2.0 Hz, 1H), 7.33-7.27 (m, 2H), 7.13 (dd, J=11.3, 8.3 Hz, 3H), 6.87-6.82 (m, 2H), 5.80-5.72 (m, 2H), 4.38 (br. s., 1H), 4.01 (dd, J=7.0, 5.0 Hz, 1H), 3.71 (dd, J=7.0, 4.0 Hz, 1H), 2.98-2.90 (m, 2H), 2.74-2.67 (m, 2H), 2.66-2.63 (m, 5H), 2.30 (s, 3H), 2.25-2.17 (m, 1H), 1.78-1.57 (m, 4H), 0.87 (d, J=6.5 Hz, 12H), 0.81 (t, J=7.3 Hz, 3H); LC-MS (ES): m/z=640 [M+H]$^+$; HPLC T$_r$: 10.0 min (Method A) and 9.9 min (Method B).

Example 14

(S)-(((4-(Phosphonooxy) butoxy)carbonyl)oxy)methyl 3-(4-(diisobutylamino)-3-(3-(p-tolyl) Ureido) Phenyl) Pentanoate

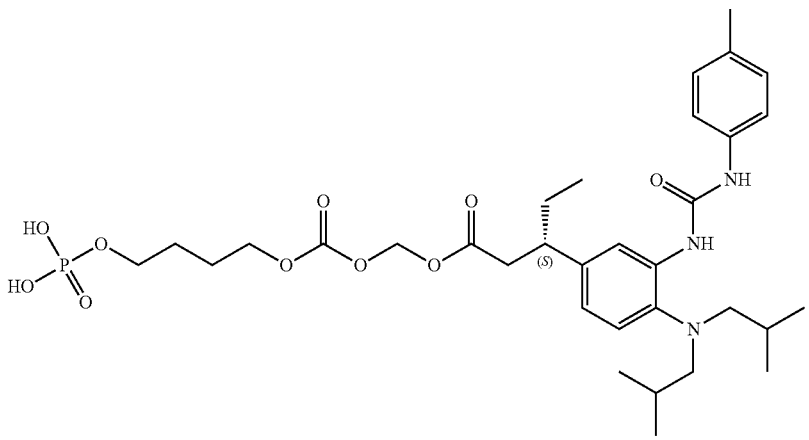

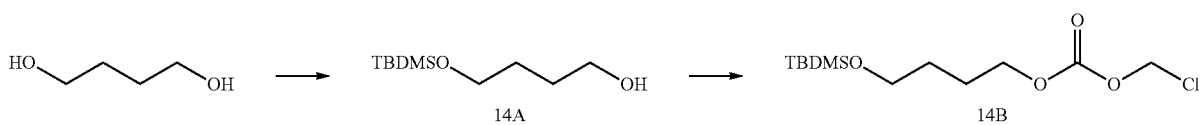

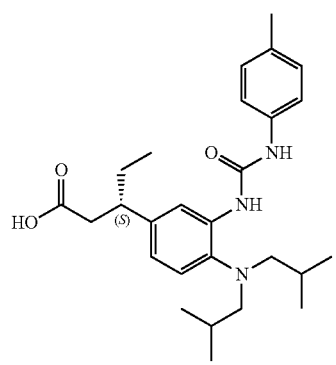

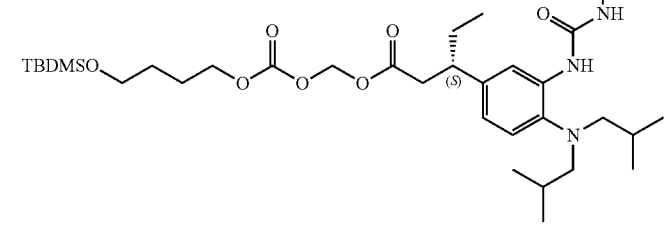

14C

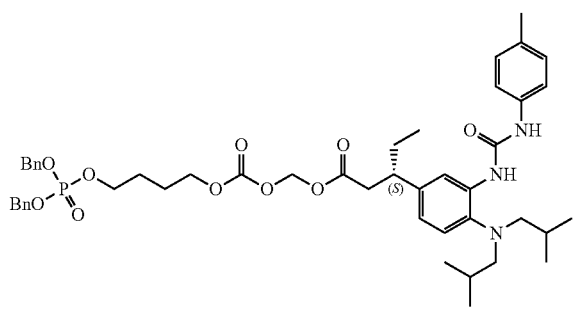

14E

↓

Example 14

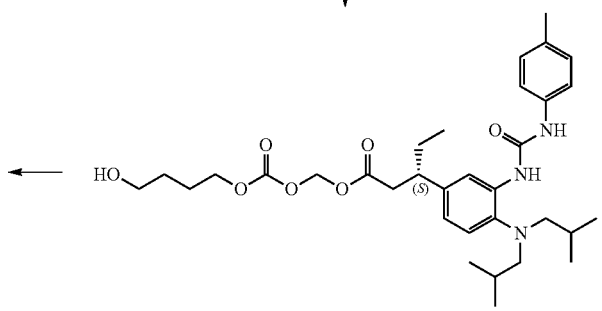

14D

14A: 4-((tert-Butyldimethylsilyl)oxy)butan-1-ol

To a suspension of sodium hydride (60%) (1.465 g, 36.6 mmol) in dry tetrahydrofuran (100 mL) at 0° C., was added a solution of butane-1,4-diol (3.000 g, 33.3 mmol) in THF (30 mL) slowly. After being stirred at room temperature for 2 h, was added tert-butyldimethylchlorosilane (5.52 g, 36.6 mmol). The reaction mixture was stirred at room temperature for 12 h. The mixture was quenched with ice water, extracted with DCM (3×100 mL). The organic layer was washed with brine solution, dried over anhydrous sodium sulphate and concentrated under vacuum to give colorless oil. The crude product was purified by ISCO (silica gel 60-120 mesh; 19% ethyl acetate in hexane as eluent) to give 4-((tert-butyldimethylsilyl)oxy)butan-1-ol (5.700 g, 27.9 mmol, 84%) as a colorless oil. $^1$H NMR (300 MHz, DMSO-$d_6$) δ ppm=4.54 (t, J=5.1 Hz, 1H), 3.78-3.69 (m, 2H), 3.61-3.53 (m, 2H), 1.71-1.54 (m, 4H), 1.04 (s, 9H), 0.86 (s, 6H).

14B: 4-((tert-Butyldimethylsilyl)oxy)butyl (chloromethyl) Carbonate

To a stirred solution of 4-((tert-butyldimethylsilyl)oxy) butan-1-ol (1.000 g, 4.89 mmol) in dry DCM (10 mL) at 0° C., pyridine (0.791 mL, 9.79 mmol) and chloromethyl chloroformate (0.871 mL, 9.79 mmol) were added slowly. After being stirred at 0° C. for 2 h, the reaction mixture was diluted with water and extracted with DCM (3×50 mL). The organic layer was dried over anhydrous sodium sulphate and concentrated under vacuum at ~30° C. to give 4-((tert-butyldimethylsilyl)oxy)butyl (chloromethyl) carbonate (1.4 g, 4.72 mmol, 96%) as a light yellowish oil. $^1$H NMR (400 MHz, DMSO-$d_6$) δ ppm=5.93 (s, 2H), 4.25 (t, J=6.5 Hz, 2H), 3.64 (t, J=6.0 Hz, 2H), 1.76-1.67 (m, 2H), 1.59-1.50 (m, 2H), 0.90 (s, 9H), 0.07 (s, 6H).

14C: (S)-10,10,11,11-Tetramethyl-3-oxo-2,4,9-trioxa-10-siladodecyl 3-(4-(diisobutylamino)-3-(3-(p-tolyl)ureido)phenyl)pentanoate A mixture of (S)-3-(4-(diisobutylamino)-3-(3-(p-tolyl) ureido)phenyl)pentanoic acid (1.000 g, 2.205 mmol) and cesium carbonate (2.155 g, 6.61 mmol) was taken in dry DMF (10 mL). After being stirred at room temperature for 30 min, were added 4-((tert-Butyldimethylsilyl)oxy)butyl (chloromethyl) carbonate (0.785 g, 2.65 mmol) and sodium iodide (0.330 g, 2.205 mmol). After being stirred at room temperature for 16 h, the mixture was diluted with water and extracted with ethyl acetate (3×50 mL). The organic layer was washed with brine solution, dried over anhydrous sodium sulphate and concentrated under vacuum at ~30° C. to give light brownish oil. The crude product was purified by ISCO (silica gel 60-120 mesh; 19% ethyl acetate in hexane as eluent) to give (S)-10,10,11,11-tetramethyl-3-oxo-2,4,9-trioxa-10-siladodecyl 3-(4-(diisobutylamino)-3-(3-(p-tolyl) ureido)phenyl)pentanoate (1.000 g, 1.373 mmol, 62.3%) as a colorless oil. $^1$H NMR (400 MHz, DMSO-$d_6$) δ ppm=9.30 (s, 1H), 7.86 (s, 1H), 7.83 (d, J=2.0 Hz, 1H), 7.35 (d, J=8.5 Hz, 2H), 7.14-7.04 (m, 3H), 6.84-6.75 (m, 1H), 5.67-5.57

(m, 2H), 4.14 (t, J=6.5 Hz, 2H), 3.63 (t, J=6.0 Hz, 2H), 2.87-2.77 (m, 1H), 2.74-2.56 (m, 6H), 2.25 (s, 3H), 1.70-1.59 (m, 2H), 1.56-1.41 (m, 6H), 0.91-0.81 (m, 21H), 0.73 (t, J=7.3 Hz, 3H), 0.04 (s, 6H); LC-MS (ES): m/z 715.2 [M+H]$^+$.

14D: (S)-(((4-Hydroxybutoxy)carbonyl)oxy)methyl 3-(4-(diisobutylamino)-3-(3-(p-tolyl)ureido)phenyl)pentanoate To a stirred solution of (S)-10,10,11,11-tetramethyl-3-oxo-2,4,9-trioxa-10-siladodecyl 3-(4-(diisobutylamino)-3-(3-(p-tolyl)ureido)phenyl)pentanoate (0.975 g, 1.366 mmol) in dry dichloromethane (5 mL) at 0° C., was added hydrogen fluoride-pyridine (0.879 mL, 6.83 mmol) slowly. After being stirred at 0° C. for 30 min. The reaction mixture was neutralized with sodium bicarbonate solution and extracted with DCM (3×50 mL). The organic layer was washed with brine solution, dried over anhydrous sodium sulphate and concentrated under vacuum at ~30° C. to give (S)-(((4-hydroxybutoxy)carbonyl)oxy) methyl 3-(4-(diisobutylamino)-3-(3-(p-tolyl)ureido)phenyl)pentanoate (0.600 g, 0.950 mmol, 69.6%) as a light yellowish oil. $^1$H NMR (400 MHz, DMSO-d$_6$) δ ppm=9.31 (s, 1H), 7.87 (s, 1H), 7.85 (d, J=2.0 Hz, 1H), 7.37 (d, J=8.5 Hz, 2H), 7.14-7.06 (m, 3H), 6.84-6.75 (m, 1H), 5.63-5.61 (m, 2H), 4.15 (t, J=6.5 Hz, 2H), 3.64 (t, J=6.0 Hz, 2H), 2.87-2.78 (m, 1H), 2.74-2.55 (m, 6H), 2.25 (s, 3H), 1.70-1.58 (m, 2H), 1.56-1.40 (m, 6H), 0.83 (d, J=6.5 Hz, 12H), 0.72 (t, J=7.3 Hz, 3H); LC-MS (ES): m/z=600.4 [M+H]$^+$ 14E: (S)-(((4-((bis(Benzyloxy)phosphoryl)oxy)butoxy)carbonyl)oxy)methyl 3-(4-(diisobutylamino)-3-(3-(p-tolyl)ureido)phenyl)pentanoate To a stirred solution of (S)-(((4-hydroxybutoxy)carbonyl)oxy)methyl 3-(4-(diisobutylamino)-3-(3-(p-tolyl)ureido)phenyl)pentanoate (0.500 g, 0.834 mmol) in dry dichloromethane (5 mL), dibenzyl N,N-diisopropylphosphoramidite (0.420 mL, 1.251 mmol) and a solution of 0.4 M 1H-tetrazole in acetonitrile (3.17 mL, 1.251 mmol) were added. The reaction mixture was stirred at room temperature for 8 h. The reaction was cooled at 0° C. H$_2$O$_2$ (0.128 mL, 4.17 mmol) was added. After being stirred at room temperature for 2 h, the reaction mixture was diluted water, extracted with DCM (3×50 mL). The organic layer was washed with brine solution, dried over anhydrous sodium sulfate, filtered and concentrated under vacuum at ~30° C. to give colorless oil. The crude product was purified by ISCO (silica gel 60-120 mesh; 36% ethyl acetate in hexane as eluent) to give (S)-(((4-((bis(benzyloxy)phosphoryl)oxy)butoxy)carbonyl)oxy)methyl 3-(4-(diisobutylamino)-3-(3-(p-tolyl)ureido)phenyl)pentanoate (0.680 g, 0.712 mmol, 85%) as a light yellowish oil. $^1$H NMR (300 MHz, DMSO-d$_6$) δ ppm=9.32 (s, 1H), 7.87 (s, 1H), 7.84 (d, J=2.3 Hz, 1H), 7.43-7.29 (m, 12H), 7.17-7.05 (m, 3H), 6.78 (dd, J=8.1, 2.1 Hz, 1H), 5.67-5.58 (m, 2H), 5.02 (d, J=8.3 Hz, 4H), 4.10 (t, J=6.5 Hz, 2H), 3.96 (t, J=6.0 Hz, 2H), 2.87-2.76 (m, 1H), 2.75-2.58 (m, 6H), 2.24 (s, 3H), 1.70-1.50 (m, 8H), 0.83 (d, J=6.8 Hz, 12H), 0.70 (t, J=7.4 Hz, 3H); LC-MS (ES): m/z=860.2 [M+H]$^+$.

Example 14

To a stirred solution of (S)-(((4-((bis(benzyloxy)phosphoryl)oxy)butoxy)carbonyl) oxy)methyl 3-(4-(diisobutylamino)-3-(3-(p-tolyl)ureido)phenyl)pentanoate (0.650 g, 0.756 mmol) in dry ethyl acetate (5 mL), was added Pd/C (10%, 0.161 g, 1.512 mmol). The mixture was degassed and then flushed with H2 and stirred at room temperature for 0.5 h under H$_2$ atmosphere. The mixture was filtered through celite bed, which was washed with ethyl acetate. The filtrate was concentrated under vacuum at ~30° C. The crude product was purified by RP HPLC (X-Bridge phenyl [250× 30 mm]; mobile phase A: 0.1% formic acid in water; mobile phase B: acetonitrile; flow rate: 18 mL/min) to afford (S)-(((4-(phosphonooxy) butoxy)carbonyl)oxy)methyl 3-(4-(diisobutylamino)-3-(3-(p-tolyl)ureido)phenyl)pentanoate (0.210 g, 0.306 mmol, 40.5%) as an off-white solid. $^1$H NMR (400 MHz, methanol-d$_4$) δ ppm=7.71 (s, 1H), 7.34-7.29 (m, 2H), 7.23 (d, J=8.5 Hz, 1H), 7.12 (d, J=8.5 Hz, 2H), 6.93 (d, J=7.0 Hz, 1H), 5.68-5.62 (m, 2H), 4.20 (t, J=6.3 Hz, 2H), 3.97 (q, J=6.0 Hz, 2H), 3.03-2.90 (m, 1H), 2.85-2.61 (m, 6H), 2.30 (s, 3H), 1.83-1.56 (m, 8H), 0.90 (d, J=6.5 Hz, 12H), 0.81 (t, J=7.3 Hz, 3H); LC-MS (ES): m/z=680.2 [M+H]$^+$; HPLC T$_r$: 10.6 min (Method A) and 8.7 min (Method B).

Example 15

(S)-(((((5-(Phosphonooxy)pentyl)oxy)carbonyl)oxy)methyl 3-(4-(diisobutylamino)-3-(3-(p-tolyl)ureido)phenyl)pentanoate

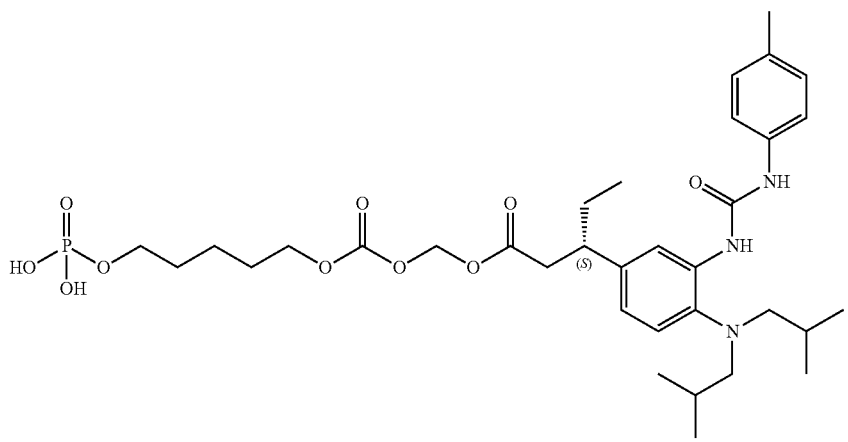

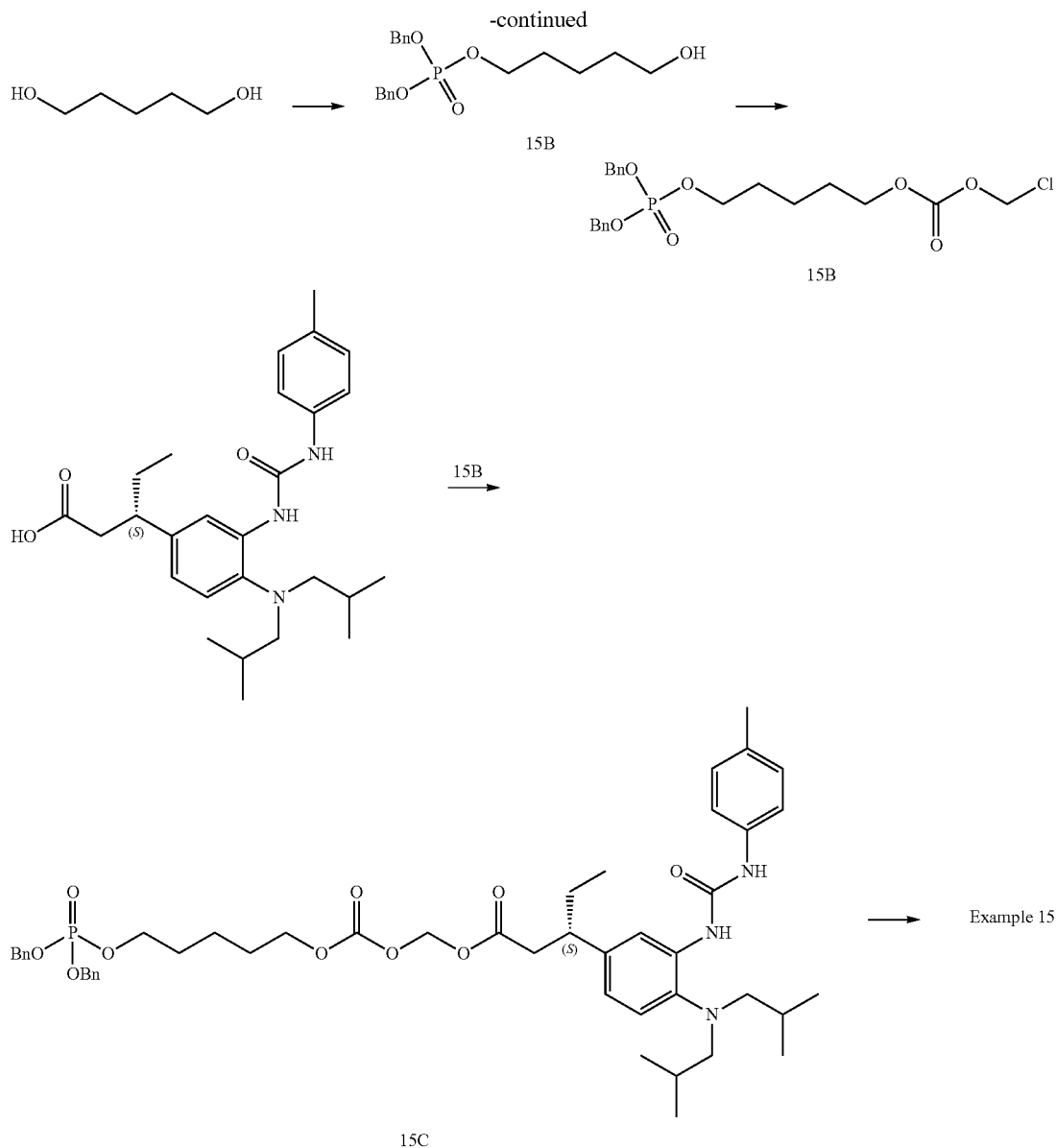

15A: Dibenzyl(5-hydroxypentyl) Phosphate

To a stirred solution of pentane-1,5-diol (2.00 g, 19.20 mmol) in dry dichloromethane (20 mL), dibenzyl N,N-diisopropylphosphoramidite (9.68 mL, 28.8 mmol and a solution of 0.4 M 1H-tetrazole in acetonitrile (73.0 mL, 28.8 mmol) were added. The reaction mixture was stirred at room temperature for 8 h. After cooling to 0° C., 30% $H_2O_2$ (2.94 mL, 96 mmol) was added. After being stirred at room temperature for 2 h, the reaction mixture was diluted with water, extracted with DCM (3×100 mL). The organic layer was washed with brine solution, dried over anhydrous sodium sulfate, filtered and concentrated under vacuum at ~30° C. to give colorless oil. The crude product was purified by RP HPLC (Kinetex C18 [250×21.2 mm]; mobile phase A: 0.1% formic acid in water; mobile phase B: acetonitrile; flow rate: 18 mL/min) to afford dibenzyl (5-hydroxypentyl) phosphate (1.700 g, 4.62 mmol, 24.05%) as colorless oil. $^1$H NMR (400 MHz, DMSO-$d_6$) δ ppm=7.44-7.32 (m, 10H), 5.06-5.01 (m, 4H), 4.35 (br. s., 1H), 3.98-3.92 (m, 2H), 3.41-3.29 (m, 2H), 1.56 (quin, J=7.0 Hz, 2H), 1.44-1.36 (m, 2H), 1.35-1.24 (m, 2H); LC-MS (ES): m/z=365.2 [M+H]$^+$.

15B: 5-((bis(Benzyloxy)phosphoryl)oxy)pentyl (chloromethyl) Carbonate

To a stirred solution of dibenzyl (5-hydroxypentyl) phosphate (0.700 g, 1.921 mmol) in dry dichloromethane (10 mL) at 0° C., pyridine (0.311 mL, 3.84 mmol) and chloromethyl chloroformate (0.342 mL, 3.84 mmol) were added slowly. After being stirred at 0° C. for 1 h, the reaction mixture was diluted with water and extracted with DCM (3×50 mL). The organic layer was washed with brine solution, dried over anhydrous sodium sulphate and concentrated under vacuum at ~30° C. to give 5-((bis(benzyloxy) phosphoryl)oxy)pentyl (chloromethyl) carbonate (0.750 g, 1.371 mmol, 71.4%) as a light yellowish oil. $^1$H NMR (400 MHz, DMSO-$d_6$) δ ppm=7.41-7.35 (m, 10H), 5.89 (s, 2H), 5.03 (dd, J=8.3, 1.3 Hz, 4H), 4.16 (t, J=6.5 Hz, 2H), 3.95 (q, J=6.5 Hz, 2H), 1.64-1.53 (m, 4H), 1.37-1.27 (m, 2H); LC-MS (ES): m/z=475.2 [M+H]$^+$ 15C: (S)-(((((5-((bis(Benzyloxy)phosphoryl)oxy)pentyl)oxy)carbonyl)oxy)methyl 3-(4-(diisobutylamino)-3-(3-(p-tolyl)ureido)phenyl)pentanoate A mixture of (S)-3-(4-(diisobutylamino)-3-(3-(p-tolyl)ureido)phenyl)pentanoic acid (0.700 g, 1.543 mmol) and cesium carbonate (1.508 g, 4.63 mmol) was taken in dry DMF (5 mL). After being stirred at room temperature for 30 min, 5-((bis(benzyloxy) phosphoryl)oxy)pentyl(chloromethyl) carbonate (0.705 g, 1.543 mmol) and sodium iodide (0.231 g, 1.543 mmol) were added. After being stirred at room temperature for 16 h, the mixture was diluted with water and extracted with ethyl acetate (3×50 mL). The organic layer was washed with brine solution, dried over sodium sulphate and concentrated under vacuum at ~30° C. to give light brownish oil. The crude product was purified by ISCO (silica gel 60-120 mesh; 40% ethyl acetate in hexane as eluent) to give (S)-(((((5-((bis(benzyloxy)phosphoryl)oxy)pentyl)oxy)carbonyl)oxy)methyl 3-(4-(diisobutylamino)-3-(3-(p-tolyl)ureido)phenyl)pentanoate (0.700 g, 0.673 mmol, 43.6%) as a light yellowish oil. $^1$H NMR (300 MHz, DMSO-d$_6$) δ ppm=9.32 (s, 1H), 7.87 (s, 1H), 7.84 (d, J=1.9 Hz, 1H), 7.41-7.32 (m, 12H), 7.14-7.05 (m, 3H), 6.78 (dd, J=8.1, 2.1 Hz, 1H), 5.67-5.57 (m, 2H), 5.01 (d, J=8.3 Hz, 4H), 4.08 (t, J=6.4 Hz, 2H), 3.92 (q, J=6.4 Hz, 2H), 2.70-2.53 (m, 7H), 2.24 (s, 3H), 1.68-1.45 (m, 5H), 1.36-1.22 (m, 2H), 1.36-1.22 (m, 3H), 0.83 (d, J=6.4 Hz, 12H), 0.70 (t, J=7.2 Hz, 3H); LC-MS (ES): m/z=875.5 [M+H]$^+$.

Example 15

To a stirred solution of (3S)-(((((5-(((benzyloxy)(phenethyl)phosphoryl)oxy)pentyl) oxy)carbonyl)oxy)methyl 3-(4-(diisobutylamino)-3-(3-(p-tolyl)ureido)phenyl)pentanoate (0.650 g, 0.745 mmol) in dry ethyl acetate (5 mL), was added Pd/C (10%; 0.159 g, 1.491 mmol). The mixture was degassed and then flushed with H2 and stirred at room temperature for 0.5 h under H$_2$ atmosphere. The reaction mixture was filtered through celite bed, which was washed with ethyl acetate. The filtrate was concentrated under vacuum at ~30° C. The crude product was purified by RP HPLC (X-Bridge phenyl [250×30 mm]; mobile phase A: 0.1% formic acid in water; mobile phase B: acetonitrile; flow rate: 18 mL/min) to afford (S)-(((((5-(phosphonooxy)pentyl)oxy)carbonyl)oxy)methyl 3-(4-(diisobutylamino)-3-(3-(p-tolyl)ureido)phenyl)pentanoate (0.235 g, 0.333 mmol, 44.6%) as an off-white solid. $^1$H NMR (400 MHz, methanol-d$_4$) δ ppm=7.73 (s, 1H), 7.34-7.29 (m, 2H), 7.23 (d, J=8.5 Hz, 1H), 7.12 (d, J=8.0 Hz, 2H), 6.92 (d, J=6.5 Hz, 1H), 5.69-5.62 (m, 2H), 4.17 (t, J=6.5 Hz, 2H), 3.96 (q, J=6.5 Hz, 2H), 3.01-2.92 (m, 1H), 2.83-2.61 (m, 6H), 2.30 (s, 3H), 1.82-1.58 (m, 8H), 1.53-1.42 (m, 2H), 0.90 (d, J=6.5 Hz, 12H), 0.81 (t, J=7.3 Hz, 3H); LC-MS (ES): m/z=694.2 [M+H]$^+$; HPLC T$_r$: 17.8 min (Method A) and 14.9 min (Method B).

Example 16

(3S)-((Hydroxy((isobutyryloxy)methoxy)phosphoryl)oxy)methyl 3-(4-(diisobutylamino)-3-(3-(p-tolyl)ureido)phenyl)pentanoate

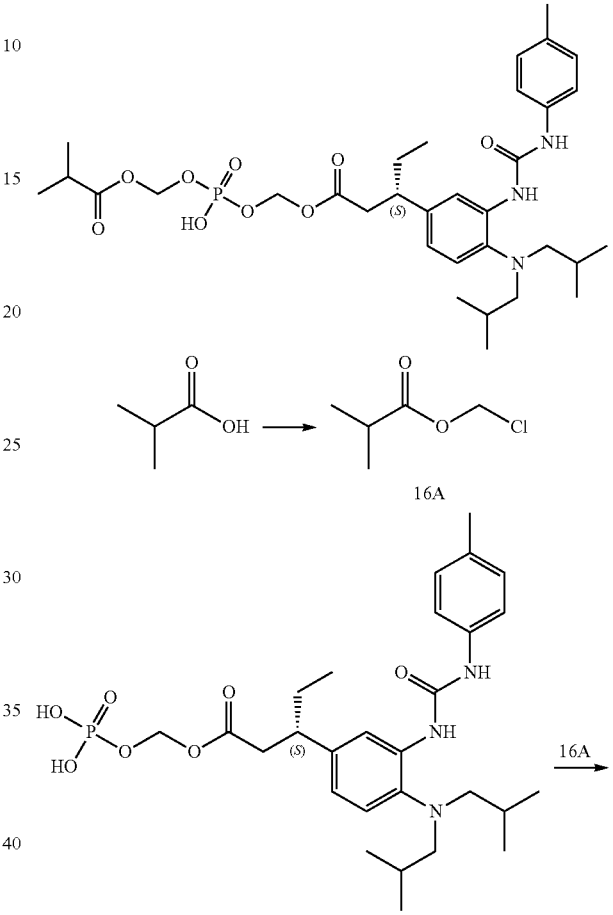

Example 16

16A: Chloromethyl Isobutyrate

To a biphasic solution of isobutyric acid (5.29 mL, 56.8 mmol), sodium bicarbonate (19.07 g, 227 mmol) and tetrabutylammonium hydrogen sulfate (1.927 g, 5.68 mmol) in dry DCM (20 mL) and water (20 mL) at 0° C., was added chloromethyl chlorosulfate (11.48 mL, 114 mmol) slowly. The reaction mixture was stirred at room temperature for 12 h. The mixture was diluted water and extracted with DCM (3×200 mL). The organic layer was washed with 10% sodium bicarbonate solution and brine solution, dried over anhydrous sodium sulphate and concentrated under vacuum at ~30° C. to give chloromethyl isobutyrate (4.300 g, 31.5 mmol, 55.5%) as a colorless liquid. $^1$H NMR (400 MHz, chloroform-d) δ ppm=5.72-5.70 (m, 2H), 5.70 (s, 2H), 2.66-2.58 (m, 1H), 1.22-1.19 (m, 6H).

Example 16

To a stirred solution of (S)-(phosphonooxy)methyl-3-(4-(diisobutylamino)-3-(3-(p-tolyl)ureido) phenyl) pentanoate (0.500 g, 0.887 mmol) in dry DMF (5 mL), were added chloromethyl isobutyrate (0.606 g, 4.44 mmol), DIPEA (0.775 mL, 4.44 mmol) and sodium iodide (0.665 g, 4.44 mmol). The reaction mixture was stirred at room temperature for 12 h. The solvent was concentrated under high vacuum at ~30° C. The crude product was purified by RP HPLC (Kinetex C18 [250×21.2 mm]; mobile phase A: 10 mM ammonium acetate in water; mobile phase B: acetonitrile; flow rate: 18 mL/min) to afford (3S)-((hydroxy((isobutyryloxy)methoxy)phosphoryl)oxy)methyl 3-(4-(diisobutylamino)-3-(3-(p-tolyl)ureido)phenyl)pentanoate (0.165 g, 0.241 mmol, 27.2%) as an off-white solid. $^1$H NMR (400 MHz, DMSO-d$_6$) δ ppm=9.30 (s, 1H), 7.85 (d, J=10.5 Hz, 2H), 7.40-7.32 (m, 2H), 7.25 (s, 1H), 7.16-7.05 (m, 2H), 7.00 (br. s., 1H), 6.80 (d, J=7.1 Hz, 1H), 5.39-5.25 (m, 4H), 2.90-2.80 (m, 1H), 2.69-2.59 (m, 5H), 2.57-2.52 (m, 2H), 2.24 (s, 3H), 1.72-1.57 (m, 3H), 1.56-1.46 (m, 1H), 1.07 (d, J=7.1 Hz, 6H), 0.83 (d, J=6.6 Hz, 12H), 0.72 (t, J=7.3 Hz, 3H); LC-MS (ES): m/z=664.2 [M+H]$^+$; HPLC T$_r$: 20.1 min (Method A) and 15.6 min (Method B).

Example 17

(3S)-((Hydroxy((propionyloxy)methoxy)phosphoryl)oxy)methyl 3-(4-(diisobutylamino)-3-(3-(p-tolyl)ureido)phenyl)pentanoate

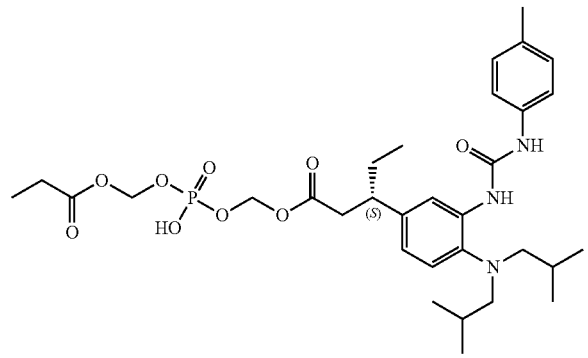

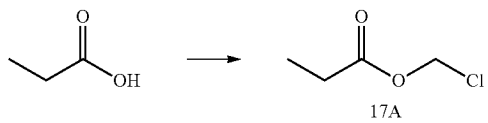

17A

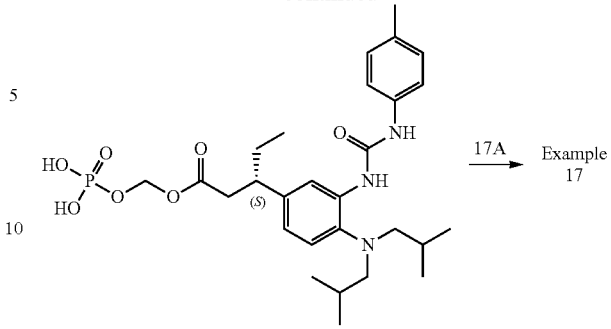

17A: Chloromethyl Propionate

To a biphasic solution of propionic acid (5.05 mL, 67.5 mmol), sodium bicarbonate (22.68 g, 270 mmol) and tetrabutylammonium hydrogen sulfate (2.292 g, 6.75 mmol) in DCM (20 mL) and water (20 mL) at 0° C., was added chloromethyl chlorosulfate (13.66 mL, 135 mmol) slowly. The reaction mixture was stirred at room temperature for 12 h. The mixture was diluted water, extracted with DCM (3×200 mL). The organic layer was washed with 10% sodium bicarbonate solution and brine, dried over anhydrous sodium sulphate and concentrated under vacuum at ~30° C. to give chloromethyl propionate (4.200 g, 34.3 mmol, 50.8%) as a colorless liquid. $^1$H NMR (300 MHz, chloroform-d) δ ppm=5.72 (s, 2H), 2.48-2.38 (m, 2H), 1.20 (t, J=7.4 Hz, 3H).

Example 17

To a stirred solution of (S)-(phosphonooxy) methyl 3-(4-(diisobutylamino)-3-(3-(p-tolyl)ureido)phenyl)pentanoate (0.500 g, 0.887 mmol) in dry DMF (5 mL), were added chloromethyl isobutyrate (0.606 g, 4.44 mmol), DIPEA (0.775 mL, 4.44 mmol) and sodium iodide (0.665 g, 4.44 mmol). The reaction mixture was stirred at room temperature for 12 h. The solvent was concentrated under high vacuum at ~30° C. The crude product was purified by RP HPLC (X-Bridge phenyl [250×30 mm]; mobile phase A: 10 mM ammonium acetate in water; mobile phase B: acetonitrile; flow rate: 18 mL/min) to afford (3S)-((hydroxy((isobutyryloxy)methoxy)phosphoryl)oxy)methyl 3-(4-(diisobutylamino)-3-(3-(p-tolyl)ureido)phenyl)pentanoate (0.050 g, 0.073 mmol, 8.24%) as an off-white solid. $^1$H NMR (400 MHz, DMSO-d$_6$) δ ppm=9.32 (s, 1H), 7.86 (s, 1H), 7.84 (d, J=2.0 Hz, 1H), 7.36 (d, J=8.5 Hz, 2H), 7.20-7.00 (m, 4H), 6.80 (dd, J=8.0, 2.0 Hz, 1H), 5.34-5.21 (m, 4H), 2.91-2.79 (m, 1H), 2.69-2.57 (m, 5H), 2.56-2.52 (m, 1H), 2.37-2.26 (m, 2H), 2.25 (s, 3H), 1.71-1.57 (m, 3H), 1.55-1.43 (m, 1H), 1.03 (t, J=7.4 Hz, 3H), 0.83 (d, J=6.5 Hz, 12H), 0.72 (t, J=7.3 Hz, 3H); LC-MS (ES): m/z=750.2 [M+H]$^+$; HPLC T$_r$: 12.0 min (Method A) and 15.0 min (Method B).

Example 18
(S)-((Methyl(3-(phosphonooxy)propyl)carbamoyl)oxy)methyl 3-(4-(diisobutylamino)-3-(3-(p-tolyl)ureido)phenyl)pentanoate
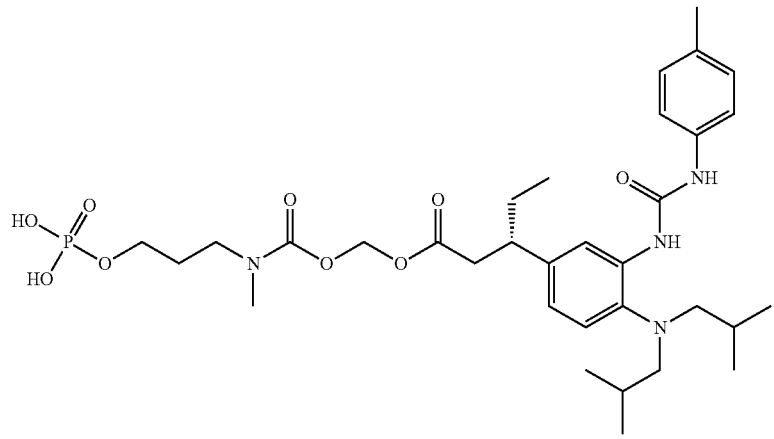
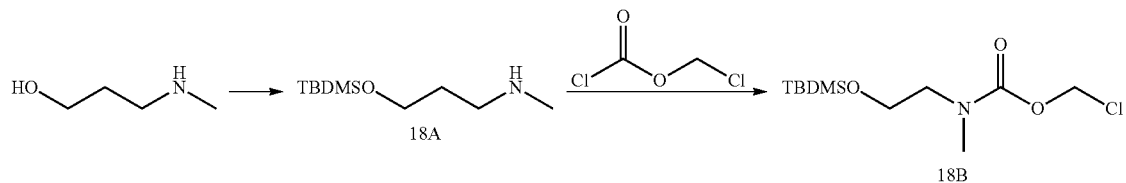
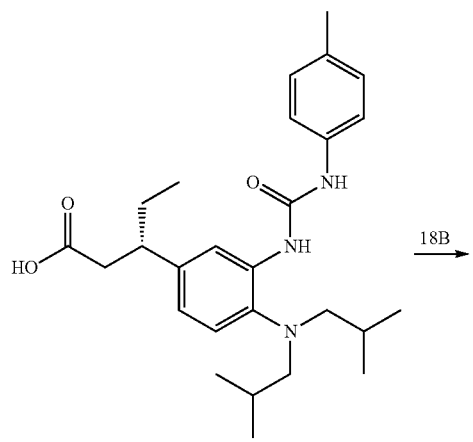

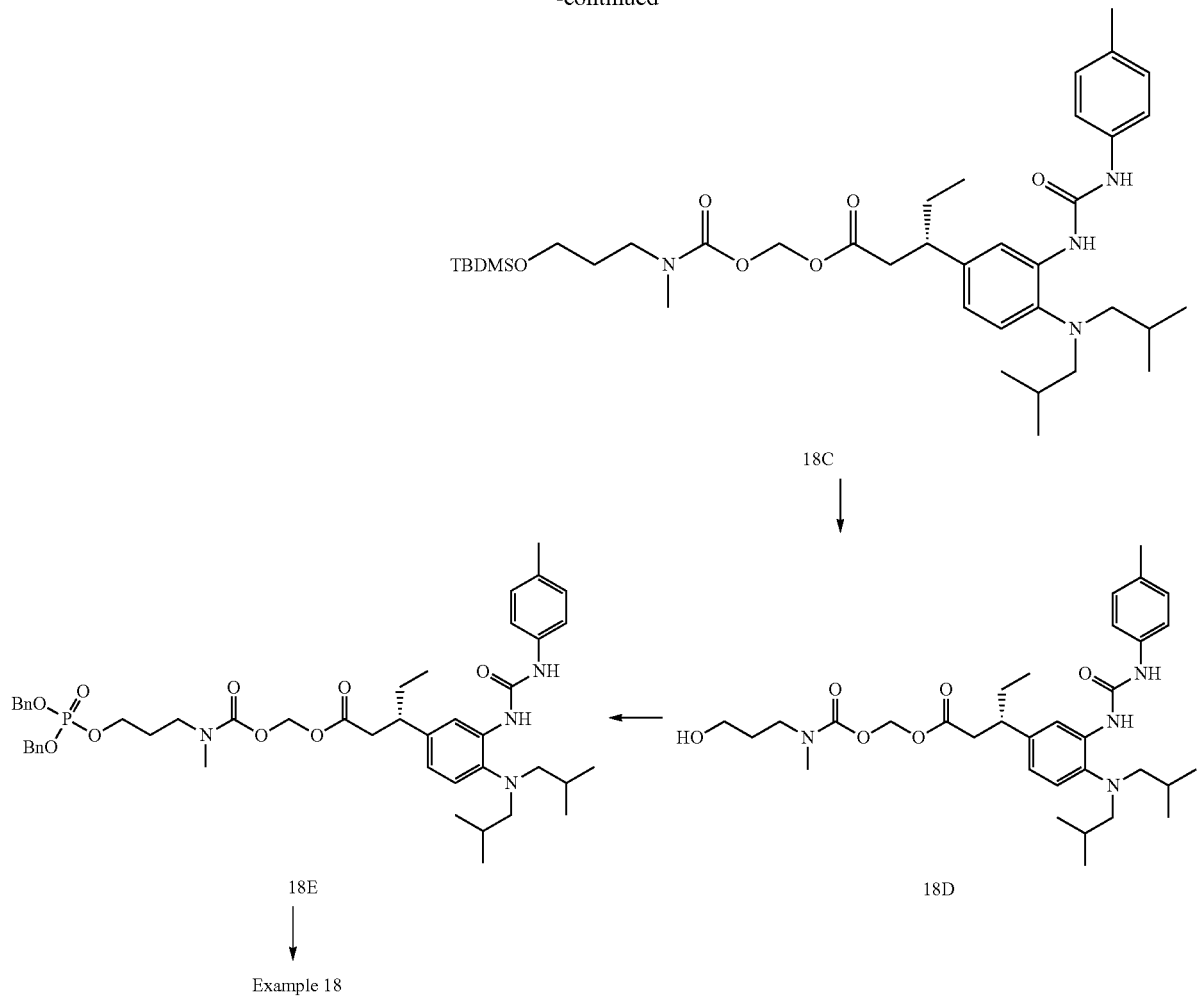

Example 18

18A: 3-((tert-Butyldimethylsilyl)oxy)-N-methylpropan-1-amine

To a stirred solution of 3-(methylamino)propan-1-ol (1.000 g, 11.22 mmol) in dry dichloromethane (10 mL) at 0° C., imidazole (0.764 g, 11.22 mmol) and tert-butyldimethylchlorosilane (1.860 g, 12.34 mmol) were added sequentially. The reaction mixture was stirred at room temperature for 12 h. The mixture was diluted with water and extracted with DCM (3×50 mL). The organic layer was washed with brine solution, dried over anhydrous sodium sulphate and concentrated under vacuum to give 3-((tert-butyldimethylsilyl)oxy)-N-methylpropan-1-amine (2.100 g, 10.32 mmol, 92%) as a colorless oil. $^1$H NMR (300 MHz, DMSO-d$_6$) δ ppm=3.62 (t, J=6.2 Hz, 2H), 3.34-3.28 (m, 2H), 2.25 (s, 3H), 1.57 (quin, J=6.6 Hz, 2H), 0.86 (s, 9H), 0.02 (s, 6H).

18B: Chloromethyl (3-((tert-butyldimethylsilyl)oxy)propyl)(methyl)carbamate

To a stirred solution of 3-((tert-butyldimethylsilyl)oxy)-N-methylpropan-1-amine (2.000 g, 9.83 mmol) in dry DCM (20 mL) at 0° C., pyridine (1.591 mL, 19.67 mmol) and chloromethyl chloroformate (1.750 mL, 19.67 mmol) were added slowly. After being stirred at 0° C. for 1 h, the reaction mixture was diluted with water and extracted with DCM (3×50 mL). The organic layer was washed with brine solution, dried over anhydrous sodium sulphate and concentrated under vacuum at ~30° C. to give light yellowish oil. The crude product was purified by ISCO (silica gel 60-120 mesh; 36% ethyl acetate in hexane as eluent) to give chloromethyl (3-((tert-butyldimethylsilyl) oxy)propyl) (methyl)carbamate (1.700 g, 5.75 mmol, 58.4%) as a light yellowish oil. $^1$H NMR (300 MHz, DMSO-d$_6$) δ=5.91 (s, 2H), 3.63 (t, J=6.0 Hz, 2H), 3.35-3.28 (m, 2H), 2.91 (s, 3H), 1.72 (quin, J=6.7 Hz, 2H), 0.94 (s, 9H), 0.01 (s, 6H).

18C: (S)-4,9,9,10,10-Pentamethyl-3-oxo-2,8-dioxa-4-aza-9-silaundecyl 3-(4-(diisobutylamino)-3-(3-(p-tolyl)ureido)phenyl)pentanoate A mixture of (S)-3-(4-(diisobutylamino)-3-(3-(p-tolyl)ureido)phenyl)pentanoic acid (1.500 g, 3.31 mmol) and cesium carbonate (3.23 g, 9.92 mmol) in dry DMF (15 mL) was stirred at room temperature for 30 min. Chloromethyl (3-((tert-butyldimethylsilyl)oxy)propyl)(methyl)carbamate (1.174 g, 3.97 mmol) and sodium iodide (0.595 g, 3.97 mmol) were added. The reaction mixture was stirred at room temperature for 16 h. The mixture was diluted with water and extracted with ethyl acetate (3×100 mL). The organic layer was dried over anhydrous sodium sulphate and concentrated under vacuum at ~30° C. to give light brownish oil. The crude product was purified by ISCO (silica gel 60-120 mesh; 15% ethyl acetate in hexane as eluent) to give (S)-4,9,9,10,10-pentamethyl-3-oxo-2,8-dioxa-4-aza-9-silaundecyl 3-(4-(diisobutylamino)-3-(3-(p-tolyl)ureido)phenyl)pentanoate (2.200 g, 2.68 mmol, 81%) as a colorless oil. $^1$H NMR (400 MHz, DMSO-d$_6$) δ ppm=9.31 (s, 1H), 7.86 (s, 1H), 7.84 (d, J=2.0 Hz, 1H), 7.36 (d, J=8.0 Hz, 2H), 7.12-7.06 (m, 3H), 6.77 (dd, J=8.0, 2.0 Hz, 1H), 5.64-5.57 (m, 2H), 3.59-3.52 (m, 2H), 3.23 (dd, J=14.6, 7.3 Hz, 2H), 2.86-2.78 (m, 3H), 2.75 (s, 3H), 2.70-2.59 (m, 4H), 2.24 (s, 3H), 1.75-1.55 (m, 5H), 1.54-1.44 (m, 1H), 0.89-0.79 (m, 21H), 0.71 (t, J=7.3 Hz, 3H), 0.01 (s, 6H); LC-MS (ES): m/z=714.2 [M+H]$^+$.

18D: (S)-(((3-Hydroxypropyl)(methyl)carbamoyl)oxy)methyl 3-(4-(diisobutylamino)-3-(3-(p-tolyl)ureido)phenyl)pentanoate To a stirred solution of (S)-4,9,9,10,10-pentamethyl-3-oxo-2,8-dioxa-4-aza-9-silaundecyl 3-(4-(diisobutylamino)-3-(3-(p-tolyl)ureido)phenyl)pentanoate (2.200 g, 3.09 mmol) in dichloromethane (25 mL) at 0° C., was added hydrogen fluoride-pyridine (1.986 mL, 15.43 mmol) slowly. After being stirred at 0° C. for 30 min, the reaction mixture was neutralized with sodium bicarbonate solution and extracted with DCM (3×50 mL). The organic layer was washed with brine solution and dried over anhydrous sodium sulphate and concentrated under vacuum at ~30° C. to give (S)-(((3-hydroxypropyl)(methyl)carbamoyl)oxy)methyl 3-(4-(diisobutylamino)-3-(3-(p-tolyl)ureido)phenyl)pentanoate (1.700 g, 2.84 mmol, 92%) as a colorless oil. $^1$H NMR (400 MHz, DMSO-d$_6$) δ ppm=9.30 (s, 1H), 7.86 (s, 1H), 7.84 (d, J=2.0 Hz, 1H), 7.38-7.33 (m, 2H), 7.13-7.06 (m, 3H), 6.78 (dd, J=8.0, 2.0 Hz, 1H), 5.65 (s, 2H), 4.46-4.41 (m, 1H), 3.42-3.33 (m, 2H), 3.23 (dd, J=15.4, 7.6 Hz, 2H), 2.88-2.79 (m, 1H), 2.77 (s, 3H), 2.71-2.54 (m, 6H), 2.25 (s, 3H), 1.69-1.55 (m, 4H), 1.55-1.44 (m, 2H), 0.84 (d, J=6.5 Hz, 12H), 0.71 (t, J=7.3 Hz, 3H); LC-MS (ES): m/z=599.3 [M+H]$^+$.

18E: (S)-(((3-((bis(Benzyloxy)phosphoryl)oxy)propyl)(methyl)carbamoyl)oxy)methyl 3-(4-(diisobutylamino)-3-(3-(p-tolyl)ureido)phenyl)pentanoate To a stirred solution of (S)-(((3-hydroxypropyl)(methyl)carbamoyl)oxy)methyl 3-(4-(diisobutylamino)-3-(3-(p-tolyl)ureido)phenyl)pentanoate (1.600 g, 2.67 mmol) in dry dichloromethane (20 mL), were added dibenzyl N,N-diisopropylphosphoramidite (1.347 ml, 4.01 mmol) and a solution of 0.4 M 1H-tetrazole in acetonitrile (10.16 ml, 4.01 mmol). The reaction mixture was stirred at room temperature for 8 h. After cooling to 0° C., 30% hydrogen peroxide solution (0.409 mL, 13.36 mmol) was added slowly. After being stirred at room temperature for 2 h, the reaction mixture was diluted with water and extracted with DCM (3×100 mL). The organic layer was washed with brine and dried over anhydrous sodium sulfate, filtered and concentrated under vacuum at ~30° C. to give yellowish oil. The crude product was purified by ISCO (silica gel 60-120 mesh; 55% ethyl acetate in hexane as eluent) to give (S)-(((3-((bis(benzyloxy)phosphoryl)oxy)propyl) (methyl)carbamoyl)oxy)methyl 3-(4-(diisobutylamino)-3-(3-(p-tolyl)ureido)phenyl) pentanoate (1.400 g, 1.173 mmol, 43.9%) as a yellowish oil. $^1$H NMR (400M Hz, DMSO-d$_6$) δ ppm=9.30 (s, 1H), 7.86 (s, 1H), 7.84 (d, J=2.0 Hz, 1H), 7.41-7.27 (m, 10H), 7.13-7.05 (m, 5H), 6.78 (dd, J=8.0, 2.0 Hz, 1H), 5.63 (s, 2H), 5.02 (d, J=8.0 Hz, 2H), 4.07-3.87 (m, 4H), 3.28-3.16 (m, 2H), 2.79 (s, 3H), 2.75-2.70 (m, 1H), 2.68-2.54 (m, 6H), 2.24 (s, 3H), 1.82-1.54 (m, 4H), 1.53-1.42 (m, 2H), 0.83 (d, J=7.0 Hz, 12H), 0.81 (t, J=7.3 Hz, 3H); LC-MS (ES): m/z=860.2 [M+H]$^+$.

Example 18

To a solution of (S)-(((3-((bis(benzyloxy)phosphoryl)oxy)propyl)(methyl) carbamoyl)oxy)methyl 3-(4-(diisobutylamino)-3-(3-(p-tolyl)ureido)phenyl)pentanoate (1.300 g, 1.513 mmol) in dry ethyl acetate (3 mL), was added Pd/C (10%, 0.322 g, 3.03 mmol). The mixture was degassed and then flushed with H2 and stirred at room temperature for 0.5 h under H$_2$ atmosphere. The mixture was filtered through celite bed, which was washed with ethyl acetate and concentrated under vacuum at ~30° C. The crude product was purified by RP HPLC (Kinetex C18 [250×21.2 mm]; mobile phase A: 10 mM ammonium acetate in water; mobile phase B: acetonitrile; flow rate: 18 mL/min) to afford (S)-((methyl (3-(phosphonooxy)propyl)carbamoyl)oxy) methyl 3-(4-(diisobutylamino)-3-(3-(p-tolyl) ureido) phenyl) pentanoate (0.255 g, 0.354 mmol, 23.38%) as an off-white solid. $^1$H NMR (400 MHz, methanol-d$_4$) δ ppm=7.80 (d, J=5.0 Hz, 1H), 7.30 (d, J=8.0 Hz, 2H), 7.17-7.08 (m, 3H), 6.86 (dd, J=8.0, 2.0 Hz, 1H), 5.65 (s, 2H), 3.88 (quin, J=6.1 Hz, 2H), 3.44-3.34 (m, 2H), 2.94 (s, 3H), 2.92-2.87 (m, 1H), 2.74-2.57 (m, 6H), 2.30 (s, 3H), 1.92-1.78 (m, 2H), 1.77-1.56 (m, 4H), 0.87 (d, J=6.5 Hz, 12H), 0.81 (t, J=7.3 Hz, 3H); LC-MS (ES): m/z=669.4 [M+H]$^+$; HPLC T$_r$: 8.3 min (Method A) and 6.8 min (Method B).

Example 19

(S)-(((S)-3-(4-(Diisobutylamino)-3-(3-(p-tolyl)ureido)phenyl)pentanoyl)oxy)methyl 2-((phosphonooxy)methyl)pyrrolidine-1-carboxylate

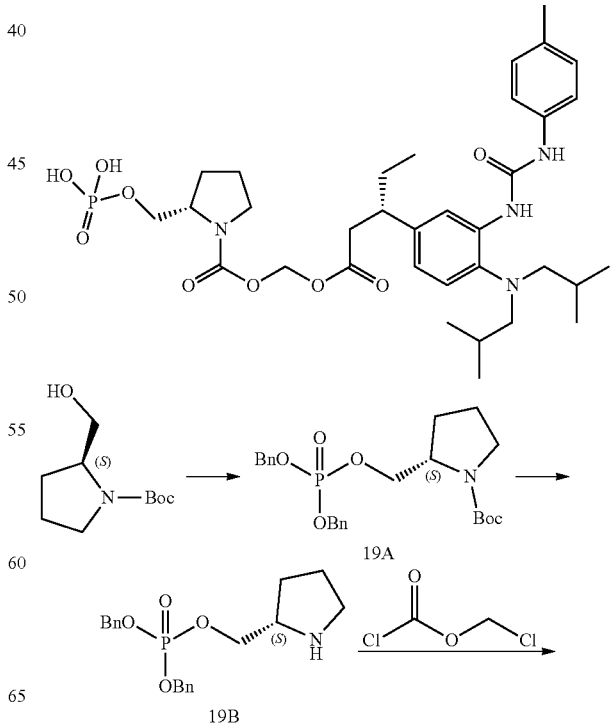

93

-continued

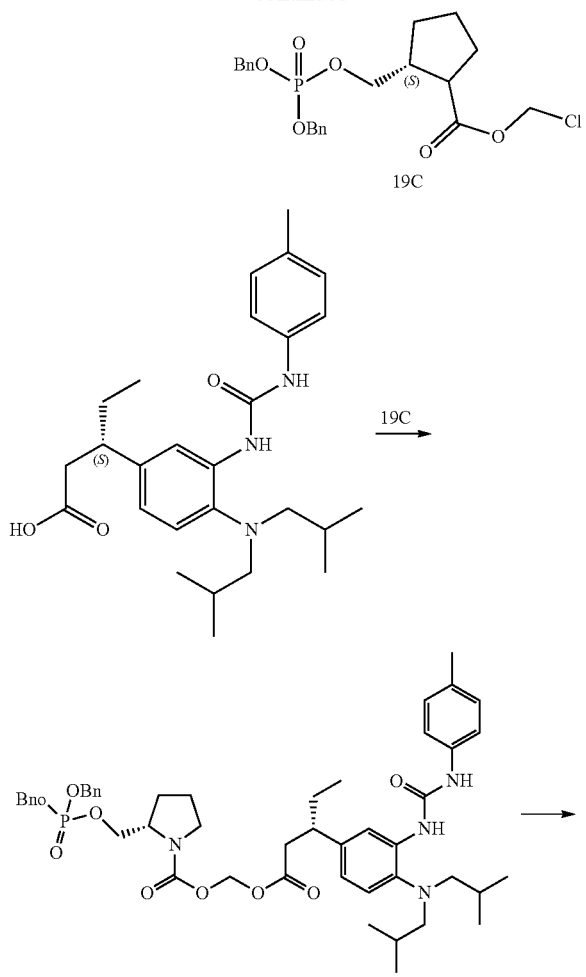

Example 19

19A: (S)-tert-Butyl 2-(((bis(benzyloxy)phosphoryl)oxy)methyl)pyrrolidine-1-carboxylate To a stirred suspension of (S)-tert-butyl 2-(hydroxymethyl)pyrrolidine-1-carboxylate (3 g, 14.91 mmol) in 1H-tetrazole in acetonitrile (57.3 mL, 19.38 mmol), was added dibenzyl N,N'-diisopropylphosphoramidite (7.72 g, 22.36 mmol) at room temperature. After being stirred for 4 h under nitrogen, the reaction mixture was cooled to 0° C. $H_2O_2$ (4.35 g, 44.7 mmol) was added. The mixture was stirred for 20 min at 0° C. The reaction mixture was partitioned between sodium bicarbonate solution and EtOAc. The EtOAc layer was washed with $H_2O$ and saturated NaCl solution, dried over anhydrous $Na_2SO_4$, filtered and concentrated under reduced pressure. The crude product was purified using CombiFlash (silica gel 60-120 mesh; 45% ethyl acetate in pet. ether as eluent) to afford (S)-tert-butyl 2-(((bis(benzyloxy)phosphoryl)oxy)methyl)pyrrolidine-1-carboxylate (6.4 g, 9.71 mmol, 65.1%) as brownish semi-solid. $^1H$ NMR (300 MHz, methanol-$d_4$) δ ppm 7.28-7.51 (m, 10H), 4.96-5.20 (m, 4H), 3.79-4.25 (m, 4H), 3.29 (m, 1H), 2.03 (m, 4H), 1.35-1.55 (m, 9H); LCMS (ES): m/z 462.2 [M+H]$^+$.

94

19B: (S)-Dibenzyl(pyrrolidin-2-ylmethyl)phosphate Hydrochloride

To a stirred solution of (S)-tert-butyl 2-(((bis(benzyloxy)phosphoryl)oxy)methyl) pyrrolidine-1-carboxylate (5 g, 10.83 mmol) in anhydrous DCM (20 mL) at 0° C., was added 4 N HCl in dioxane (20 mL, 658 mmol). After being stirred for 20 min at 0° C., the reaction mixture was concentrated to dryness under high vacuum to afford (S)-dibenzyl(pyrrolidin-2-ylmethyl) phosphate hydrochloride (4.3 g, 8.32 mmol, 77%) as pale yellow oil. $^1H$ NMR (400 MHz, methanol-$d_4$) δ ppm 7.27-7.57 (m, 10H), 5.00-5.23 (m, 4H), 3.95-4.35 (m, 3H), 3.20-3.30 (m, 2H), 1.93-2.31 (m, 4H); LCMS (ES): m/z 362.2 [M+H]$^+$.

19C: (S)-Chloromethyl 2-(((bis(benzyloxy)phosphoryl)oxy)methyl)pyrrolidine-1-carboxylate To a stirred solution of (S)-dibenzyl(pyrrolidin-2-ylmethyl) phosphate (4.3 g, 11.90 mmol) in anhydrous DCM (15 mL) at 0° C., was added $Et_3N$ (8.29 mL, 59.5 mmol) and subsequently drop-wise chloromethyl chloroformate (4.60 g, 35.7 mmol). The reaction mixture was slowly warmed to room temperature and stirred for 5 h under nitrogen. The reaction mixture was cooled to 0° C., partitioned between sodium bicarbonate solution (25 mL) and DCM. The organic layer was washed with $H_2O$, and brine, dried over anhydrous $Na_2SO_4$, filtered and concentrated under reduced pressure. The residue was purified using CombiFlash (silica gel 60-120 mesh; 55% ethyl acetate in pet. ether as eluent) to afford (S)-chloromethyl 2-(((bis(benzyloxy)phosphoryl) oxy) methyl)pyrrolidine-1-carboxylate (1.2 g, 2.59 mmol, 21.78%) as brownish semi-solid. $^1H$ NMR (300 MHz, methanol-$d_4$) δ ppm 7.39 (s, 10H), 5.75-5.80 (m, 2H), 5.06 (d, J=9.07 Hz, 4H), 3.99-4.22 (m, 3H), 3.36 (s, 2H), 1.85-2.03 (m, 4H); LCMS (ES): m/z 454.2 [M+H]$^+$.

19D: (S)-(((S)-3-(4-(Diisobutylamino)-3-(3-(p-tolyl)ureido)phenyl)pentanoyl)oxy)methyl 2-(((bis(benzyloxy)phosphoryl)oxy)methyl)pyrrolidine-1-carboxylate To a stirred solution of (S)-3-(4-(diisobutylamino)-3-(3-(p-tolyl)ureido)phenyl) pentanoic acid (150 mg, 0.331 mmol) in anhydrous acetonitrile (2.5 mL), were added potassium carbonate (137 mg, 0.992 mmol), sodium iodide (74.3 mg, 0.496 mmol) and (S)-chloromethyl 2-(((bis(benzyloxy)phosphoryl)oxy)methyl)pyrrolidine-1-carboxylate (300 mg, 0.661 mmol). The reaction mixture was stirred for 16 h at room temperature, diluted with water (10 mL) and extracted with ethyl acetate (2×25 mL). The organic layer was washed with $H_2O$, and saturated NaCl solution, dried over anhydrous $Na_2SO_4$, filtered and concentrated under high vacuum at 30° C. The crude product was purified using CombiFlash (silica gel 60-120 mesh; 55% ethyl acetate in pet. ether as eluent) to afford (S)-(((S)-3-(4-(diisobutylamino)-3-(3-(p-tolyl)ureido)phenyl)pentanoyl)oxy)methyl 2-(((bis(benzyloxy)phosphoryl)oxy)methyl)pyrrolidine-1-carboxylate (200 mg, 0.184 mmol, 55.6%) as brownish semi-solid. $^1H$ NMR (400 MHz, DMSO-$d_6$) δ ppm 9.31 (s, 1H), 7.82-7.90 (m, 2H), 7.33-7.42 (m, 12H), 7.05-7.14 (m, 3H), 6.76 (d, J=8.53 Hz, 1H), 5.63 (d, J=5.52 Hz, 2H), 5.02 (d, J=8.03 Hz, 4H), 3.97-4.09 (m, 3H), 3.83-3.97 (m, 7H), 3.27 (s, 1H), 2.31-2.36 (m, 1H), 2.25 (s, 3H), 2.00 (s, 1H), 1.46-1.69 (m, 6H), 1.18 (s, 1H), 0.83 (d, J=6.53 Hz, 12H), 0.69 (t, J=7.53 Hz, 3H); LCMS (ES): m/z=872.4 [M+H]$^+$.

Example 19

To a stirred solution of (S)-(((S)-3-(4-(diisobutylamino)-3-(3-(p-tolyl)ureido)phenyl) pentanoyl)oxy)methyl 2 (((bis(benzyloxy)phosphoryl)oxy)methyl)pyrrolidine-1-carboxylate (200 mg, 0.230 mmol) in anhydrous DCE (2 mL) at 0° C., was added TFA (4 mL, 51.9 mmol) followed by anisole (1 mL, 9.15 mmol). The reaction mixture was heated to 50° C. and stirred for 16 h. The reaction mixture was concentrated to dryness at 30° C. under high vacuum. The crude product (brownish solid) was purified in RP HPLC (X-Bridge phenyl [250×19 mm]; mobile phase A: 0.1% formic acid in water; mobile phase B: $CH_3CN$; Flow rate: 18 mL/min). The prep. fraction was concentrated under high vacuum at 30° C. The residue was dissolved in a mixture of MeCN and water, frozen and lyophilized for 12 h to afford (S)-(((S)-3-(4-(diisobutylamino)-3-(3-(p-tolyl)ureido) phenyl)pentanoyl)oxy)methyl 2-((phosphonooxy)methyl)pyrrolidine-1-carboxylate (50 mg, 0.069 mmol, 30.3%) as an off-white solid. $^1$H NMR (300 MHz, DMSO-$d_6$; $D_2O$ exchange) δ ppm 7.81 (br. s., 1H), 7.34 (d, J=8.31 Hz, 2H), 7.05-7.16 (m, 3H), 6.78 (d, J=7.93 Hz, 1H), 5.53-5.66 (m, 2H), 3.67-3.94 (m, 2H), 3.19-3.33 (m, 2H), 2.80 (d, J=5.67 Hz, 1H), 2.68-2.75 (m, 1H), 2.57-2.67 (m, 6H), 2.24 (s, 3H), 1.86 (m, 4H), 1.57-1.66 (m, 4H), 0.82 (d, J=6.42 Hz, 12H), 0.70 (t, J=7.18 Hz, 3H); LCMS (ES): m/z=691.3[M+H]$^+$; HPLC T$_r$: 9.1 min (Method A) and 9.7 min (Method B).

Example 20

(3S)-1-((Methyl(3-((phosphonooxy)methyl)pyridin-2-yl)carbamoyl)oxy)ethyl 3-(4-(diisobutylamino)-3-(3-(p-tolyl)ureido)phenyl)pentanoate

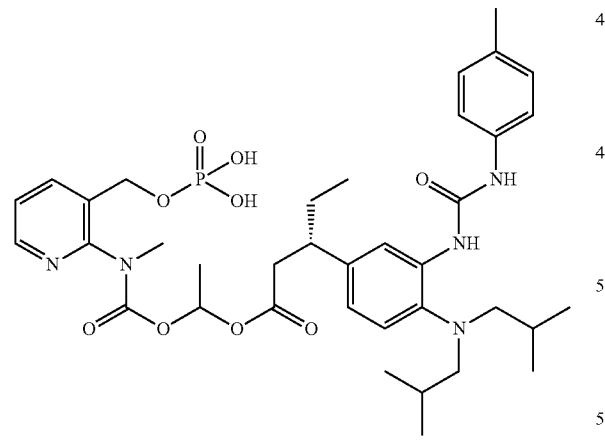

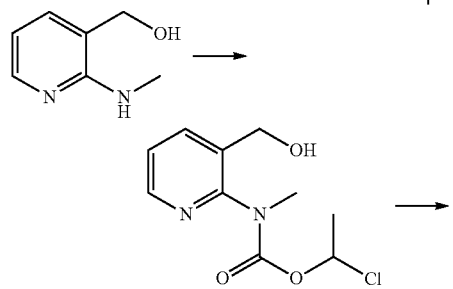

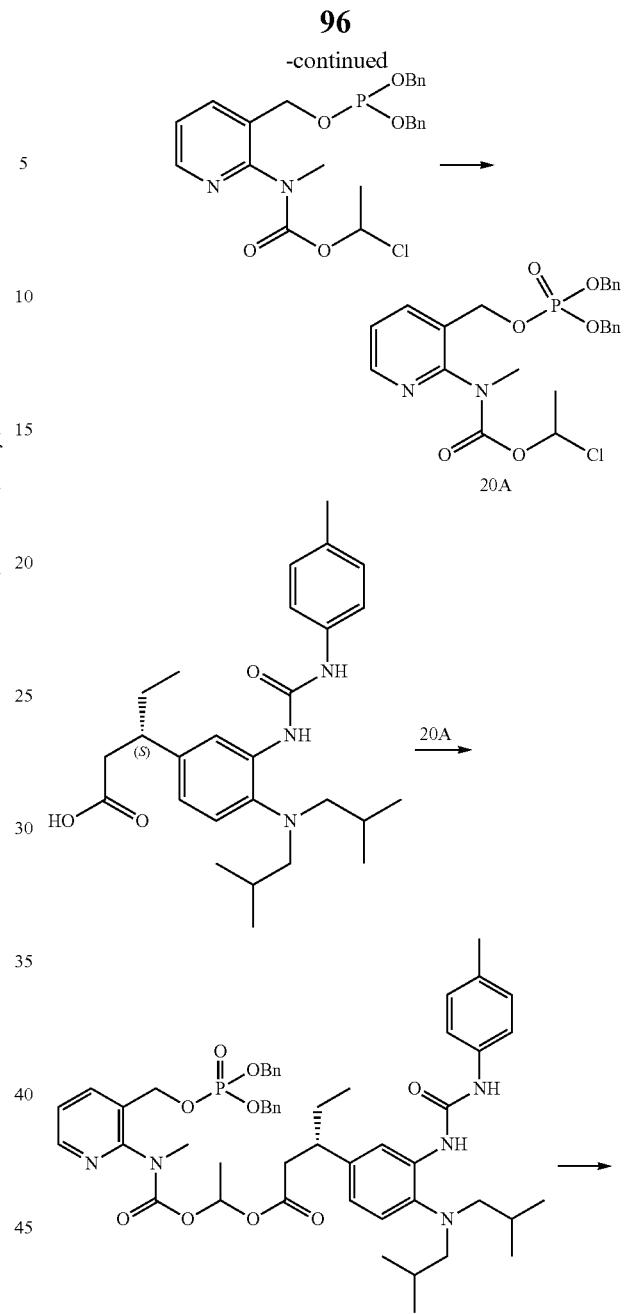

Example 20

20A: 1-Chloroethyl (3-(((bis(benzyloxy)phosphoryl)oxy)methyl)pyridin-2-yl)(methyl)carbamate To a stirred solution of (2-(methylamino)pyridin-3-yl)methanol (100 mg, 0.724 mmol) in anhydrous DCM (1 mL) at −10° C., was added DIPEA (0.164 mL, 0.941 mmol), followed by drop wise 1-chloroethyl chloroformate (0.088 mL, 0.796 mmol). After being stirred for 1 h at −10° C., the reaction mixture warmed to 0° C. Dibenzyl N,N′-diisopropylphosphoramidite (500 mg, 1.448 mmol) and 1H-tetrazole (3.21 mL, 1.086 mmol) were added. The reaction mixture was stirred for 1 h at 0° C. After adding $H_2O_2$ (0.222 mL, 2.171 mmol) dropwise, the mixture was stirred for 30 min. and subsequently partitioned between sodium bicarbonate solution (10 mL) and DCM (2×20 mL). The organic layer was washed with H$_2$O, and saturated NaCl solution, dried over anhydrous Na$_2$SO$_4$, filtered and concentrated under reduced pressure to get the crude product, which was purified using CombiFlash (silica gel 60-120 mesh; 55% ethyl acetate in pet. ether as eluent) to afford 1-chloroethyl (3-(((bis(benzyloxy)phosphoryl)oxy)methyl)pyridin-2-yl)(methyl)carbamate (80 mg, 0.125 mmol, 17.29%) as pale yellow oil. LCMS (ES): m/z=505.3[M+H]$^+$.

20B: (3S)-1-(((3-(((bis(Benzyloxy)phosphoryl)oxy)methyl)pyridin-2-yl)(methyl)carbamoyl)oxy)ethyl 3-(4-(diisobutylamino)-3-(3-(p-tolyl)ureido)phenyl)pentanoate To a stirred solution of (S)-3-(4-(diisobutylamino)-3-(3-(p-tolyl)ureido)phenyl) pentanoic acid (300 mg, 0.661 mmol) in anhydrous acetonitrile (5 mL), were added K$_2$CO$_3$ (274 mg, 1.984 mmol), sodium iodide (149 mg, 0.992 mmol) and 1-chloroethyl (3-(((bis(benzyloxy)phosphoryl)oxy)methyl)pyridin-2-yl)(methyl)carbamate (668 mg, 1.323 mmol). The reaction mixture was stirred for 16 h at 50° C. The reaction mixture was cooled to room temperature and partitioned between water (10 mL) and ethyl acetate (2×20 mL). The organic layer was washed with H$_2$O, and saturated NaCl solution, dried over anhydrous Na$_2$SO$_4$, filtered and concentrated under reduced pressure. The crude compound was purified in RP HPLC. The prep. fraction was concentrated under high vacuum at 30° C. The residue was dissolved in a mixture of MeCN and water, frozen and lyophilized for 12 h to afford (3S)-1-(((3-(((bis(benzyloxy)phosphoryl)oxy)methyl) pyridin-2-yl)(methyl)carbamoyl)oxy)ethyl 3-(4-(diisobutylamino)-3-(3-(p-tolyl)ureido)phenyl)pentanoate (140 mg, 0.140 mmol, 21.12%) as an off-white solid. $^1$H NMR (300 MHz, DMSO-d$_6$) δ ppm 9.29-9.35 (m, 1H), 8.39-8.52 (m, 1H), 7.78-7.90 (m, 3H), 7.18-7.56 (m, 13H), 7.00-7.14 (m, 3H), 6.71-6.81 (m, 1H), 6.53-6.67 (m, 1H), 4.85-5.09 (m, 6H), 3.03-3.16 (m, 3H), 2.56-2.78 (m, 7H), 1.92-2.01 (m, 3H) 1.37-1.69 (m, 4H), 1.09-1.24 (m, 3H), 0.77-0.86 (m, 12H), 0.60-0.74 (m, 3H); LCMS(ES): m/z=922.4[M+H]$^+$.

Example 20

To a stirred solution of (3S)-1-(((3-(((bis(benzyloxy)phosphoryl)oxy)methyl) pyridin-2-yl)(methyl)carbamoyl)oxy)ethyl 3-(4-(diisobutylamino)-3-(3-(p-tolyl)ureido)phenyl)pentanoate (130 mg, 0.141 mmol) in anhydrous ethyl acetate (2.5 mL), was added Pd/C (10%, 150 mg, 0.141 mmol) and stirred for 3 h under hydrogen bladder at room temperature. The black suspension was filtered through celite bed and the bed was washed with ethyl acetate (50 mL). The filtrate was concentrated under reduced pressure to afford the crude product as brownish semi-solid. The crude compound was purified by RP HPLC (X-Bridge phenyl [250×19 mm]; mobile phase A: 0.1% formic acid in water; mobile phase B: CH$_3$CN; Flow rate: 18 mL/min). The prep. fraction was concentrated under high vacuum at 30° C. The residue was dissolved in a mixture of MeCN and water, frozen and lyophilized for 12 h to afford (3S)-1-((methyl(3-((phosphonooxy)methyl)pyridin-2-yl)carbamoyl)oxy)ethyl 3-(4-(diisobutylamino)-3-(3-(p-tolyl)ureido)phenyl)pentanoate (25 mg, 0.033 mmol, 23.66%) as an off-white solid. $^1$H NMR (400 MHz, methanol-d$_4$) δ ppm 9.26 (d, J=3.51 Hz, 1H), 8.76 (d, J=8.03 Hz, 1H), 8.69 (br. s., 2H), 8.25 (br. s., 1H), 8.17 (d, J=8.53 Hz, 2H), 7.932-7.952 (m, 1H), 7.88-7.96 (m, 3H), 7.63 (br. s., 1H), 7.43 (br. s., 1H), 5.60 (br. s., 2H), 3.40-3.59 (m, 7H), 3.07 (s, 3H), 2.42 (dd, J=12.80, 6.27 Hz, 3H), 1.45-1.71 (m, 3H), 1.77-2.13 (m, 4H), 1.64 (d, J=6.02 Hz, 12H), 1.52 (br. s., 3H); LCMS(ES): m/z=724.4[M+H]$^+$; HPLC T$_r$: 9.0 min (Method A) and 9.7 min (Method B)

Example 21

(S)-(((S)-3-Methyl-2-(phosphonooxy)butanoyl)oxy)methyl 3-(4-(diisobutylamino)-3-(3-(p-tolyl)ureido)phenyl)pentanoate

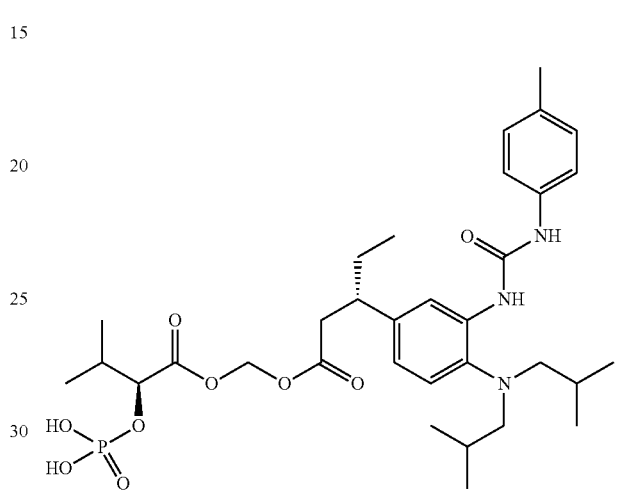

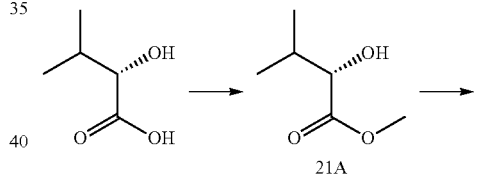

21A

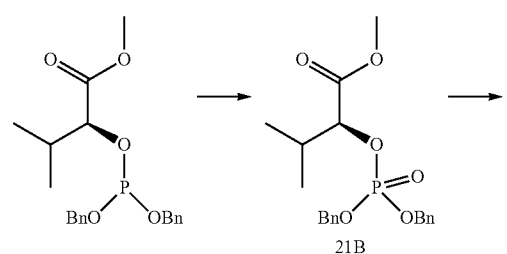

21B

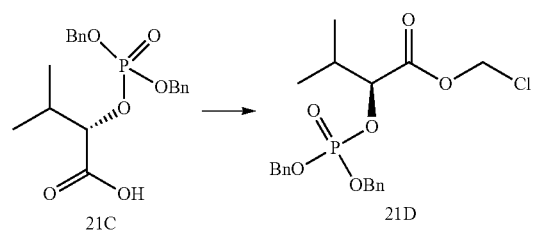

21C

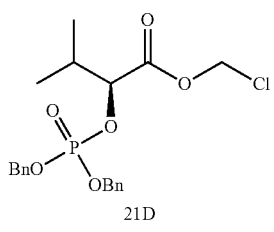

21D

-continued

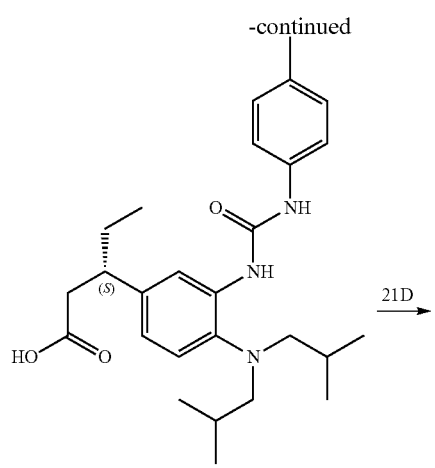

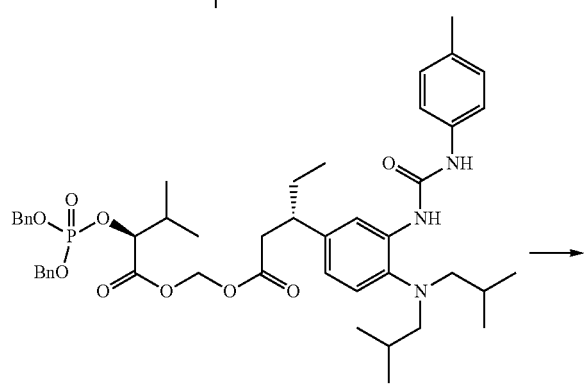

Example 21

21A: (S)-Methyl 2-hydroxy-3-methylbutanoate

To a stirred solution of (S)-2-hydroxy-3-methylbutanoic acid (1 g, 8.47 mmol) in anhydrous methanol (25 mL) at 0° C., was added thionyl chloride (1.236 mL, 16.93 mmol). The reaction mixture was allowed to warm to room temperature and stirred for 2 h. The reaction mixture was concentrated to dryness under high vacuum. The residue was partitioned between sodium bicarbonate solution (25 ml) and DCM (50 mL). The organic layer was washed with $H_2O$ and saturated NaCl solution, dried over anhydrous $Na_2SO_4$, filtered and concentrated under reduced pressure to afford (S)-methyl 2-hydroxy-3-methylbutanoate (1.2 g, 5.27 mmol, 62.2%) as colourless oil. $^1H$ NMR (300 MHz, methanol-$d_4$) δ ppm 3.96 (d, J=4.91 Hz, 1H), 3.74 (s, 3H), 1.95-2.12 (m, 1H), 0.98 (d, J=6.80 Hz, 3H), 0.92 (d, J=6.80 Hz, 3H); LCMS(ES): m/z=133.2[M+H]$^+$.

21B: (S)-Methyl 2-((bis(benzyloxy)phosphoryl)oxy)-3-methylbutanoate

To a stirred solution of (S)-methyl 2-hydroxy-3-methylbutanoate (600 mg, 4.54 mmol) in anhydrous acetonitrile (10 mL) at 0° C., was added 1H-tetrazole (232 mg, 6.81 mmol), followed by dibenzyl N,N'-diisopropylphosphoramidite (2352 mg, 6.81 mmol) dropwise. The reaction mixture was brought to room temperature and stirred for 5 h. After cooling the reaction mixture to 0° C., $H_2O_2$ (0.795 mL, 9.08 mmol) was added dropwise. After being stirred for 30 min., the reaction mixture was diluted with water (10 mL) and extracted with ethyl acetate (2×25 mL). EtOAc layer was washed with $H_2O$ and saturated NaCl solution. The organic layer was dried over anhydrous $Na_2SO_4$, filtered and concentrated under reduced pressure. The residue was purified using CombiFlash (silica gel 60-120 mesh; 40% ethyl acetate in pet. ether as eluent) to afford (S)-methyl 2-((bis(benzyloxy)phosphoryl)oxy)-3-methylbutanoate (2.2 g, 3.81 mmol, 84%) as colourless oil. $^1H$ NMR (400 MHz, chloroform-d) δ ppm 7.32-7.37 (m, 10H), 5.02-5.14 (m, 4H), 4.65 (dd, J=8.01, 4.25 Hz, 1H), 3.70 (s, 3H), 2.11-2.23 (m, 1H), 0.99 (d, J=7.00 Hz, 3H), 0.93 (d, J=7.00 Hz, 3H); LCMS(ES): m/z=393.8 [M+H]$^+$.

21C: (S)-2-((Bis(Benzyloxy)phosphoryl)oxy)-3-methylbutanoic Acid

To a mixed stirred suspension of (S)-methyl 2-((bis(benzyloxy)phosphoryl)oxy)-3-methylbutanoate (1.0 g, 2.55 mmol) in anhydrous THF (5 mL) and water (5 mL) at 0° C., was added LiOH (0.122 g, 5.10 mmol). After being stirred for 30 min., the reaction mixture was diluted with water (5 mL) and acidified with 1.5N HCl (20 ml), and extracted with ethyl acetate (2×50 mL). The organic layer was washed with $H_2O$ and saturated NaCl solution, dried over anhydrous $Na_2SO_4$, filtered and concentrated under reduced pressure at 30° C. to afford (S)-2-((bis(benzyloxy)phosphoryl)oxy)-3-methylbutanoic acid (900 mg, 1.308 mmol, 51.3%) as brown semi-solid. LCMS (ES): m/z=379.1[M+H]$^+$.

21D: (S)-Chloromethyl 2-((bis(benzyloxy)phosphoryl)oxy)-3-methylbutanoate

To a solution of (S)-2-((bis(benzyloxy)phosphoryl)oxy)-3-methylbutanoic acid (900 mg, 2.379 mmol) in anhydrous DCM (10 mL) and water (10 mL) at 0° C., were sequentially added tetrabutylammonium hydrogen sulfate (81 mg, 0.238 mmol), sodium bicarbonate (799 mg, 9.51 mmol) and chloromethyl chlorosulfate (0.361 mL, 3.57 mmol) dropwise. The reaction mixture was allowed to warm to room temperature and stirred for 16 h. The reaction mixture was diluted with water (20 mL) and extracted with DCM (2×50 mL). The organic layer was washed with $H_2O$ and saturated NaCl solution, dried over anhydrous $Na_2SO_4$, filtered and concentrated under reduced pressure to afford (S)-chloromethyl 2-((bis(benzyloxy)phosphoryl)oxy)-3-methylbutanoate (900 mg, 2.109 mmol, 89%) as pale yellow oil. $^1H$ NMR (400 MHz, chloroform-d) δ ppm 7.32-7.39 (m, 10H), 5.56-5.78 (m, 2H), 5.04-5.19 (m, 4H), 2.14-2.27 (m, 1H), 1.39-1.41 (m, 1H), 0.93-1.03 (m, 6H); LCMS (ES): m/z=427.2 [M+H]$^+$.

21E: (S)-(((S)-2-((bis(Benzyloxy)phosphoryl)oxy)-3-methylbutanoyl)oxy)methyl 3-(4-(diisobutylamino)-3-(3-(p-tolyl)ureido)phenyl)pentanoate To a stirred solution of (S)-3-(4-(diisobutylamino)-3-(3-(p-tolyl)ureido)phenyl) pentanoic acid (300 mg, 0.661 mmol) in anhydrous acetonitrile (10 mL), were added $K_2CO_3$ (366 mg, 2.65 mmol) and (S)-chloromethyl 2-((bis(benzyloxy)phosphoryl)oxy)-3-methylbutanoate (565 mg, 1.323 mmol). The reaction mixture was stirred for 16 h at room temperature, diluted with water (20 mL) and extracted with ethyl acetate (2×50 mL). The organic layer was washed with $H_2O$ and saturated NaCl solution. The organic layer was dried over anhydrous $Na_2SO_4$, filtered and concentrated under reduced pressure to afford (S)-(((S)-2-((bis(benzyloxy)phosphoryl)oxy)-3-methylbutanoyl)oxy)methyl 3-(4-

(diisobutylamino)-3-(3-(p-tolyl)ureido)phenyl)pentanoate (550 mg, 0.241 mmol, 36.5%) as brownish semi-solid. $^1$H NMR (300 MHz, DMSO-$d_6$) δ ppm 9.25-9.35 (m, 1H), 7.80-7.90 (m, 1H), 7.32-7.40 (m, 14H), 7.03-7.15 (m, 2H), 6.72-6.87 (m, 1H), 5.94-5.99 (m, 1H), 5.86-5.92 (m, 1H), 4.69-4.79 (m, 4H), 3.93-4.12 (m, 1H), 2.59-2.77 (m, 4H), 2.21-2.34 (m, 3H), 1.92-2.05 (s, 3H), 1.40-1.75 (m, 5H), 0.75-0.97 (m, 18H), 0.61-0.76 (m, 3H); LCMS(ES): m/z=845.3[M+H]$^+$.

Example 21

To a stirred solution of (S)-(((S)-2-((bis(benzyloxy)phosphoryl)oxy)-3-methylbutanoyl)oxy)methyl 3-(4-(diisobutylamino)-3-(3-(p-tolyl)ureido)phenyl)pentanoate (550 mg, 0.652 mmol) in anhydrous ethyl acetate (15 mL), was added Pd/C (10%; 694 mg, 0.652 mmol) at room temperature and then stirred for 1 h under hydrogen bladder. The black suspension was filtered through celite bed and the bed was washed with ethyl acetate (50 mL). The filtrate was concentrated under reduced pressure. The crude product was purified in RP HPLC (DAD-1 Luna C18 [250×4.6 mm]; mobile phase A: 10 mM Ammonium acetate in water; mobile phase B: CH$_3$CN; Flow rate: 18 mL/min). The prep. fraction was concentrated under high vacuum at 30° C. The residue was dissolved in a mixture of MeCN and water, frozen and lyophilized for 12 h to afford (S)-(((S)-3-methyl-2-(phosphonooxy)butanoyl)oxy)methyl 3-(4-(diisobutylamino)-3-(3-(p-tolyl)ureido)phenyl)pentanoate (38 mg, 0.056 mmol, 8.52%) as off-white solid. $^1$H NMR (300 MHz, DMSO-d6; D$_2$O exchange) δ ppm 7.78 (s, 1H), 7.33 (d, J=8.31 Hz, 2H), 7.04-7.14 (m, 3H), 6.78 (d, J=8.31 Hz, 1H), 5.56-5.71 (m, 2H), 4.21 (br. s., 1H), 2.81 (br. s., 1H), 2.56-2.74 (m, 6H), 2.23 (s, 3H), 1.822-1.863 (m, 1H), 1.45-1.71 (m, 4H), 0.81 (d, J=6.42 Hz, 18H), 0.64-0.74 (m, 3H); LCMS (ES): m/z=664.4[M+H]$^+$; HPLC T$_r$: 16.7 min (Method A) and 16.3 min (Method B)

Example 22

(3S)-(((2-(Phosphonooxy)propoxy)carbonyl)oxy)methyl 3-(4-(diisobutylamino)-3-(3-(p-tolyl)ureido)phenyl)pentanoate

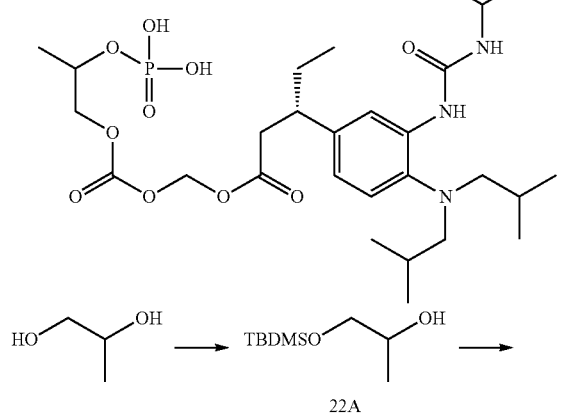

22A

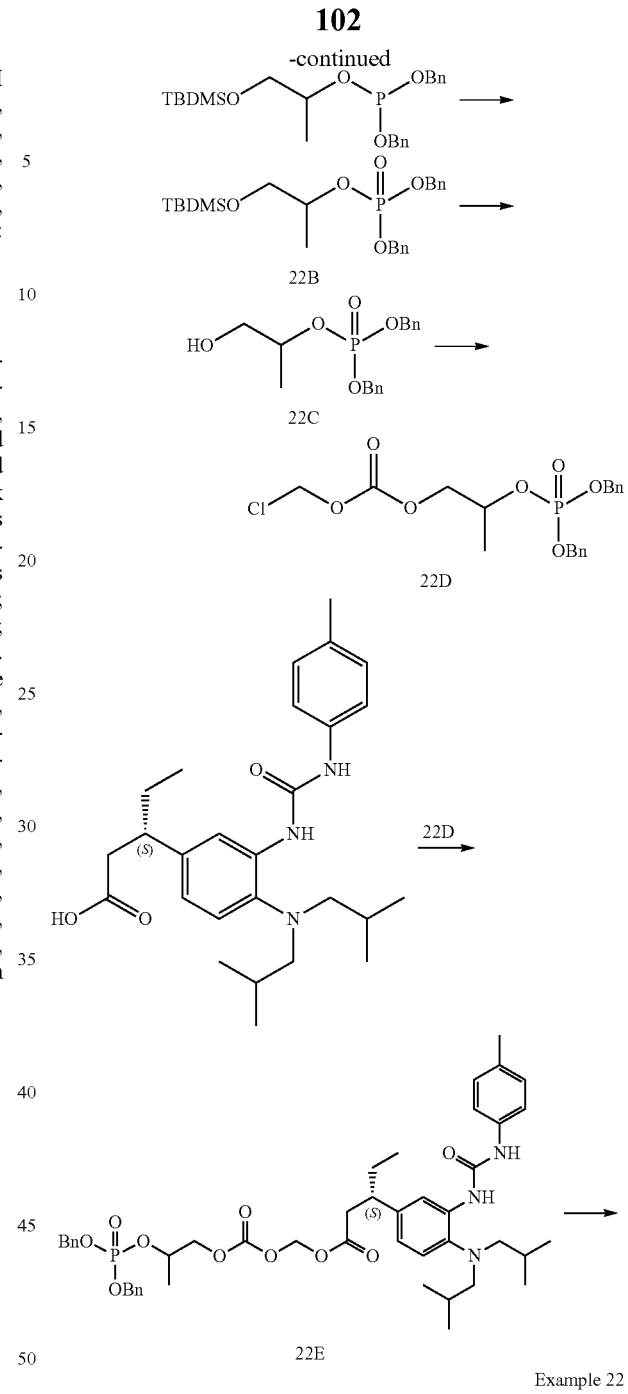

Example 22

22A: 1-((tert-butyldimethylsilyl)oxy)propan-2-ol

To a stirred solution of propane-1,2-diol (10 g, 131 mmol) in anhydrous DCM (40 mL) at 0° C., was added imidazole (8.95 g, 131 mmol), followed by TBDMS-Cl (21.79 g, 145 mmol). The reaction mixture was stirred at room temperature for 4 h, cooled to 0° C., and partitioned between sodium bicarbonate solution (50 mL) and DCM (200 mL). The organic layer was washed with H$_2$O and saturated NaCl solution, dried over anhydrous Na$_2$SO$_4$, filtered and concentrated under reduced pressure to afford 1-((tert-butyldimethylsilyl)oxy)propan-2-ol (19 g, 85 mmol, 64.6%) as colourless oil. $^1$H NMR (300 MHz, chloroform-d) δ ppm 3.78-3.89 (m, 1H), 3.52-3.66 (m, 1H), 3.33-3.42 (m, 1H), 1.13 (d, J=6.04 Hz, 3H), 0.90-0.95 (m, 9H), 0.04-0.23 (m, 6H).

22B: Dibenzyl (1-((tert-butyldimethylsilyl)oxy)propan-2-yl) Phosphate

A stirred solution of 1-((tert-butyldimethylsilyl)oxy)propan-2-ol (5 g, 26.3 mmol) and dibenzyl N,N'-diisopropylphosphoramidite (13.61 g, 39.4 mmol) in 1H-tetrazole in acetonitrile (86 ml, 39.4 mmol) was stirred for 1 h at room temperature. After 1 h, reaction mixture was cooled to 0° C., $H_2O_2$ (5.75 ml, 65.7 mmol) was added dropwise and stirred for 30 min at 0° C. The reaction mixture was partitioned between sodiumbicarbonate solution (50 mL) and DCM (100 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 40% ethyl acetate in pet. ether as eluent) to afford dibenzyl (1-((tert-butyldimethylsilyl)oxy)propan-2-yl) phosphate (9 g, 11.98 mmol, 45.6%) as pale yellow oil. $^1$H NMR (300 MHz, chloroform-d) δ ppm 7.33-7.39 (m, 10H), 5.05 (td, J=5.10, 2.64 Hz, 4H), 4.44-4.59 (m, 1H), 3.65-3.73 (m, 1H), 3.49-3.60 (m, 1H), 1.31 (d, J=6.04 Hz, 3H), 0.87-0.90 (m, 9H), 0.03-0.11 (m, 6H); LCMS (ES): m/z=451.3 [M+H]$^+$.

22C: Dibenzyl(1-hydroxypropan-2-yl) Phosphate

To a stirred solution of dibenzyl(1-((tert-butyldimethylsilyl)oxy)propan-2-yl) phosphate (9 g, 19.97 mmol) in anhydrous DCM (50 mL) at 0° C., was added dropwise 70% HF-pyridine (11.31 g, 80 mmol). The reaction mixture was warmed to room temperature, and stirred for 15 min. The reaction mixture was cooled to 0° C. and partitioned between sodium bicarbonate solution (50 mL) and DCM (2×50 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 65% ethyl acetate in pet. ether as eluent) to afford dibenzyl (1-hydroxypropan-2-yl) phosphate (3.5 g, 9.89 mmol, 49.5) as pale yellow oil. $^1$H NMR (400 MHz, chloroform-d) δ ppm 7.35 (d, J=1.00 Hz, 10H), 4.94-5.20 (m, 4H), 4.46-4.60 (m, 1H), 3.51-3.70 (m, 2H), 1.20-1.31 (m, 3H); LCMS(ES): m/z=337.1 [M+H]$^+$.

22D: 2-((bis(Benzyloxy)phosphoryl)oxy)propyl (chloromethyl) Carbonate

To a stirred solution of dibenzyl (1-hydroxypropan-2-yl) phosphate (3.5 g, 10.41 mmol) in anhydrous DCM (30 mL) at 0° C., was added DIPEA (10.91 mL, 62.4 mmol), followed by chloromethyl chloroformate (4.03 g, 31.2 mmol). The reaction mixture was warmed to room temperature and stirred for 4 h, cooled to 0° C. and partitioned between sodium bicarbonate solution (50 mL) and DCM (100 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 50% ethyl acetate in pet. ether as eluent) to afford 2-((bis(benzyloxy) phosphoryl)oxy)propyl (chloromethyl) carbonate (2 g, 4.38 mmol, 42.1%) as pale yellow oil. $^1$H NMR (400 MHz, chloroform-d) δ ppm 7.28-7.38 (m, 10H), 5.56-5.76 (m, 2H), 4.99-5.11 (m, 4H), 4.65-4.79 (m, 1H), 4.20 (d, J=6.53 Hz, 2H), 1.32 (d, J=6.53 Hz, 3H); LCMS(ES): m/z=429.2 [M+H]$^+$.

22E: (3S)-(((2-((bis(Benzyloxy)phosphoryl)oxy) propoxy)carbonyl)oxy)methyl 3-(4-(diisobutylamino)-3-(3-(p-tolyl)ureido)phenyl)pentanoate To a stirred solution of (S)-3-(4-(diisobutylamino)-3-(3-(p-tolyl)ureido)phenyl) pentanoic acid (500 mg, 1.102 mmol) in anhydrous DMF (10 mL), were added $Cs_2CO_3$ (1077 mg, 3.31 mmol), sodium iodide (248 mg, 1.653 mmol) and 2-((bis(benzyloxy) phosphoryl)oxy)propyl (chloromethyl) carbonate (945 mg, 2.205 mmol). The reaction mixture was stirred for 6 h at room temperature. The reaction mixture was diluted with water (20 mL) and extracted with ethyl acetate (2×50 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 35% ethyl acetate in pet. ether as eluent) to afford (3S)-(((2-((bis(benzyloxy)phosphoryl) oxy)propoxy)carbonyl)oxy)methyl 3-(4-(diisobutylamino)-3-(3-(p-tolyl)ureido)phenyl)pentanoate (850 mg, 0.834 mmol, 76%) as brownish semi-solid. LCMS(ES): m/z=846.4 [M+H]$^+$.

Example 22

To a stirred solution of (3S)-(((2-((bis(benzyloxy)phosphoryl)oxy)propoxy) carbonyl)oxy)methyl 3-(4-(diisobutylamino)-3-(3-(p-tolyl)ureido)phenyl)pentanoate (200 mg, 0.236 mmol) in anhydrous ethyl acetate (10 mL), was added Pd/C (10%; 252 mg, 0.118 mmol). The mixture was stirred for 1 h under hydrogen bladder at room temperature. The black suspension was filtered through celite bed and the bed was washed with ethyl acetate (20 mL). The filtrate was concentrated under reduced pressure. The crude compound was purified in RP HPLC (XB C18 [150×19 mm]; mobile phase A: 0.1% formic acid in water; mobile phase B: $CH_3CN$; flow rate: 18 mL/min). The prep. fraction was concentrated under high vacuum at 30° C. The residue was dissolved in a mixture of MeCN and water, frozen and lyophilized for 12 h to afford afford (3S)-(((2-(phosphonooxy)propoxy)carbonyl)oxy)methyl 3-(4-(diisobutylamino)-3-(3-(p-tolyl)ureido)phenyl)pentanoate (35 mg, 0.050 mmol, 21.13%) as off-white solid. $^1$H NMR (300 MHz, DMSO-$d_6$; $D_2O$ exchange) δ ppm 7.76-7.82 (m, 1H), 7.25-7.39 (m, 2H), 7.02-7.17 (m, 3H), 6.69-6.85 (m, 1H), 5.47-5.79 (m, 2H), 4.36-4.55 (m, 1H), 3.99-4.22 (m, 2H), 2.54-2.92 (m, 7H), 2.20-2.25 (m, 3H), 1.45-1.71 (m, 4H), 1.12-1.26 (m, 3H), 0.81 (d, J=6.42 Hz, 12H), 0.64-0.74 (m, 3H); LCMS(ES): m/z=664.4 [M+H]$^+$; HPLC $T_r$: 9.5 min (Method A) and 9.8 min (Method B)

Example 23

(S)-((Methyl(3-((phosphonooxy)methyl)pyridin-2-yl)carbamoyl)oxy)methyl 3-(4-(diisobutylamino)-3-(3-(p-tolyl)ureido)phenyl)pentanoate

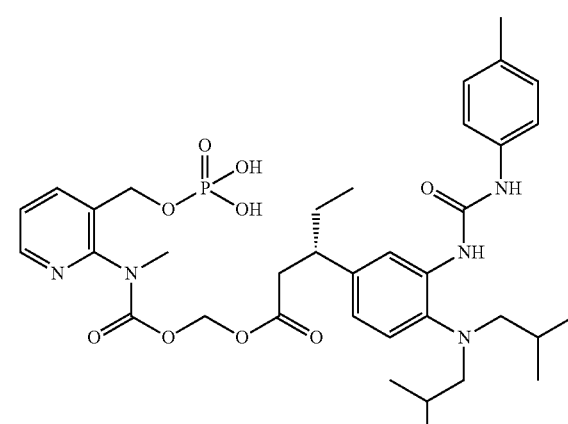

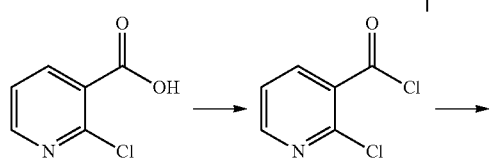
23A

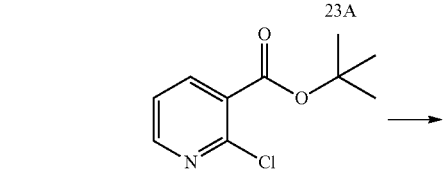
23B

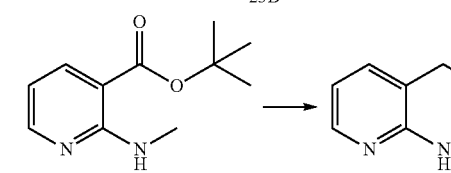
23C          23D

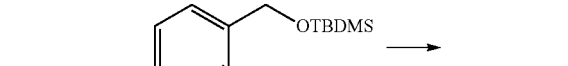
23E

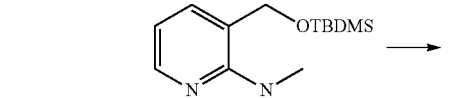
23F

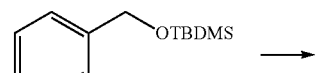
23G

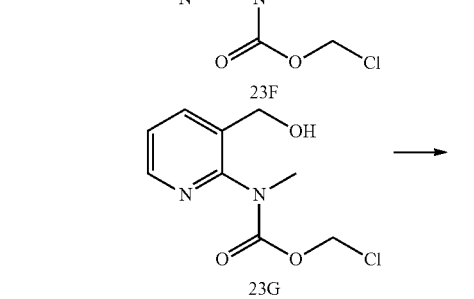

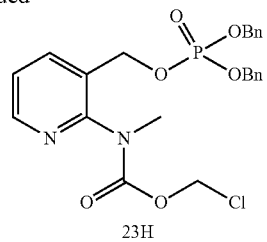
23H

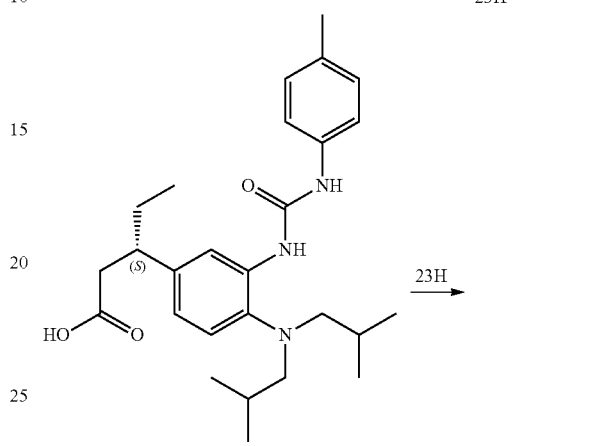
23I

Example 23

23A: 2-Chloronicotinoyl Chloride

To the 2-chloronicotinic acid (5 g, 31.7 mmol), was added thionyl chloride (10 mL, 137 mmol) dropwise at room temperature and the solution was heated to reflux for 2 h. The reaction mixture was brought to room temperature and then concentrated under high vacuum to afford 2-chloronicotinoyl chloride (5.6 g, 28.6 mmol, 90%) as brown solid.

23B: Tert-butyl 2-Chloronicotinate

A stirred solution of 2-chloronicotinoyl chloride (5.6 g, 31.8 mmol) in anhydrous THF (60 mL) was cooled to −5° C., to which was added 1.0 M potassium tert-butoxide in THF (35.0 mL, 35.0 mmol) dropwise. After the addition, the reaction mixture was stirred for 2 h at 0° C. The reaction mixture was diluted with water (50 mL) and extracted with ethyl acetate (2×100 mL). The organic layer was washed with H$_2$O and saturated NaCl solution, dried over anhydrous Na$_2$SO$_4$, filtered and concentrated under reduced pressure to afford tert-butyl 2-chloronicotinate (6 g, 26.7 mmol, 84%) as brown solid. ¹H NMR (400 MHz, methanol-d₄) δ ppm 8.41-8.60 (m, 1H), 8.01-8.19 (m, 1H), 7.39-7.62 (m, 1H), 1.63 (s, 9H). MS(ES): m/z=214.2 [M+H]⁺.

23C: Tert-butyl 2-(methylamino)nicotinate

To a stirred solution of tert-butyl 2-chloronicotinate (5 g, 23.40 mmol) in anhydrous MeOH (15 mL), was added 40% methylamine in water (50 mL, 23.40 mmol), heated to 100° C. and stirred for 2 h. The reaction mixture was concentrated under reduced pressure to remove MeOH. The remaining aqueous solution was extracted with ethyl acetate (2×100 mL). The organic layer was washed with H₂O and saturated NaCl solution, dried over anhydrous Na₂SO₄, filtered and concentrated under reduced pressure. The residue was purified using CombiFlash (silica gel 60-120 mesh; 15% ethyl acetate in pet. ether as eluent) to afford tert-butyl 2-(methylamino)nicotinate (4 g, 19.01 mmol, 81%) as pale yellow oil. ¹H NMR (400 MHz, DMSO-d₆) δ ppm 8.24-8.29 (m, 1H), 7.98-8.04 (m, 1H), 7.82-7.92 (m, 1H), 6.50-6.62 (m, 1H), 2.94 (d, J=5.02 Hz, 3H), 1.54 (s, 9H); LCMS(ES): m/z=209.4 [M+H]⁺.

23S: (2-(Methylamino)pyridin-3-yl)methanol

To a stirred solution of tert-butyl 2-(methylamino)nicotinate (1 g, 4.80 mmol) in anhydrous THF (20 mL) at 0° C., was added dropwise 1 M LiAlH₄ in THF (4.80 mL, 4.80 mmol). The reaction mixture was warmed to room temperature and stirred for 2 h. The reaction mixture was cooled to 0° C. Water (5 mL) and 10% NaOH solution (20 mL) were sequentially added dropwise. The reaction mixture was stirred for 10 min and filtered. The filtrate was extracted with ethyl acetate (2×50 mL). The organic layer was washed with H₂O and saturated NaCl solution, dried over anhydrous Na₂SO₄, filtered and concentrated under reduced pressure to (2-(methylamino)pyridin-3-yl)methanol (550 mg, 3.58 mmol, 74.6%) as pale yellow oil. ¹H NMR (400 MHz, DMSO-d₆) δ ppm 7.93 (dd, J=5.02, 2.01 Hz, 1H), 7.26-7.45 (m, 1H), 6.49 (dd, J=7.03, 5.02 Hz, 1H), 5.68-5.90 (m, 1H), 5.14 (t, J=5.27 Hz, 1H), 4.34 (d, J=5.52 Hz, 2H), 2.83 (d, J=5.02 Hz, 3H); LCMS(ES): m/z=139.2 [M+H]⁺.

23E: 3-(((tert-Butyldimethylsilyl)oxy)methyl)-N-methylpyridin-2-amine

To a stirred solution of (2-(methylamino)pyridin-3-yl) methanol (600 mg, 4.34 mmol) in anhydrous DCM (15 mL), were added imidazole (591 mg, 8.69 mmol) and TBDMS-Cl (785 mg, 5.21 mmol) at room temperature. After being stirred for 4 h at room temperature, the reaction mixture was diluted with water (10 mL) and extracted with ethyl acetate (2×25 mL). The organic layer was washed with H₂O and brine, dried over anhydrous Na₂SO₄, filtered and concentrated under reduced pressure to afford 3-(((tert-butyldimethylsilyl)oxy)methyl)-N-methylpyridin-2-amine (1.1 g, 4.36 mmol, 100%) as light brown oil. ¹H NMR (400 MHz, DMSO-d₆) δ ppm 7.82-8.01 (m, 1H), 7.26-7.44 (m, 1H), 6.25-6.65 (m, 1H), 5.57-5.82 (m, 1H), 4.53 (s, 2H), 2.83 (d, J=4.52 Hz, 3H), 0.90 (s, 9H), 0.08 (s, 6H); LCMS (ES): m/z=253.2 [M+H]⁺.

23F: Chloromethyl (3-(((tert-butyldimethylsilyl) oxy)methyl)pyridin-2-yl)(methyl)carbamate To a stirred solution of 3-(((tert-butyldimethylsilyl)oxy) methyl)-N-methylpyridin-2-amine (1.1 g, 4.36 mmol) in anhydrous DCM (15 mL) at 0° C., were sequentially added DIPEA (0.989 mL, 5.66 mmol) and chloromethyl chloroformate (0.618 g, 4.79 mmol). The reaction mixture was diluted with water (15 mL) and extracted with DCM (2×50 mL). The organic layer was washed with H₂O and saturated NaCl solution, dried over anhydrous Na₂SO₄, filtered and concentrated under reduced pressure. The residue was purified using CombiFlash (silica gel 60-120 mesh; 15% ethyl acetate in pet. ether as eluent) to afford chloromethyl (3-(((tert-butyldimethylsilyl)oxy)methyl)pyridin-2-yl)(methyl) carbamate (1.4 g, 3.73 mmol, 86%) as brownish semi-solid. ¹H NMR (400 MHz, DMSO-d₆) δ ppm 8.47-8.55 (m, 1H), 7.81-8.06 (m, 1H) 7.33-7.58 (m, 1H), 6.54-6.95 (m, 2H), 5.01-5.26 (m, 2H), 3.86-4.12 (m, 3H), 1.23-1.32 (m, 9H), 0.23 (s, 6H); LCMS (ES): m/z=345.4 [M+H]⁺.

23G: Chloromethyl (3-(hydroxymethyl)pyridin-2-yl)(methyl)carbamate

To a stirred solution of chloromethyl (3-(((tert-butyldimethylsilyl)oxy)methyl) pyridin-2-yl)(methyl)carbamate (1 g, 2.90 mmol) in anhydrous DCM (10 mL) at 0° C., was added 70% HF-pyridine (0.718 g, 7.25 mmol). After being stirred for 30 min, the reaction mixture was cooled to 0° C., and partitioned between sodium bicarbonate solution (50 mL) and DCM (100 mL). The organic layer was washed with H₂O and saturated NaCl solution, dried over anhydrous Na₂SO₄, filtered and concentrated under reduced pressure to afford chloromethyl (3-(hydroxymethyl)pyridin-2-yl) (methyl)carbamate (600 mg, 2.60 mmol, 90%) as brownish semi-solid. LCMS (ES): m/z=231.1 [M+H]⁺.

23H: Chloromethyl (3-(((bis(benzyloxy)phosphoryl) oxy)methyl)pyridin-2-yl)(methyl)carbamate To a mixture of of chloromethyl (3-(hydroxymethyl) pyridin-2-yl)(methyl)carbamate (600 mg, 2.60 mmol) and 3.5% 1H-tetrazole in acetonitrile (40 mL, 457 mmol) at 0° C., was added dibenzyl N,N'diisopropylphosphoramidite (0.856 mL, 2.60 mmol). The reaction mixture was stirred for 1 h at room temperature and then cooled to 0° C. H₂O₂ (2.218 mL, 21.71 mmol) was added dropwise at 0° C. After being stirred for 30 min., the reaction mixture was partitioned between sodium bicarbonate solution (20 ml) and DCM (100 mL). The organic layer was washed with H₂O and saturated NaCl solution, dried over anhydrous Na₂SO₄, filtered and concentrated under reduced pressure. The crude product was purified using CombiFlash (silica gel 60-120 mesh; 45% ethyl acetate in pet. ether as eluent) to afford chloromethyl (3-(((bis(benzyloxy)phosphoryl) oxy)methyl) pyridin-2-yl)(methyl)carbamate (900 mg, 1.815 mmol, 69.8%) as pale yellowish oil. ¹H NMR (300 MHz, DMSO-d₆) δ ppm 8.45-8.57 (m, 1H), 7.81-7.93 (m, 1H), 7.40-7.55 (m, 1H), 7.27-7.40 (m, 10H), 5.77-6.01 (m, 2H), 5.00-5.12 (m, 4H), 4.89-4.99 (m, 2H), 3.10-3.20 (m, 3H); LCMS(ES): m/z=490.8 [M+H]⁺.

23I: (S)-(((3-(((Bis(Benzyloxy)phosphoryl)oxy) methyl)pyridin-2-yl)(methyl)carbamoyl)oxy)methyl 3-(4-(diisobutylamino)-3-(3-(p-tolyl)ureido)phenyl) pentanoate To a stirred solution of (S)-3-(4-(diisobutylamino)-3-(3-(p-tolyl)ureido)phenyl) pentanoic acid (500 mg, 1.102 mmol) in anhydrous DMF (10 mL), were added Cs₂CO₃ (1077 mg, 3.31 mmol), sodium iodide (248 mg, 1.653 mmol) and chloromethyl (3-(((bis(benzyloxy)phosphoryl) oxy)methyl)pyridin-2-yl)(methyl)carbamate (812 mg, 1.653 mmol). After being stirred for 16 h, the reaction mixture was diluted with water (25 mL) and extracted with ethyl acetate (2×50 mL). The organic layer was washed with H₂O and saturated NaCl solution, dried over anhydrous Na₂SO₄, filtered and concentrated under reduced pressure. The residue was purified using CombiFlash (silica gel 60-120 mesh;

40% ethyl acetate in pet. ether as eluent) to afford (S)-(((3-(((bis(benzyloxy)phosphoryl) oxy)methyl)pyridin-2-yl)(methyl)carbamoyl)oxy)methyl 3-(4-(diisobutylamino)-3-(3-(p-tolyl)ureido)phenyl)pentanoate (1.25 g, 1.074 mmol, 97%) as brownish semi-solid. $^1$H NMR (400 MHz, DMSO-d$_6$) δ ppm 9.29-9.38 (m, 1H), 8.44-8.52 (m, 1H), 7.93-8.00 (m, 8H), 7.81-7.91 (m, 2H), 7.31-7.36 (m, 7H), 7.04-7.17 (m, 3H), 5.32-5.73 (m, 2H), 5.00-5.10 (m, 4H), 4.87-4.96 (m, 2H), 3.09-3.16 (m, 3H), 2.56-2.72 (m, 7H), 2.19-2.29 (m, 3H), 1.50-1.67 (m, 4H), 0.78-0.87 (m, 12H), 0.65-0.72 (m, 3H); LCMS (ES): m/z=908.4 [M+H]$^+$.

Example 23

To a stirred solution of (S)-(((3-(((bis(benzyloxy)phosphoryl)oxy)methyl)pyridin-2-yl)(methyl)carbamoyl)oxy)methyl 3-(4-(diisobutylamino)-3-(3-(p-tolyl)ureido)phenyl)pentanoate (1.15 g, 0.988 mmol) in anhydrous IPA (20 mL), was added Pd/C (10%; 0.841 g, 0.395 mmol). After being stirred for 1 h under hydrogen bladder at room temperature, the black suspension was filtered through celite bed and the bed was washed with ethyl acetate (50 mL). The filtrate was concentrated under reduced pressure to afford the crude product. The crude product was purified using RP HPLC (Kinetex C18 [250×21 mm]; mobile phase A: 10 mM ammonium acetate in water; mobile phase B: CH$_3$CN; Flow rate: 18 mL/min). The prep. fraction was concentrated under high vacuum at 30° C. The residue was dissolved in a mixture of MeCN and water, frozen and lyophilized for 12 h to afford (S)-((methyl(3-((phosphonooxy)methyl)pyridin-2-yl)carbamoyl)oxy)methyl 3-(4-(diisobutylamino)-3-(3-(p-tolyl)ureido)phenyl)pentanoate (100 mg, 0.132 mmol, 13.35%) as off-white solid. $^1$H NMR (300 MHz, DMSO-d$_6$) δ ppm 9.346 (s, 1H), 8.29-8.41 (m, 1H), 7.94-8.07 (m, 1H), 7.69-7.81 (m, 1H), 7.36-7.45 (m, 1H), 7.25-7.35 (m, 3H), 7.01-7.17 (m, 3H), 6.72-6.84 (m, 1H), 5.33-5.75 (m, 2H), 4.54-4.70 (m, 2H), 3.00-3.19 (m, 3H), 2.53-2.84 (m, 7H), 2.16-2.24 (m, 3H), 1.46-1.70 (m, 4H), 0.75-0.86 (m, 12H), 0.60-0.72 (m, 3H); LCMS (ES): m/z=728.0 [M+H]$^+$; HPLC T$_r$: 8.8 min (Method A) and 9.5 min (Method B).

Example 24

(3S)-1-((Methyl(3-((2-(methylamino)acetoxy)methyl)pyridin-2-yl)carbamoyl)oxy)ethyl 3-(4-(diisobutylamino)-3-(3-(p-tolyl)ureido)phenyl)pentanoate Dihydrochloride

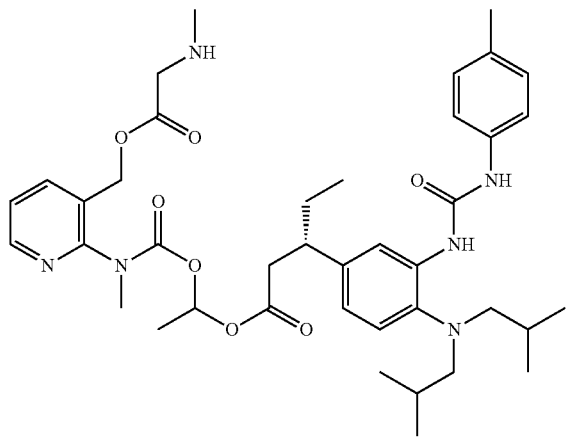

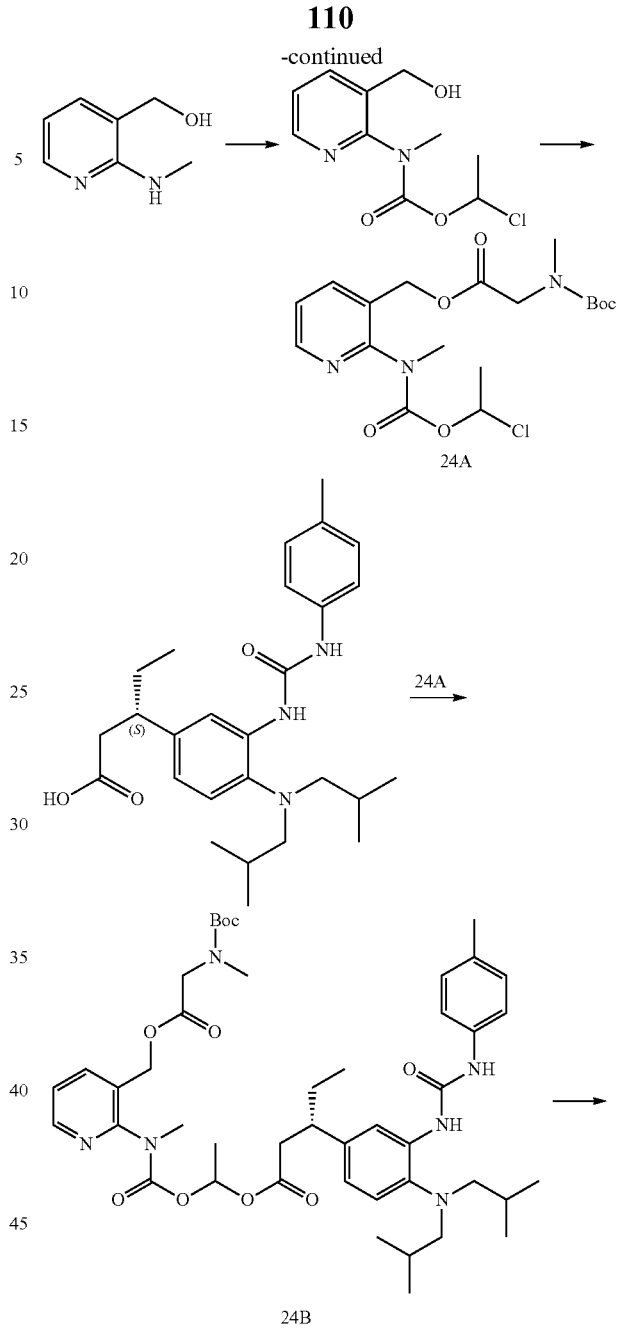

Example 24

24A: (2-(((1-Chloroethoxy)carbonyl)(methyl)amino)pyridin-3-yl)methyl 2-((tert-butoxycarbonyl)(methyl)amino)acetate To a stirred solution of (2-(methylamino)pyridin-3-yl)methanol (1 g, 5.79 mmol) in anhydrous DCM (10 mL) at −10° C., were added, DIPEA (1.315 mL, 7.53 mmol) and 1-chloroethyl chloroformate (0.700 mL, 6.37 mmol). After being stirred for 1 h, were sequentially added 2-((tert-butoxycarbonyl)(methyl)amino)acetic acid (1.424 g, 7.53 mmol), EDC (1.443 g, 7.53 mmol), and DMAP (0.212 g, 1.737 mmol). The reaction mixture was stirred for 2 h at −10° C. The reaction mixture was allowed to warm to room temperature, diluted with water (20 mL) and extracted with DCM (2×50 mL). The organic layer was washed with H₂O and saturated NaCl solution, dried over anhydrous Na₂SO₄, filtered and concentrated under reduced pressure. The residue was purified using CombiFlash (silica gel 60-120 mesh; 50% ethyl acetate in pet. ether as eluent) to afford (2-(((1-chloroethoxy)carbonyl)(methyl)amino)pyridin-3-yl)methyl 2-((tert-butoxycarbonyl)(methyl)amino)acetate (800 mg, 1.462 mmol, 25.3%) as pale yellow oil. $^1$H NMR (400 MHz, DMSO-d₆) δ ppm 8.49-8.56 (m, 1H), 7.91-7.97 (m, 1H), 7.43-7.53 (m, 1H), 6.53-6.65 (m, 1H), 5.01-5.24 (m, 2H), 3.97-4.10 (m, 3H), 3.17-3.29 (m, 3H), 2.79-2.88 (m, 3H), 1.45-1.63 (m, 2H), 1.24-1.41 (m, 9H); LCMS (ES): m/z=416.2 [M+H]⁺.

24B: (3S)-1-(((3-((2-((tert-Butoxycarbonyl)(methyl) amino)acetoxy)methyl)pyridin-2-yl)(methyl)carbamoyl)oxy)ethyl 3-(4-(diisobutylamino)-3-(3-(p-tolyl) ureido)phenyl) Pentanoate To a stirred solution of (S)-3-(4-(diisobutylamino)-3-(3-(p-tolyl)ureido)phenyl) pentanoic acid (550 mg, 1.212 mmol) in anhydrous DMF (10 mL), were added sodium iodide (273 mg, 1.819 mmol), Cs₂CO₃ (1185 mg, 3.64 mmol) and (2-(((1-chloroethoxy)carbonyl)(methyl)amino) pyridin-3-yl)methyl 2-((tert-butoxycarbonyl) (methyl)amino)acetate (756 mg, 1.819 mmol). After being stirred for 16 h at room temperature, the reaction mixture was diluted with water (20 mL) and extracted with ethyl acetate (2×25 mL). The organic layer was washed with H₂O and saturated NaCl solution, dried over anhydrous Na₂SO₄, filtered and concentrated under reduced pressure. The residue was purified using CombiFlash (silica gel 60-120 mesh; 40% ethyl acetate in pet. ether as eluent) to afford (3S)-1-(((3-((2-((tert-butoxycarbonyl)(methyl)amino) acetoxy)methyl)pyridin-2-yl)(methyl)carbamoyl)oxy)ethyl 3-(4-(diisobutylamino)-3-(3-(p-tolyl)ureido)phenyl)pentanoate (800 mg, 0.807 mmol, 66.5%) as brownish semi-solid; LCMS (ES): m/z=833.4 [M+H]⁺.

Example 24

To a stirred solution of (3S)-1-(((3-((2-((tert-butoxycarbonyl)(methyl)amino) acetoxy)methyl)pyridin-2-yl) (methyl)carbamoyl)oxy)ethyl 3-(4-(diisobutylamino)-3-(3-(p-tolyl)ureido)phenyl)pentanoate (700 mg, 0.840 mmol) in anhydrous DCM (10 mL) at 0° C., was added 4 N HCl in dioxane (13 mL, 52.0 mmol) and stirred for 30 min. The reaction mixture was concentrated to dryness under high vacuum. The crude compound was purified using RP HPLC (DAD:1-Kinetex C18 [150×4.6 mm]; DAD:2-Sunfire C18 [150×4.6]; mobile phase A: water; mobile phase B: CH₃CN; Flow rate: 2 mL/min). The prep. fraction was concentrated under high vacuum at 30° C. The residue was dissolved in a mixture of MeCN and water, frozen and lyophilized for 12 h to afford (3S)-1-((methyl(3-((2-(methylamino)acetoxy) methyl)pyridin-2-yl)carbamoyl)oxy)ethyl 3-(4-(diisobutylamino)-3-(3-(p-tolyl)ureido)phenyl)pentanoate dihydrochloride (310 mg, 0.365 mmol, 43.5%) as off-white solid. $^1$H NMR (300 MHz, methanol-d₄) δ ppm 8.42-8.52 (m, 1H), 7.90-8.04 (m, 1H), 7.59-7.80 (m, 1H), 7.40-7.51 (m, 1H), 7.23-7.37 (m, 3H), 7.04-7.17 (m, 2H), 6.80-6.98 (m, 1H), 6.50-6.69 (m, 1H), 4.99-5.31 (m, 2H), 3.96-4.06 (m, 2H), 3.15 (s, 3H), 2.67-2.93 (m, 5H), 2.58 (s, 5H), 2.23 (s, 3H), 1.40-1.83 (m, 4H), 0.97-1.28 (m, 3H), 0.79 (d, J=6.04 Hz, 12H), 0.60-0.73 (m, 3H); LCMS(ES): m/z=733.4 [M+H]⁺; HPLC T$_r$: 7.5 min (Method A) and 9.8 min (Method B).

Example 25

(S)-((Methyl(3-((2-(methylamino)acetoxy)methyl) pyridin-2-yl)carbamoyl)oxy)methyl 3-(4-(diisobutylamino)-3-(3-(p-tolyl)ureido)phenyl)pentanoate Dihydrochloride

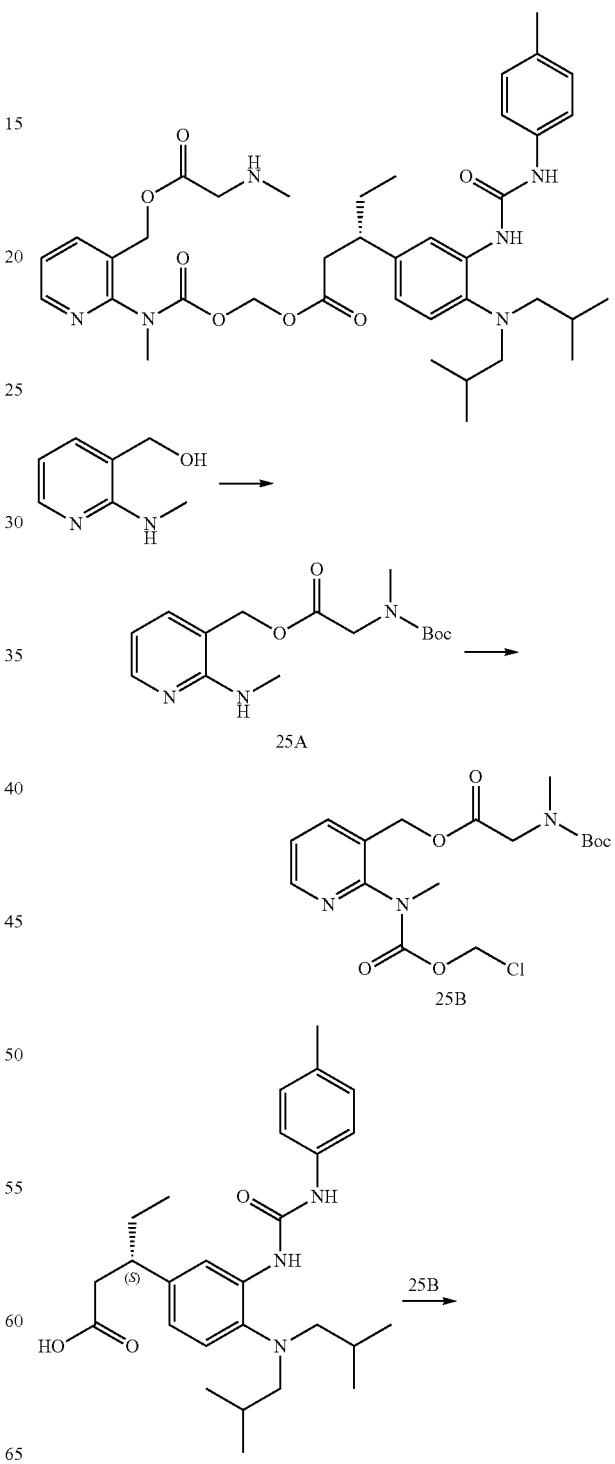

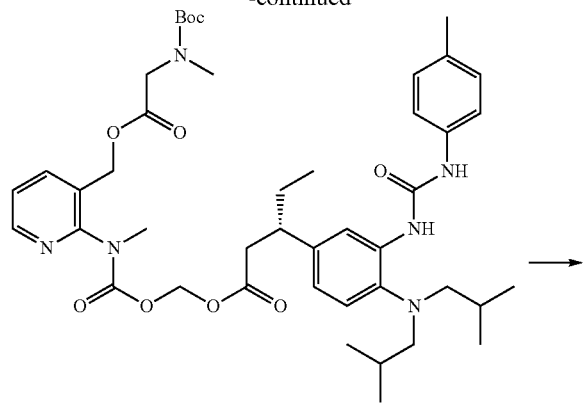

Example 25

25A: (2-(Methylamino)pyridin-3-yl)methyl 2-((tert-butoxycarbonyl)(methyl) Amino)acetate To a stirred solution of (2-(methylamino)pyridin-3-yl) methanol (1 g, 7.24 mmol) in anhydrous DCM (15 mL), were added 2-((tert-butoxycarbonyl)(methyl)amino)acetic acid (1.506 g, 7.96 mmol), EDC (1.804 g, 9.41 mmol) and finally DMAP (0.884 g, 7.24 mmol). After being stirred for 16 h at room temperature, the reaction mixture was diluted with water (20 mL) and extracted with DCM (2×50 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 70% ethyl acetate in pet. ether) to afford (2-(methylamino)pyridin-3-yl)methyl 2-((tert-butoxycarbonyl)(methyl)amino)acetate (1.7 g, 5.17 mmol, 71.4%) as brown solid. $^1H$ NMR (400 MHz, DMSO-$d_6$) δ ppm 8.01-8.02 (m, 1H), 7.37-7.38 (m, 1H), 6.40-6.54 (m, 1H), 6.19 (m, 1H), 4.94-5.06 (m, 2H), 3.94-4.04 (m, 2H), 2.83 (m, 6H), 1.27-1.41 (m, 9H); LCMS (ES): m/z=310.2 [M+H]$^+$.

25B: (2-(((Chloromethoxy)carbonyl)(methyl)amino)pyridin-3-yl)methyl 2-((tert-butoxycarbonyl)(methyl)amino)acetate To a stirred solution of (2-(methylamino)pyridin-3-yl) methyl 2-((tert-butoxycarbonyl)(methyl)amino)acetate (1.7 g, 5.50 mmol) in anhydrous DCM (20 mL) at 0° C., was added DIPEA (4.80 mL, 27.5 mmol) followed by chloromethyl chloroformate (2.126 g, 16.49 mmol). The reaction mixture was warmed to room temperature and stirred for 4 h, cooled to 0° C., and partitioned between sodium bicarbonate solution (25 mL) and DCM (100 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 30% ethyl acetate in pet. ether as eluent) to afford the (2-(((chloromethoxy)carbonyl)(methyl)amino)pyridin-3-yl)methyl 2-((tert-butoxycarbonyl)(methyl)amino)acetate (2 g, 4.23 mmol, 77%) as pale yellow oil. $^1H$ NMR (400 MHz, DMSO-$d_6$) δ ppm 8.39-8.56 (m, 1H), 7.85-8.01 (m, 1H), 7.31-7.55 (m, 1H), 5.72-6.07 (m, 2H), 5.02-5.15 (m, 2H), 4.03 (d, J=7.03 Hz, 3H), 3.18-3.25 (m, 2H), 2.83 (d, J=14.56 Hz, 3H), 1.21-1.44 (m, 9H); LCMS (ES): m/z=402.2 [M+H]$^+$.

25C: (S)-(((3-((2-((tert-Butoxycarbonyl)(methyl)amino)acetoxy)methyl)pyridin-2-yl)(methyl)carbamoyl)oxy)methyl 3-(4-(diisobutylamino)-3-(3-(p-tolyl)ureido)phenyl)pentanoate To a stirred solution of (S)-3-(4-(diisobutylamino)-3-(3-(p-tolyl)ureido)phenyl) pentanoic acid (500 mg, 1.102 mmol) in anhydrous DMF (10 mL), were added $Cs_2CO_3$ (1077 mg, 3.31 mmol) and (2-(((chloromethoxy)carbonyl)(methyl)amino)pyridin-3-yl)methyl 2-((tert-butoxycarbonyl)(methyl)amino)acetate (886 mg, 2.205 mmol). After being stirred for 16 h at room temperature, the reaction mixture was diluted with water (25 mL) and extracted with ethyl acetate (2×50 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 40% ethyl acetate in pet. ether as eluent) to afford (S)-(((3-((2-((tert-butoxycarbonyl)(methyl)amino)acetoxy)methyl)pyridin-2-yl)(methyl)carbamoyl) oxy)methyl 3-(4-(diisobutylamino)-3-(3-(p-tolyl)ureido)phenyl)pentanoate (150 mg, 0.179 mmol, 16.28%) as brown solid. $^1H$ NMR (300 MHz, DMSO-$d_6$) δ ppm 9.13-9.40 (m, 1H), 8.41-8.54 (m, 1H), 7.77-8.04 (m, 3H), 7.27-7.66 (m, 3H), 6.95-7.23 (m, 3H), 6.69-6.88 (m, 1H), 5.60-5.68 (m, 2H), 4.97-5.22 (m, 2H), 3.91-4.23 (m, 2H), 3.11-3.26 (m, 3H), 2.54-2.94 (m, 7H), 2.17-2.33 (m, 3H), 2.07 (s, 3H), 1.40-1.74 (m, 4H), 1.15-1.45 (m, 9H), 0.82 (d, J=6.42 Hz, 12H), 0.63-0.73 (m, 3H); LCMS (ES): m/z=819.4 [M+H]$^+$.

Example 25

To a stirred solution of (S)-(((3-((2-((tert-butoxycarbonyl)(methyl)amino)acetoxy) methyl)pyridin-2-yl)(methyl)carbamoyl)oxy)methyl 3-(4-(diisobutylamino)-3-(3-(p-tolyl)ureido)phenyl)pentanoate (130 mg, 0.159 mmol) in anhydrous DCM (10 mL) at 0° C., was added 4 N HCl in dioxane (5 mL, 20.00 mmol). After being stirred for 30 min., the reaction mixture was concentrated to dryness under high vacuum. The residue was dissolved in a mixture of MeCN and water, frozen and lyophilized for 12 h to afford (S)-((methyl(3-((2-(methylamino)acetoxy)methyl)pyridin-2-yl) carbamoyl)oxy)methyl 3-(4-(diisobutylamino)-3-(3-(p-tolyl)ureido)phenyl)pentanoate dihydrochloride (100 mg, 0.119 mmol, 74.8%) as an off-white solid. $^1H$ NMR (400 MHz, methanol-$d_4$) δ ppm 8.40-8.52 (m, 1H), 7.93-8.09 (m, 1H), 7.64-7.82 (m, 1H), 7.43-7.52 (m, 1H), 7.21-7.43 (m, 4H), 7.13-7.19 (m, 2H), 5.42-5.89 (m, 2H), 5.13-5.34 (m, 2H), 4.00-4.14 (m, 2H), 3.40-3.60 (m, 3H), 3.29 (s, 5H), 2.78 (s, 5H), 2.33 (s, 3H), 1.99-2.16 (m, 2H), 1.59-1.89 (m, 2H), 0.97-1.16 (m, 12H), 0.75-0.89 (m, 3H); LCMS(ES): m/z=719.2 [M+H]$^+$; HPLC $T_r$: 7.3 min (Method A) and 9.6 min (Method B).

Example 26

(S)-((Methyl(2-(phosphonooxy)ethyl)carbamoyl)oxy)methyl 3-(4-(diisobutylamino)-3-(3-(p-tolyl)ureido)phenyl)pentanoate

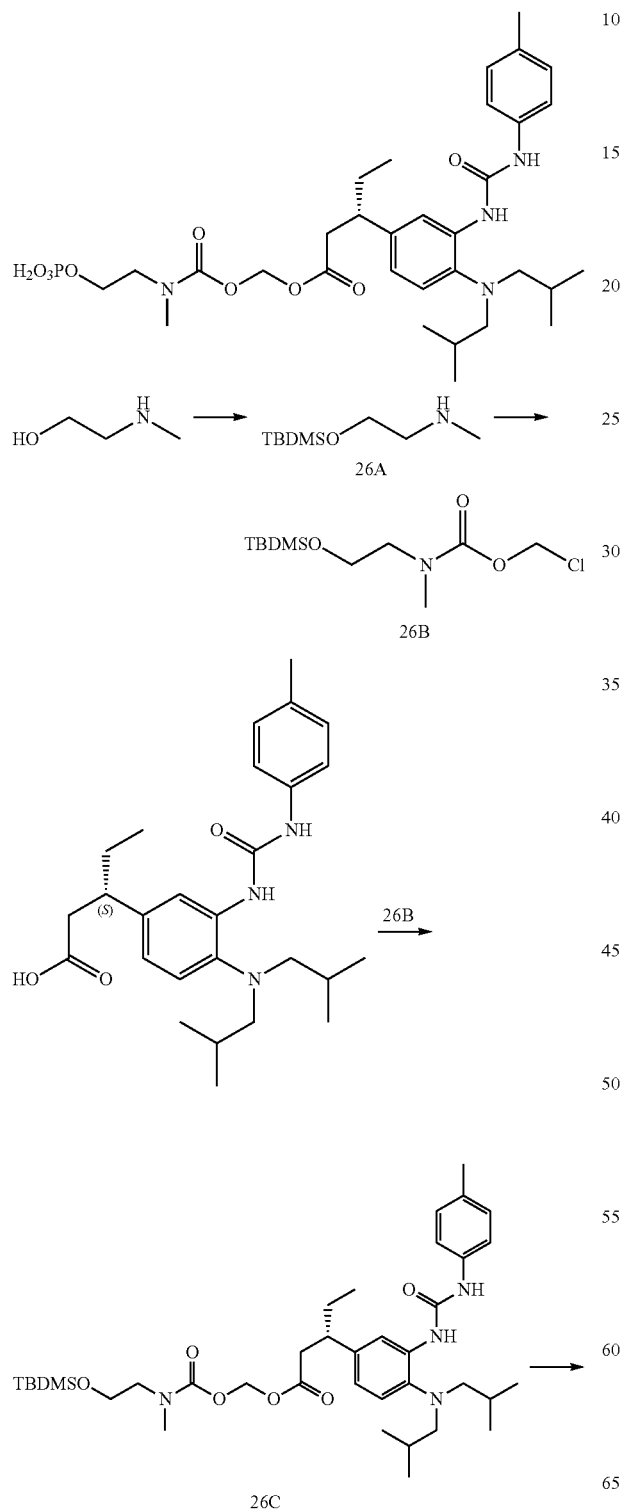

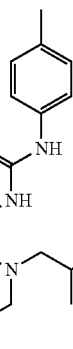

26D

Example 26

26A: 2-((tert-Butyldimethylsilyl)oxy)-N-methylethanamine

To a stirred solution of 2-(methylamino)ethanol (3 g, 39.9 mmol) in anhydrous DCM (50 mL) at 0° C., was added imidazole (2.72 g, 39.9 mmol), followed by TBDMS-Cl (6.62 g, 43.9 mmol). After being stirred for 4 h at room temperature, the reaction mixture was cooled to 0° C., and partitioned between sodium bicarbonate solution (50 mL) and DCM (200 mL). The organic layer was washed with $H_2O$ and saturated NaCl solution, dried over anhydrous $Na_2SO_4$, filtered and concentrated under reduced pressure to afford 2-((tert-butyldimethylsilyl)oxy)-N-methylethanamine (7 g, 33.3 mmol, 83%) as colourless oil. $^1H$ NMR (300 MHz, chloroform-d) δ ppm 3.65-3.79 (m, 2H), 2.92 (d, J=0.76 Hz, 3H), 2.60-2.75 (m, 2H), 0.89-0.95 (m, 9H), 0.05-0.15 (m, 6H).

26B: Chloromethyl (2-((tert-butyldimethylsilyl)oxy)ethyl)(methyl)carbamate

To a stirred solution of 2-((tert-butyldimethylsilyl)oxy)-N-methylethanamine (2 g, 10.56 mmol) in anhydrous DCM (20 mL) at 0° C., was added DIPEA (9.22 mL, 52.8 mmol), followed by chloromethyl chloroformate (2.03 g, 15.84 mmol). The reaction mixture was warmed to room temperature. After being stirred for 16 h, the reaction mixture was cooled to 0° C., and partitioned between sodium bicarbonate solution (50 mL) and DCM (100 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 12% ethyl acetate in pet. ether as eluent) to afford chloromethyl (2-((tert-butyldimethylsilyl)oxy)ethyl) (methyl)carbamate (2.5 g, 8.87 mmol, 84%) as colourless oil. $^1H$ NMR (300 MHz, DMSO-$d_6$) δ ppm 5.89 (d, J=8.31 Hz, 2H), 3.93-4.23 (m, 1H), 3.69 (d, J=5.67 Hz, 2H), 3.11-3.24 (m, 1H), 2.92 (d, J=0.76 Hz, 3H), 0.77-0.88 (m, 9H), 0.07-0.10 (m, 6H).

26C: (S)-4,8,8,9,9-Pentamethyl-3-oxo-2,7-dioxa-4-aza-8-siladecyl 3-(4-(diisobutylamino)-3-(3-(p-tolyl)ureido)phenyl)pentanoate To a stirred solution of (S)-3-(4-(diisobutylamino)-3-(3-(p-tolyl)ureido)phenyl) pentanoic acid (500 mg, 1.102 mmol) in anhydrous DMF (8 mL), were added $Cs_2CO_3$ (1077 mg, 3.31 mmol) and chloromethyl (2-((tert-butyldimethylsilyl)oxy)ethyl)(methyl) carbamate (466 mg, 1.653 mmol). After being stirred for 6 h at room temperature, the reaction mixture was diluted with water (50 mL) and extracted with ethyl acetate (2×50 mL). The organic layer was washed with H₂O and saturated NaCl solution, dried over anhydrous Na₂SO₄, filtered and concentrated under reduced pressure to afford (S)-4,8,8,9,9-pentamethyl-3-oxo-2,7-dioxa-4-aza-8-siladecyl 3-(4-(diisobutylamino)-3-(3-(p-tolyl)ureido)phenyl)pentanoate (1 g, 0.587 mmol, 53.2%) as brownish semi-solid. LCMS (ES): m/z=699.5 [M+H]⁺.

26D: (S)-(((2-Hydroxyethyl)(methyl)carbamoyl)oxy)methyl 3-(4-(diisobutylamino)-3-(3-(p-tolyl)ureido)phenyl)pentanoate To a stirred solution of (S)-4,8,8,9,9-pentamethyl-3-oxo-2,7-dioxa-4-aza-8-siladecyl 3-(4-(diisobutylamino)-3-(3-(p-tolyl)ureido)phenyl)pentanoate (950 mg, 0.557 mmol) in anhydrous DCM (20 mL) at 0° C., was added drop-wise 70% HF-pyridine (316 mg, 2.229 mmol). The reaction mixture was brought to room temperature. After being stirred for 15 min., the reaction mixture was cooled to 0° C., partitioned between sodium bicarbonate solution (50 ml)) and DCM (100 mL). The organic layer was washed with H₂O saturated NaCl solution, dried over anhydrous Na₂SO₄, filtered and concentrated under reduced pressure. The residue was purified using CombiFlash (silica gel 60-120 mesh; 65% ethyl acetate in pet. ether as eluent) to afford (S)-(((2-hydroxyethyl)(methyl) carbamoyl)oxy)methyl 3-(4-(diisobutylamino)-3-(3-(p-tolyl)ureido)phenyl)pentanoate (230 mg, 0.366 mmol, 65.6%) as brown solid. ¹H NMR (300 MHz, DMSO-d₆) δ ppm 9.14-9.33 (m, 1H), 7.77-7.91 (m, 2H), 7.29-7.47 (m, 2H), 6.91-7.20 (m, 3H), 6.67-6.83 (m, 1H), 5.84-5.95 (m, 1H), 5.71-5.80 (m, 1H), 5.53-5.66 (m, 2H), 4.64-4.75 (m, 1H), 3.42-3.53 (m, 3H), 2.77-2.97 (m, 6H), 2.57-2.70 (m, 5H), 2.21-2.30 (m, 3H), 1.36-1.67 (m, 4H), 0.78-0.91 (m, 12H), 0.64-0.74 (m, 3H); LCMS(ES): m/z=629.4 [M+H]⁺.

Example 26

To a stirred solution of (S)-(((2-hydroxyethyl)(methyl) carbamoyl)oxy)methyl 3-(4-(diisobutylamino)-3-(3-(p-tolyl)ureido)phenyl)pentanoate (180 mg, 0.308 mmol) in anhydrous THF (3 mL) at −10° C., were sequentially added pyridine (0.025 mL, 0.308 mmol), POCl₃ (0.029 mL, 0.308 mmol) and DMAP (37.6 mg, 0.308 mmol). After being stirred for 1 h at −10° C., the reaction mixture was diluted with water (10 mL). After being stirred for 5 min, the mixture was concentrated to dryness at 30° C. under high vacuum. The crude compound was purified using RP HPLC HPLC (Kinetex Biphenyl [250×21 mm]; mobile phase A: 0.1% formic acid in water; mobile phase B: CH₃CN; Flow rate: 18 mL/min). The prep. fraction was concentrated under high vacuum at 30° C. The residue was dissolved in a mixture of MeCN and water, frozen and lyophilized for 12 h to afford (S)-((methyl(2-(phosphonooxy)ethyl)carbamoyl)oxy)methyl 3-(4-(diisobutylamino)-3-(3-(p-tolyl)ureido)phenyl)pentanoate (60 mg, 0.088 mmol, 28.4%) as off-white solid. ¹H NMR (400 MHz, methanol-d₄) δ ppm 7.57-7.73 (m, 1H), 7.28-7.49 (m, 3H), 7.09-7.19 (m, 2H), 6.93-7.08 (m, 1H), 5.52-5.70 (m, 2H), 3.92-4.19 (m, 2H), 3.44-3.59 (m, 2H), 2.92-3.03 (m, 5H), 2.70-2.76 (m, 2H), 2.32 (s, 3H), 1.58-1.93 (m, 4H), 0.95 (d, J=6.53 Hz, 12H), 0.80-0.86 (m, 3H); LCMS (ES): m/z=665.2 [M+H]⁺; HPLC T_r: 8.8 min (Method A) and 9.5 min (Method B).

Example 27

(S)-((((S)-2-(Phosphonooxy)propoxy)carbonyl)oxy) methyl 3-(4-(diisobutylamino)-3-(3-(p-tolyl)ureido) phenyl)pentanoate

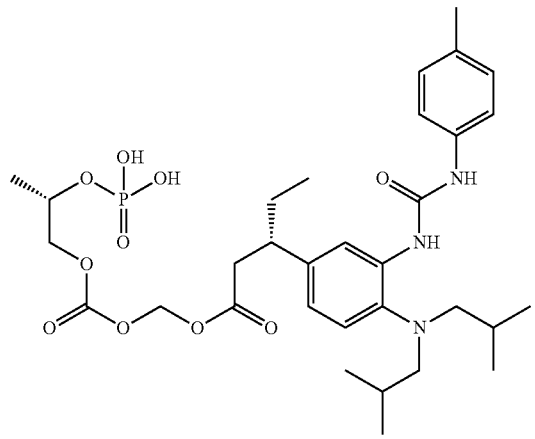

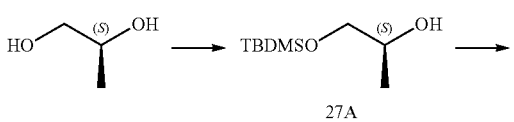

27A

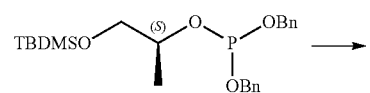

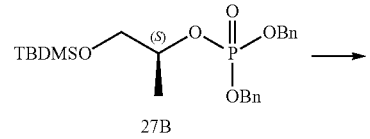

27B

27C

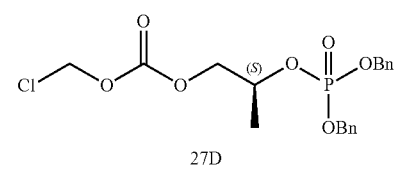

27D

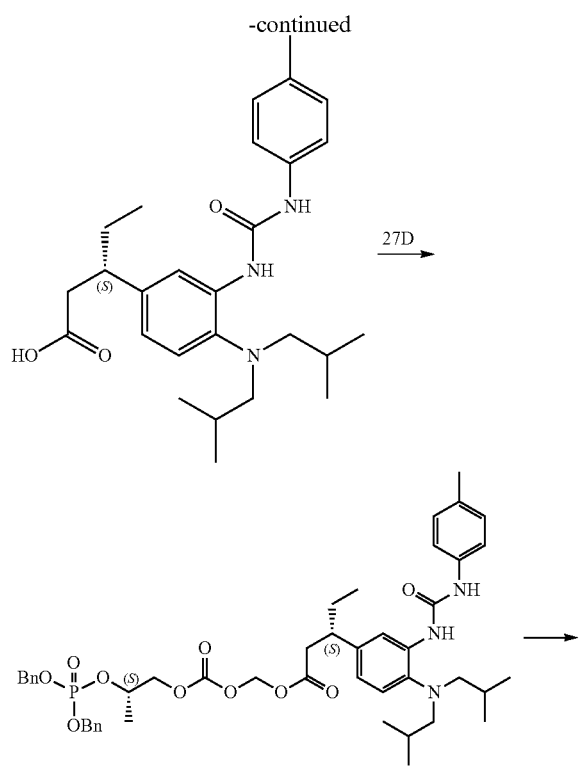

Example 27

27A: (S)-1-((tert-butyldimethylsilyl)oxy)propan-2-ol

To a stirred solution of (S)-propane-1,2-diol (5 g, 65.7 mmol) in anhydrous DCM (40 mL) at 0° C., was added imidazole (4.47 g, 65.7 mmol), followed by TBDMS-Cl (10.89 g, 72.3 mmol). After being stirred at room temperature for 4 h, the reaction mixture was cooled to 0° C., and partitioned between sodium bicarbonate solution (50 ml) and DCM (200 mL). The organic layer was washed with $H_2O$, and saturated NaCl solution, dried over anhydrous $Na_2SO_4$, filtered and concentrated under reduced pressure (S)-1-((tert-butyldimethylsilyl)oxy)propan-2-ol (12 g, 63.0 mmol, 96%) as colourless oil. $^1$H NMR (400 MHz, chloroform-d) δ ppm 3.73-3.88 (m, 1H), 3.51-3.65 (m, 1H), 3.29-3.46 (m, 1H), 2.36-2.56 (m, 1H), 1.12 (d, J=6.53 Hz, 3H), 0.90-0.96 (m, 9H), 0.06-0.13 (m, 6H).

27B: (S)-Dibenzyl (1-((tert-butyldimethylsilyl)oxy)propan-2-yl) phosphate

A solution of (S)-1-((tert-butyldimethylsilyl)oxy)propan-2-ol (5 g, 26.3 mmol) and dibenzyl diisopropylphosphoramidite (13.61 g, 39.4 mmol), and 1H-tetrazole in acetonitrile (250 ml, 114 mmol) was stirred at room temperature. After 1 h, the reaction mixture was cooled to 0° C. to which $H_2O_2$ was added dropwise (5.75 ml, 65.7 mmol). After being stirred for 30 min at 0° C., the reaction mixture was cooled to 0° C., and partitioned between sodium bicarbonate solution (50 mL) and DCM (2×50 mL). The organic layer was washed with $H_2O$, and saturated NaCl solution, dried over anhydrous $Na_2SO_4$, filtered and concentrated under reduced pressure. The residue was purified using CombiFlash (silica gel 60-120 mesh; 25% ethyl acetate in pet. ether as eluent) to afford (S)-dibenzyl (1-((tert-butyldimethylsilyl)oxy)pro-pan-2-yl) phosphate (8.2 g, 17.29 mmol, 65.8%) as colourless oil. $^1$H NMR (300 MHz, DMSO-$d_6$) δ ppm 7.09-7.71 (m, 10H), 5.02 (dd, J=7.93, 2.64 Hz, 4H), 4.05-4.53 (m, 1H), 3.59 (d, J=5.29 Hz, 2H), 1.20 (d, J=6.42 Hz, 3H), 0.84 (s, 9H), 0.09-0.13 (m, 6H); LCMS(ES): m/z=451.2 $[M+H]^+$.

27C: (S)-Dibenzyl (1-hydroxypropan-2-yl)phosphate

To a stirred solution of (S)-dibenzyl (1-((tert-butyldimethylsilyl)oxy)propan-2-yl) phosphate (8.2 g, 18.20 mmol) in anhydrous DCM (100 mL) at 0° C., was added dropwise 70% HF-pyridine (10.31 g, 72.8 mmol). The reaction mixture was warmed to room temperature and stirred for 15 min. The reaction mixture was cooled to 0° C. and partitioned between sodium bicarbonate solution (50 ml) and with DCM (2×50 mL). The organic layer was washed with $H_2O$, and saturated NaCl solution, dried over anhydrous $Na_2SO_4$, filtered and concentrated under reduced pressure. The residue was purified using CombiFlash (silica gel 60-120 mesh; 65% ethyl acetate in pet. ether as eluent) to afford (S)-dibenzyl (1-hydroxypropan-2-yl) phosphate (5.2 g, 14.38 mmol, 79%) as colourless oil. $^1$H NMR (400 MHz, DMSO-$d_6$) δ ppm 7.23-7.47 (m, 10H), 5.03 (dd, J=7.65, 6.40, 1.00 Hz, 4H), 4.31-4.43 (m, 1H), 3.39-3.53 (m, 2H), 1.20 (d, J=6.02 Hz, 3H); LCMS (ES): m/z=377.3 $[M+H]^+$.

27D: (S)-2-((bis(Benzyloxy)phosphoryl)oxy)propyl (chloromethyl) carbonate

To a stirred solution of (S)-dibenzyl (1-hydroxypropan-2-yl) phosphate (5.2 g, 15.46 mmol) in anhydrous DCM (50 mL) at 0° C., was added DIPEA (16.20 mL, 93 mmol), followed by chloromethyl chloroformate (5.98 g, 46.4 mmol). After being stirred at room temperature for 4 h, the reaction mixture was cooled to 0° C. and partitioned between sodium bicarbonate solution (50 ml)) and DCM (100 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 30% ethyl acetate in pet. ether as eluent) to afford (S)-2-((bis(benzyloxy)phosphoryl)oxy)propyl (chloromethyl) carbonate (3.5 g, 8.08 mmol, 52.3%) as pale yellow oil. $^1$H NMR (400 MHz, DMSO-$d_6$) δ ppm 7.38 (d, J=2.01 Hz, 10H), 5.90 (s, 2H), 5.03 (d, J=8.53 Hz, 4H), 4.15-4.35 (m, 2H), 1.26 (d, J=6.53 Hz, 3H); LCMS (ES): m/z=429.0 $[M+H]^+$.

27E: (S)-((((S)-2-((bis(Benzyloxy)phosphoryl)oxy)propoxy)carbonyl)oxy)methyl 3-(4-(diisobutylamino)-3-(3-(p-tolyl)ureido)phenyl)pentanoate To a stirred solution of (S)-3-(4-(diisobutylamino)-3-(3-(p-tolyl)ureido)phenyl) pentanoic acid (500 mg, 1.102 mmol) in anhydrous DMF (10 mL), were added $Cs_2CO_3$ (1077 mg, 3.31 mmol), sodium iodide (248 mg, 1.653 mmol) and (S)-2-((bis(benzyloxy) phosphoryl)oxy)propyl (chloromethyl) carbonate (709 mg, 1.653 mmol). After being stirred for 6 h at room temperature, the reaction mixture was diluted with water (25 mL) and extracted with ethyl acetate (2×50 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 35% ethyl acetate in pet. ether as eluent) to afford (S)-((((S)-2-((bis(benzyloxy) phosphoryl)oxy)

propoxy)carbonyl)oxy)methyl 3-(4-(diisobutylamino)-3-(3-(p-tolyl)ureido)phenyl)pentanoate (650 mg, 0.684 mmol, 62.0%) as brown semi solid. $^1$H NMR (300 MHz, DMSO-$d_6$) δ ppm 9.30-9.39 (m, 1H), 7.80-7.96 (m, 2H), 7.35 (s, 12H), 7.03-7.16 (m, 3H), 6.70-6.85 (m, 1H), 5.54-5.68 (m, 2H), 4.93-5.06 (m, 4H), 4.56-4.75 (m, 1H), 4.11-4.31 (m, 2H), 2.54-2.98 (m, 7H), 2.19-2.28 (m, 3H), 1.36-1.72 (m, 4H), 1.09-1.29 (m, 3H), 0.78-0.88 (m, 12H), 0.62-0.74 (m, 3H); LCMS(ES): m/z=846.2 [M+H]$^+$.

Example 27

To a stirred solution of (S)-((((S)-2-((bis(benzyloxy)phosphoryl)oxy) propoxy) carbonyl)oxy)methyl 3-(4-(diisobutylamino)-3-(3-(p-tolyl)ureido)phenyl)pentanoate (650 mg, 0.768 mmol) in anhydrous ethyl acetate (10 mL), was added Pd/C (10%, 736 mg, 0.346 mmol). After being stirred for 1 h at room temperature, the black suspension was filtered through celite bed and the bed was washed with ethyl acetate (20 mL). The filtrate was concentrated under reduced pressure to afford the crude product. The crude compound was purified using RP HPLC (Kinetex Biphenyl [250×21 mm]; mobile phase A: 10 mm Ammonium acetate in water; mobile phase B: CH$_3$CN; flow rate: 18 mL/min). The prep. fraction was concentrated under high vacuum at 30° C. The residue was dissolved in a mixture of MeCN and water, frozen and lyophilized for 12 h to afford (S)-((((S)-2-(phosphonooxy) propoxy)carbonyl)oxy)methyl 3-(4-(diisobutylamino)-3-(3-(p-tolyl)ureido)phenyl)pentanoate (60 mg, 0.087 mmol, 11.38%) as off-white solid. $^1$H NMR (400 MHz, DMSO-$d_6$) δ ppm 9.58-9.69 (m, 1H), 7.87-7.95 (m, 1H), 7.69-7.77 (m, 1H), 7.36-7.48 (m, 2H), 7.03-7.13 (m, 3H), 6.75-6.86 (m, 1H), 5.57-5.64 (m, 2H), 3.96-4.29 (m, 3H), 2.59-2.77 (m, 7H), 2.24 (s, 3H), 1.44-1.69 (m, 4H), 1.06-1.13 (m, 3H), 0.83 (dd, J=6.53, 1.51 Hz, 12H), 0.72 (s, 3H); LCMS (ES): m/z=666.1 [M+H]$^+$; HPLC T$_r$: 15.9 min (Method A) and 15.7 min (Method B).

Example 28

(S)-((4-((S)-2-(Phosphonooxy)propanamido)butanoyl)oxy)methyl 3-(4-(diisobutylamino)-3-(3-(p-tolyl)ureido)phenyl)pentanoate

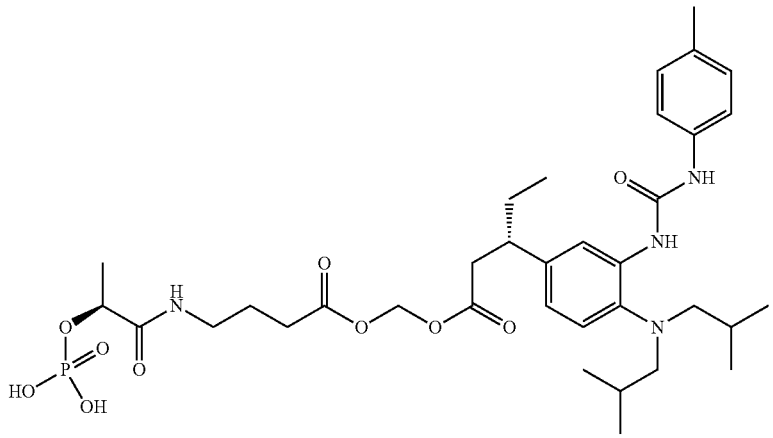

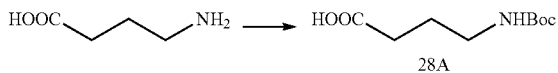

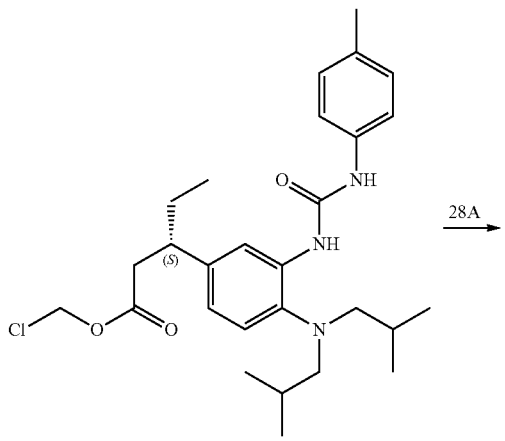

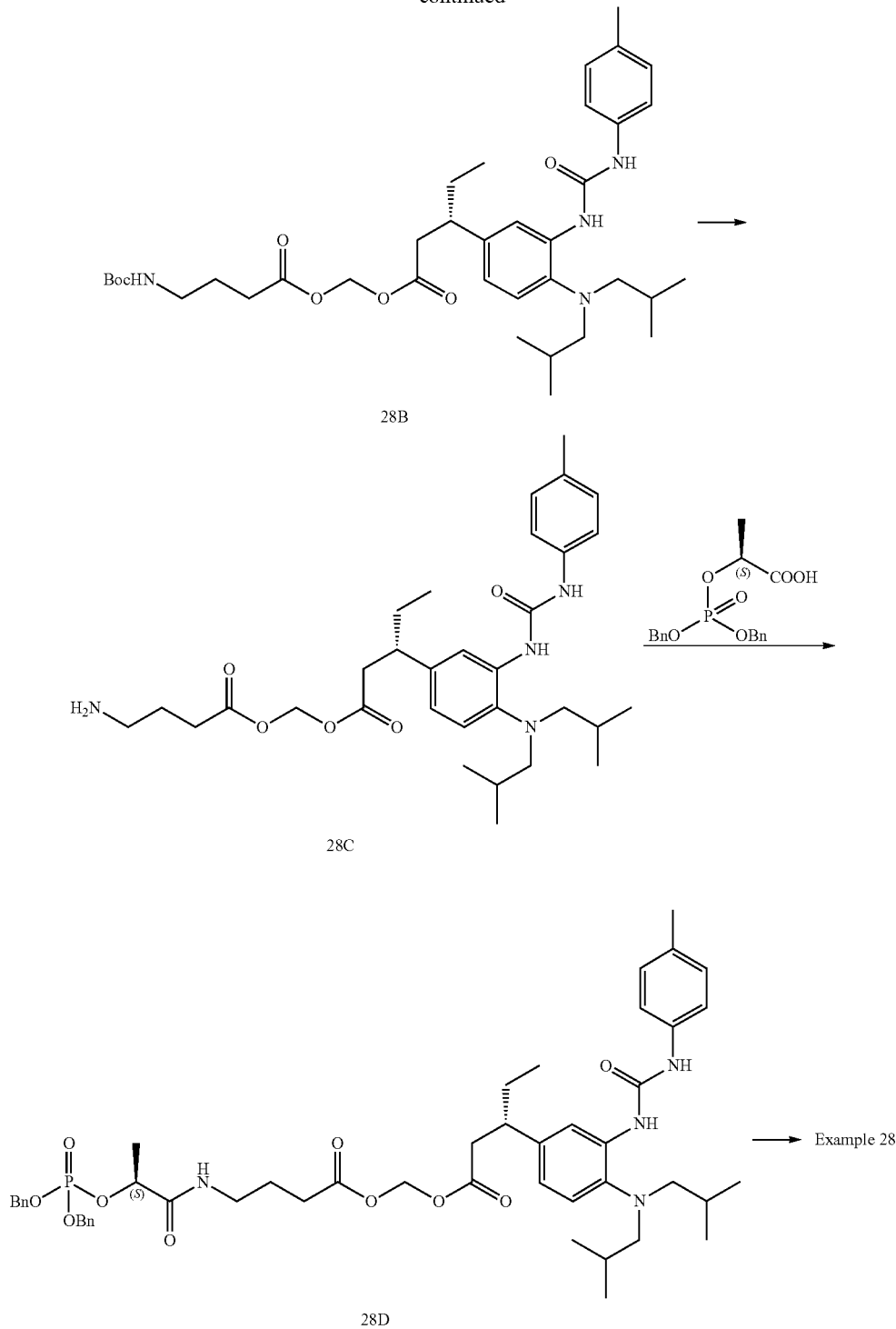

28A: 4-((tert-Butoxycarbonyl)amino)butanoic Acid

To a stirred solution of 4-aminobutanoic acid (2.3 g, 22.30 mmol) in tetrahydrofuran (10 mL) and water (10 mL), was added NaH (1.784 g, 44.6 mmol), followed by di-tert-butyl dicarbonate (10.36 mL, 44.6 mmol) at room temperature. After being stirred for 16 h, the reaction mixture was cooled to 0° C. After adding 1.5 N HCl (30 mL) dropwise, the mixture was extracted with EtOAc (2×50 mL). The organic layer was washed with $H_2O$, and saturated NaCl solution, dried over anhydrous $Na_2SO_4$, filtered and concentrated under reduced pressure. The residue was purified using CombiFlash (silica gel 60-120 mesh; 40% ethyl acetate in pet. ether as eluent) to afford 4-((tert-butoxycarbonyl)amino)butanoic acid (4.5 g, 18.82 mmol, 840%) as off-white solid. $^1$H NMR (400 MHz, DMSO-$d_6$) δ ppm 11.89-12.08 (m, 1H), 6.75-6.82 (m, 1H), 2.87-2.97 (m, 2H), 2.15-2.24 (m, 2H), 1.54-1.66 (m, 2H), 1.38 (s, 9H).

28B: (S)-((4-((tert-Butoxycarbonyl)amino)butanoyl)oxy)methyl 3-(4-(diisobutylamino)-3-(3-(p-tolyl)ureido)phenyl)pentanoate To a stirred solution of (S)-chloromethyl 3-(4-(diisobutylamino)-3-(3-(p-tolyl)ureido)phenyl)pentanoate (1 g, 1.992 mmol) in anhydrous DMF (10 mL), was added $Cs_2CO_3$ (1.298 g, 3.98 mmol) and 4-((tert-butoxycarbonyl)amino) butanoic acid (0.607 g, 2.99 mmol). After being stirred for 16 h at room temperature, the reaction mixture was diluted with water (25 mL) and extracted with ethyl acetate (2×50 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 55% ethyl acetate in pet. ether as eluent) to afford (S)-((4-((tert-butoxycarbonyl)amino)butanoyl)oxy)methyl 3-(4-(diisobutylamino)-3-(3-(p-tolyl)ureido)phenyl)pentanoate (1.3 g, 1.497 mmol, 75%) as brownish semi-solid. $^1$H NMR (300 MHz, DMSO-$d_6$) δ ppm 9.22-9.36 (m, 1H), 7.77-7.94 (m, 2H), 7.31-7.44 (m, 2H), 7.02-7.29 (m, 2H), 6.61-6.88 (m, 2H), 5.52-5.68 (m, 2H), 3.90-4.10 (m, 1H), 2.58-3.06 (m, 9H), 2.22-2.36 (m, 4H), 2.08 (s, 3H), 1.56-1.70 (m, 4H), 1.36 (s, 9H), 0.79-0.87 (m, 12H), 0.65-0.76 (m, 3H); LCMS (ES): m/z=669.3 [M+H]$^+$.

28C: (S)-((4-Aminobutanoyl)oxy)methyl 3-(4-(diisobutylamino)-3-(3-(p-tolyl)ureido)phenyl)pentanoate Dihydrochloride To a stirred solution of (S)-((4-((tert-butoxycarbonyl) amino)butanoyl)oxy)methyl 3-(4-(diisobutylamino)-3-(3-(p-tolyl)ureido)phenyl)pentanoate (1.3 g, 1.944 mmol) in anhydrous DCM (10 mL) at 0° C., was added 4 M HCl in dioxane (10 mL, 40.0 mmol). The reaction mixture was warmed to room temperature. After being stirred for 30 min., the reaction mixture was concentrated to dryness under high vacuum to afford (S)-((4-aminobutanoyl)oxy)methyl 3-(4-(diisobutylamino)-3-(3-(p-tolyl)ureido)phenyl) pentanoate dihydrochloride (1.3 g, 1.803 mmol, 93%) as brownish semi-solid. $^1$H NMR (300 MHz, DMSO-$d_6$) δ ppm 9.29-9.43 (m, 1H), 7.72-7.94 (m, 3H), 7.30-7.45 (m, 2H), 7.05-7.20 (m, 2H), 6.71-6.89 (m, 1H), 5.40-5.85 (m, 2H), 3.57 (s, 8H), 2.58-2.90 (m, 5H), 2.19-2.29 (m, 3H), 1.43-1.87 (m, 6H), 0.78-0.88 (m, 12H), 0.67-0.75 (m, 3H); LCMS (ES): m/z=569.4 [M+H]$^+$.

28D: (S)-((4-((S)-2-((bis(Benzyloxy)phosphoryl)oxy)propanamido)butanoyl)oxy)methyl 3-(4-(diisobutylamino)-3-(3-(p-tolyl)ureido)phenyl)pentanoate To a stirred solution of (S)-((4-aminobutanoyl)oxy) methyl 3-(4-(diisobutylamino)-3-(3-(p-tolyl)ureido)phenyl) pentanoate (460 mg, 0.809 mmol) in anhydrous DMF (10 mL), were added HATU (615 mg, 1.618 mmol), DIPEA (0.706 mL, 4.04 mmol) and finally (S)-2-((bis(benzyloxy) phosphoryl)oxy)propanoic acid (283 mg, 0.809 mmol) at room temperature. The reaction mixture was stirred for 30 min at room temperature. The reaction mixture was diluted with water (20 mL) and extracted with ethyl acetate (2×50 mL). The organic layer was washed with $H_2O$ and saturated NaCl solution, dried over anhydrous $Na_2SO_4$, filtered and concentrated under reduced pressure. The residue was purified using CombiFlash (silica gel 60-120 mesh; 40% ethyl acetate in pet. ether) to afford (S)-((4-((S)-2-((bis(benzyloxy)phosphoryl)oxy)propanamido)butanoyl)oxy)methyl 3-(4-(diisobutylamino)-3-(3-(p-tolyl)ureido)phenyl)pentanoate (260 mg, 0.277 mmol, 34.3%) as brownish semi-solid. $^1$H NMR (400 MHz, DMSO-$d_6$) δ ppm 9.25-9.34 (m, 1H), 7.96-8.09 (m, 1H), 7.77-7.90 (m, 2H), 7.28-7.46 (m, 11H), 7.00-7.19 (m, 3H), 6.77-6.82 (m, 1H), 5.52-5.71 (m, 2H), 4.96-5.11 (m, 4H), 4.57-4.81 (m, 1H), 3.84-4.10 (m, 2H), 2.75-2.90 (m, 1H), 2.56-2.71 (m, 8H), 2.30-2.36 (m, 2H), 2.20-2.27 (m, 3H), 1.58-1.67 (m, 4H), 1.08-1.24 (m, 3H), 0.80-0.90 (m, 12H) 0.65-0.74 (m, 3H); LCMS(ES): m/z=902.4 [M+H]$^+$.

Example 28

To a stirred solution of (S)-((4-((S)-2-((bis(benzyloxy) phosphoryl)oxy) propanamido)butanoyl)oxy)methyl-3-(4-(diisobutylamino)-3-(3-(p-tolyl)ureido)phenyl) pentanoate (260 mg, 0.289 mmol) in anhydrous ethyl acetate (10 mL), was added Pd/C (10%, 123 mg, 0.115 mmol). After being stirred for 1 h at room temperature under hydrogen atmosphere, the black suspension was filtered through celite bed and the bed was washed with ethyl acetate (20 mL). The filtrate was concentrated under reduced pressure to afford the crude product as brown semi solid. The crude compound was purified using RP HPLC (Kinetex C18 [150×21 mm]; mobile phase A: 10 mM Ammonium acetate in water; mobile phase: $CH_3CN$; flow rate: 17 mL/min). The prep. fraction was concentrated under high vacuum at 30° C. The residue was dissolved in a mixture of MeCN and water, frozen and lyophilized for 12 h to afford (S)-((4-((S)-2-(phosphonooxy)propanamido)butanoyl)oxy)methyl 3-(4-(diisobutylamino)-3-(3-(p-tolyl)ureido)phenyl)pentanoate (60 mg, 0.081 mmol, 28.0%) as off-white solid. $^1$H NMR (300 MHz, methanol-$d_4$) δ ppm 7.70-7.79 (m, 1H), 7.27-7.39 (m, 2H), 7.01-7.14 (m, 3H), 6.72-6.82 (m, 1H), 5.49-5.64 (m, 2H), 4.23-4.46 (m, 1H), 2.97-3.14 (m, 2H), 2.55-2.89 (m, 9H), 2.22 (s, 3H), 1.46-1.70 (m, 6H), 1.14-1.26 (m, 3H), 0.80 (d, J=6.42 Hz, 12H), 0.63-0.74 (m, 3H); LCMS (ES): m/z=721.2 [M+H]$^+$; HPLC T$_r$: 10.7 min (Method A) and 9.2 min (Method B).

Example 29

(S)-((4-((S)-2-Hydroxypropanamido)butanoyl)oxy)methyl 3-(4-(diisobutylamino)-3-(3-(p-tolyl)ureido)phenyl)pentanoate

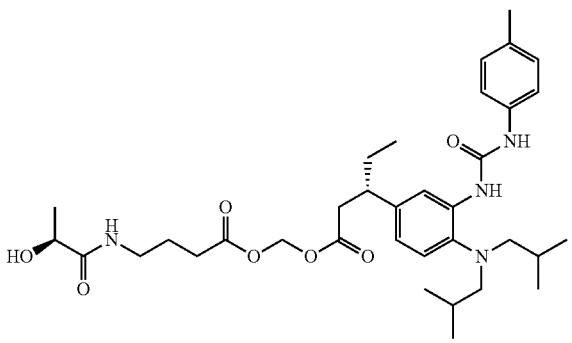 [SMILES: CC[C@@H](CC(=O)OCOC(=O)CCCNC(=O)[C@H](C)O)c1ccc(N(CC(C)C)CC(C)C)c(NC(=O)Nc2ccc(C)cc2)c1]

To a stirred solution of (S)-((4-aminobutanoyl)oxy) methyl 3-(4-(diisobutylamino)-3-(3-(p-tolyl)ureido)phenyl) pentanoate (100 mg, 0.176 mmol) in anhydrous DMF (4 mL), were added HATU (134 mg, 0.352 mmol), DIPEA (0.154 mL, 0.879 mmol) and finally L-(+)-lactic acid (15.84 mg, 0.176 mmol) at room temperature for 1 h. The reaction mixture was diluted with water (5 mL) and extracted with ethyl acetate (2×25 mL). The organic layer was washed with $H_2O$ and saturated NaCl solution, dried over anhydrous $Na_2SO_4$, filtered and concentrated under reduced pressure. The crude compound was purified in RP HPLC (X-Bridge Biphenyl [250×19 mm]; mobile phase A: 10 mm Ammonium acetate in water; mobile phase B: $CH_3CN$; flow rate: 17 mL/min). The prep. fraction was concentrated under high vacuum at 30° C. The residue was dissolved in a mixture of MeCN and water, frozen and lyophilized for 12 h to afford (S)-((4-((S)-2-hydroxypropanamido)butanoyl)oxy)methyl 3-(4-(diisobutylamino)-3-(3-(p-tolyl)ureido)phenyl)pentanoate (20 mg, 0.031 mmol, 17.57%) as off-white solid. $^1$H NMR (300 MHz, DMSO-d$_6$) δ ppm 9.31 (s, 1H), 7.70-7.84 (m, 1H), 7.22-7.44 (m, 2H), 6.91-7.17 (m, 5H) 6.59-6.85 (m, 1H), 5.45-5.70 (m, 2H), 3.81-4.07 (m, 1H), 3.01-3.24 (m, 2H), 2.56-2.90 (m, 7H), 2.09-2.39 (m, 5H), 1.45-1.74 (m, 6H), 1.12-1.23 (m, 3H), 0.82 (d, J=6.42 Hz, 12H), 0.64-0.75 (m, 3H); LCMS (ES): m/z=641.4 [M+H]$^+$; HPLC T$_r$: 18.0 min (Method A) and 15.1 min (Method B).

Example 30

(S)-((3-((S)-2-(Phosphonooxy)propanamido)propanoyl)oxy)methyl 3-(4-(diisobutylamino)-3-(3-(p-tolyl)ureido)phenyl)pentanoate

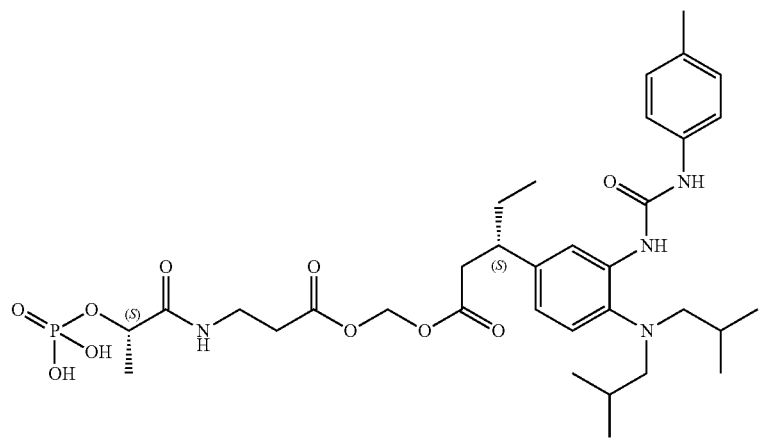

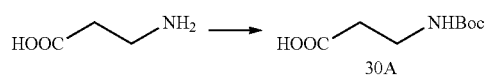

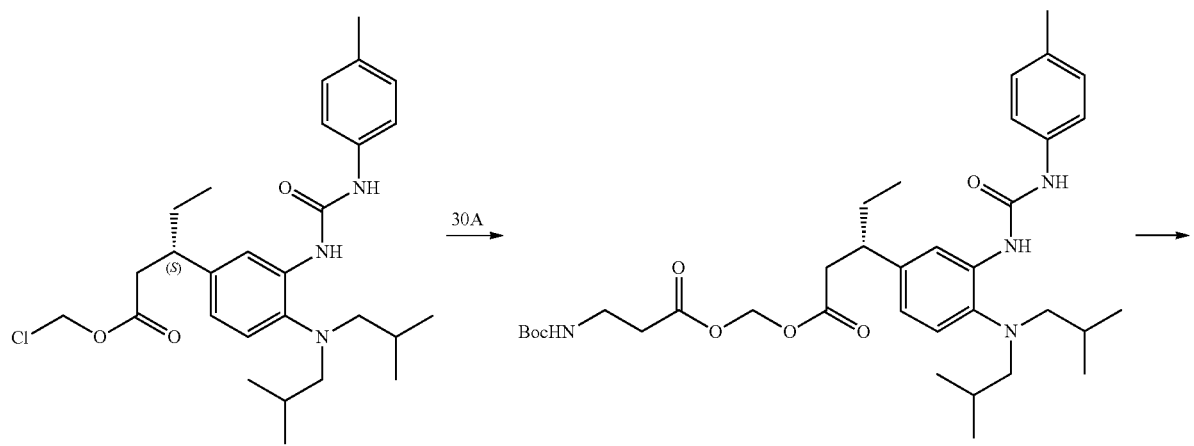

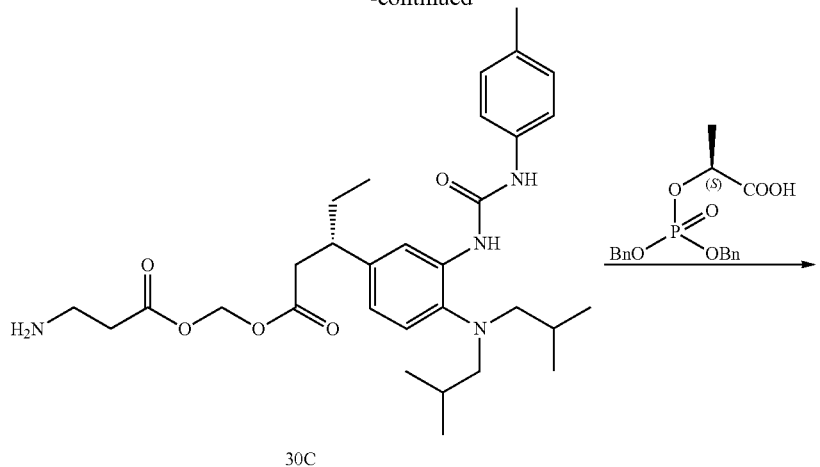

30C

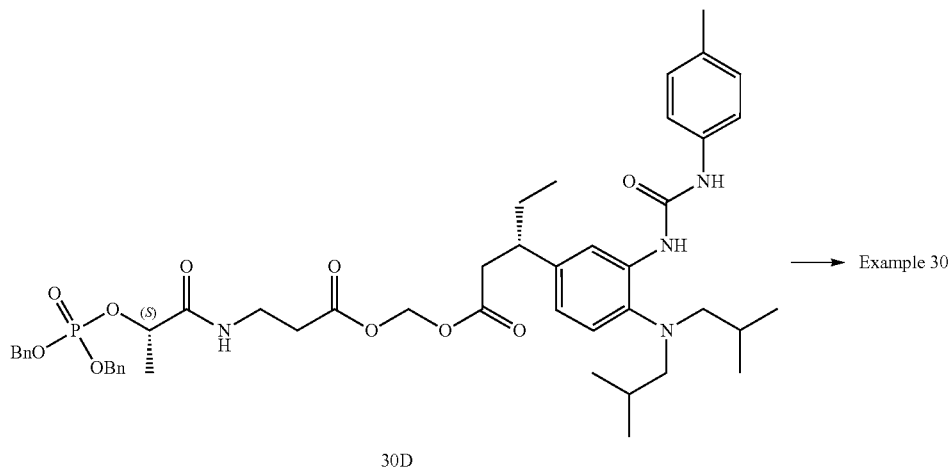

30D

30A: 3-((tert-Butoxycarbonyl)amino)propanoic Acid

To a mixed stirred suspension of 3-aminopropanoic acid (2.5 g, 28.1 mmol) in tetrahydrofuran (10 mL) and water (10 mL), was added NaOH (2.245 g, 56.1 mmol), followed by di-tert-butyl dicarbonate (13.03 mL, 56.1 mmol) at room temperature. The reaction mixture was stirred for 16 h at room temperature. The reaction mixture was diluted with water (30 mL) and washed with EtOAc (2×25 mL). After adding 1.5 N HCl (100 mL) to the aqueous layer, it was extracted with ethyl acetate (2×25 mL). The organic layer was washed with $H_2O$ (10 mL), saturated NaCl (10 mL), dried over anhydrous $Na_2SO_4$, filtered and concentrated under reduced pressure to afford 3-((tert-butoxycarbonyl)amino)propanoic acid (4.5 g, 21.40 mmol, 76%) as off-white solid. $^1$H NMR (300 MHz, DMSO-$d_6$) δ ppm 12.01-12.31 (m, 1H), 6.69-6.93 (m, 1H), 3.11 (d, J=6.04 Hz, 2H), 2.34 (t, J=6.99 Hz, 2H), 1.37 (s, 9H).

30B: (S)-((3-((tert-Butoxycarbonyl)amino)propanoyl)oxy)methyl 3-(4-(diisobutylamino)-3-(3-(p-tolyl)ureido)phenyl)pentanoate To a stirred solution of (S)-chloromethyl 3-(4-(diisobutylamino)-3-(3-(p-tolyl)ureido)phenyl)pentanoate (850 mg, 1.693 mmol) in anhydrous DMF (10 mL), were added $Cs_2CO_3$ (1103 mg, 3.39 mmol) and 3-((tert-butoxycarbonyl)amino)propanoic acid (480 mg, 2.54 mmol). After being stirred for 16 h at room temperature, the reaction mixture was diluted with water (25 mL) and extracted with ethyl acetate (2×50 mL). The organic layer was washed with $H_2O$, and saturated NaCl solution, dried over anhydrous $Na_2SO_4$, filtered and concentrated under reduced pressure. The residue was purified using CombiFlash (silica gel 60-120 mesh; 40% ethyl acetate in pet. ether as eluent) to (S)-((3-((tert-butoxycarbonyl)amino)propanoyl)oxy)methyl 3-(4-(diisobutylamino)-3-(3-(p-tolyl)ureido)phenyl)pentanoate (800 mg, 1.209 mmol, 71.4%) as brownish semi-solid. $^1$H NMR (400 MHz, DMSO-$d_6$) δ ppm 9.26-9.36 (m, 1H), 7.78-8.03 (m, 2H), 7.30-7.46 (m, 2H), 7.02-7.19 (m, 2H), 6.73-6.96 (m, 2H), 5.55-5.65 (m, 2H), 3.12-3.15 (m, 2H), 2.81-2.87 (m, 1H), 2.61-2.70 (m, 9H), 2.21-2.29 (s, 3H), 1.54-1.72 (m, 4H), 1.36 (s, 9H), 0.84 (d, J=6.53 Hz, 12H), 0.67-0.75 (m, 3H); LCMS (ES): m/z=655.4 [M+H]$^+$.

30C: (S)-((3-Aminopropanoyl)oxy)methyl 3-(4-(diisobutylamino)-3-(3-(p-tolyl)ureido)phenyl)pentanoate Dihydrochloride To a stirred solution of (S)-((3-((tert-butoxycarbonyl)amino)propanoyl)oxy) methyl 3-(4-(diisobutylamino)-3-(3-(p-tolyl)ureido)phenyl)pentanoate (700 mg, 1.069 mmol) in anhydrous DCM (2 mL) at 0° C., was added dropwise 4 N HCl in dioxane (2.5 mL, 10.00 mmol). After being stirred for 30 min., the reaction mixture was concentrated under high vacuum. The residue was dissolved in a mixture of MeCN and water, frozen and lyophilized for 12 h to afford (S)-((3-aminopropanoyl)oxy)methyl 3-(4-(diisobutylamino)-3-(3-(p-tolyl)ureido)phenyl)pentanoate dihydrochloride (700 mg, 1.060 mmol, 99%) as off-white solid. $^1$H NMR (400 MHz, DMSO-d$_6$) δ ppm 9.37-9.48 (m, 1H), 7.90-7.98 (m, 3H), 7.33-7.43 (m, 2H), 7.07-7.11 (m, 2H), 6.70-6.87 (m, 1H), 5.64-5.71 (m, 2H), 2.98-3.09 (m, 2H), 2.81-2.89 (m, 1H), 2.61-2.73 (m, 8H), 2.25 (s, 3H), 1.48-1.74 (m, 4H), 0.84 (d, J=6.53 Hz, 12H), 0.68-0.76 (m, 3H).

30D: (S)-((3-((S)-2-((bis(Benzyloxy)phosphoryl)oxy)propanamido) Propanoyl)oxy)methyl 3-(4-(diisobutylamino)-3-(3-(p-tolyl)ureido)phenyl)pentanoate To a stirred solution of (S)-((3-aminopropanoyl)oxy)methyl 3-(4-(diisobutylamino)-3-(3-(p-tolyl)ureido)phenyl)pentanoate (600 mg, 1.082 mmol) in anhydrous DMF (10 mL), were added HATU (823 mg, 2.163 mmol), DIPEA (0.945 mL, 5.41 mmol) and finally (S)-2-((bis(benzyloxy)phosphoryl)oxy)propanoic acid (455 mg, 1.298 mmol) at room temperature. After being stirred for 20 min, the reaction mixture was diluted with water (25 mL) and extracted with ethyl acetate (2×50 mL). The organic layer was washed with H$_2$O and saturated NaCl solution, dried over anhydrous Na$_2$SO$_4$, filtered and concentrated under reduced pressure. The crude product was purified using CombiFlash (silica gel 60-120 mesh; 40% ethyl acetate in pet. ether as eluent) to afford (S)-((3-((S)-2-((bis(benzyloxy)phosphoryl)oxy)propanamido)propanoyl)oxy)methyl 3-(4-(diisobutylamino)-3-(3-(p-tolyl)ureido)phenyl)pentanoate (120 mg, 0.131 mmol, 12.13%) as brownish semi-solid. LCMS (ES): m/z=887.7 [M+H]$^+$.

Example 30

To a stirred solution of (S)-((3-((S)-2-((bis(benzyloxy)phosphoryl)oxy) propanamido)propanoyl)oxy)methyl 3-(4-(diisobutylamino)-3-(3-(p-tolyl)ureido)phenyl) pentanoate (120 mg, 0.135 mmol) in anhydrous ethyl acetate (5 mL), was added Pd/C (10%, 72.0 mg, 0.068 mmol) and stirred for 1 h at room temperature under hydrogen bladder. The black suspension was filtered through celite bed and the bed was washed with ethyl acetate (20 mL). The filtrate was concentrated under reduced pressure to afford the crude product. The crude compound was purified using RP HPLC (Kinetex Bi phenyl [250×21 mm]; mobile phase A: 0.1% formic acid in water; mobile phase B: CH$_3$CN; flow rate: 17 mL/min). The prep. fraction was concentrated under high vacuum at 30° C. The residue was dissolved in a mixture of MeCN and water, frozen and lyophilized for 12 h to afford (S)-((3-((S)-2-(phosphonooxy)propanamido)propanoyl)oxy)methyl 3-(4-(diisobutylamino)-3-(3-(p-tolyl)ureido)phenyl)pentanoate (30 mg, 0.041 mmol, 30.4%) as an off-white solid. $^1$H NMR (300 MHz, methanol-d$_4$) δ ppm 7.71-7.84 (m, 1H), 7.25-7.38 (m, 3H), 7.01-7.16 (m, 3H), 6.72-6.81 (m, 1H), 5.43-5.72 (m, 2H), 4.33-4.59 (m, 1H), 3.19-3.49 (m, 3H), 2.57-2.78 (m, 8H), 2.30 (s, 3H), 1.42-1.68 (m, 4H) 1.27-1.33 (m, 3H) 0.76-0.85 (m, 12H) 0.63-0.74 (m, 3H); LCMS (ES): m/z=707.2 [M+H]$^+$; HPLC T$_r$: 10.2 min (Method A) and 8.0 min (Method B).

Example 31

(3S)-2-Methyl-1-(((S)-3-methyl-2-((S)-2-(phosphonooxy)propanamido)butanoyl)oxy)propyl 3-(4-(diisobutylamino)-3-(3-(p-tolyl)ureido)phenyl)pentanoate

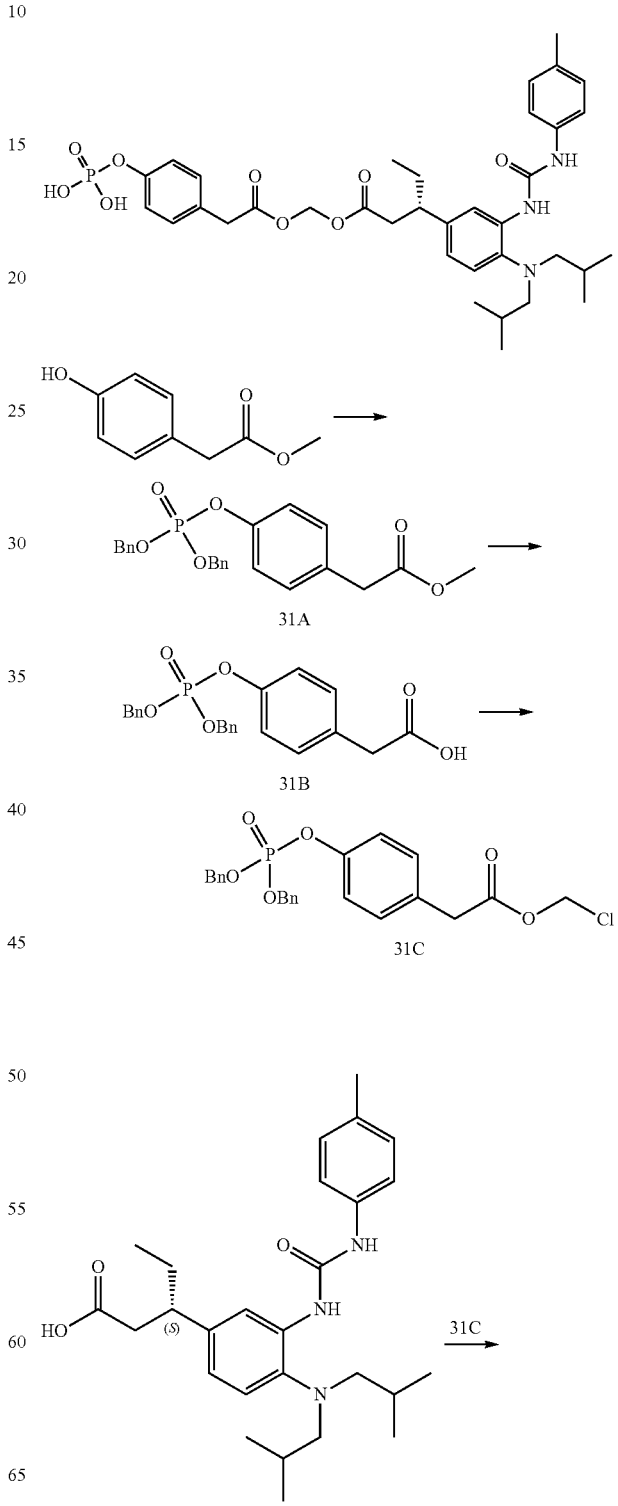

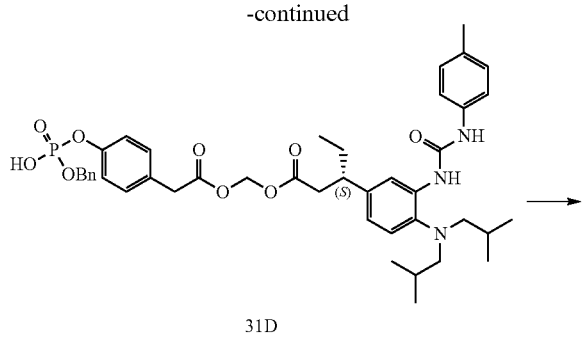

31D

Example 31

31A: Methyl 2-(4-((bis(benzyloxy)phosphoryl)oxy)phenyl)acetate

A mixture of methyl 4-hydroxyphenylacetate (5.5 g, 33.1 mmol), dibenzyl N,N-diisopropylphosphoramidite (16.68 ml, 49.6 mmol) and 1H-Tetrazole (0.45 M in acetonitrile) (110 ml, 49.6 mmol) was stirred at room temperature for 8 h. The reaction was cooled to 0° C., to which was added $H_2O_2$ (2.028 ml, 66.2 mmol). After being stirred for 10 min, the reaction mixture was partitioned between ethyl acetate (200 mL) and water. The organic layer was washed with brine, dried over anhydrous sodium sulfate, filtered and concentrated under vacuum to get colorless oil. The crude material was purified by CombiFlash (silica gel 60-120 mesh; 30% ethyl acetate in hexane as eluent) to get methyl 2-(4-((bis(benzyloxy)phosphoryl)oxy)phenyl)acetate (7.2 g, 16.89 mmol, 51.0%) as a colorless oil. $^1$H NMR (300 MHz, chloroform-d) δ ppm 7.27-7.40 (m, 10H), 7.19-7.26 (m, 2H), 7.08-7.16 (m, 2H), 5.14 (d, J=8.31 Hz, 4H), 3.72 (s, 3H), 3.61 (s, 2H); LCMS (ES): m/z 427.4 [M+H]$^+$.

31B: 2-(4-((bis(Benzyloxy)phosphoryl)oxy)phenyl)acetic Acid

To a stirred mixture of methyl 2-(4-((bis(benzyloxy)phosphoryl)oxy)phenyl) acetate (3 g, 7.04 mmol) in THF (10 mL) and methanol (2 mL), was added aqueous solution of LiOH (0.337 g, 14.07 mmol; 10 mL of water). The reaction mixture was stirred at room temperature for 2 h. The reaction mixture was concentrated to remove organic solvents under vacuum. The remaining aqueous layer was diluted with water, washed with DCM (50 mL), acidified using 1.5 N HCl at 0° C. and extracted with ethyl acetate (2*100 mL). The combined organic layer was washed with brine, dried over anhydrous sodium sulfate, filtered and concentrated under vacuum to get 2-(4-((bis(benzyloxy)phosphoryl)oxy)phenyl)acetic acid (2.5 g, 6.06 mmol, 86%) as a colorless liquid. $^1$H NMR (300 MHz, DMSO-d$_6$) δ ppm 7.31-7.42 (m, 10H), 7.27 (d, J=8.31 Hz, 2H), 7.13 (dd, J=8.69, 1.13 Hz, 2H), 5.16 (d, J=8.31 Hz, 4H), 3.56 (s, 2H); LCMS (ES): m/z 413.4 [M+H]$^+$.

31C: Chloromethyl 2-(4-((bis(benzyloxy)phosphoryl)oxy)phenyl)acetate

To a stirred mixture of 2-(4-((bis(benzyloxy)phosphoryl)oxy)phenyl)acetic acid (0.6 g, 1.455 mmol) in dichloromethane (10 mL) and water (10 mL), were added sodium bicarbonate (0.489 g, 5.82 mmol) and tetrabutylammonium hydrogen sulfate (0.049 g, 0.145 mmol). The reaction mixture was stirred at 0° C. for 15 min. Chloromethyl chlorosulfate (0.294 mL, 2.91 mmol) was added. The reaction mixture was brought to room temperature, stirred for 8 h and diluted with DCM (100 mL). The organic layer was washed with water (3*100 mL) and brine, dried over anhydrous sodium sulfate, filtered and concentrated under vacuum to get as colorless liquid. The crude material was purified by CombiFlash (ELSD) (silica gel 60-120 mesh; 35% ethyl acetate in hexane as eluent) to get chloromethyl 2-(4-((bis(benzyloxy)phosphoryl)oxy)phenyl)acetate (0.55 g, 1.193 mmol, 82%) as a colorless gum. $^1$H NMR (300 MHz, chloroform-d) δ ppm 7.30-7.40 (m, 10H), 7.20-7.25 (m, 2H), 7.10-7.16 (m, 2H), 5.72 (s, 2H), 5.14 (d, J=8.31 Hz, 4H), 3.68 (s, 2H); LCMS (ES): m/z 478.3 [M+H]$^+$.

31D: (3S)-(2-(4-(((Benzyloxy)(hydroxy)phosphoryl)oxy)phenyl)acetoxy)methyl 3-(4-(diisobutylamino)-3-(3-(p-tolyl)ureido)phenyl)pentanoate To a stirred solution of ((S)-3-(4-(diisobutylamino)-3-(3-(p-tolyl)ureido)phenyl) pentanoic acid (0.35 g, 0.772 mmol) in acetonitrile (10 mL), K$_2$CO$_3$ (0.427 g, 3.09 mmol) was added. The reaction mixture was stirred at room temperature for 5 min. Then chloromethyl 2-(4-((bis(benzyloxy)phosphoryl)oxy)phenyl)acetate (0.711 g, 1.543 mmol) and sodium iodide (0.231 g, 1.543 mmol) were added. The reaction mixture was heated at 60° C. for 8 h and partitioned between ethyl acetate and water. The organic layer was washed with brine, dried over anhydrous sodium sulfate, filtered and concentrated to get brownish gum. The material was purified using RP-HPLC (Symmetry C8 (19*250 mm); Mobile phase A: 10 mM ammonium acetate-4.5 pH Mobile phase B: acetonitrile; flow rate 20.0 mL/min.). The fraction was concentrated using high vacuum at 30° C. The residue was dissolved in a mixture of acetonitrile and water, frozen and lyophilized for 12 h to get (3S)-(2-(4-(((benzyloxy)(hydroxy)phosphoryl)oxy)phenyl)acetoxy)methyl 3-(4-(diisobutylamino)-3-(3-(p-tolyl)ureido)phenyl)pentanoate (0.1 g, 0.127 mmol, 16.45%) as a white solid. $^1$H NMR (400 MHz, methanol-d$_4$) δ ppm 7.22-7.41 (m, 10H), 7.08-7.24 (m, 6H), 5.63-5.71 (m, 2H), 4.95-5.06 (m, 2H), 3.57 (s, 2H), 2.54-3.00 (m, 7H), 2.26-2.45 (m, 3H), 1.54-1.75 (m, 4H), 1.29-1.46 (m, 2H), 0.68-1.16 (m, 15H); LCMS (ES): m/z 788.6 [M+H]$^+$.

Example 31

To a stirred solution of (S)-(2-(4-((bis(benzyloxy)phosphoryl)oxy)phenyl) acetoxy)methyl 3-(4-(diisobutylamino)-3-(3-(p-tolyl)ureido)phenyl)pentanoate (100 mg, 0.114 mmol) in 2-propanol (5 mL), Pd/C (5%; 121 mg, 0.057 mmol) was added. After being stirred at room temperature under hydrogen atm. for 1 h, the reaction mixture was filtered through a pad of celite, which was washed with ethyl acetate. The filtrate was concentrated under high vacuum at 30° C. to get the colorless gum. The crude product was purified using RP-HPLC (X Bridge phenyl [250×19 mm]; mobile phase A: 10 mM ammonium acetate in water; mobile phase B: acetonitrile; flow rate: 18 mL/min.). The fraction was concentrated using high vacuum at 30° C. The residue was dissolved in a mixture of acetonitrile and water, frozen and lyophilized for 12 h to get the product (S)-(2-(4-(phosphonooxy)phenyl)acetoxy)methyl 3-(4-(diisobutylamino)-3-(3-(p-tolyl)ureido)phenyl)pentanoate (25 mg, 0.036 mmol, 31.2%) as a white solid. $^1$H NMR (300 MHz, DMSO-d$_6$; D$_2$O exchange) δ ppm 7.78 (d, J=2.27 Hz, 1H), 7.34 (d, J=8.31 Hz, 2H), 6.99-7.14 (m, 7H), 6.74-6.82 (m, 1H), 5.55-5.65 (m, 2H), 3.53 (s, 2H), 2.66 (d, J=6.80 Hz, 1H), 2.55-2.63 (m, 6H), 2.23 (s, 3H), 1.44-1.64 (m, 4H), 0.79 (d, J=6.42 Hz, 12H), 0.70 (t, J=7.18 Hz, 3H); LCMS (ES): m/z 698.2 [M+H]+; HPLC T,: 17.68 min (Method A) and 16.19 min (Method B).

Example 32

(S)-(S)-2-(Phosphonooxy)propyl 3-(4-(diisobutylamino)-3-(3-(p-tolyl)ureido)phenyl)pentanoate

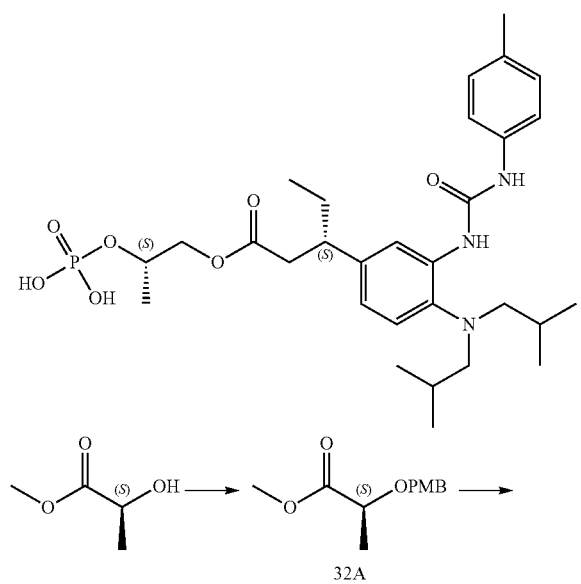

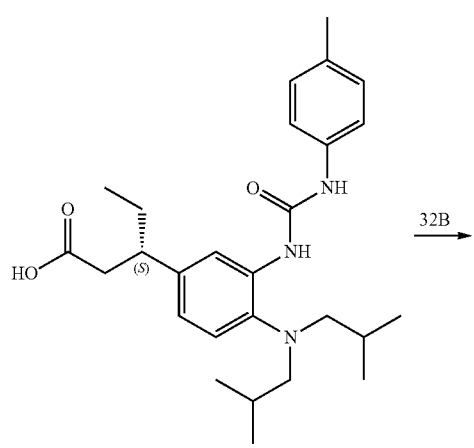

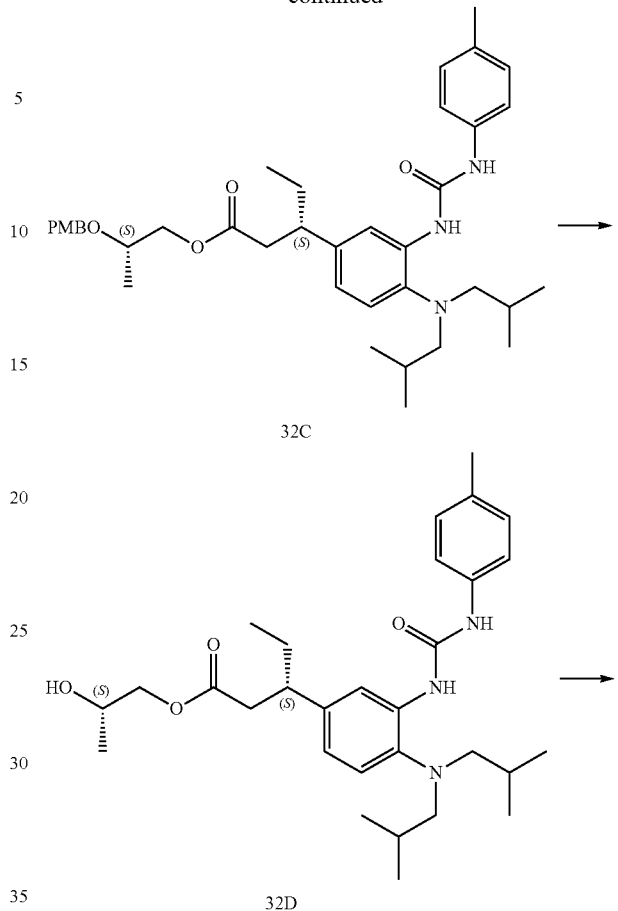

Example 32

32A: (S)-Methyl 2-((4-methoxybenzyl)oxy)propanoate

To a mixture of (S)-methyl 2-hydroxypropanoate (3 g, 28.8 mmol) and 4-methoxybenzyl chloride (5.89 mL, 43.2 mmol), were added DIPEA (8.05 mL, 46.1 mmol) and sodium iodide (0.432 g, 2.88 mmol). After being heated at 150° C. for 3 h, the reaction mixture was cooled to room temperature and partitioned between ethyl acetate (200 mL) and 10% sodium bicarbonate solution (200 mL). The organic layer was washed with brine, dried over anhydrous sodium sulfate, filtered and concentrated under vacuum to get brownish liquid. The crude material was purified by CombiFlash (silica gel 60-120 mesh; 30% ethyl acetate in pet. ether as eluent) to get (S)-methyl 2-((4-methoxybenzyl)oxy)propanoate (3 g, 13.38 mmol, 46.4%) colorless liquid. 1H NMR (400 MHz, chloroform-d) δ=7.32-7.21 (m, 2H), 6.93-6.83 (m, 2H), 4.62 (d, J=11.5 Hz, 1H), 4.46-4.32 (m, 1H), 4.05 (q, J=6.7 Hz, 1H), 3.84-3.77 (m, 3H), 3.75 (s, 3H), 1.42 (d, J=7.0 Hz, 3H).

32B: (S)-2-((4-Methoxybenzyl)oxy)propan-1-ol

Lithium borohydride (2 M solution in THF) (13.38 mL, 26.8 mmol) was added dropwise to a solution of (S)-methyl 2-((4-methoxybenzyl)oxy)propanoate (4 g, 17.84 mmol) in methanol (0.938 mL, 23.19 mmol) and diethyl ether (50 mL)

at 0° C. The reaction mixture was stirred at 0° C. for 1 h and then at room temperature for 5 h. The reaction mixture was cooled to 0° C., and quenched with water. The reaction mixture was filtered and the filtrate was extracted with diethyl ether (2*100 mL). The organic layer was washed with brine, dried over anhydrous sodium sulfate, filtered and concentrated under vacuum. The crude product was purified by CombiFlash (ELSD: silica gel 60-120 mesh; 40% ethyl acetate in pet. ether as eluent) to get (S)-2-((4-methoxybenzyl)oxy) propan-1-ol (3, 15.29 mmol, 86%) as a colorless gum. $^1$H NMR (400 MHz, chloroform-d) δ=7.30-7.24 (m, 2H), 6.91-6.86 (m, 2H), 4.59 (d, J=11.3 Hz, 1H), 4.41 (d, J=11.3 Hz, 1H), 3.80 (s, 3H), 3.70-3.60 (m, 2H), 3.51-3.45 (m, 1H), 2.04 (br. s., 1H), 1.16 (d, J=6.3 Hz, 3H).

32C: (S)-(S)-2-((4-Methoxybenzyl)oxy)propyl 3-(4-(diisobutylamino)-3-(3-(p-tolyl)ureido)phenyl)pentanoate To a solution of (S)-3-(4-(diisobutylamino)-3-(3-(p-tolyl)ureido)phenyl)pentanoic acid (0.5 g, 1.102 mmol) in DCM (10 mL), (S)-2-((4-methoxybenzyl)oxy)propan-1-ol (0.260 g, 1.323 mmol), DMAP (0.135 g, 1.102 mmol) and DCC (0.341 g, 1.653 mmol) were added After being stirred at room temperature for 8 h, the reaction mixture was filtered through a pad of celite and the celite pad was washed with DCM (3*50 mL). The combined organic layer was concentrated to get colorless gum. The crude product was purified by CombiFlash (silica gel 60-120 mesh; 40% ethyl acetate in pet. ether as eluent) to get (S)-(S)-2-((4-methoxybenzyl)oxy)propyl 3-(4-(diisobutylamino)-3-(3-(p-tolyl)ureido) phenyl)pentanoate (0.58 g, 83%) as a colorless gum. $^1$H NMR (400 MHz, methanol-d$_4$) δ=7.88 (d, J=2.0 Hz, 1H), 7.34-7.29 (m, 2H), 7.26-7.21 (m, 2H), 7.13 (s, 3H), 6.90-6.83 (m, 3H), 4.45 (d, J=1.0 Hz, 2H), 4.04-3.93 (m, 2H), 3.78-3.74 (m, 3H), 3.70-3.62 (m, 1H), 2.96 (s, 1H), 2.72-2.57 (m, 6H), 2.31 (s, 3H), 1.77-1.59 (m, 4H), 1.08 (d, J=6.0 Hz, 3H), 0.88 (d, J=6.5 Hz, 12H), 0.83 (t, J=7.3 Hz, 3H); LCMS (ES): m/z 632.5 [M+H]$^+$.

32D: (S)-(S)-2-Hydroxypropyl 3-(4-(diisobutylamino)-3-(3-(p-tolyl)ureido)phenyl) pentanoate To a solution of (S)-(S)-2-((4-methoxybenzyl)oxy)propyl 3-(4-(diisobutylamino)-3-(3-(p-tolyl)ureido)phenyl)pentanoate (0.5 g, 0.791 mmol) in DCM (5 mL) at 0° C., were added anisole (0.6 mL, 5.49 mmol) and TFA (1 mL, 12.98 mmol). After being stirred at room temperature for 8 h, the reaction mixture was concentrated under vacuum. The residue was dissolved in methanol. Aqueous ammonia solution was added. After being stirred for 1 h, the mixture was concentrated to get brownish gum. The crude product was purified using RP HPLC (Column-Gemini nx-C18 [50×4.6 mm)]; mobile phase A: 10 mM ammonium formate in water; mobile phase B: acetonitrile; flow rate: 1 mL/min.). The fraction was concentrated using high vacuum at 30° C. The residue was dissolved in a mixture of acetonitrile and water, frozen and lyophilized for 12 h to get (S)-(S)-2-hydroxypropyl 3-(4-(diisobutylamino)-3-(3-(p-tolyl)ureido)phenyl) pentanoate (0.2 g, 49.0%) as a white solid. $^1$H NMR (400 MHz, DMSO-d$_6$) δ=9.31 (s, 1H), 7.91-7.83 (m, 2H), 7.41-7.32 (m, 2H), 7.16-7.04 (m, 3H), 6.82-6.76 (m, 1H), 4.75-4.62 (m, 2H), 3.89-3.77 (m, 1H), 3.75-3.61 (m, 1H), 3.29-3.19 (m, 1H), 2.93-2.77 (m, 1H), 2.70-2.57 (m, 5H), 2.26 (s, 3H), 1.70-1.41 (m, 4H), 1.02-0.90 (m, 3H), 0.84 (d, J=6.5 Hz, 12H), 0.74 (t, J=7.5 Hz, 3H); LCMS (ES): m/z 512.2 [M+H]$^+$.

Example 32

To a stirred solution of (S)-(S)-2-hydroxypropyl 3-(4-(diisobutylamino)-3-(3-(p-tolyl)ureido)phenyl)pentanoate (290 mg, 0.567 mmol) in THF (5 mL), TEA (0.395 mL, 2.83 mmol) and DMAP (69.2 mg, 0.567 mmol) were added. After cooling the reaction mixture 0° C., POCl$_3$ (0.528 mL, 5.67 mmol) was added. After being stirred at 0° C. for 30 min, the reaction mixture was cooled to −10° C. and quenched with ice-cold water. The reaction mixture was concentrated under vacuum at 30° C. The residue was purified using RP HPLC (Symmetry C8 (19*250 mm); Mobile phase A: 10 mM ammonium acetate −4.5 pH; Mobile phase B: acetonitrile; flow rate: 20.0 mL/min). The fraction was concentrated using high vacuum at 30° C. The residue was dissolved in a mixture of acetonitrile and water, frozen and lyophilized for 12 h to get (S)-(S)-2-(phosphonooxy) propyl 3-(4-(diisobutylamino)-3-(3-(p-tolyl)ureido)phenyl)pentanoate (25 mg, 0.040 mmol, 7.14%) as a white solid. $^1$H NMR (400 MHz, methanol-d$_4$) δ=7.73 (br. s., 1H), 7.34 (d, J=8.0 Hz, 2H), 7.25 (br. s., 1H), 7.14 (s, 2H), 6.97 (br. s., 1H), 4.47 (br. s., 1H), 4.04 (d, J=3.5 Hz, 2H), 3.02 (br. s., 1H), 2.83-2.71 (m, 4H), 2.65-2.57 (m, 2H), 2.32 (s, 3H), 1.76 (dd, J=13.8, 6.8 Hz, 4H), 1.24 (br. s., 3H), 0.92 (d, J=6.5 Hz, 12H), 0.85 (t, J=7.3 Hz, 3H); LCMS (ES): m/z 592.4 [M+H]$^+$; HPLC T$_r$: 9.78 min (Method A) and 9.48 min (Method B).

Example 33

(S)-((3-(4-(Diisobutylamino)-3-(3-(p-tolyl)ureido) phenyl)pentanoyl)oxy)methyl 1-(phosphonooxy) cyclopropanecarboxylate

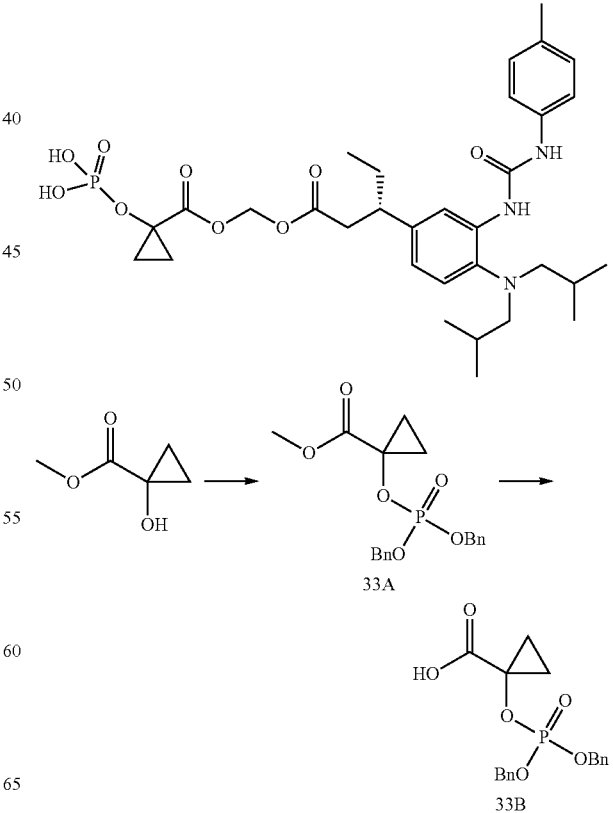

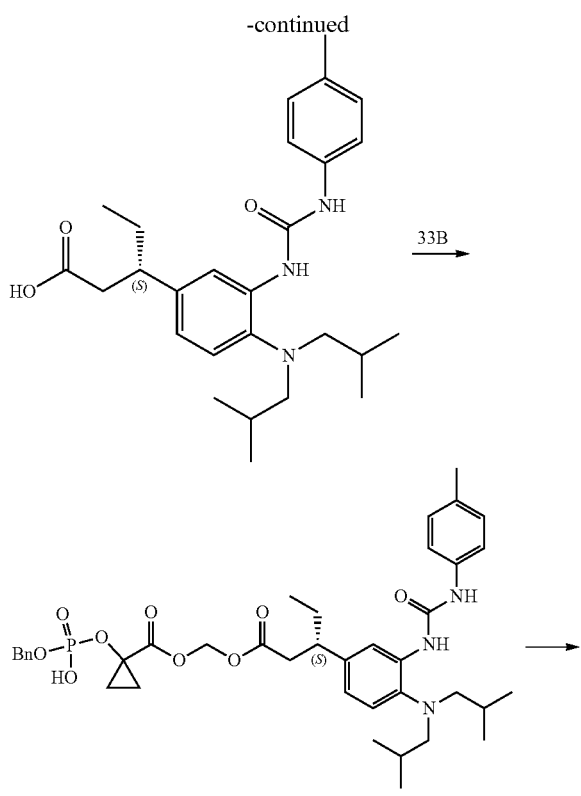

33C

Example 33

33A: Methyl 1-((bis(benzyloxy)phosphoryl)oxy)cyclopropanecarboxylate

A mixture of methyl 1-hydroxycyclopropanecarboxylate (1.1 g, 9.47 mmol), dibenzyl N,N-diisopropylphosphoramidite (4.77 mL, 14.21 mmol) and 1H-tetrazole (0.45 M in acetonitrile) (31.6 mL, 14.21 mmol) was stirred at room temperature for 8 h. The reaction was cooled to 0° C. was added hydrogen peroxide (0.581 mL, 18.95 mmol). The mixture was partitioned between ethyl acetate (100 mL) and water. The organic layer was washed with brine, dried over anhydrous sodium sulfate, filtered and concentrated under vacuum. The crude material was purified by CombiFlash (silica gel 60-120 mesh; 30% ethyl acetate in hexane as eluent) to get methyl 1-((bis(benzyloxy)phosphoryl)oxy) cyclopropanecarboxylate (2.5 g, 6.64 mmol, 70.1%) as a colorless oil. $^1$H NMR (400 MHz, chloroform-d) δ=7.41-7.30 (m, 10H), 5.17-5.05 (m, 4H), 3.71 (s, 3H), 1.48-1.31 (m, 4H); LCMS (ES): m/z 378.0 [M+H]$^+$.

33B: 1-((bis(Benzyloxy)phosphoryl)oxy)cyclopropanecarboxylic Acid

To a stirred mixture of methyl 1-((bis(benzyloxy)phosphoryl)oxy) cyclopropanecarboxylate (2.5 g, 6.64 mmol) in THF (10 mL) and water (10 mL) at 0° C., LiOH (0.318 g, 13.29 mmol) was added. After being stirred at room temperature for 3 h, the reaction mixture was concentrated to remove organic solvents under vacuum. The remaining aqueous layer was diluted with water, washed with DCM (50 mL), and acidified using 1.5 N HCl at 0° C. and extracted with ethyl acetate (2*100 mL). The combined organic layer was washed with brine, dried over anhydrous sodium sulfate, filtered and concentrated under high vacuum at 30° C. to get 1-((bis(benzyloxy) phosphoryl)oxy)cyclopropanecarboxylic acid (1.9 g, 5.24 mmol, 79%) as a colorless liquid. $^1$H NMR (400 MHz, methanol-d$_4$) δ=7.45-7.20 (m, 10H), 5.22-5.03 (m, 2H), 4.61 (s, 2H), 1.42 (d, J=3.5 Hz, 4H); LCMS (ES): m/z 363.2 [M+H]$^+$.

33C: (((S)-3-(4-(Diisobutylamino)-3-(3-(p-tolyl)ureido)phenyl)pentanoyl)oxy)methyl 1-(((benzyloxy)(hydroxy)phosphoryl)oxy)cyclopropanecarboxylate To a solution of 1-((bis(benzyloxy)phosphoryl)oxy)cyclopropanecarboxylic acid (0.289 g, 0.797 mmol) in DMF (5 mL), cesium carbonate (0.260 g, 0.797 mmol) was added. After being stirred at room temperature for 5 min, (S)-chloromethyl 3-(4-(diisobutylamino)-3-(3-(p-tolyl)ureido)phenyl)pentanoate (0.2 g, 0.398 mmol) and sodium iodide (0.119 g, 0.797 mmol), were added. The reaction mixture was stirred at room temperature for 8 h and concentrated under high vacuum. The residue was partitioned between ethyl acetate and water. The organic layer was washed with brine, dried over anhydrous sodium sulfate, filtered and concentrated to get brownish gum. The crude product was purified using RP HPLC (X Bridge phenyl C18 [150×19 mm]; mobile phase A: 10 mM ammonium acetate in water; mobile phase B: acetonitrile; flow rate: 18 mL/min.). The fraction was concentrated using high vacuum at 30° C. The residue was dissolved in a mixture of acetonitrile and water, frozen and lyophilized for 12 h to get (S)-((3-(4-(diisobutylamino)-3-(3-(p-tolyl)ureido)phenyl)pentanoyl)oxy)methyl 1-((bis(benzyloxy)phosphoryl)oxy)cyclopropanecarboxylate (0.12 g, 0.138 mmol, 34.6%) as a white solid. $^1$H NMR (300 MHz, methanol-d$_4$) δ=7.89-7.74 (m, 1H), 7.49-7.20 (m, 7H), 7.12 (d, J=7.9 Hz, 3H), 6.87 (br. s., 1H), 5.77-5.62 (m, 2H), 4.98 (d, J=5.7 Hz, 2H), 2.99-2.86 (m, 1H), 2.81-2.51 (m, 6H), 2.31 (s, 3H), 1.81-1.58 (m, 4H), 1.51-1.43 (m, 2H), 1.35-1.24 (m, 2H), 0.89 (d, J=6.4 Hz, 12H), 0.83-0.64 (m, 3H); LCMS (ES): m/z 738.4 [M+H]$^+$.

Example 33

To a stirred solution of (((S)-3-(4-(diisobutylamino)-3-(3-(p-tolyl)ureido)phenyl) pentanoyl)oxy)methyl 1-(((benzyloxy)(hydroxy)phosphoryl)oxy) cyclopropanecarboxylate (0.11 g, 0.149 mmol) in 2-propanol (5 mL), Pd—C (10%, 0.127 g, 0.060 mmol) was added and the reaction mixture was stirred room temperature under hydrogen atm for 1 h. The reaction mixture was filtered through a pad of celite, which was washed with ethyl acetate. The filtrate was concentrated under high vacuum at 30° C. to get the colorless gum. The crude product was purified using RP HPLC (Kinetex Biphenyl [250×21 mm]; mobile phase A: 10 mM ammonium acetate in water; mobile phase B: acetonitrile; flow rate: 18 mL/min.). The fraction was concentrated using high vacuum at 30° C. The residue was dissolved in a mixture of acetonitrile and water, frozen and lyophilized for 12 h to get (S)-((3-(4-(diisobutylamino)-3-(3-(p-tolyl)ureido)phenyl) pentanoyl)oxy)methyl 1-(phosphonooxy)cyclopropanecarboxylate (25 mg, 0.037 mmol, 25.05%) as a white solid. $^1$H NMR (300 MHz, methanol-d$_4$) δ=7.79 (br. s., 1H), 7.32 (br. s., 2H), 7.13 (br. s., 3H), 6.88 (br. s., 1H), 5.71 (br. s., 2H), 2.97 (br. s., 1H), 2.69 (br. s., 6H), 2.32 (br. s., 3H), 1.72 (br. s., 4H), 1.53 (br. s., 2H), 1.29 (br. s., 2H), 1.03-0.77 (m, 15H); LCMS (ES): m/z 648.1 [M+H]$^+$. HPLC T$_r$: 17.00 min (Method A) and 9.50 min (Method B).

Example 34
Diastereomer 1 and Diastereomer 2
(3S)-2-Methyl-1-(((S)-3-methyl-2-((S)-2-(phosphonooxy)propanamido)butanoyl) oxy)propyl 3-(4-(diisobutylamino)-3-(3-(p-tolyl)ureido)phenyl)pentanoate—Relative Stereochemistry not Confirmed
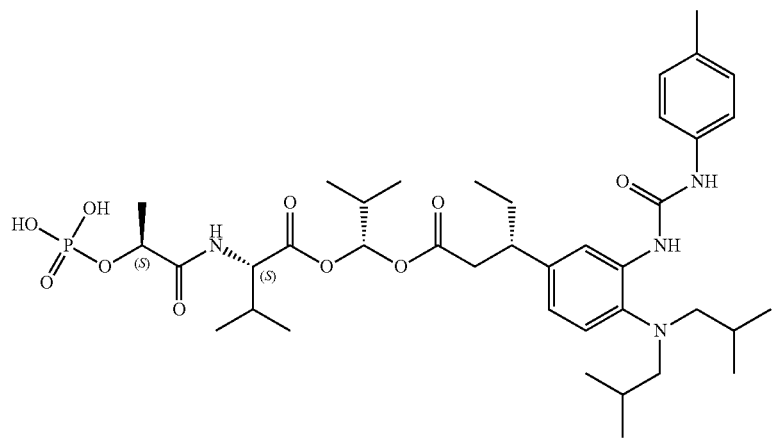
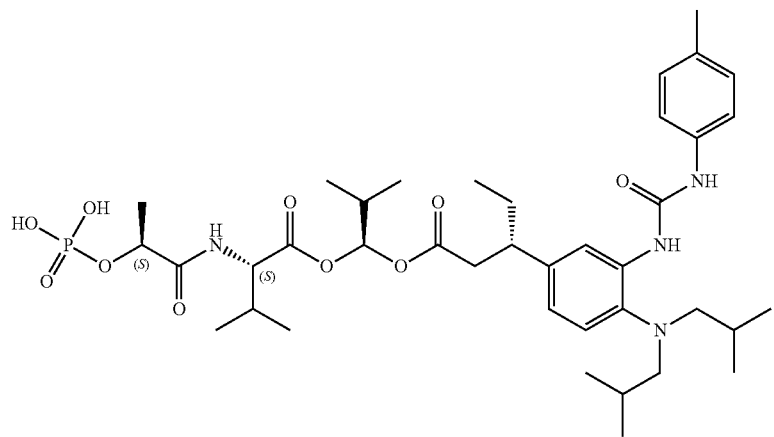
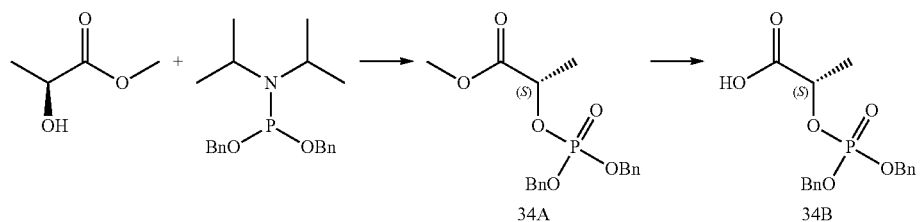

143 144
-continued
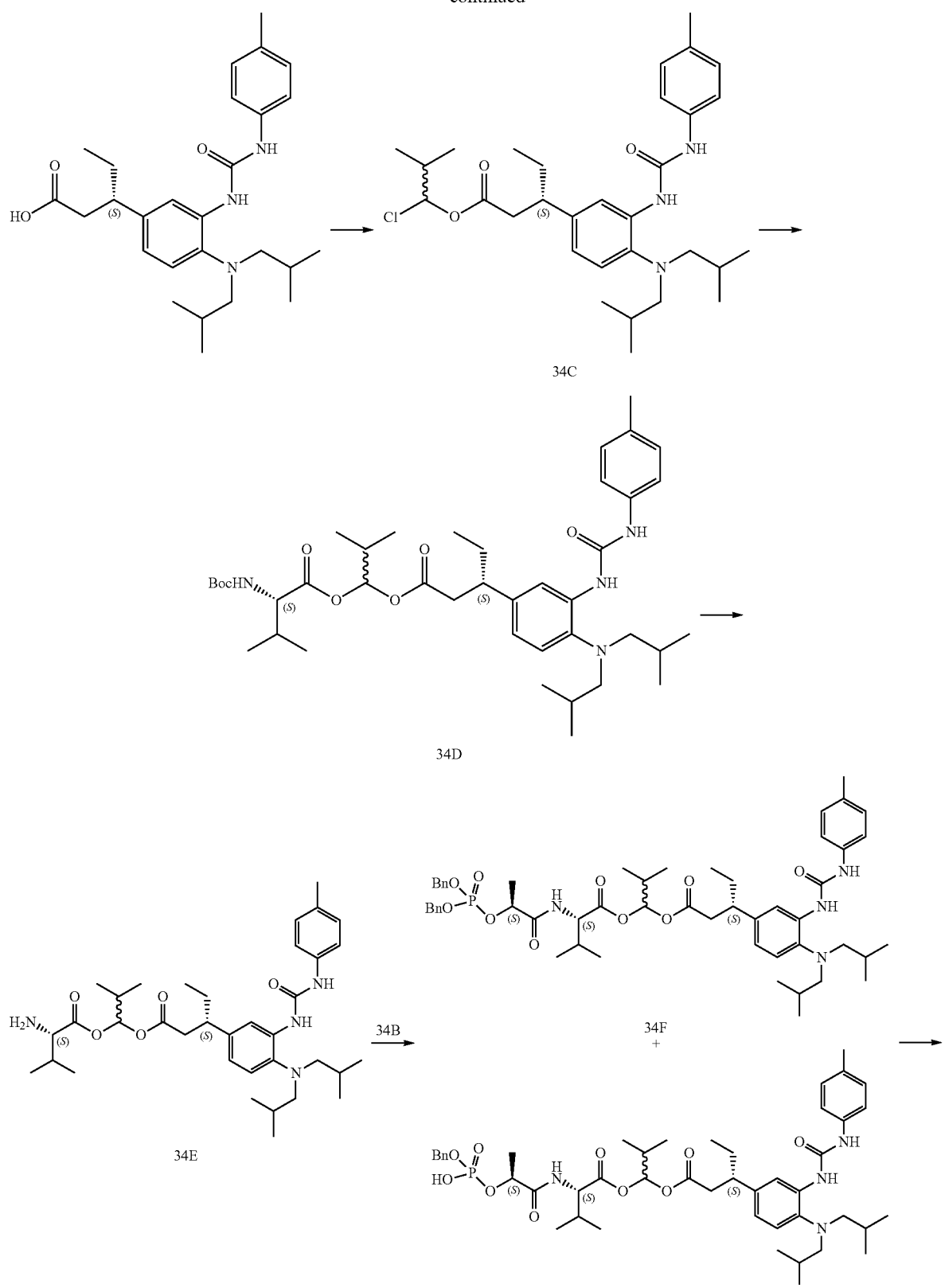
34C
34D
34E → 34B → 34F +
Example 34
Diasteromer-1
Diastereomer-2

34A: (S)-Methyl 2-((bis(benzyloxy)phosphoryl)oxy)propanoate

To a stirred solution of (S)-methyl 2-hydroxypropanoate (6 g, 57.6 mmol) in DCM (10 mL), dibenzyl N,N-diisopropylphosphoramidite (29.0 mL, 86 mmol), and 1H-tetrazole (0.45 M in acetonitrile) (192 mL, 86 mmol) were added. The reaction mixture was stirred at room temperature for 8 h and cooled to 0° C., to which was added $H_2O_2$ (3.53 mL, 115 mmol). After being stirred for 10 min, the reaction mixture was partitioned between ethyl acetate and water. The organic layer was washed with brine, dried over anhydrous sodium sulfate, filtered and concentrated under vacuum to get colorless oil. The crude material was purified by CombiFlash (silica gel 60-120 mesh; 20% ethyl acetate in hexane as eluent) to get the (S)-methyl 2-((bis(benzyloxy)phosphoryl)oxy) propanoate (15 g, 41.2 mmol, 71.4%) as a colorless oil. $^1$H NMR (300 MHz, chloroform-d) δ=7.47-7.30 (m, 10H), 5.19-5.04 (m, 4H), 4.91 (dd, J=8.1, 7.0 Hz, 1H), 3.74 (s, 3H), 1.50 (d, J=6.8 Hz, 3H); LCMS (ES): m/z 365.1 $[M+H]^+$.

34B: (S)-2-((bis(Benzyloxy)phosphoryl)oxy)propanoic Acid

To a stirred solution of (S)-methyl 2-((bis(benzyloxy) phosphoryl)oxy)propanoate (5 g, 10.98 mmol) in THF (20 mL) and water (20 mL) at 0° C., was added LiOH (0.526 g, 21.96 mmol). The reaction mixture was stirred at room temperature for 2 h and concentrated to remove organic solvents under vacuum. The remaining aqueous layer was diluted with water, washed with DCM (100 mL), acidified using 1.5 N HCl at 0° C. and extracted with ethyl acetate (2*150 mL). The combined organic layer was washed with brine, dried over anhydrous sodium sulfate, filtered and concentrated under vacuum to get (S)-2-((bis(benzyloxy) phosphoryl)oxy)propanoic acid (3.8 g, 10.85 mmol, 99%) as a colorless liquid. $^1$H NMR (300 MHz, methanol-$d_4$) δ=7.46-7.29 (m, 10H), 5.11 (dd, J=17.2, 8.5 Hz, 4H), 4.90-4.76 (m, 1H), 1.48 (dd, J=6.8, 0.8 Hz, 3H); LCMS (ES): m/z 351.3 $[M+H]^+$.

34C: (3S)-1-Chloro-2-methylpropyl 3-(4-(diisobutylamino)-3-(3-(p-tolyl)ureido)phenyl) Pentanoate To a stirred solution of (S)-3-(4-(diisobutylamino)-3-(3-(p-tolyl)ureido)phenyl) pentanoic acid (2 g, 4.41 mmol) in DCM (10 mL) at −10° C., was added 1-chloro-N,N 2-trimethylpropenylamine (1.167 mL, 8.82 mmol). The reaction mixture was stirred at 0° C. for 1 h and cooled to −10° C. Zinc chloride (0.721 g, 5.29 mmol) and isobutyraldehyde (2.012 mL, 22.05 mmol) were added. After being stirred at −10° C. for 1 h, the reaction mixture was partitioned between DCM and water. The organic layer was washed with water (2*100 mL), brine, dried over anhydrous sodium sulfate, filtered and concentrated to get yellowish gum. The crude material was purified by CombiFlash (silica gel 60-120 mesh; 15% ethyl acetate in hexane as eluent) to get (3S)-1-chloro-2-methylpropyl 3-(4-(diisobutylamino)-3-(3-(p-tolyl)ureido)phenyl)pentanoate (1 g, 1.838 mmol, 41.7%) as a colorless semi-solid. $^1$H NMR (400 MHz, methanol-$d_4$) δ=7.86 (s, 1H), 7.32 (d, J=8.0 Hz, 2H), 7.18-7.10 (m, 3H), 6.87 (d, J=7.5 Hz, 1H), 6.24 (dd, J=11.0, 4.5 Hz, 1H), 2.96 (d, J=6.0 Hz, 1H), 2.78-2.62 (m, 6H), 2.32 (s, 3H), 2.12-1.93 (m, 1H), 1.79-1.61 (m, 4H), 0.95-0.82 (m, 21H); LCMS (ES): m/z 546.6 $[M+H]^+$.

34D: (3S)-1-(((S)-2-((tert-Butoxycarbonyl)amino)-3-methylbutanoyl)oxy)-2-methylpropyl 3-(4-(diisobutylamino)-3-(3-(p-tolyl)ureido)phenyl)pentanoate To a solution of (S)-2-((tert-Butoxycarbonyl)amino)-3-methylbutanoic acid (0.898 g, 4.13 mmol) in MeOH (3 mL), cesium carbonate (1.347 g, 4.13 mmol) was added. The reaction mixture was stirred at room temperature for 2 h. The reaction mixture was concentrated under high vacuum at low temperature to get colorless solid. After adding DMF (1 mL), (3S)-1-chloro-2-methylpropyl 3-(4-(diisobutylamino)-3-(3-(p-tolyl)ureido) phenyl)pentanoate (0.75 g, 1.378 mmol) and sodium iodide (0.207 g, 1.378 mmol) were added. The reaction mixture was heated at 70° C. for 8 h. The reaction mixture was concentrated under vacuum to get colorless gum. The residue was dissolved in ethyl acetate and the solution was washed with brine, dried over anhydrous sodium sulfate, filtered and concentrated. The crude material was purified by CombiFlash (silica gel 60-120 mesh; 20% ethyl acetate in hexane as eluent) to get (3S)-1-(((S)-2-((tert-butoxycarbonyl)amino)-3-methylbutanoyl) oxy)-2-methylpropyl 3-(4-(diisobutylamino)-3-(3-(p-tolyl) ureido)phenyl)pentanoate (0.45 g, 0.621 mmol, 45.0%) as a white solid. LCMS (ES): m/z 726.8 $[M+H]^+$.

34E: (3S)-1-(((S)-2-Amino-3-methylbutanoyl)oxy)-2-methylpropyl 3-(4-(diisobutylamino)-3-(3-(p-tolyl)ureido)phenyl)pentanoate Hydrochloride A solution of HCl (4M, 5 mL, 165 mmol) in dioxane was added to (3S)-1-(((S)-2-((tert-butoxycarbonyl)amino)-3-methylbutanoyl)oxy)-2-methylpropyl 3-(4-(diisobutylamino)-3-(3-(p-tolyl)ureido)phenyl)pentanoate (0.45 g, 0.621 mmol) at 0° C. The reaction mixture was brought to room temperature and stirred for 2 h. The reaction mixture was concentrated under high vacuum at 30° C. The residue was triturated with diethyl ether to get (3S)-1-(((S)-2-amino-3-methylbutanoyl)oxy)-2-methylpropyl 3-(4-(diisobutylamino)-3-(3-(p-tolyl)ureido)phenyl)pentanoate hydrochloride (0.5 g, 0.756 mmol, 122%) as a colorless gum. The crude material was as such taken to the next step without purification. LCMS (ES): m/z 625.6 $[M+H]^+$.

34F: (3S)-1-(((S)-2-((S)-2-((bis(Benzyloxy)phosphoryl)oxy)propanamido)-3-methylbutanoyl)oxy)-2-methylpropyl 3-(4-(diisobutylamino)-3-(3-(p-tolyl) ureido) Phenyl)pentanoate To a stirred solution of (3S)-1-(((S)-2-amino-3-methylbutanoyl)oxy)-2-methylpropyl 3-(4-(diisobutylamino)-3-(3-(p-tolyl)ureido)phenyl)pentanoate hydrochloride (650 mg, 0.983 mmol) in DMF (10 mL), were added DIPEA (0.858 mL, 4.91 mmol), HATU (561 mg, 1.474 mmol) and (S)-2-((bis(benzyloxy)phosphoryl) oxy)propanoic acid (516 mg, 1.474 mmol). After being stirred at room temperature for 4 h, the reaction mixture was diluted in water and extracted with ethyl acetate. The organic layer was washed with brine, dried over anhydrous sodium sulfate, filtered and concentrated to get brownish gum. The crude product was purified using RP HPLC (X-Bridge phenyl [250×19 mm]; mobile phase A: 10 mM ammonium acetate in water; mobile phase B: acetonitrile; flow rate: 18 mL/min.). The fraction was concentrated using high vacuum at 30° C. The residue was dissolved in a mixture of acetonitrile and water, frozen and lyophilized for 12 h to get (3S)-1-(((S)-2-((S)-2-((bis(benzyloxy)phosphoryl)oxy)propanamido)-3-methylbutanoyl)oxy)-2-methylpropyl 3-(4-(diisobutylamino)-3-(3-(p-tolyl)ureido)phenyl)pentanoate (300 mg, 0.298 mmol, 30.3%) and (3S)-1-(((2S)-2-((2S)-2-(((benzyloxy)(hydroxy)phosphoryl)oxy) propanamido)-3-methylbutanoyl)oxy)-2-methylpropyl 3-(4-(diisobutylamino)-3-(3-(p-tolyl)ureido)phenyl)pentanoate (220 mg, 0.241 mmol, 24.53%) as a white solid. LCMS (ES): m/z 867.6 [M+H]+.

Example 34 Diastereomer 1 and Diastereomer 2 (Relative Stereochemistry not Confirmed)

To a stirred solution of (3S)-1-(((S)-2-((S)-2-((bis(benzyloxy)phosphoryl)oxy) propanamido)-3-methylbutanoyl)oxy)-2-methylpropyl 3-(4-(diisobutylamino)-3-(3-(p-tolyl)ureido)phenyl)pentanoate (0.22 g, 0.230 mmol) in 2-propanol (10 mL), Pd/C (0.196 g, 0.092 mmol) was added. The reaction mixture was stirred room temperature under hydrogen atm for 2 h. The reaction mixture was filtered through a pad of celite, which was washed with ethyl acetate. The filtrate was concentrated under high vacuum at 30° C. to get the colorless gum. The crude product was purified using RP HPLC (Kinetex Biphenyl [250×21 mm]; mobile phase A: 10 mM formic acid in water; mobile phase B: acetonitrile; flow rate: 18 mL/min.) to obtain two diastereomers. The fractions were separately concentrated using high vacuum at 30° C. The residues were dissolved in a mixture of acetonitrile and water, frozen and lyophilized for 12 h to get the product Diastereomer-1 (3S)-2-methyl-1-(((S)-3-methyl-2-((S)-2-(phosphonooxy)propanamido)butanoyl)oxy)propyl 3-(4-(diisobutylamino)-3-(3-(p-tolyl)ureido)phenyl)pentanoate (118.24 mg, 0.144 mmol, 62.9%) and Diastereomer-2 (3S)-2-methyl-1-(((S)-3-methyl-2-((S)-2-(phosphonooxy)propanamido)butanoyl)oxy)propyl 3-(4-(diisobutylamino)-3-(3-(p-tolyl)ureido)phenyl)pentanoate (152 mg, 0.185 mmol, 80%) as a white solid.

Diastereomer-1: $^1$H NMR (400 MHz, methanol-$d_4$) δ=7.79-7.55 (m, 1H), 7.37 (d, J=8.0 Hz, 3H), 7.14 (d, J=8.0 Hz, 3H), 6.53 (d, J=4.5 Hz, 1H), 4.77 (t, J=7.0 Hz, 1H), 4.34 (d, J=6.0 Hz, 1H), 3.09-2.88 (m, 4H), 2.83-2.60 (m, 3H), 2.32 (s, 3H), 2.25-2.14 (m, 1H), 1.91 (dq, J=11.6, 6.8 Hz, 2H), 1.81-1.58 (m, 3H), 1.52 (d, J=6.5 Hz, 3H), 1.07-0.91 (m, 18H), 0.89-0.81 (m, 9H); LCMS (ES): m/z 777.2 [M+H]+; HPLC T$_r$: 21.28 min (Method A) and 17.40 min (Method B).

Diastereomer-2: $^1$H NMR (400 MHz, methanol-$d_4$) δ=7.42 (d, J=7.5 Hz, 4H), 7.13 (d, J=8.5 Hz, 3H), 6.44 (br. s., 1H), 4.82-4.71 (m, 1H), 4.27 (d, J=6.5 Hz, 1H), 3.15 (dt, J=3.4, 1.6 Hz, 2H), 3.08-2.92 (m, 2H), 2.83-2.66 (m, 2H), 2.32 (s, 3H), 2.15-1.85 (m, 4H), 1.82-1.57 (m, 4H), 1.52 (d, J=6.5 Hz, 3H), 1.00 (d, J=5.0 Hz, 12H), 0.96-0.80 (m, 15H); LCMS (ES): m/z 777.2 [M+H]+; HPLC T$_r$: 19.88 min (Method A) and 17.44 min (Method B).

Example 35

(3S)-2-Methyl-1-(((S)-2-(phosphonooxy)propanoyl)oxy)propyl 3-(4-(diisobutylamino)-3-(3-(p-tolyl)ureido)phenyl)pentanoate

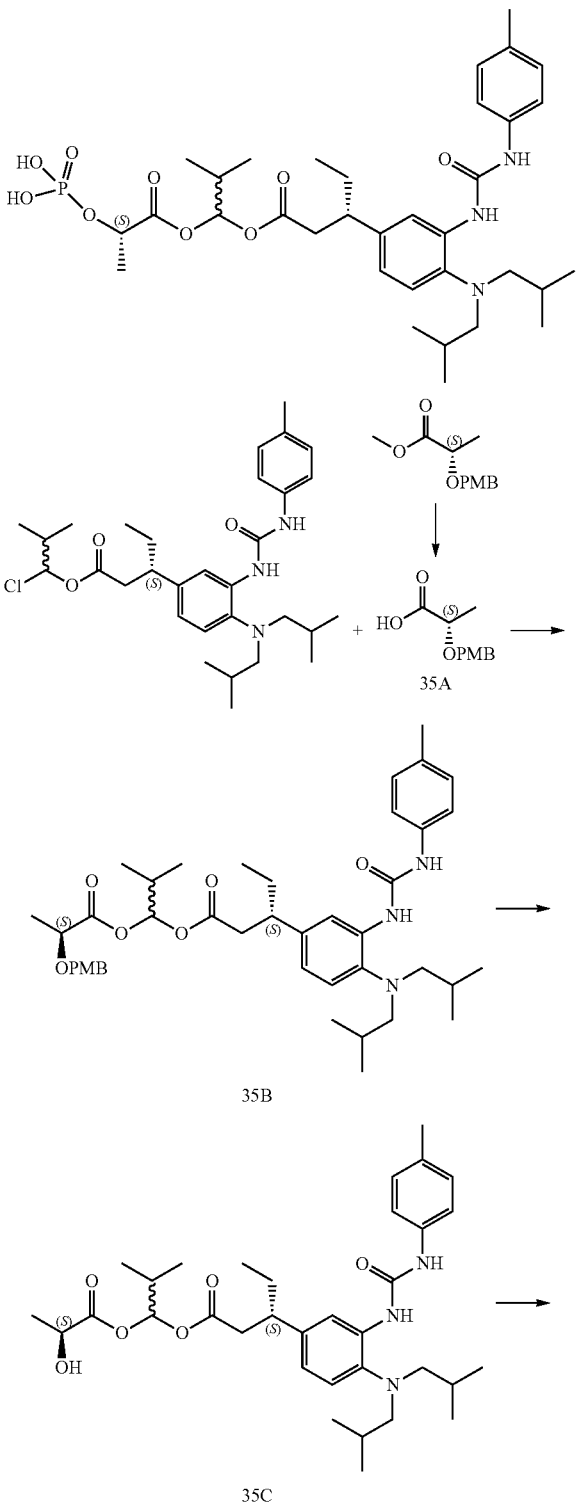

149

-continued

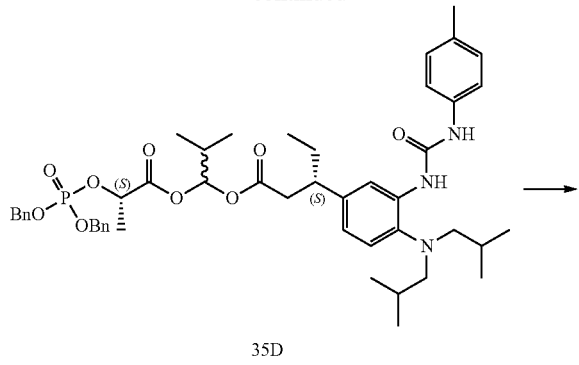

35D

Example 35

35A: (S)-2-((4-Methoxybenzyl)oxy)propanoic Acid

To a stirred mixture of (S)-methyl 2-((4-methoxybenzyl)oxy)propanoate (5 g, 18.95 mmol) in THF (15 mL) and water (15 mL), was added LiOH (0.908 g, 37.9 mmol). The reaction mixture was stirred at room temperature for 5 h and then concentrated to remove organic solvents under vacuum. The remaining aqueous layer was diluted with water, washed with DCM (50 mL), acidified using 1.5 N HCl at 0° C. and extracted with ethyl acetate (2*100 mL). The combined organic layer was washed with brine, dried over anhydrous sodium sulfate, filtered and concentrated under vacuum to get (S)-2-((4-methoxybenzyl)oxy)propanoic acid (3.5 g, 16.65 mmol, 88%) as a colorless liquid. $^1$H NMR (400 MHz, DMSO-$d_6$) δ=7.29-7.21 (m, 2H), 6.95-6.84 (m, 2H), 4.51 (d, J=11.0 Hz, 1H), 4.32 (d, J=11.0 Hz, 1H), 3.94 (q, J=6.7 Hz, 1H), 1.28 (d, J=7.0 Hz, 3H); LCMS (ES): m/z 209.2 [M−H]$^+$.

35B: (3S)-1-(((S)-2-((4-Methoxybenzyl)oxy)propanoyl)oxy)-2-methylpropyl 3-(4-(diisobutylamino)-3-(3-(p-tolyl)ureido)phenyl)pentanoate (S)-2-((4-Methoxybenzyl)oxy)propanoic acid (0.865 g, 4.12 mmol) was dissolved in DMF (15 mL). Cesium carbonate (1.341 g, 4.12 mmol) was added. After being stirred at room temperature for 10 min, were added (3S)-1-chloro-2-methylpropyl 3-(4-(diisobutylamino)-3-(3-(p-tolyl)ureido)phenyl)pentanoate (1.12 g, 2.058 mmol) and sodium iodide (0.309 g, 2.058 mmol). The reaction mixture was heated at 70° C. for 8 h. The reaction mixture was concentrated under high vacuum to get brownish residue. The crude product was purified using RP HPLC (Luna C18 [250×30 mm]; mobile phase A: 10 mM formic acid in water; mobile phase B: acetonitrile; flow rate: 18 mL/min.). The fraction was concentrated using high vacuum at 30° C. The residue was dissolved in a mixture of acetonitrile and water, frozen and lyophilized for 12 h to get (3S)-1-(((S)-2-((4-methoxybenzyl)oxy)propanoyl)oxy)-2-methylpropyl 3-(4-(diisobutylamino)-3-(3-(p-tolyl)ureido)phenyl)pentanoate (0.6 g, 0.836 mmol, 40.6%) as a white solid. $^1$H NMR (300 MHz, methanol-$d_4$) δ=7.88 (dd, J=5.7, 1.9 Hz, 1H), 7.37-7.22 (m, 4H), 7.18-7.07 (m, 3H), 6.94-6.79 (m, 3H), 6.55 (dd, J=4.9, 4.2 Hz, 1H), 4.61-4.48 (m, 1H), 4.34 (dd, J=13.8, 11.1 Hz, 1H), 4.08-3.89 (m, 1H), 3.82-3.73 (m, 3H), 2.94 (d, J=5.7 Hz, 1H), 2.74-2.59 (m, 6H), 2.31 (s, 3H), 2.01-1.85 (m, 1H), 1.69 (tt, J=13.4, 7.0 Hz, 4H), 1.31 (dd, J=6.8, 4.2 Hz, 3H), 0.97-0.65 (m, 21H); LCMS (ES): m/z 718.4 [M+H]$^+$.

150

35C: (3S)-1-(((S)-2-Hydroxypropanoyl)oxy)-2-methylpropyl 3-(4-(diisobutylamino)-3-(3-(p-tolyl)ureido)phenyl)pentanoate To a stirred solution of (3S)-1-(((S)-2-((4-methoxybenzyl)oxy)propanoyl)oxy)-2-methylpropyl 3-(4-(diisobutylamino)-3-(3-(p-tolyl)ureido)phenyl)pentanoate (600 mg, 0.836 mmol) in 2-propanol (10 mL), Pd/C (10%; 889 mg, 0.418 mmol) was added. After being stirred at room temperature under hydrogen atm for 2 h, the reaction mixture was filtered through a pad of celite, which was washed with ethyl acetate. The filtrate was concentrated under high vacuum at 30° C. to get the colorless gum. The crude product was purified using RP HPLC (Kinetex Biphenyl [250×21 mm]; mobile phase A: 10 mM formic acid in water; mobile phase B: acetonitrile; flow rate: 18 mL/min.). The fraction was concentrated using high vacuum at 30° C. The residue was dissolved in a mixture of acetonitrile and water, frozen and lyophilized for 12 h to get the product (3S)-1-(((S)-2-hydroxypropanoyl)oxy)-2-methylpropyl 3-(4-(diisobutylamino)-3-(3-(p-tolyl)ureido) phenyl)pentanoate (0.3 g, 0.492 mmol, 58.8%) as a colorless gum. $^1$H NMR (400 MHz, methanol-$d_4$) δ=7.87 (dd, J=3.8, 2.3 Hz, 1H), 7.36-7.26 (m, 2H), 7.20-7.07 (m, 3H), 6.87 (dt, J=8.0, 1.8 Hz, 1H), 6.57 (dd, J=15.3, 4.8 Hz, 1H), 4.28-4.14 (m, 1H), 2.95 (m, 1H), 2.76-2.59 (m, 6H), 2.32 (s, 3H), 2.00-1.85 (m, 1H), 1.70 (dt, J=13.4, 6.6 Hz, 4H), 1.34 (dd, J=15.6, 7.0 Hz, 3H), 0.91-0.88 (m, 15H), 0.87-0.82 (m, 6H); LCMS (ES): m/z 598.3 [M+H]$^+$.

35D: (3S)-1-(((S)-2-((bis(Benzyloxy)phosphoryl)oxy)propanoyl)oxy)-2-methylpropyl 3-(4-(diisobutylamino)-3-(3-(p-tolyl)ureido)phenyl)pentanoate To a stirred solution of ((3S)-1-(((S)-2-hydroxypropanoyl)oxy)-2-methylpropyl 3-(4-(diisobutylamino)-3-(3-(p-tolyl)ureido)phenyl)pentanoate (0.23 g, 0.385 mmol) in DCM (5 mL), dibenzyl N,N-diisopropylphosphoramidite (0.259 mL, 0.770 mmol), 1H-tetrazole (0.45 M in acetonitrile) (1.710 mL, 0.770 mmol) and phenyl isocyanate (0.050 g, 0.423 mmol) were added. The reaction mixture was stirred at room temperature for 8 h and cooled to 0° C., to which was added $H_2O_2$ (2.028 ml, 66.2 mmol). After being stirred for 10 min, the reaction mixture was partitioned between ethyl acetate and water. The organic layer was washed with brine, dried over anhydrous sodium sulfate, filtered and concentrated under vacuum to get colorless oil. The crude product was purified using RP-HPLC (Kinetex C18 [150×20 mm]; mobile phase A: 10 mM formic acid in water; mobile phase B: acetonitrile; flow rate: 16 mL/min.). The fraction was concentrated using high vacuum at 30° C. The residue was dissolved in a mixture of acetonitrile and water, frozen and lyophilized for 12 h to get (3S)-1-(((S)-2-((bis(benzyloxy)phosphoryl)oxy) propanoyl)oxy)-2-methylpropyl 3-(4-(diisobutylamino)-3-(3-(p-tolyl)ureido) phenyl) pentanoate (0.2 g, 0.221 mmol, 57.6%) as a white solid. $^1$H NMR (400 MHz, methanol-$d_4$) δ=7.86 (d, J=2.0 Hz, 1H), 7.42-7.27 (m, 12H), 7.17-7.08 (m, 3H), 6.83 (td, J=8.0, 2.0 Hz, 1H), 6.63-6.50 (m, 1H), 5.17-5.04 (m, 4H), 4.87-4.74 (m, 1H), 3.00-2.83 (m, 1H), 2.75-2.55 (m, 6H), 2.31 (s, 3H), 2.00-1.82 (m, 1H), 1.75-1.57 (m, 4H), 1.49-1.33 (m, 3H), 0.94-0.85 (m, 15H), 0.84-0.74 (m, 6H); LCMS (ES): m/z 858.5 [M+H]$^+$.

Example 35

To a stirred solution of (3S)-1-(((S)-2-((bis(benzyloxy)phosphoryl)oxy) propanoyl)oxy)-2-methylpropyl 3-(4-(diisobutylamino)-3-(3-(p-tolyl)ureido)phenyl) pentanoate (0.2 g, 0.233 mmol) in 2-propanol (5 mL), Pd/C (10%; 0.198 g, 0.093 mmol) was added. The reaction mixture was stirred at room temperature under hydrogen atm for 2 h. The reaction mixture was filtered through a pad of celite, which was washed with ethyl acetate. The filtrate was concentrated under high vacuum at 30° C. to get the colorless gum. The crude product was purified using RP-HPLC (Kinetex Biphenyl [250×21 mm]; mobile phase A: 10 mM formic acid in water; mobile phase B: acetonitrile; flow rate: 18 mL/min.). The fraction was concentrated using high vacuum at 30° C. The residue was dissolved in a mixture of acetonitrile and water, frozen and lyophilized for 12 h to get the product (3S)-2-methyl-1-(((S)-2-(phosphonooxy)propanoyl)oxy) propyl 3-(4-(diisobutylamino)-3-(3-(p-tolyl)ureido)phenyl) pentanoate (0.125 g, 0.178 mmol, 76%) as a white solid (mixture of diastereomers). $^1$H NMR (400 MHz, methanol-d$_4$) δ=7.82 (br. s., 1H), 7.39-7.27 (m, 2H), 7.25-7.08 (m, 3H), 6.89 (d, J=7.5 Hz, 1H), 6.55 (d, J=5.0 Hz, 1H), 4.80-4.68 (m, 1H), 3.03-2.88 (m, 1H), 2.82-2.55 (m, 6H), 2.32 (s, 3H), 2.02-1.88 (m, 1H), 1.82-1.60 (m, 4H), 1.44 (dd, J=14.8, 6.8 Hz, 3H), 0.95-0.86 (m, 15H), 0.87-0.82 (m, 6H); LCMS (ES): m/z 678.2 [M+H]$^+$. HPLC T$_r$: 18.51, 19.23 min (Method A) and 14.89, 15.02 min (Method B).

Example 36

(S)-(2-((S)—N-Methyl-2-(phosphonooxy)propanamido)acetoxy)methyl 3-(4-(diisobutylamino)-3-(3-(p-tolyl)ureido)phenyl)pentanoate

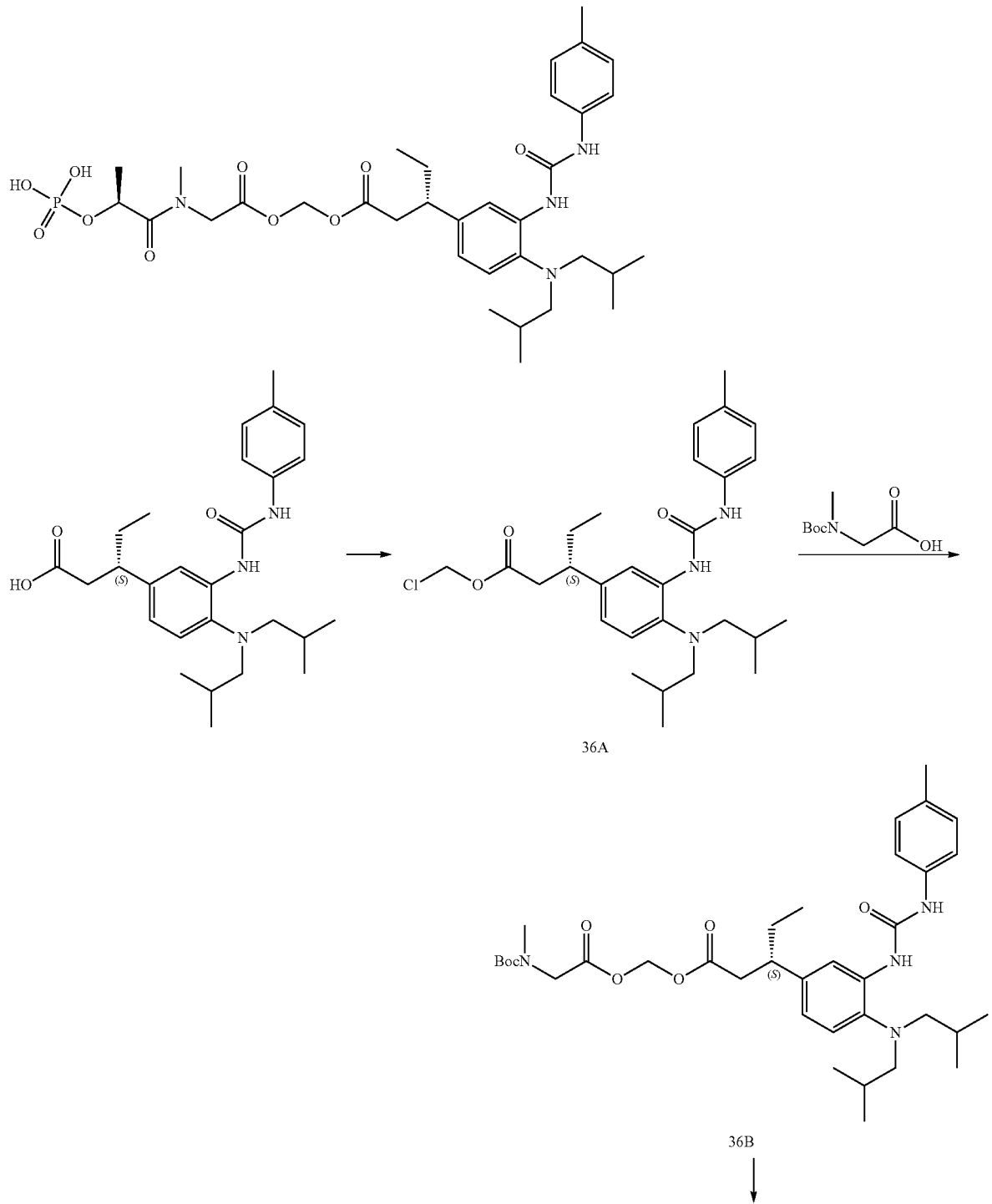

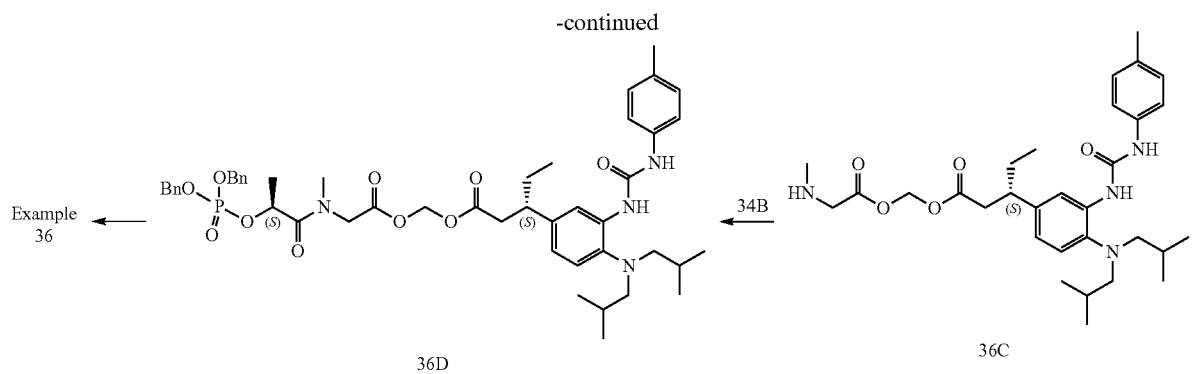

36A: (S)-Chloromethyl 3-(4-(diisobutylamino)-3-(3-(p-tolyl)ureido)phenyl)pentanoate To a mixture of (S)-3-(4-(diisobutylamino)-3-(3-(p-tolyl)ureido)phenyl)pentanoic acid (3 g, 6.61 mmol) in DCM (10 mL) and water (10 mL), were added sodium bicarbonate (2.222 g, 26.5 mmol) and tetrabutylammonium hydrogen sulfate (0.449 g, 1.323 mmol). The reaction mixture was stirred at 0° C. for 15 min. chloromethyl chlorosulfate (1.338 mL, 13.23 mmol) was added. The reaction mixture was brought to room temperature and stirred for 8 h. The reaction mixture was diluted with DCM (100 mL). The organic layer was washed with water (3×100 mL) and brine, dried over anhydrous sodium sulfate, filtered and concentrated under vacuum to get as colorless liquid. The crude material was purified by CombiFlash (ELSD) (silica gel 60-120 mesh; 35% ethyl acetate in hexane as eluent) to get (S)-chloromethyl 3-(4-(diisobutylamino)-3-(3-(p-tolyl)ureido)phenyl)pentanoate (2.6 g, 4.92 mmol, 74.4%) as a white solid. $^1$H NMR (300 MHz, methanol-$d_4$) δ=7.83 (d, J=1.9 Hz, 1H), 7.32 (d, J=8.7 Hz, 2H), 7.20-7.08 (m, 3H), 6.87 (dd, J=8.1, 1.7 Hz, 1H), 5.70 (d, J=0.8 Hz, 2H), 3.07-2.91 (m, 1H), 2.81-2.59 (m, 6H), 2.32 (s, 3H), 1.80-1.57 (m, 4H), 0.96-0.77 (m, 15H); LCMS (ES): m/z 504.3 [M+H]$^+$.

36B: (S)-(2-((tert-Butoxycarbonyl)(methyl)amino)acetoxy)methyl 3-(4-(diisobutylamino)-3-(3-(p-tolyl)ureido)phenyl)pentanoate Boc-SAR-OH (0.226 g, 1.195 mmol) was dissolved in DMF (5 mL). Cesium carbonate (0.389 g, 1.195 mmol) was added. After being stirred at room temperature for 5 min, were added (S)-chloromethyl 3-(4-(diisobutylamino)-3-(3-(p-tolyl)ureido)phenyl)pentanoate (0.3 g, 0.598 mmol) and sodium iodide (0.090 g, 0.598 mmol). The reaction mixture was stirred at room temperature for 8 h and concentrated under high vacuum to get brownish residue. The residue was dissolved in ethyl acetate. The solution was washed with water and brine, dried over anhydrous sodium sulfate, filtered and concentrated to get colorless semi-solid. The crude product was purified using RP-HPLC (Kinetex Biphenyl [250×21 mm]; mobile phase A: 10 mM formic acid in water; mobile phase B: acetonitrile; flow rate: 18 mL/min.). The fraction was concentrated using high vacuum at 30° C. The residue was dissolved in a mixture of acetonitrile and water, frozen and lyophilized for 12 h to get (S)-(2-((tert-butoxycarbonyl)(methyl)amino)acetoxy)methyl 3-(4-(diisobutylamino)-3-(3-(p-tolyl)ureido)phenyl)pentanoate (0.32 g, 0.489 mmol, 82%) as a white solid. $^1$H NMR (400 MHz, methanol-$d_4$) δ=7.88-7.76 (m, 1H), 7.32 (d, J=8.5 Hz, 2H), 7.19-7.06 (m, 3H), 6.87 (d, J=8.5 Hz, 1H), 5.85-5.68 (m, 2H), 4.01-3.88 (m, 2H), 3.04-2.94 (m, 1H), 2.92-2.88 (m, 3H), 2.78-2.62 (m, 6H), 2.32 (s, 3H), 1.80-1.59 (m, 4H), 1.49-1.40 (m, 9H), 0.89 (d, J=6.5 Hz, 12H), 0.83 (t, J=7.3 Hz, 3H); LCMS (ES): m/z 655.5 [M+H]$^+$.

36C: (S)-(2-(Methylamino)acetoxy)methyl 3-(4-(diisobutylamino)-3-(3-(p-tolyl)ureido)phenyl)pentanoate Hydrochloride To (S)-(2-((tert-butoxycarbonyl)(methyl)amino)acetoxy)methyl 3-(4-(diisobutylamino)-3-(3-(p-tolyl)ureido)phenyl)pentanoate (0.4 g, 0.611 mmol) at 0° C., 4M solution of hydrogen chloride in dioxane (5 mL, 165 mmol) was added. The reaction mixture was brought to room temperature and stirred for 2 h. The reaction mixture was concentrated under high vacuum. The residue was triturated with diethyl ether to get (S)-(2-(methylamino)acetoxy)methyl 3-(4-(diisobutylamino)-3-(3-(p-tolyl)ureido)phenyl)pentanoate hydrochloride (0.36 g, 0.609 mmol, 100%) as a white solid. $^1$H NMR (300 MHz, methanol-$d_4$) δ=7.72 (br. s., 1H), 7.48-7.07 (m, 6H), 5.95-5.69 (m, 2H), 4.06 (s, 2H), 3.50 (d, J=7.2 Hz, 3H), 3.10 (br. s., 1H), 2.99-2.61 (m, 6H), 2.33 (s, 3H), 1.90-1.58 (m, 4H), 1.36-0.93 (m, 12H), 0.91-0.73 (m, 3H); LCMS (ES): m/z 555.4 [M+H]$^+$.

36D: (S)-(2-((S)-2-((bis(Benzyloxy)phosphoryl)oxy)-N-methylpropanamido)acetoxy) methyl 3-(4-(diisobutylamino)-3-(3-(p-tolyl)ureido)phenyl)pentanoate To a stirred solution of (S)-(2-(methylamino)acetoxy)methyl 3-(4-(diisobutylamino)-3-(3-(p-tolyl)ureido)phenyl)pentanoate hydrochloride (280 mg, 0.426 mmol) in DMF (5 mL), HATU (243 mg, 0.639 mmol), (S)-2-((bis(benzyloxy)phosphoryl) oxy)propanoic acid (224 mg, 0.639 mmol) and DIPEA (0.372 mL, 2.131 mmol) were added. After being stirred at 0° C. for 30 min, the reaction mixture was diluted in water and extracted with ethyl acetate. The organic layer was washed with brine, dried over anhydrous sodium sulfate, filtered and concentrated to get brownish semi-solid. The material was purified using RP HPLC (Kinetex C18 [150×21.2 mm]; mobile phase A: 10 mM formic acid in water; mobile phase B: acetonitrile; flow rate: 17 mL/min.). The fraction was concentrated using high vacuum at 30° C. The residue was dissolved in a mixture of acetonitrile and water, frozen and lyophilized for 12 h to get the product (S)-(2-((S)-2-((bis(benzyloxy)phosphoryl)oxy)-N methylpropanamido)acetoxy)methyl 3-(4-(diisobutylamino)-3-(3-(p-tolyl)ureido)phenyl)pentanoate (230 mg, 0.259 mmol, 60.8%) as a white solid. $^1$H NMR (400 MHz, methanol-$d_4$) δ=7.88-7.76 (m, 1H), 7.41-7.35 (m, 10H), 7.32 (d, J=8.0 Hz, 2H), 7.18-7.10 (m, 3H), 6.86 (dd, J=8.5, 2.0 Hz, 1H), 5.75-5.67 (m, 2H), 5.30-5.23 (m, 1H), 5.11-5.06 (m, 4H), 4.23 (d, J=17.1 Hz, 1H), 3.99 (d, J=17.6 Hz, 1H), 3.05 (s, 3H), 2.91 (s, 1H), 2.72-2.61 (m, 6H), 2.31 (s, 3H), 1.76-1.58 (m, 4H), 1.46-1.36 (m, 3H), 0.89 (d, J=6.5 Hz, 12H), 0.82 (t, J=7.3 Hz, 3H); LCMS (ES): m/z 887.5 [M+H]$^+$.

Example 36

To a stirred solution of (S)-(2-((S)-2-((bis(benzyloxy)phosphoryl)oxy)-N-methylpropanamido)acetoxy)methyl 3-(4-(diisobutylamino)-3-(3-(p-tolyl)ureido)phenyl) pentanoate (0.23 g, 0.259 mmol) in 2-propanol (5 mL), Pd/C (10%; 0.221 g, 0.104 mmol) was added and the reaction mixture was stirred room temperature under hydrogen atm for 2 h. The reaction mixture was filtered through a pad of celite, which was washed with ethyl acetate. The filtrate was concentrated under high vacuum at 30° C. to get the colorless gum. The crude product was purified using RP-HPLC (Luna C18 [250×30 mm]; mobile phase A: 10 mM formic acid in water; mobile phase B: acetonitrile; flow rate: 25 mL/min.). The fraction was concentrated using high vacuum at 30° C. The residue was dissolved in a mixture of acetonitrile and water, frozen and lyophilized for 12 h to get the product (S)-(2-((S)—N-methyl-2-(phosphonooxy)propanamido)acetoxy) methyl 3-(4-(diisobutylamino)-3-(3-(p-tolyl)ureido)phenyl)pentanoate (131 mg, 0.178 mmol, 68.8%) as a white solid. $^1$H NMR (400 MHz, methanol-$d_4$) δ=7.88-7.76 (m, 1H), 7.37-7.28 (m, 2H), 7.22-7.07 (m, 3H), 6.89 (dd, J=8.0, 2.0 Hz, 1H), 5.84-5.63 (m, 2H), 5.13 (dd, J=8.3, 6.8 Hz, 1H), 4.41-4.21 (m, 1H), 3.98 (d, J=17.6 Hz, 1H), 3.22 (s, 3H), 3.01-2.87 (m, 1H), 2.82-2.57 (m, 6H), 2.32 (s, 3H), 1.81-1.56 (m, 4H), 1.43 (d, J=6.5 Hz, 3H), 0.90 (d, J=6.5 Hz, 12H), 0.84 (t, J=7.3 Hz, 3H); LCMS (ES): m/z 705.5 [M+H]$^+$. HPLC T$_r$: 16.48 min (Method A) and 13.33 min (Method B).

Example 37

(((S)-3-(4-(Diisobutylamino)-3-(3-(p-tolyl)ureido)phenyl)pentanoyl)oxy)methyl trans-4-(phosphonooxy)cyclohexanecarboxylate

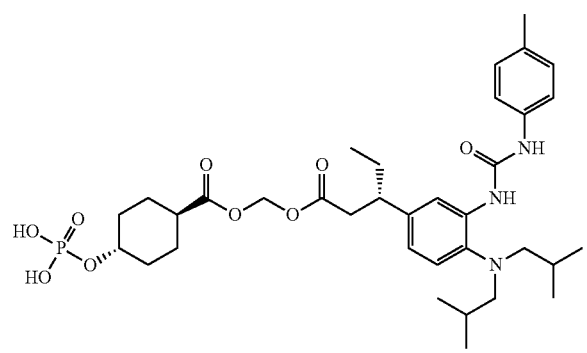

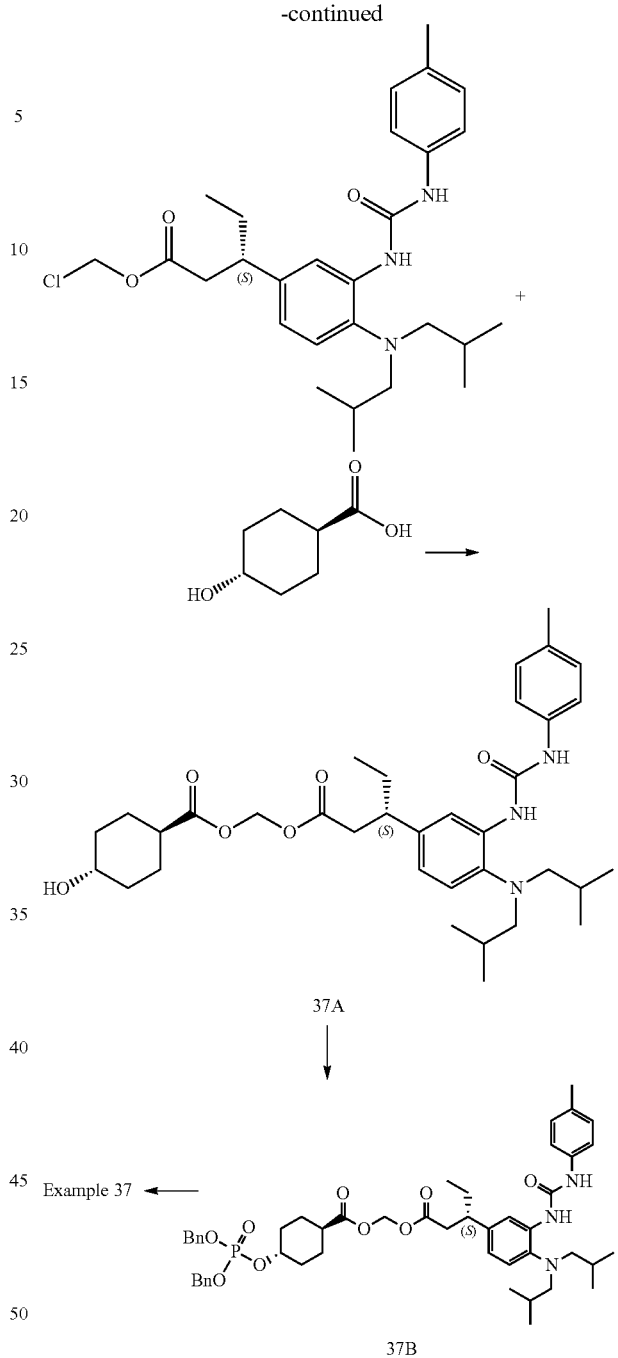

37A: (((S)-3-(4-(Diisobutylamino)-3-(3-(p-tolyl)ureido)phenyl)pentanoyl)oxy)methyl trans-4-hydroxycyclohexanecarboxylate To a solution of trans-4-hydroxycyclohexanecarboxylic acid (0.287 g, 1.992 mmol) in DMF (6 mL), cesium carbonate (0.649 g, 1.992 mmol) was added. After being stirred at room temperature for 5 min, were added (S)-chloromethyl 3-(4-(diisobutylamino)-3-(3-(p-tolyl)ureido)phenyl)pentanoate (0.5 g, 0.996 mmol) and sodium iodide (0.149 g, 0.996 mmol). After being stirred at room temperature for 8 h, the reaction mixture was concentrated under high vacuum to get brownish residue, which was partitioned between water and ethyl acetate. The organic layer was washed with brine, dried over anhydrous sodium sulfate, filtered and concentrated to get brownish gum. The crude product was purified using RP HPLC (Kinetex C18 [150×21.2 mm]; mobile phase A: 10 mM formic acid in water in water; mobile phase B: acetonitrile; flow rate: 18 mL/min.). The fraction was concentrated using high vacuum at 30° C. The residue was dissolved in a mixture of acetonitrile and water, frozen and lyophilized for 12 h to get (((S)-3-(4-(diisobutylamino)-3-(3-(p-tolyl)ureido)phenyl)pentanoyl)oxy)methyl trans-4-hydroxycyclohexanecarboxylate (0.37 g, 0.607 mmol, 60.9%) as a white solid. $^1$H NMR (300 MHz, methanol-d$_4$) δ=7.84 (d, J=1.9 Hz, 1H), 7.35-7.29 (m, 2H), 7.14 (dd, J=7.9, 5.7 Hz, 3H), 6.86 (dd, J=8.3, 1.9 Hz, 1H), 5.68 (q, J=5.7 Hz, 2H), 3.57-3.45 (m, 1H), 3.01-2.89 (m, 1H), 2.76-2.59 (m, 6H), 2.34-2.22 (m, 4H), 1.98 (d, J=10.6 Hz, 4H), 1.79-1.60 (m, 4H), 1.54-1.37 (m, 2H), 1.29 (t, J=11.0 Hz, 2H), 0.94-0.86 (m, 12H), 0.82 (t, J=7.4 Hz, 3H); LCMS (ES): m/z 610.4 [M+H]$^+$.

37B: (((S)-3-(4-(Diisobutylamino)-3-(3-(p-tolyl)ureido)phenyl)pentanoyl)oxy)methyl trans-4-((bis(benzyloxy)phosphoryl)oxy)cyclohexanecarboxylate A solution of (((S)-3-(4-(diisobutylamino)-3-(3-(p-tolyl)ureido)phenyl)pentanoyl) oxy)methyl trans-4-hydroxycyclohexanecarboxylate (0.3 g, 0.492 mmol) in DCM (5 mL), were added dibenzyl diisopropylphosphoramidite (0.331 mL, 0.984 mmol), 1H-tetrazole (2.187 mL, 0.984 mmol) and phenyl isocyanate (0.059 g, 0.492 mmol). The reaction mixture was stirred at room temperature for 8 h. The reaction was cooled to 0° C., to which was added H$_2$O$_2$ (0.030 mL, 0.984 mmol). After being stirred for 10 min, the reaction mixture was partitioned between ethyl acetate (75 mL) and water (50 mL). The organic layer was washed with brine, dried over anhydrous sodium sulfate, filtered and concentrated under vacuum to get colorless oil. The crude material was purified by CombiFlash (silica gel 60-120 mesh; 30% ethyl acetate in hexane as eluent) to get (((S)-3-(4-(diisobutylamino)-3-(3-(p-tolyl)ureido)phenyl)pentanoyl)oxy)methyl trans-4-((bis(benzyloxy)phosphoryl)oxy)cyclohexanecarboxylate (0.33 g, 0.360 mmol, 73.2%) as a colorless brownish gum. LCMS (ES): m/z 870.5 [M+H]$^+$.

Example 37

To a stirred solution of (((S)-3-(4-(diisobutylamino)-3-(3-(p-tolyl)ureido)phenyl) pentanoyl)oxy)methyl trans-4-((bis(benzyloxy)phosphoryl)oxy)cyclohexanecarboxylate (0.32 g, 0.368 mmol) in 2-propanol (8 mL), Pd/C (10%; 0.196 g, 0.184 mmol) was added and the reaction mixture was stirred room temperature under hydrogen atm for 1 h. The reaction mixture was filtered through a pad of celite, which was washed with ethyl acetate. The filtrate was concentrated under high vacuum at 30° C. to get the colorless gum. The crude product was purified using RP HPLC (Kinetex C18 [250×21 mm]; mobile phase A: 10 mM amm0nium acetate in water; mobile phase B: acetonitrile; flow rate: 17 mL/min.) The fraction was concentrated using high vacuum at 30° C. The residue was dissolved in a mixture of acetonitrile and water, frozen and lyophilized for 12 h to get the product (((S)-3-(4-(diisobutylamino)-3-(3-(p-tolyl)ureido)phenyl)pentanoyl)oxy) methyl trans-4-(phosphonooxy)cyclohexanecarboxylate (35 mg, 0.050 mmol, 13.59%) as a white solid. $^1$H NMR (400 MHz, methanol-d$_4$) δ=7.85-7.69 (m, 1H), 7.44 (d, J=8.0 Hz, 3H), 7.26 (d, J=8.5 Hz, 3H), 7.13 (br. s., 1H), 5.79 (q, J=6.0 Hz, 2H), 4.39-4.24 (m, 1H), 3.16-2.97 (m, 4H), 2.92-2.71 (m, 3H), 2.54-2.41 (m, 4H), 2.32-2.09 (m, 4H), 2.02-1.68 (m, 5H), 1.66-1.54 (m, 4H), 1.05 (d, J=6.5 Hz, 12H), 0.94 (t, J=7.3 Hz, 3H); LCMS (ES): m/z 690.4 [M+H]$^+$; HPLC T$_r$: 11.20 min (Method A) and 10.01 min (Method B).

Example 38

(S)-(2-(N-Methyl-4-(phosphonooxy)butanamido)acetoxy)methyl 3-(4-(diisobutylamino)-3-(3-(p-tolyl)ureido)phenyl)pentanoate

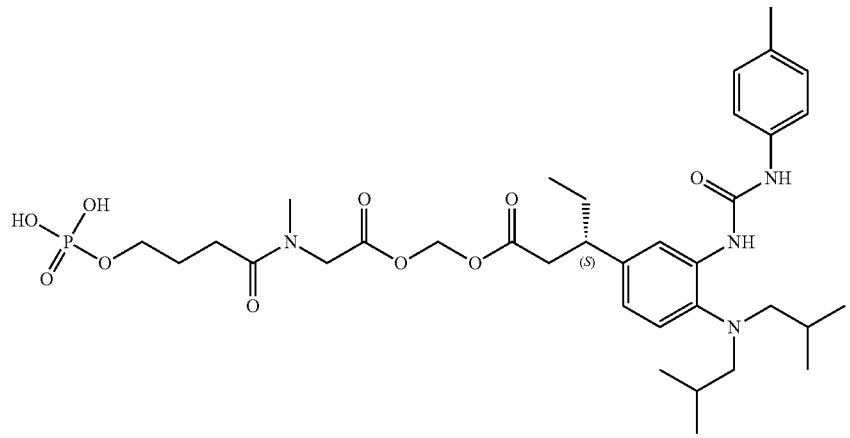

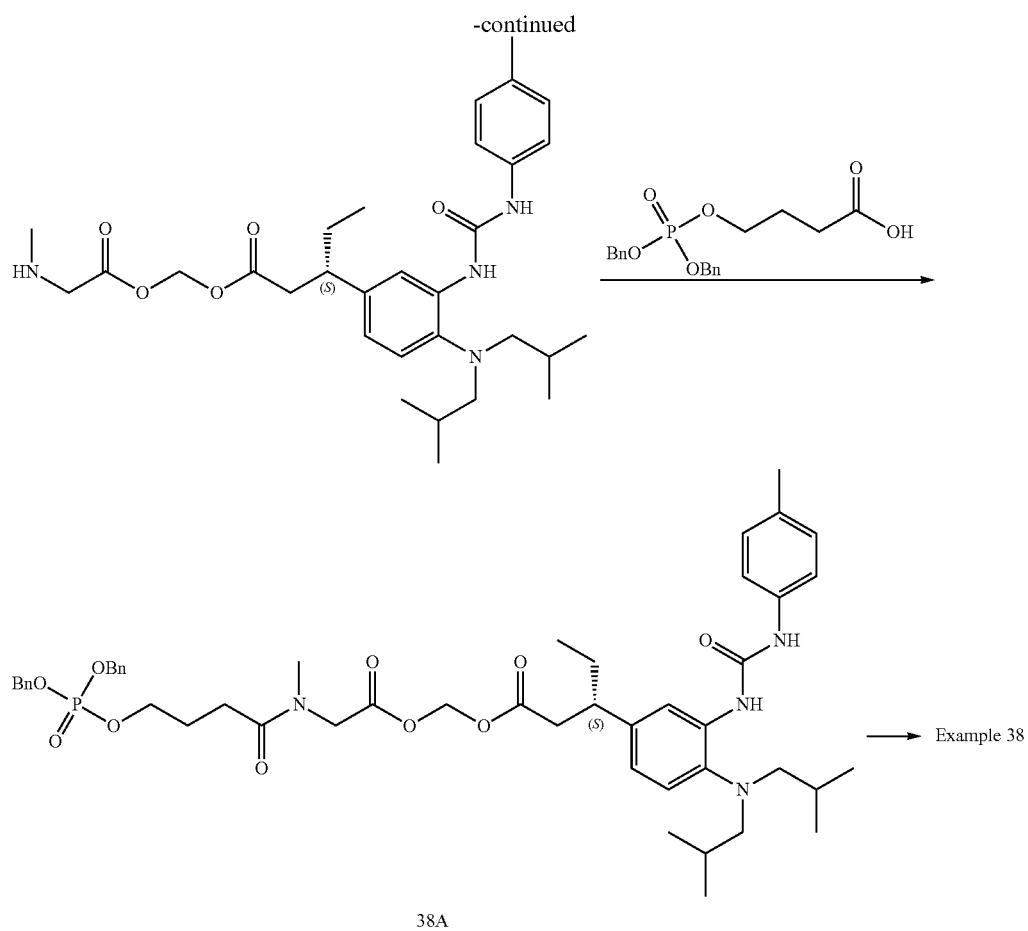

38A

38A: (S)-(2-(4-((bis(Benzyloxy)phosphoryl)oxy)-N-methylbutanamido)acetoxy)methyl 3-(4-(diisobutylamino)-3-(3-(p-tolyl)ureido)phenyl)pentanoate To a stirred solution of (S)-(2-(methylamino)acetoxy)methyl 3-(4-(diisobutylamino)-3-(3-(P-tolyl)ureido)phenyl)pentanoate hydrochloride (250 mg, 0.381 mmol) in DMF (8 mL), were added HATU (217 mg, 0.571 mmol), 4-((bis(benzyloxy) phosphoryl)oxy)butanoic acid (277 mg, 0.761 mmol) and DIPEA (0.332 mL, 1.903 mmol). The reaction mixture was stirred at 0° C. for 30 min. The reaction mixture was partitioned between ethyl acetate and water. The organic layer was washed with brine, dried over anhydrous sodium sulfate, filtered and concentrated to get brownish gum. The material was purified using RP HPLC (Kinetex C18 [250×21 mm]; mobile phase A: 10 mM amm0nium acetate in water; mobile phase B: acetonitrile; flow rate: 17 mL/min.). The fraction was concentrated using high vacuum at 30° C. The residue was dissolved in a mixture of acetonitrile and water, frozen and lyophilized for 12 h to get the product (S)-(2-(4-((bis(benzyloxy)phosphoryl)oxy)-N-methylbutanamido) acetoxy)methyl 3-(4-(diisobutylamino)-3-(3-(p-tolyl) ureido)phenyl)pentanoate (220 mg, 0.232 mmol, 60.9%) as a white solid. $^1$H NMR (400 MHz, methanol-$d_4$) δ=7.85-7.81 (m, 1H), 7.41-7.34 (m, 10H), 7.33-7.29 (m, 2H), 7.19-7.10 (m, 3H), 6.89-6.83 (m, 1H), 5.74-5.68 (m, 2H), 5.09-5.02 (m, 4H), 4.18-4.02 (m, 4H), 3.01 (s, 3H), 2.95 (d, J=6.0 Hz, 1H), 2.90 (s, 1H), 2.76-2.64 (m, 5H), 2.44 (t, J=7.3 Hz, 1H), 2.35-2.26 (m, 4H), 1.95-1.87 (m, 2H), 1.77-1.58 (m, 4H), 0.93-0.85 (m, 12H), 0.85-0.77 (m, 3H); LCMS (ES): m/z 901.6 [M+H]$^+$.

Example 38

To a stirred solution of (S)-(2-(4-((bis(benzyloxy)phosphoryl)oxy)-N-methylbutanamido)acetoxy)methyl 3-(4-(diisobutylamino)-3-(3-(p-tolyl)ureido)phenyl) pentanoate (0.18 g, 0.200 mmol) in 2-propanol (8 mL), was added Pd/C (10%; 0.106 g, 0.100 mmol) and the reaction mixture was stirred room temperature under hydrogen atm. for 1 h. The reaction mixture was filtered through a pad of celite, which was washed with ethyl acetate. The filtrate was concentrated under high vacuum at 30° C. to get the colorless gum. The crude product was purified using RP HPLC (Kinetex C18 [150×20 mm]; mobile phase A: 10 mM ammonium acetate in water; mobile phase B: acetonitrile; flow rate: 17 mL/min.). The fraction was concentrated using high vacuum at 30° C. The residue was dissolved in a mixture of acetonitrile and water, frozen and lyophilized for 12 h to get the product (S)-(2-(N-methyl-4-(phosphonooxy)butanamido) acetoxy)methyl 3-(4-(diisobutylamino)-3-(3-(p-tolyl) ureido)phenyl)pentanoate (110 mg, 0.147 mmol, 73.7%) as a white solid. $^1$H NMR (400 MHz, methanol-$d_4$) δ=7.81 (d, J=2.5 Hz, 1H), 7.35-7.27 (m, 2H), 7.14 (dd, J=15.8, 8.3 Hz, 3H), 6.86 (dd, J=8.3, 2.3 Hz, 1H), 5.81-5.66 (m, 2H), 4.11 (d, J=1.5 Hz, 2H), 3.96-3.84 (m, 2H), 3.10 (s, 3H), 2.95 (br. s., 1H), 2.89 (s, 1H), 2.78-2.69 (m, 1H), 2.67-2.61 (m, 4H), 2.61-2.52 (m, 2H), 2.30 (s, 3H), 1.94-1.83 (m, 2H), 1.77-1.56 (m, 4H), 0.87 (d, J=6.5 Hz, 12H), 0.82 (t, J=7.3 Hz, 3H); LCMS (ES): m/z 721.4 [M+H]$^+$; HPLC T$_r$: 9.57 min (Method A) and 8.07 min (Method B).

Example 39

(S)-(2-Oxo-5-((phosphonooxy)methyl)-1,3-dioxol-4-yl)methyl 3-(4-(diisobutylamino)-3-(3-(p-tolyl) ureido)phenyl)pentanoate

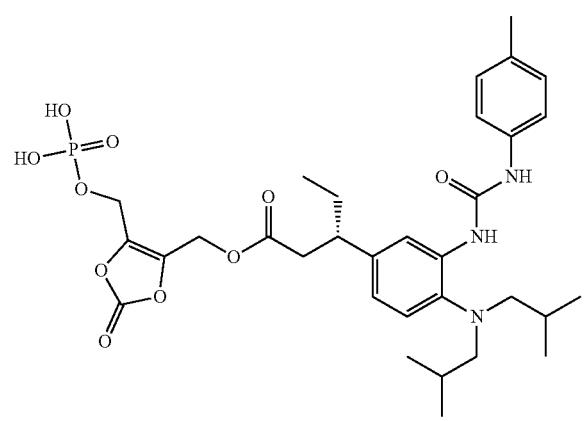

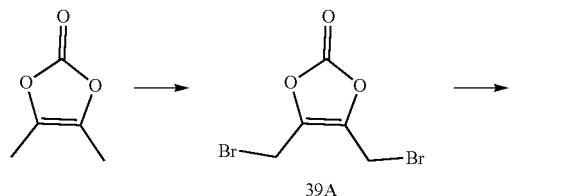

39A

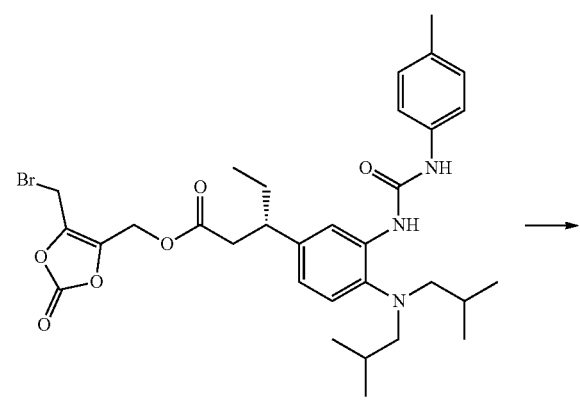

39B

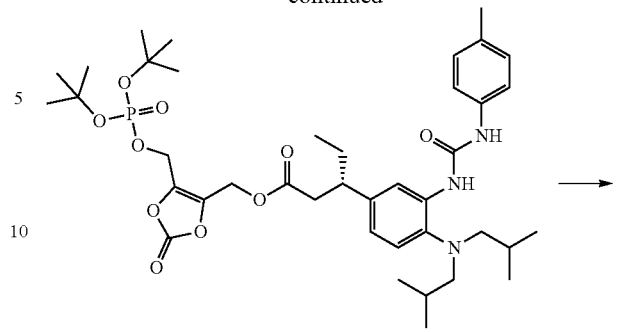

39C

Example 39A

39A: 4,5-bis(Bromomethyl)-1,3-dioxol-2-one

To a stirred solution of 4,5-dimethyl-1,3-dioxol-2-one (4.5 g, 39.4 mmol) in benzene (150 mL), were added NBS (15.44 g, 87 mmol) and AIBN (0.648 g, 3.94 mmol). The reaction mixture was stirred at 110° C. for 2 h under nitrogen atmosphere and subsequently concentrated in vacuo. The residue was dissolved in ethyl acetate (200 mL). The solution was washed with water (2*150 mL) and brine (100 mL), dried over anhydrous sodium sulphate and concentrated in vacuo to get the crude product as a light brownish oil, which was purified by CombiFlash chromatography (60-120 silica gel; 5-55% ethyl acetate in pet. ether as eluent) to afford 4,5-bis (bromomethyl)-1,3-dioxol-2-one (7 g, 66%) as a light yellowish oil. $^1$H NMR (400 MHz, Chloroform-d) δ ppm 4.22 (s, 4H).

39B: (S)-(5-(Bromomethyl)-2-oxo-1,3-dioxol-4-yl)methyl 3-(4-(diisobutylamino)-3-(3-(p-tolyl)ureido)phenyl)pentanoate To a solution of (S)-3-(4-(diisobutylamino)-3-(3-(p-tolyl) ureido)phenyl)pentanoic acid (0.8 g, 1.764 mmol) in anhydrous DMF (5 mL) at 0° C., were added cesium carbonate (1.72 g, 5.29 mmol) and 4,5-bis(bromomethyl)-1,3-dioxol-2-one (0.719 g, 2.65 mmol). After being stirred at room temperature for 2 h under nitrogen atmosphere, the reaction mixture was partitioned between ethyl acetate (25 mL) and water (30 mL). The organic layer was washed with brine (20 mL), dried over anhydrous sodium sulphate and concentrated to get the crude product as a light yellowish solid, which was purified by CombiFlash chromatography (60-120 silica gel; 10-15% ethyl acetate in pet. ether a eluent) to afford (S)-(5-(bromomethyl)-2-oxo-1,3-dioxol-4-yl)methyl 3-(4-(diisobutylamino)-3-(3-(p-tolyl)ureido)phenyl)pentanoate (0.6 g, 52.8%) as a white semi-solid. $^1$H NMR (400 MHz, Methanol-d$_4$) δ ppm 7.80 (d, J=2.01 Hz, 1H), 7.32 (d, J=8.53 Hz, 2H), 7.12 (d, J=8.53 Hz, 3H), 6.84 (dd, J=8.03, 2.01 Hz, 1H), 5.49 (s, 1H), 4.92-5.03 (m, 2H), 4.40 (s, 2H), 2.72-2.83 (m, 1H), 2.67-2.9 (m, 2H), 2.62-2.64 (m, 3H), 2.30 (s, 1H), 2.15 (s, 1H), 1.55-1.82 (m, 3H), 1.22-1.38 (m, 2H), 0.91 (s, 12H), 0.83 (t, J=7.28 Hz, 3H); LCMS (ES): m/z 646.4 [M+H]$^+$.

39C: (S)-(5-((((Di-tert-butoxyphosphoryl)oxy)methyl)-2-oxo-1,3-dioxol-4-yl)methyl 3-(4-(diisobutylamino)-3-(3-(p-tolyl)ureido)phenyl)pentanoate To a solution of (S)-(5-(bromomethyl)-2-oxo-1,3-dioxol-4-yl)methyl 3-(4-(diisobutylamino)-3-(3-(p-tolyl)ureido)

phenyl)pentanoate (550 mg, 0.853 mmol) in anhydrous acetonitrile (5 mL), was added tetra-n-butylammonium di-tert-butylphosphate (771 mg, 1.706 mmol) under nitrogen atmosphere. The reaction mixture was stirred at room temperature for 5 h and partitioned between sodium bicarbonate solution and DCM. The organic layer was washed with water and brine, dried over anhydrous sodium sulphate and concentrated to get crude product as a light yellowish oil, which was purified by CombiFlash chromatography (60-120 silica gel; 10-50% ethyl acetate in pet. ether as eluent) to afford (S)-(5-(((di-tert-butoxyphosphoryl)oxy)methyl)-2-oxo-1,3-dioxol-4-yl)methyl 3-(4-(diisobutylamino)-3-(3-(p-tolyl)ureido)phenyl)pentanoate (380 mg, 0.491 mmol, 57.5%) as an off-white solid. $^1$H NMR (300 MHz, MeOH-d4) δ ppm 7.83 (d, J=1.89 Hz, 1H), 7.32 (d, J=8.31 Hz, 2H), 7.13 (d, J=8.31 Hz, 3H), 6.83 (dd, J=8.12, 2.08 Hz, 1H), 4.96 (d, J=4.15 Hz, 2H), 4.82 (s, 2H), 2.89-3.06 (m, 1H), 2.71-2.81 (m, 1H), 2.61-2.70 (m, 5H), 2.3 (s, 3H), 1.69 (dt, J=13.13, 6.47 Hz, 4H), 1.44-1.53 (m, 18H), 0.90 (d, J=6.42 Hz, 12H), 0.83 (t, J=7.37 Hz, 3H); LCMS (ES): m/z 774.6 [M+H]$^+$.

Example 39

To a solution of (S)-(5-((((di-tert-butoxyphosphoryl)oxy)methyl)-2-oxo-1,3-dioxol-4-yl)methyl 3-(4-(diisobutylamino)-3-(3-(p-tolyl)ureido)phenyl)pentanoate (150 mg, 0.194 mmol) in dry CH$_2$Cl$_2$ (1 mL) at 0° C. under nitrogen atmosphere, was added TFA (0.075 mL, 0.969 mmol). After being stirred for 30 min., the reaction mixture was concentrated in vacuo. The crude product was purified by RP HPLC (kinetex C18 (150×21.2 mm); mobile phase A: 10 mM ammonium acetate in water; mobile phase B: acetonitrile; flow rate: 18 mL/min.) to afford (S)-(2-oxo-5-((phosphonooxy)methyl)-1,3-dioxol-4-yl)methyl 3-(4-(diisobutylamino)-3-(3-(p-tolyl)ureido)phenyl)pentanoate (70.82 mg, 53%) as a white solid. $^1$H NMR (300 MHz, DMSO-d$_6$-D$_2$O exchange) δ ppm 7.75 (s, 1H), 7.33 (d, J=8.69 Hz, 2H), 7.02-7.15 (m, 3H), 6.78 (d, J=6.42 Hz, 1H), 4.92 (d, J=7.18 Hz, 2H), 4.73 (d, J=9.82 Hz, 2H), 2.73 (s, 1H), 2.58-2.68 (m, 6H), 2.23 (s, 3H), 1.48-1.69 (m, 4H), 0.81 (d, J=6.80 Hz, 12H), 0.70 (t, J=7.18 Hz, 3H); MS (ES): m/z 662.2 [M+H]$^+$; HPLC T$_r$=9.46 min (Method A) and 9.71 min (Method B).

Example 40

(S)-(((S)-2-(Phosphonooxy)propanoyl)oxy)methyl 3-(4-(diisobutylamino)-3-(3-(p-tolyl)ureido)phenyl)pentanoate

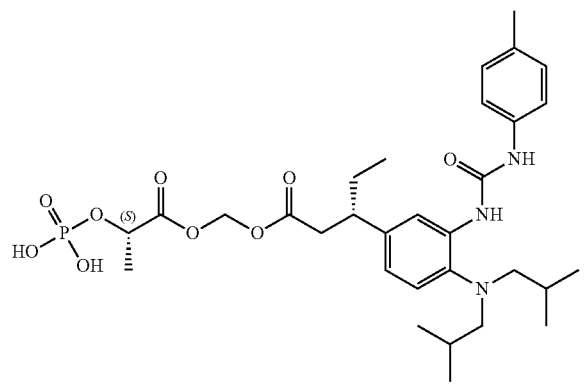

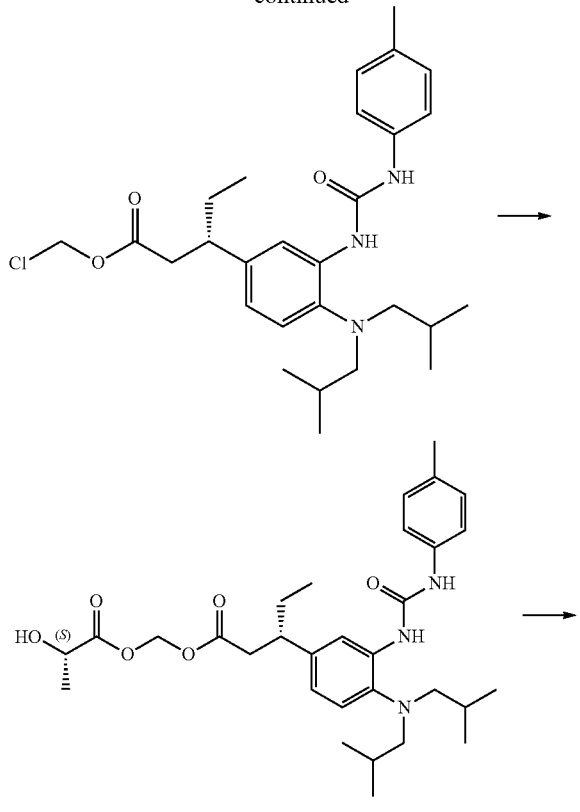

Example 40

40A: (S)-(((S)-2-Hydroxypropanoyl)oxy)methyl 3-(4-(diisobutylamino)-3-(3-(p-tolyl)ureido)phenyl)pentanoate To a solution of (S)-chloromethyl 3-(4-(diisobutylamino)-3-(3-(p-tolyl)ureido) phenyl)pentanoate (400 mg, 0.797 mmol) in dry DMF (5 mL), were added cesium carbonate (389 mg, 1.195 mmol), sodium iodide (119 mg, 0.797 mmol) and L-(+)-Lactic acid (144 mg, 1.593 mmol). After being stirred at room temperature under nitrogen atmosphere for 7 h, the reaction mixture was diluted with ethyl acetate (50 mL) and washed with water (2*30 mL) and brine, dried over anhydrous sodium sulphate and concentrated get crude product as light yellowish oil, which was purified by RP HPLC (X Bridge C18 (250×19 mm); mobile phase A: 10 mM ammonium acetate in water; mobile phase B: acetonitrile; flow rate: 18 mL/min.) to afford (S)-(((S)-2-hydroxypropanoyl) oxy)methyl 3-(4-(diisobutylamino)-3-(3-(p-tolyl)ureido)phenyl)pentanoate (100 mg, 0.175 mmol, 22.03%) as a white semi-solid. $^1$H NMR (300 MHz, DMSO-d$_6$) δ ppm 7.79 (s, 1H), 7.33 (d, J=8.31 Hz, 2H), 7.02-7.14 (m, 3H), 6.77 (d, J=8.31 Hz, 1H), 5.48-5.75 (m, 2H), 4.00-4.18 (m, 1H), 2.62 (br.s, 1H), 2.58-2.74 (m, 6H), 2.25-2.29 (m, 3H), 1.57-1.66 (m, 4H), 1.2 (d, J=7.18 Hz, 3H), 0.81 (d, J=6.80 Hz, 12H), 0.69 (t, J=7.37 Hz, 3H); LCMS (ES): m/z 556.4 [M+H]$^+$; HPLC T$_r$=18.16 min (Method A) and 17.73 min (Method B).

Example 40

To a solution of (S)-(((S)-2-hydroxypropanoyl)oxy) methyl 3-(4-(diisobutylamino)-3-(3-(p-tolyl)ureido)phenyl)

pentanoate (150 mg, 0.270 mmol) in dry tetrahydrofuran (5 mL)) at ~30° C., were added pyridine (0.065 mL, 0.810 mmol), DMAP (3.30 mg, 0.027 mmol) and POCl₃ (0.075 mL, 0.810 mmol) under nitrogen atmosphere. The reaction mixture was stirred for 1 h. Water (0.8 mL) was added. The reaction mixture was concentrated in vacuo. The residue was purified by RP HPLC (X-Bridge C18 (250×19 mm); mobile phase A: water; mobile phase B: acetonitrile; flow rate: 18 mL/min.) to afford (S)-(((S)-2-(phosphonooxy)propanoyl)oxy) methyl 3-(4-(diisobutylamino)-3-(3-(p-tolyl)ureido)phenyl)pentanoate (66.06 mg, 36%) as a white solid. ¹H NMR (400 MHz, DMSO-d₆) δ ppm 9.31 (s, 1H), 7.74-7.91 (m, 2H), 7.25-7.43 (m, 2H), 6.94-7.17 (m, 3H), 6.79 (dd, J=8.03, 2.01 Hz, 1H), 5.51-5.81 (m, 2H), 4.35-4.85 (m, 1H), 2.78-3.03 (m, 1H), 2.66-2.75 (m, 1H), 2.56-2.65 (m, 5H), 2.25 (s, 3H), 1.54-1.72 (m, 3H), 1.40-1.54 (m, 1H), 1.32 (d, J=7.03 Hz, 3H), 0.83 (d, J=6.53 Hz, 12H), 0.71 (t, J=7.28 Hz, 3H); LCMS (ES): m/z 636.4 [M+H]⁺; HPLC T$_r$=9.23 min (Method A) and 9.60 min (Method B).

Example 41

(((S)-3-(4-(Diisobutylamino)-3-(3-(p-tolyl)ureido)phenyl)pentanoyl)oxy)methyl 4-(((S)-2-(phosphonooxy)propanamido)methyl)benzoate

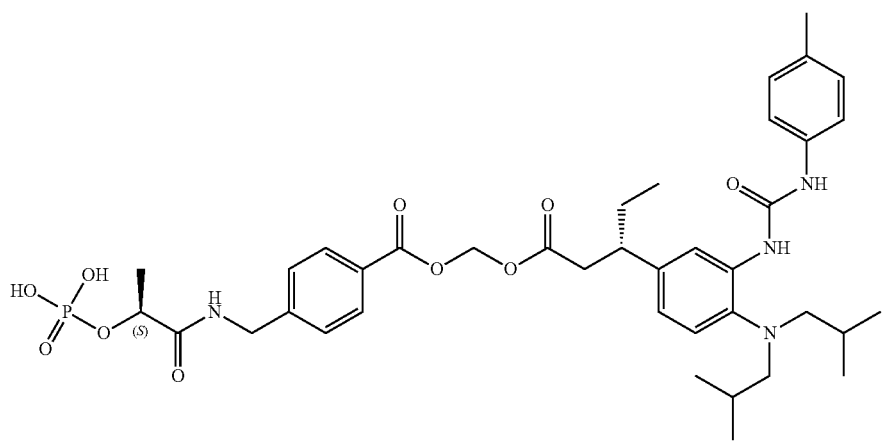

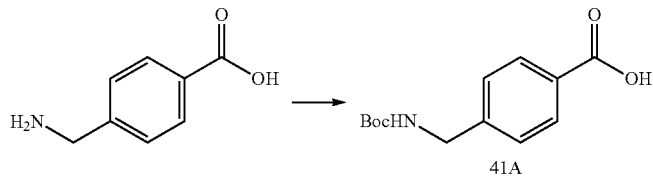

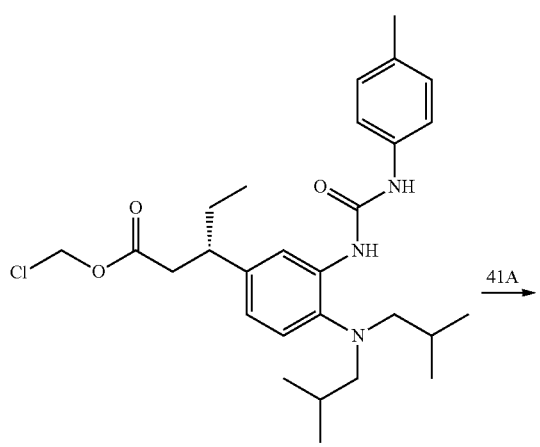

-continued
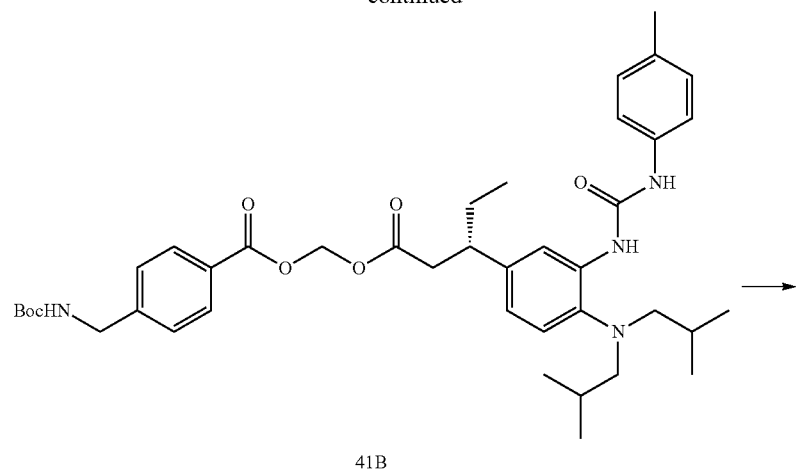
41B
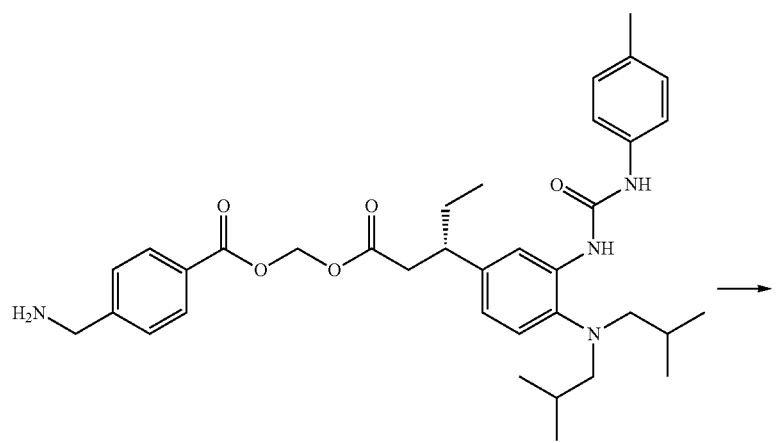
41C
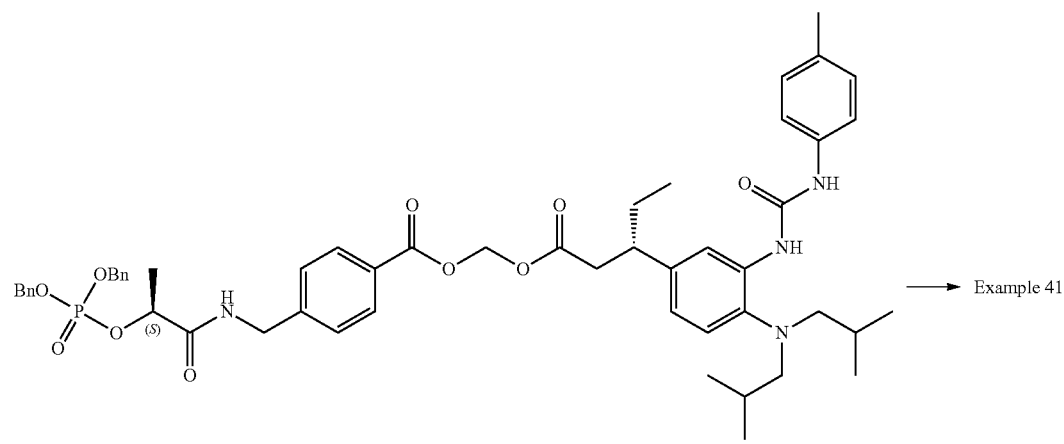
41D
→ Example 41

41A: 4-(((tert-Butoxycarbonyl)amino)methyl)benzoic Acid

To a solution of 4-(aminomethyl)benzoic acid (3.000 g, 19.85 mmol) in a solvent mixture of tetrahydrofuran (25 mL) and water (25 mL), was added di-tert-butyl dicarbonate (9.22 mL, 39.7 mmol) followed by sodium bicarbonate solution (pH>8) at room temperature. After being stirred for 16 h under nitrogen atmosphere, the reaction mixture was extracted with ethyl acetate (2*100 mL). The aqueous layer was acidified with 1.5N HCl solution (pH=1) and extracted with ethyl acetate (3*100 mL). The combined organic layer was washed with brine dried over anhydrous $Na_2SO_4$ and concentrated in vacuo to afford 4-(((tert-butoxycarbonyl)amino)methyl)benzoic acid (4.200 g, 81%) as an off-white solid. $^1$H NMR (300 MHz, chloroform-d) δ ppm 8.08 (d, J=8.31 Hz, 2H), 7.39 (d, J=8.31 Hz, 2H), 5.00 (br. s, 1H), 4.41 (d, J=5.67 Hz, 2H), 1.49 (s, 9H); LCMS (ES); m/z 252.4 [M+H]$^+$.

41B: (S)-((3-(4-(Diisobutylamino)-3-(3-(p-tolyl)ureido)phenyl)pentanoyl)oxy)methyl 4-(((tert-butoxycarbonyl)amino)methyl)benzoate To a solution of 4-(((tert-butoxycarbonyl)amino)methyl) benzoic acid (0.601 g, 2.390 mmol) in dry DMF (5 mL), were added cesium carbonate (1.038 g, 3.19 mmol) and (S)-chloromethyl 3-(4-(diisobutylamino)-3-(3-(p-tolyl)ureido)phenyl)pentanoate (0.8 g, 1.593 mmol)) at room temperature. After being stirred for 16 h under nitrogen atmosphere, the reaction mixture was concentrated in vacuo at 30° C. The residue was diluted with ethyl acetate (50 mL) and washed with water (2*30 mL) and brine, dried over anhydrous sodium sulphate and concentrated to get crude product as a colorless oil, which was purified by CombiFlash chromatography (60-120 silica gel; 10-30% ethyl acetate in pet. ether as eluent) to afford (S)-((3-(4-(diisobutylamino)-3-(3-(p-tolyl)ureido)phenyl)pentanoyl)oxy)methyl 4-(((tert-butoxycarbonyl)amino) methyl)benzoate (0.85 g, 74.4%) as a colorless oil. $^1$H NMR (300 MHz, methanol-d$_4$) δ ppm 7.97 (d, J=7.93 Hz, 2H), 7.83 (d, J=2.27 Hz, 1H) 7.40 (d, J=7.93 Hz, 2H), 7.31 (d, J=8.31 Hz, 2H), 6.99-7.18 (m, 3H), 6.83 (d, J=6.04 Hz, 1H), 5.81-6.01 (m, 2H), 4.29 (br, s, 2H), 2.56-2.84 (m, 7H), 2.02 (s, 3H), 1.57-1.83 (m, 4H), 1.47 (s, 9H), 0.88 (s, 12H), 0.80 (t, J=7.37 Hz, 3H); LCMS (ES): m/z 717.5[M+H]$^+$.

41C: (S)-((3-(4-(Diisobutylamino)-3-(3-(p-tolyl)ureido)phenyl)pentanoyl)oxy)methyl 4-(aminomethyl)benzoate Hydrochloride To the solid of (S)-((3-(4-(diisobutylamino)-3-(3-(p-tolyl)ureido)phenyl)pentanoyl oxy)methyl 4-(((tert-butoxycarbonyl)amino)methyl)benzoate (0.7 g, 0.976 mmol), was added 4N HCl in dioxane (2 mL, 8.00 mmol) at 0° C. under nitrogen atmosphere. After being stirred at 0° C. for 1 h., the reaction mixture was concentrated in vacuo at 30° C. The residue was stirred with ether. The solvent was carefully decanted. The resultant solid was dried under vacuum to get crude product as an off-white solid. The solid was dissolved in a mixture of acetonitrile and water. The resulting mixture was frozen and lyophilized for 12.0 h to afford (S)-((3-(4-(diisobutylamino)-3-(3-(p-tolyl)ureido)phenyl) pentanoyl) oxy)methyl 4-(aminomethyl)benzoate hydrochloride (550 mg, 84%) as a white solid. $^1$H NMR (300 MHz, methanol-d$_4$) δ ppm 8.05-8.14 (m, 2H), 7.59 (d, J=8.69 Hz, 3H), 7.36 (d, J=8.31 Hz, 3H), 7.17 (d, J=7.93 Hz, 3H), 5.85-5.99 (m, 2H), 4.17 (s, 2H), 3.3 (br.s, 4H), 3.10 (br. s. 1H), 2.68-2.93 (m, 2H), 2.33 (s, 3H), 2.08 (br. s., 2H), 1.55-1.89 (m, 2H), 1.01 (br. s., 12H), 0.71-0.86 (m, 3H); LCMS (ES): m/z 617.4 [M+H]$^+$; HPLC T$_r$=8.71 min (Method A) and 8.50 min. (Method B).

41D: (((S)-3-(4-(Diisobutylamino)-3-(3-(p-tolyl)ureido)phenyl)pentanoyl)oxy)methyl 4-(((S)-2-((bis(benzyloxy)phosphoryl)oxy)propanamido)methyl) benzoate To a stirred solution of (S)-((3-(4-(diisobutylamino)-3-(3-(p-tolyl)ureido)phenyl) pentanoyl)oxy)methyl 4-(aminomethyl)benzoate (300 mg, 0.486 mmol) in dry DMF (0.8 mL), were added (S)-2-((bis(benzyloxy)phosphoryl)oxy)propanoic acid (187 mg, 0.535 mmol), HATU (222 mg, 0.584 mmol) and DIPEA (0.255 mL, 1.459 mmol) at 0° C. under nitrogen atmosphere. The reaction mixture was stirred at room temperature for 1 h. The reaction mixture was diluted with water (20 mL) and extracted with EtOAc (3*20 mL). The organic layer was washed with water and brine, dried over anhydrous sodium sulphate and concentrated in vacuo at 30° C. The crude product was purified by CombiFlash chromatography (60-120 silica gel; 10-70% ethyl acetate in pet. ether as eluent) to afford (((S)-3-(4-(diisobutylamino)-3-(3-(p-tolyl)ureido)phenyl)pentanoyl) oxy)methyl 4-(((S)-2-((bis(benzyloxy)phosphoryl)oxy) propanamido)methyl) benzoate (250 mg, 54.2%) as a white solid. LCMS (ES): m/z 949.8 [M+H]$^+$

Example 41

To a solution of (((S)-3-(4-(diisobutylamino)-3-(3-(p-tolyl)ureido)phenyl) pentanoyl)oxy)methyl 4-(((S)-2-(bis(benzyloxy)phosphoryl)oxy)propanamido) methyl)benzoate (0.250 g, 0.263 mmol) in dry 2-propanol (2 mL), was added 10% palladium on carbon (0.140 g, 0.132 mmol). The mixture was degassed and then flushed with H2 gas. The reaction mixture was stirred for 1 h under H2 atmosphere, filtered through celite bed and the bed was washed with EtOAc. The filtrate was concentrated in vacuo at 30° C. The crude product was purified by RP HPLC (HSS CN (250×19 mm); mobile phase A: 10 mM ammonium acetate in water; mobile phase B: acetonitrile; flow rate: 17 mL/min.) to afford (((S)-3-(4-(diisobutylamino)-3-(3-(p-tolyl)ureido) phenyl) pentanoyl)oxy)methyl 4-(((S)-2-(phosphonooxy) propanamido)methyl) benzoate (21.49 mg, 11%) as a white solid. $^1$H NMR (400 MHz, methanol-d$_4$) δ ppm 7.92-8.06 (m, 2H), 7.81 (d, J=2.01 Hz, 1H), 7.43 (d, J=8.53 Hz, 2H), 7.21-7.35 (m, 2H), 7.01-7.17 (m, 3H), 6.84 (dd, J=8.53, 2.01 Hz, 1H), 5.79-6.06 (m, 2H), 4.61-4.79 (m, 1H), 4.37-4.55 (m, 2H), 2.86-3.05 (m, 1H), 2.55-2.83 (m, 6H), 2.30 (s, 3H), 1.58-1.83 (m, 4H), 1.49 (d, J=6.53 Hz, 3H), 0.85 (d, J=7.03 Hz, 12H), 0.79 (t, J=7.28 Hz, 3H); LCMS (ES); m/z 769.4 [M+H]$^+$; HPLC T$_r$=18.49 min. (Method A) and RT=15.39 min. (Method B).

Example 42
(S)-((3-(4-(Diisobutylamino)-3-(3-(p-tolyl)ureido)phenyl)pentanoyl)oxy)methyl 5-(phosphonooxy)pentanoate
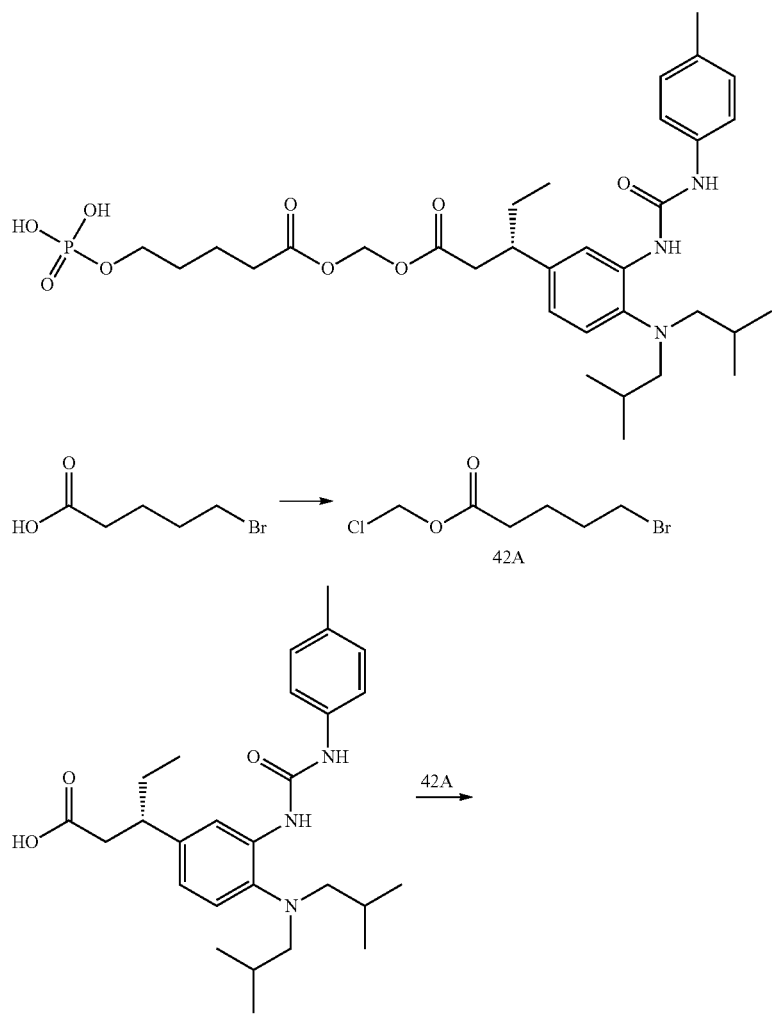

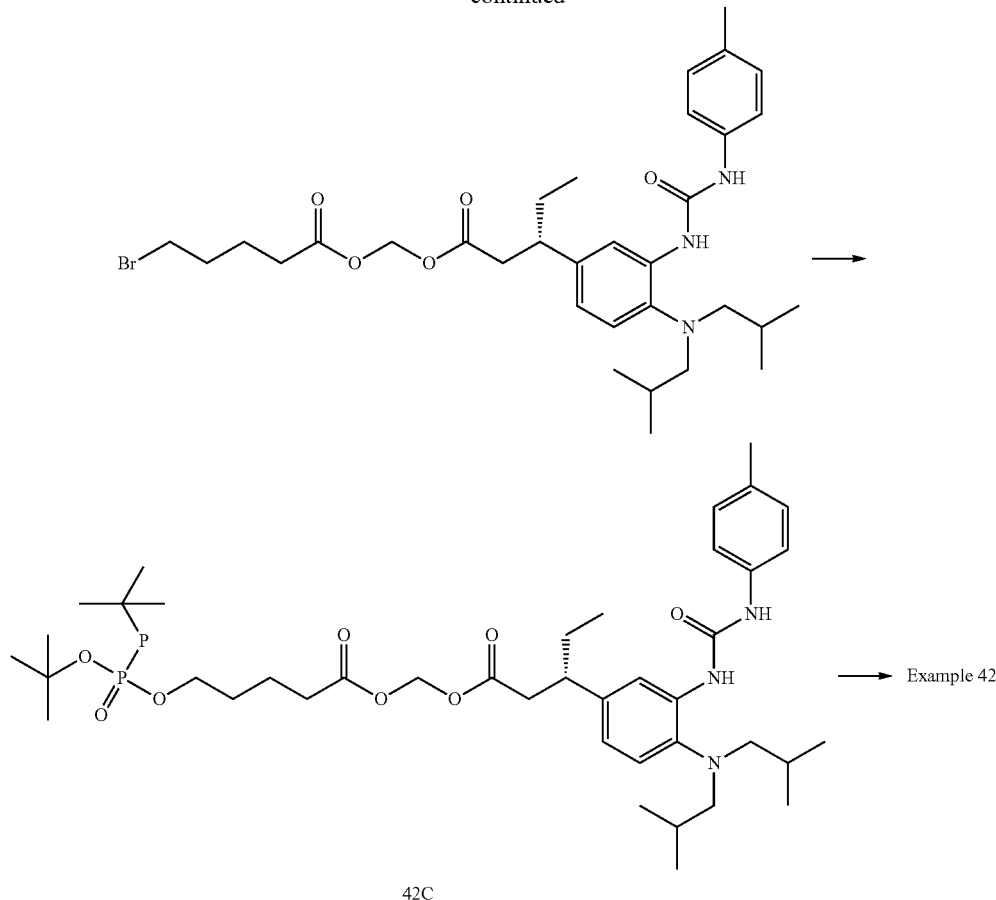

42C

42A: Chloromethyl 5-bromopentanoate

To a solution of 5-bromopentanoic acid (2 g, 11.05 mmol) in DCM (50 mL) and water (40 mL) at 0° C., were added sodium bicarbonate (3.71 g, 44.2 mmol), tetrabutylammonium hydrogen sulfate (0.375 g, 1.105 mmol) and chloromethyl chlorosulfate (2.235 mL, 22.10 mmol). The reaction mixture was stirred at room temperature for 16 h, diluted with DCM and washed with water (3*100 mL) and brine. The organic layer was dried over anhydrous sodium sulphate and concentrated to afford chloromethyl 5-bromopentanoate (1.6 g, 6.97 mmol, 63.1%) as a brownish oil. $^1$H NMR (300 MHz, chloroform-d) δ ppm 3.22-3.51 (m, 2H), 2.35-2.50 (m, 2H), 1.76-2.10 (m, 4H), 1.34-1.74 (m, 1H), 1.02 (t, J=7.18 Hz, 1H).

42B: (S)-((5-Bromopentanoyl)oxy)methyl 3-(4-(diisobutylamino)-3-(3-(p-tolyl)ureido)phenyl)pentanoate To a stirred solution of chloromethyl 5-bromopentanoate (0.506 g, 2.205 mmol) in anhydrous DMF (2 mL), were added cesium carbonate (0.359 g, 1.102 mmol) and (S)-3-(4-(diisobutylamino)-3-(3-(p-tolyl)ureido)phenyl)pentanoic acid (0.5 g, 1.102 mmol) under nitrogen atmosphere. The reaction mixture was stirred at room temperature for 7 h. The solid was filtered. The filtrate was removed under vacuum. The residue was partitioned between water and EtOAc. The organic layer was dried over anhydrous sodium sulphate and concentrated in vacuo to get light yellow oil. The crude product was purified by RP-HPLC (kinetex C18 (250×21.2 mm); mobile phase A: 10 mM ammonium acetate in water; mobile phase B: acetonitrile; flow rate: 17 mL/min.) to get (S)-((5-bromopentanoyl)oxy)methyl 3-(4-(diisobutylamino)-3-(3-(p-tolyl)ureido)phenyl) pentanoate (300 mg, 42%) as a colorless oil. $^1$H NMR (300 MHz, methanol-d$_4$) δ ppm 7.80-7.88 (m, 1H), 7.28-7.37 (m, 2H), 7.14 (t, J=7.74 Hz, 3H), 6.86 (dd, J=8.31, 2.27 Hz, 1H), 5.61-5.76 (m, 2H), 3.43 (t, J=6.42 Hz, 2H), 2.85-3.05 (m, 1H), 2.58-2.79 (m, 6H), 2.38 (t, J=6.99 Hz, 2H), 2.32 (s, 3H), 1.52-1.95 (m, 8H), 0.89 (d, J=6.80 Hz, 12H), 0.79-0.85 (m, 3H); LCMS (ES): m/z=648.3[M+H]$^+$.

42C: (S)-((5-((Di-tert-butoxyphosphoryl)oxy)pentanoyl)oxy)methyl 3-(4-(diisobutylamino)-3-(3-(p-tolyl)ureido)phenyl)pentanoate To a solution of (S)-((5-bromopentanoyl)oxy)methyl 3-(4-(diisobutylamino)-3-(3-(p-tolyl)ureido)phenyl)pentanoate (0.350 g, 0.541 mmol) in dry acetonitrile (5 mL) were added tetra-n-butyl ammonium di-tert-butyl phosphate (0.489 g, 1.082 mmol), sodium iodide (0.081 g, 0.541 mmol) and K$_2$CO$_3$ (0.112 g, 0.812 mmol) under nitrogen atmosphere. The reaction mixture was heated at 85° C. for 5 h. The reaction mixture was partitioned between sodium bicarbonate solution and DCM. The organic layer was washed with water and brine, dried over anhydrous sodium sulphate and concentrated to get crude product as a light yellowish oil, which was purified by CombiFlash chromatography (60-120 silica gel; 10-30% ethyl acetate in pet. ether to get (S)-((5-((di-tert-butoxyphosphoryl)oxy)pentanoyl)oxy)methyl 3-(4-(diisobutylamino)-3-(3-(p-tolyl)ureido)phenyl)pentanoate (250 mg, 59.5%) as a colorless oil. $^1$H NMR (400 MHz, methanol-$d_4$) δ ppm 7.82 (d, J=2.51 Hz, 1H), 7.26-7.35 (m, 2H), 7.13 (t, J=8.78 Hz, 3H), 6.84 (dd, J=8.03, 2.01 Hz, 1H), 5.62-5.73 (m, 2H), 4.10 (q, J=7.03 Hz, 1H), 3.87-3.99 (m, 2H), 2.87-3.04 (m, 1H), 2.55-2.76 (m, 5H), 2.38 (t, J=7.03 Hz, 2H), 2.31 (s, 3H), 1.57-1.80 (m, 8H), 1.44-1.50 (m, 18H), 0.88 (d, J=6.53 Hz, 12H), 0.76-0.84 (m, 3H); LCMS (ES): m/z 776.7 [M+H]$^+$.

Example 42

To a solution of (S)-((5-((di-tert-butoxyphosphoryl)oxy)pentanoyl)oxy)methyl 3-(4-(diisobutylamino)-3-(3-(p-tolyl)ureido)phenyl)pentanoate (250 mg, 0.322 mmol) in anhydrous DCM (1 mL) at 0° C. under nitrogen atmosphere, was added TFA (0.2 mL, 2.60 mmol). The reaction mixture was stirred for 1 h and concentrated in vacuo. The crude product was purified by RP HPLC (X-Bridge Phenyl (250×21.2 mm); mobile phase A: 10 mM ammonium acetate in water; mobile phase B: acetonitrile; flow rate: 17 mL/min.) to afford (S)-((3-(4-(diisobutylamino)-3-(3-(p-tolyl)ureido)phenyl) pentanoyl)oxy)methyl 5-(phosphonooxy)pentanoate (192.41 mg, 88%) as a white solid. $^1$H NMR (300 MHz, methanol-$d_4$) δ ppm 7.80 (d, J=1.89 Hz, 1H), 7.29-7.32 (m, 2H), 7.13-7.17 (m, 3H), 6.86 (dd, J=8.31, 1.89 Hz, 1H), 5.64-5.70 (m, 2H), 3.87 (q, J=6.04 Hz, 2H), 2.90-3.08 (m, 1H), 2.60-2.77 (m, 6H), 2.37-2.41 (m, 2H), 2.31 (s, 3H), 1.58-1.77 (m, 8H), 0.80-0.88 (m, 15H); LCMS (ES): m/z 664.2[M+H]$^+$; HPLC T$_r$=10.49 min. (Method A) and 8.69 min. (Method B).

Example 43

(((S)-3-(4-(Diisobutylamino)-3-(3-(p-tolyl)ureido) phenyl)pentanoyl)oxy)methyl 5-((S)-2-(phosphonooxy)propanamido)pentanoate

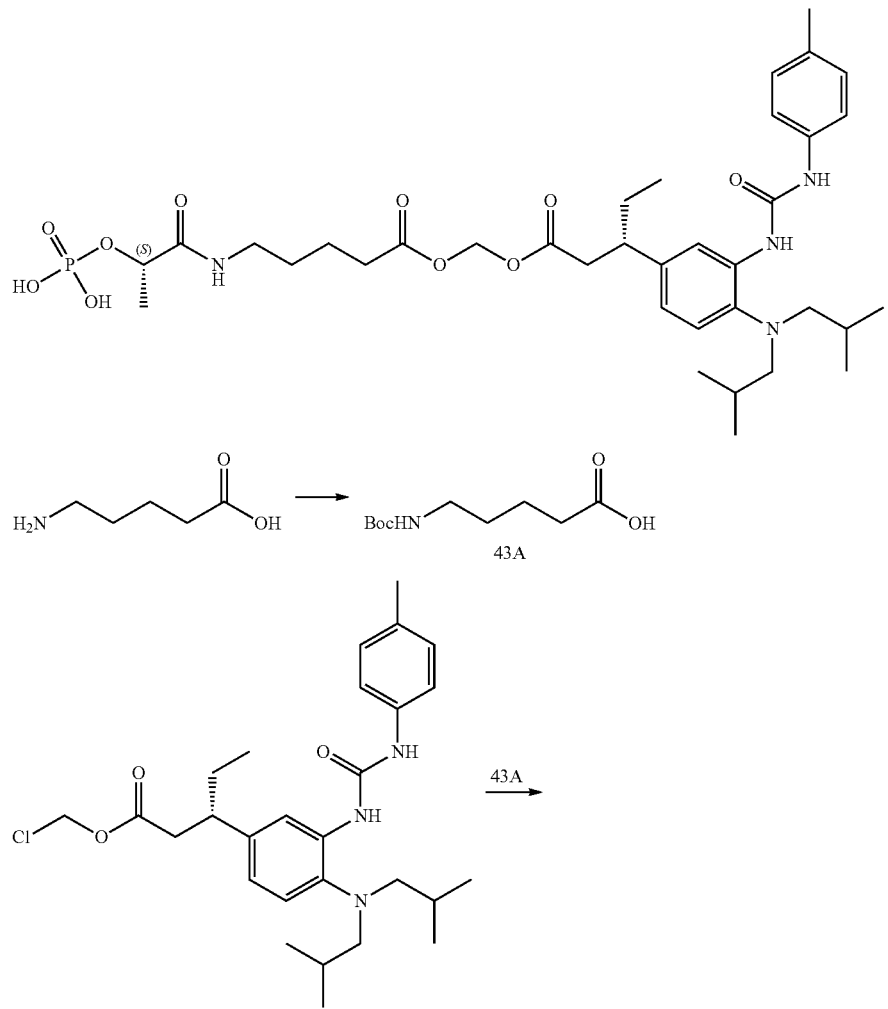

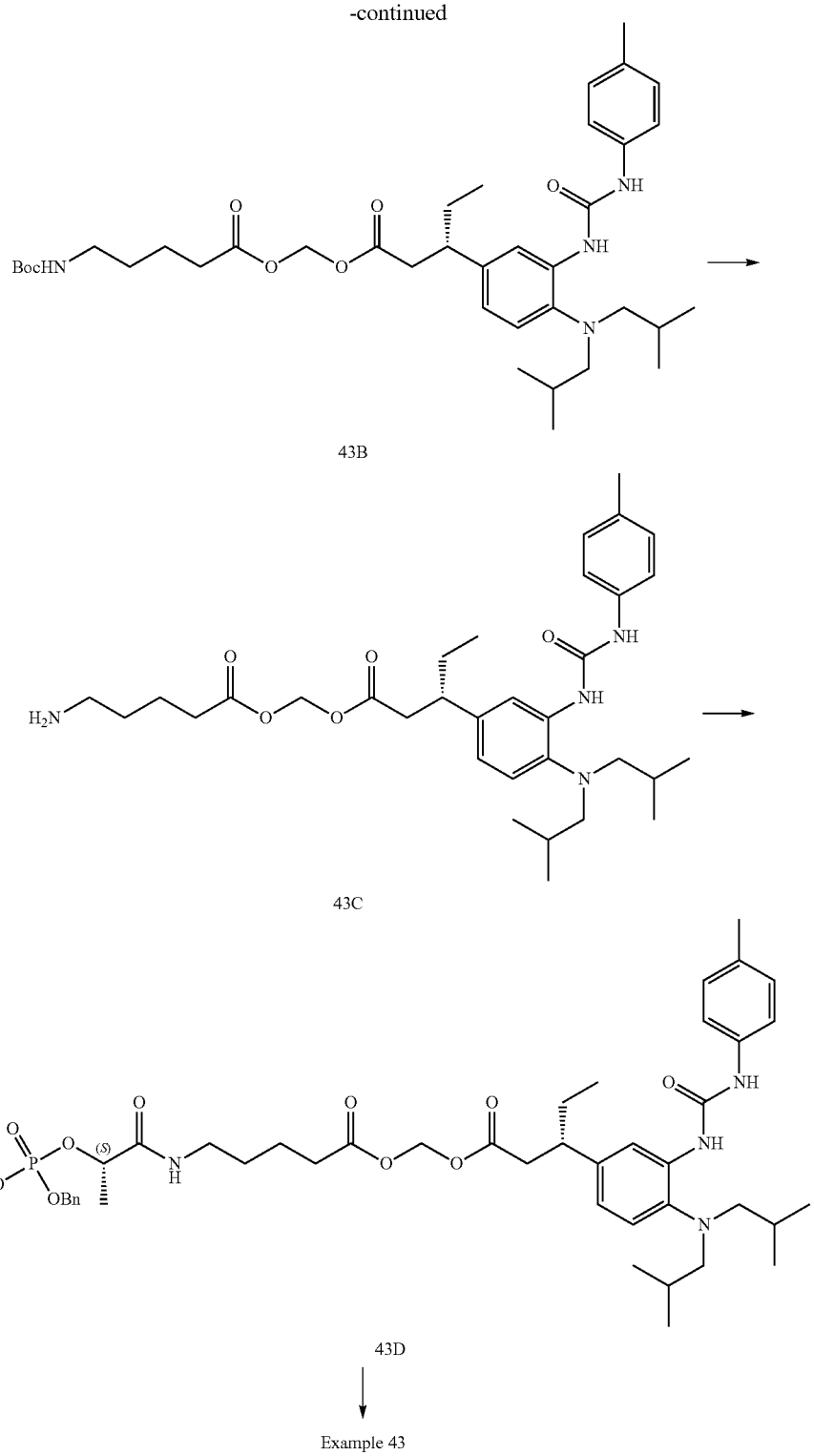

43A: 5-((tert-butoxycarbonyl)amino)pentanoic Acid

To a solution of 5-aminopentanoic acid (1 g, 8.54 mmol) in a solvent mixture of 1,4-dioxane (16 mL) and water (8 mL), was added 1M solution of sodium carbonate (8.4 mL) followed by di-tert-butyl dicarbonate (1.982 mL, 8.54 mmol) at 0° C. The reaction mixture was stirred at room temperature for 16 h. After evaporation of solvent in vacuo, the residue was partitioned between ethyl acetate and water. The aqueous layer was acidified with aqueous citric acid solution (pH=3) and extracted with ethyl acetate (3*100 mL). The organic layer was washed with water and brine, dried over anhydrous $Na_2SO_4$ and concentrated in vacuo to afford 5-((tert-butoxycarbonyl)amino)pentanoic acid (1.5 g, 81%) as a colorless oil. $^1$H NMR (300 MHz, Chloroform-d) δ ppm 3.15 (d, J=6.42 Hz, 2H), 2.39 (t, J=7.18 Hz, 2H), 1.22-1.7 (m, 13H).

43B: (S)-((5-((tert-Butoxycarbonyl)amino)pentanoyl)oxy)methyl 3-(4-(diisobutylamino)-3-(3-(p-tolyl)ureido)phenyl)pentanoate To a solution of (S)-chloromethyl 3-(4-(diisobutylamino)-3-(3-(p-tolyl)ureido) phenyl)pentanoate (0.8 g, 1.593 mmol) in dry DMF (8 mL), were added cesium carbonate (1.038 g, 3.19 mmol) and 5-((tert-butoxycarbonyl)amino)pentanoic acid (0.692 g, 3.19 mmol) at room temperature for 16 h under nitrogen atmosphere. The reaction mixture was concentrated in vacuo at 30° C. The residue was partitioned between ethyl acetate and water. The organic layer was washed with brine, dried over anhydrous sodium sulphate and concentrated in vacuo to get crude product as a colorless oil, which was purified by CombiFlash chromatography (60-120 silica gel; 10-30% ethyl acetate in pet. ether as eluent) to afford (S)-((5-((tert-butoxycarbonyl)amino)pentanoyl)oxy)methyl 3-(4-(diisobutylamino)-3-(3-(p-tolyl)ureido)phenyl)pentanoate (0.8 g, 73.5%) as a colorless oil. $^1$H NMR (300 MHz, methanol-d$_4$) δ ppm 7.83 (d, J=2.27 Hz, 1H) 7.24-7.39 (m, 2H), 7.14 (t, J=8.12 Hz, 3H), 6.86 (dd, J=8.12, 2.08 Hz, 1H), 5.68-5.70 (m, 2H), 4.12 (q, J=7.18 Hz, 2H), 2.86-3.12 (m, 3H), 2.57-2.78 (m, 6H), 2.27-2.43 (m, 5H), 1.55-1.86 (m, 6H), 1.39-1.54 (m, 9H), 0.90 (br, s, 12H), 0.78-0.86 (m, 3H); LCMS (ES): m/z 683.5 [M+H]$^+$

43C: (S)-((5-Aminopentanoyl)oxy)methyl 3-(4-(diisobutylamino)-3-(3-(p-tolyl)ureido)phenyl)pentanoate Hydrochloride To the solid of (S)-((5-((tert-butoxycarbonyl)amino)pentanoyl)oxy)methyl 3-(4-(diisobutylamino)-3-(3-(p-tolyl)ureido)phenyl)pentanoate (0.7 g, 1.025 mmol), was added 4N HCl in dioxane at 0° C. under nitrogen atmosphere. The reaction mixture was stirred at 0° C. for 1 h and subsequently concentrated in vacuo at 30° C. The residue was stirred with ether. The ether layer was decanted. The resultant solid was dried in vacuo to get crude product as an off-white solid. The solid was dissolved in a mixture of acetonitrile and water. The resulting mixture was frozen and lyophilized for 12 h to afford (S)-((5-aminopentanoyl)oxy)methyl 3-(4-(diisobutylamino)-3-(3-(p-tolyl)ureido)phenyl)pentanoate hydrochloride (0.6 g, 91%) as a white solid. $^1$H NMR (400 MHz, methanol-d4) δ ppm 7.69 (br. s., 1H), 7.25-7.32 (m, 4H), 7.13 (d, J=8.53 Hz, 2H), 5.51-5.78 (m, 2H), 3.65-3.84 (m, 1H), 3.52-3.64 (m, 2H), 3.02-3.19 (m, 1H), 2.89-2.98 (m, 2H), 2.63-2.87 (m, 2H), 2.30 (m, 2H), 2.37 (s, 3H), 1.99 (br, s, 2H), 1.58-1.90 (m, 7H), 1.04 (br. s., 12H), 0.84 (t, J=7.53 Hz, 3H); LCMS (ES): m/z 583.2[M+H]$^+$; HPLC T$_r$=8.46 min (Method A) and 9.4 min (Method B).

43D: (S)-((5-((S)-2-((bis(Benzyloxy)phosphoryl)oxy)propanamido) Pentanoyl)oxy)methyl 3-(4-(diisobutylamino)-3-(3-(p-tolyl)ureido)phenyl)pentanoate To a stirred solution of (S)-((5-aminopentanoyl)oxy)methyl 3-(4-(diisobutylamino)-3-(3-(p-tolyl)ureido)phenyl)pentanoate (220 mg, 0.378 mmol) in dry DMF (2 mL) at 0° C., were added (S)-2-((bis(benzyloxy)phosphoryl)oxy)propanoic acid (145 mg, 0.415 mmol), HATU (172 mg, 0.453 mmol) and DIPEA (0.198 mL, 1.133 mmol) under nitrogen atmosphere. The reaction mixture was stirred at 0° C. for 1 h. The reaction mixture was partitioned between ethyl acetate and water. The organic layer was washed with water and brine, dried over anhydrous sodium sulphate and concentrated in vacuo at 30° C. The crude product was purified by CombiFlash chromatography (60-120 silica gel; 20-60% ethyl acetate in pet. ether as eluent) to afford (S)-((5-((S)-2-((bis(benzyloxy)phosphoryl)oxy)propanamido)pentanoyl)oxy)methyl 3-(4-(diisobutylamino)-3-(3-(p-tolyl)ureido)phenyl)pentanoate (120 mg, 34.7%) as a colorless oil. LCMS (ES): m/z 915.8 [M+H]$^+$

Example 43

To a stirred solution of (S)-((5-((S)-2-((bis(benzyloxy)phosphoryl)oxy) propanamido)pentanoyl)oxy)methyl 3-(4-(diisobutylamino)-3-(3-(p-tolyl)ureido)phenyl) pentanoate (120 mg, 0.131 mmol) in dry 2-propanol (2 mL), was added 10% palladium on carbon (140 mg, 0.131 mmol). The mixture was degassed and then flushed with H2 gas. After being stirred for 1 h under H2 atmosphere, the reaction mixture was filtered through celite bed and the bed was washed with EtOAc. The filtrate was concentrated in vacuo at 30° C. The crude product was purified by RP HPLC (Kinetex Biphenyl (250×21.2 mm); mobile phase A: 10 mM ammonium acetate in water; mobile phase B: acetonitrile; flow rate: 17 mL/min.) to afford (((S)-3-(4-(diisobutylamino)-3-(3-(p-tolyl)ureido)phenyl)pentanoyl)oxy)methyl 5-((S)-2-(phosphonooxy)propanamido) pentanoate (17.77 mg, 18%) as a white solid. $^1$H NMR (400 MHz, methanol-d$_4$) δ ppm 7.68 (br. s., 1H), 7.21 (d, J=8.53 Hz, 2H), 7.02 (br. s., 1H), 7.0 (d, J=8.03 Hz, 2H), 6.77 (br. s., 1H), 5.53-5.58 (m, 2H), 4.58-4.65 (m, 1H), 3.11-3.27 (m, 2H), 2.91-2.99 (m, 1H), 2.59-2.78 (m, 5H), 2.32-2.38 (m, 2H), 2.30 (s, 3H), 1.50-1.79 (m, 9H), 1.46 (d, J=6.53 Hz, 3H), 0.89 (d, J=6.53 Hz, 12H), 0.81 (t, J=7.28 Hz, 3H); LCMS (ES); m/z 735.4 [M+H]$^+$; HPLC T$_r$=11.15 min (Method A) and 9.28 min (Method B).

Example 44

((S)-2-Morpholinoethyl 3-(4-(diisobutylamino)-3-(3-(p-tolyl)ureido)phenyl)pentanoate, HCl

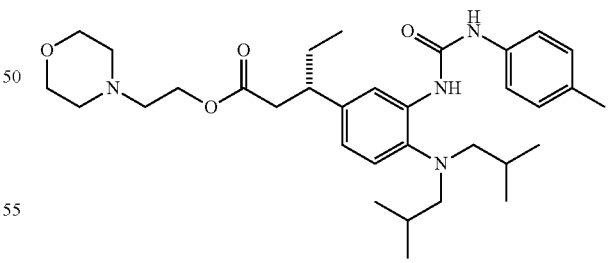

To a homogeneous mixture of (S)-3-(4-(diisobutylamino)-3-(3-(p-tolyl)ureido) phenyl)pentanoic acid (50 mg, 0.11 mmol) in anhydrous DCM (1 mL) was added 2-morpholinoethanol (0.015 mL, 0.12 mmol) followed by DMAP (5.4 mg, 0.04 mmol). The resulting solution was cooled to 0° C., in an ice bath, before 1-(3-dimethylaminopropyl)-3-ethylcarbodiimide (25.4 mg, 0.13 mmol) was added. The mixture was then stirred at 0° C. for 2 hours before the ice bath was removed and the reaction was stirred at room temperature. After 25 hours, the reaction was partitioned between EtOAc and 1N HCl (aq). Brine was added to facilitate clarification of the layers which were then separated. The aqueous layer was twice extracted with 5% MeOH in CHCl$_3$ and these organic extracts were combined with the original organic layer and were washed with water then brine, before being concentrated in vacuo to afford a gold oil which was purified via preparative HPLC. Fractions consistent for the presence of product were combined and concentrated in vacuo to remove volatiles. The resulting residue was treated with HCl (4M in dioxane, 0.03 mL, 0.12 mmol) and stirred at 5° C. before being lyophilized overnight to afford the title compound as a white solid (55.9 mg; 81% yield). MS (ES): m/z=567 [M+H]$^+$. T$_r$=0.97 min (Method C). $^1$H NMR (400 MHz, DMSO-d$_6$) δ 9.38 (s, 1H), 7.95-7.78 (m, 2H), 7.35 (d, J=8.4 Hz, 2H), 7.18-7.06 (m, 3H), 6.81 (d, J=7.0 Hz, 1H), 4.35-4.31 (m, 2H), 3.98-3.87 (m, 2H), 3.80-3.68 (m, 2H), 3.44-3.32 (m, 4H), 3.15-3.00 (m, 2H), 2.94-2.82 (m, 1H), 2.73-2.57 (m, 6H), 2.25 (s, 3H), 1.69-1.44 (m, 4H), 0.87-0.80 (m, 12H), 0.72 (t, J=7.3 Hz, 3H).

Example 45

(S)-(((R)-2-Amino-3-methylbutanoyl)oxy)methyl 3-(4-(diisobutylamino)-3-(3-(p-tolyl)ureido)phenyl)pentanoate, HCl

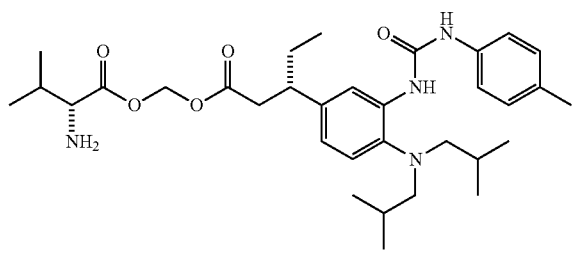 [SMILES: CC[C@@H](CC(=O)OCOC(=O)[C@H](N)C(C)C)c1ccc(N(CC(C)C)CC(C)C)c(NC(=O)Nc2ccc(C)cc2)c1]

45A. (S)-(((R)-2-((tert-Butoxycarbonyl)amino)-3-methylbutanoyl)oxy)methyl 3-(4-(diisobutylamino)-3-(3-(p-tolyl)ureido)phenyl)pentanoate To a homogeneous mixture of (S)-3-(4-(diisobutylamino)-3-(3-(p-tolyl)ureido)phenyl)pentanoic acid (50 mg, 0.11 mmol) in anhydrous MeCN (1.1 mL) was added K$_2$CO$_3$ (45.7 mg, 0.33 mmol). The resulting mixture was stirred at room temperature for 20 minutes before (R)-chloromethyl 2-((tert-butoxycarbonyl)amino)-3-methylbutanoate (58.6 mg, 0.22 mmol) was added followed by sodium iodide (16.5 mg, 0.11 mmol). The resulting heterogeneous mixture was stirred for 7 hours before a solution of (R)-chloromethyl 2-((tert-butoxycarbonyl)amino)-3-methylbutanoate (58.6 mg, 0.22 mmol) in anhydrous MeCN (0.5 mL) was added to the reaction and stirring continued. After 19 hours the reaction was partitioned between EtOAc and brine. The layers were separated and the aqueous layer was extracted with EtOAc. These organic extracts were combined with the original organic layer and were concentrated in vacuo to afford the title compound which was used in the next step without further purification. MS (ES): m/z=683 [M+H]$^+$. T$_r$=1.16 min (Method C).

Example 45

To a homogeneous mixture of (S)-(((R)-2-((tert-butoxycarbonyl)amino)-3-methylbutanoyl)oxy)methyl 3-(4-(di-isobutylamino)-3-(3-(p-tolyl)ureido)phenyl)pentanoate (75 mg, 0.11 mmol) in anhydrous dioxane (2 ml), cooled in an ice bath and under nitrogen atmosphere, was added HCl (4N in dioxane) (0.11 ml, 0.44 mmol). The resulting mixture was stirred at 0° C. for 10 minutes before the ice bath was removed and the reaction stirred at ambient temperature. After 4 hours, HCl (4N in dioxane) (0.11 ml, 0.44 mmol) was added and stirring continued. After 45 minutes, the reaction mixture was diluted with MeOH, filtered through an Acrodisc 0.45 m syringe filter then purified via preparative HPLC. Fractions consistent for the presence of product were combined and concentrated in vacuo to remove volatiles. The resulting residue was treated with HCl (4M in dioxane, 0.03 mL, 0.12 mmol) and stirred at room temperature before being lyophilized to afford the title compound as a white solid (19.3 mg; 27% yield). MS (ES): m/z=583 [M+H]$^+$. T$_r$=0.96 min (Method C). H NMR (400 MHz, DMSO-d$_6$) δ 9.34 (s, 1H), 8.39 (br. s., 2H), 7.91-7.79 (m, 2H), 7.35 (d, J=8.4 Hz, 2H), 7.17-7.03 (m, 3H), 6.82-6.76 (m, 1H), 5.96-5.68 (m, 2H), 4.02-3.98 (m, 1H), 2.90-2.80 (m, 1H), 2.69-2.59 (m, 6H), 2.25 (s, 3H), 2.17-2.08 (m, 1H), 1.68-1.59 (m, 3H), 1.57-1.45 (m, 1H), 0.95-0.89 (m, 6H), 0.83 (d, J=6.6 Hz, 12H), 0.71 (t, J=7.3 Hz, 3H).

Example 46

(S)-(Phosphonooxy)methyl 3-(4-(diisobutylamino)-3-(3-(p-tolyl)ureido)phenyl)pentanoate

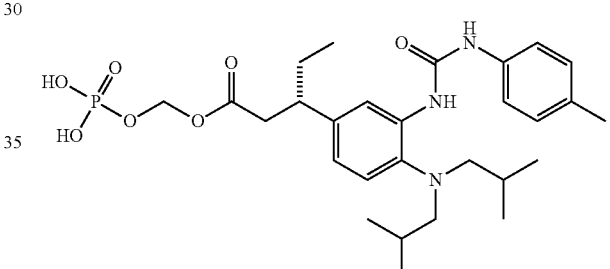

46A. (S)-((Bis(benzyloxy)phosphoryl)oxy)methyl 3-(4-(diisobutylamino)-3-(3-(p-tolyl)ureido)phenyl)pentanoate To a homogeneous mixture of (S)-3-(4-(diisobutylamino)-3-(3-(p-tolyl)ureido)phenyl)pentanoic acid (3.00 g, 6.6 mmol) in anhydrous DMF (60 mL), under nitrogen atmosphere, was added dibenzyl (chloromethyl) phosphate (4.32 g, 13.2 mmol) followed by K$_2$CO$_3$ (2.74 g, 19.8 mmol). The resulting mixture was stirred at room temperature for 10 minutes before being warmed to 40° C. After 3.5 hours the reaction mixture was cooled to room temperature, diluted with water, then thoroughly extracted with EtOAc. The organic extracts were combined, washed with brine, dried (Na$_2$SO$_4$), filtered and concentrated in vacuo to afford the crude product. This material was filtered to remove any solids before the filtrate was purified by Isco chromatography to afford the title compound as a colorless oil (4.60 g; 93% yield). MS (ES): m/z=744 [M+H]$^+$. T$_r$=1.14 min (Method C).

Example 46

To a flask charged with (S)-((bis(benzyloxy)phosphoryl)oxy)methyl 3-(4-(diisobutylamino)-3-(3-(p-tolyl)ureido)

phenyl)pentanoate (4.60 g, 6.18 mmol) and 10% Pd—C (1.32 g, 1.24 mmol), and under a flow of nitrogen, was carefully added MeOH (30 mL). The nitrogen line was replaced with a balloon filled with hydrogen and the resulting mixture was stirred at ambient temperature. After 1.5 hours, the balloon was refilled with hydrogen and stirring was continued. After 2 hours, the reaction mixture was purged with nitrogen before being filtered through a pad of Celite, which was then thoroughly rinsed with MeOH. The combined filtrates were concentrated in vacuo to afford the title compound as a white solid (3.18 g, 91%). MS (ES): m/z=564 [M+H]$^+$. T$_r$=0.90 min (Method C). $^1$H NMR (400 MHz, DMSO-d$_6$) δ 9.31 (s, 1H), 7.94-7.79 (m, 2H), 7.36 (d, J=8.3 Hz, 2H), 7.17-7.04 (m, 3H), 6.83-6.76 (m, 1H), 5.52-5.30 (m, 2H), 2.91-2.82 (m, 1H), 2.70-2.57 (m, 6H), 2.25 (s, 3H), 1.70-1.58 (m, 3H), 1.55-1.46 (m, 1H), 0.83 (d, J=6.6 Hz, 12H), 0.71 (t, J=7.3 Hz, 3H).

Thermodynamic Equilibrium Aqueous Solubility Evaluation

Standards Preparation

The calibration standard is prepared by accurately weighing 0.3-0.7 mg of sample into 5 ml volumetric flask and then dissolved in pure methanol. If the standard material is not fully soluble in methanol, other solvents such as DMSO or mixed solvent systems can used.

The calibration standard is typically prepared fresh, before the start of the assay. Note the calibration standard must be fully dissolved. A single point calibration curve is used to determine the concentration of the final saturated solution.

Test Sample Preparation

The saturated solution is prepared by adding 1.0 ml of the appropriate aqueous solvent to the remaining portion/portions of material (~1 mg/1 ml) into the 1 dram submission vial. The solution is sonicated and vortexed for ~30 seconds. The sample solution is placed on an orbiter that continually agitates the sample solutions for 18-24 hours at room temperature. The saturated solution is then transferred to a 1.5 ml eppendorf tube and centrifuged for ~2 min. at 10000 rpms. The supernatant from the saturated solution is filtered, using a 0.45 µm PTFE syringe filter, into a 1.5 mL glass HPLC.

LC Quantitation:

The standards and sample are analyzed by HPLC using either UV/Vis diode array or variable wavelength detection. Typical quantitation wavelengths are 210 or 254 nm; detection wavelength can be individually customized to optimize sensitivity. In addition to UV detection, mass spectrometry detection is recommended in order to confirm the Mass of the peak of interest.

Dilutions of saturated aqueous test solutions are performed if HPLC-UV peak is beyond the linear portion of the standard calibration curve. Typical dilutions include 100 µl/900 µl (×10) or 500 µl/500 µl (2×), as required.

Reagents

HPLC grade solvents are employed.

TABLE 1

Thermodynamic Equilibrium Aqueous Solubility

| Example | Solubility (µg/mL) pH 1.0, 4.0, 6.5, 7.4 buffers |
|---|---|
| 4 | 24, >500, >500, 158 |

TABLE 1-continued

Thermodynamic Equilibrium Aqueous Solubility

| Example | Solubility (µg/mL) pH 1.0, 4.0, 6.5, 7.4 buffers |
|---|---|
| 9 | 215, >1100, >2000, >2000 |
| 20 | 35, >500, >500, >500 |
| 22 | 15, >500, 22, 16 |
| 1E | 630, NT, NT, 1 |

Evaluation of Biological Activity

Materials and Methods

The following general materials and methods were used, where indicated, or may be used in the Examples below:

Standard methods in molecular biology are described in the scientific literature (see, e.g., Sambrook et al., *Molecular Cloning*, Third Edition, Cold Spring Harbor Laboratory Press, Cold Spring Harbor, N.Y. (2001); and Ausubel et al., *Current Protocols in Molecular Biology*, Vols. 1-4, John Wiley and Sons, Inc. New York, N.Y. (2001), which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan et al., *Current Protocols in Protein Science*, Vols. 1-2, John Wiley and Sons, Inc., NY (2000)).

Software packages and databases for determining, e.g., antigenic fragments, leader sequences, protein folding, functional domains, glycosylation sites, and sequence alignments, are available (see, e.g., GCG® Wisconsin Package (Accelrys, Inc., San Diego, Calif.); and DECYPHER® (TimeLogic Corp., Crystal Bay, Nev.).

The literature is replete with assays and other experimental techniques that can serve as a basis for evaluation of the compounds described herein.

An IDO enzyme assay and cellular production of kynurenine (KYN) is described in Sarkar, S. A. et al., *Diabetes*, 56:72-79 (2007). Briefly, all chemicals can be purchased from Sigma-Aldrich (St. Louis, Mo.) unless specified otherwise. Groups of 1,000 human islets can be cultured for 24 h in 1 mL medium with cytokines, recovered by centrifugation for 5 min at 800×g and sonicated in 150 µL PBS containing a protease inhibitor cocktail (Set 2; Calbiochem, EMD Biosciences, San Diego, Calif.). The sonicate can be centrifuged for 10 min at 10,000×g, and the supernatant can be assayed in triplicate by incubating a 40 µl sample with an equal volume of 100 mmol/L potassium phosphate buffer, pH 6.5, containing 40 mmol/L ascorbic acid (neutralized to pH 7.0), 100 µmol/L methylene blue, 200 µg/mL catalase, and 400 µmol/l L-Trp for 30 min at 37° C. The assay can be terminated by the addition of 16 µL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 µg/mL; 500-2,000 units/mL) and 1-α-methyl Trp (1-MT; 40 µmol/L) can be added to the incubation media as indicated. This assay can also form the basis of a cell-based assay, and may be quantified via LCMS/MS as an alternative to UV/Vis detection.

Western Blot Analyses. Groups of 1,000-1,200 islets incubated for 24 h in Miami medium in the presence of cytokines can be harvested and sonicated in PBS as above, and 50 µg protein samples can be electrophoresed on 10% SDS-PAGE gels. COS7 cells ($0.6 \times 10^6$ cells/60 mm3 petri dish) transfected with human-IDO plasmid (3 µg) or empty vector cells can be used as positive and negative controls, respectively. Proteins can be transferred electrophoretically onto polyvinylidine fluoride membranes by semidry method and blocked for 1 h with 5% (w/v) nonfat dry milk in Tris-buffered saline and 0.1% Tween and then incubated overnight with anti-human mouse IDO antibody (1:500; Chemicon, Temecula, Calif.), phospho-STAT$_{1\alpha}$ p91, and STAT$_{1\alpha}$ p91 (1:500; Zymed, San Francisco, Calif.). Immunoreactive proteins can be visualized with ECL PLUS® Western blotting detection reagent (Amersham BioSciences, Buckinghamshire, U.K.) after incubation for 1 h with anti-mouse horseradish peroxidase-conjugated secondary antibody (Jackson Immunolabs, West Grove, Pa.).

Immunohistochemical Detection of IDO. Islets can be fixed in 4% paraformaldehyde in PBS (Invitrogen) for 1 h, immobilized in molten 10% porcine skin gelatin blocks (37° C.), and embedded in optimal cutting temperature compound. Immunofluorescent staining on islet tissue can be performed on 7 µm sections that were stained with antibodies raised against pancreatic duodenal homeobox 1 (PDX1) and IDO. Antigen retrieval can be performed in a water bath for 30 min in a buffer containing 10 mmol/l Tris and 1 mmol/l EDTA (pH 9.0) at 97° C. The sections can be blocked for 1 h with 5% normal goat serum in PBS. The tissues can then be reacted with mouse monoclonal anti-human IDO antibody (1:20; Chemicon) and goat polyclonal anti-human PDX1 antibody (1:2,000; which may be requested from Dr. Chris Wright, School of Medicine, Vanderbilt, Tenn.) overnight at room temperature in a humid chamber. Secondary antibodies anti-goat (labeled with Cy3) and anti-mouse (labeled with Cy2) can be purchased from Jackson Immunolabs and can be used at a concentration of 1:200. The nuclei can be stained with Hoechst 33258 (Molecular Probes, Eugene, Oreg.). Images can be acquired by Intelligent Imaging System software from an Olympus 1X81 inverted motorized microscope equipped with Olympus DSU (spinning disk confocal) and Hamamatsu ORCA IIER monochromatic CCD camera.

Alternative means for evaluating the IDO inhibitors of the present invention are described in WO 2010/0233166 and are summarized hereafter.

Biochemical Assay. cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K. et al., *Prot. Exp. Purif.*, 19:22-29 (2000)). To screen for IDO inhibitory activity, compounds can be evaluated at a single concentration of, for example, 200 µM against 50 ng of IDO enzyme in 100 µL reaction volumes with tryptophan added at increasing concentrations at, for example, 0, 2, 20, and 200 µM. Kynurenine production can be measured at 1 hour.

Cell-based Assay. COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at $6 \times 10^4$ cells per well. The following day, the wells can be washed and new media (phenol red free) containing 20 µg/mL tryptophan can be added together with inhibitor. The reaction can be stopped at 5 hours and the supernatant removed and spectrophotometrically-assayed for kynurenine as previously described for the enzyme assay. To obtain initial confirmation of IDO activity, compounds can be evaluated at a single concentration of, for example, 100 µM. More extensive dose-escalation profiles can be collected for select compounds.

Pharmacodynamic and Pharmacokinetic Evaluation. A pharmacodynamic assay can be based on measuring serum levels of both kynurenine and tryptophan, and calculating the kynurenine/tryptophan ratio provides an estimate of IDO activity that is independent of baseline tryptophan levels. Serum tryptophan and kynurenine levels can be determined by HPLC analysis, and serum compound levels can optionally also be determined in the same HPLC run.

Compounds can be initially evaluated by challenging mice with LPS and then subsequently administering a bolus dose of compound at the time that the serum kynurenine level plateaus. As the kynurenine pool is rapidly turned over with a half-life in serum of less than 10 minutes, pre-existing kynurenine is not expected to unduly mask the impact that an IDO inhibitor has on kynurenine production. Each experiment can include non-LPS-exposed mice (to determine baseline kynurenine levels against which to compare the other mice) and a set of LPS-exposed mice dosed with vehicle alone (to provide a positive control for IDO activation). Each compound can initially be evaluated in mice at a single high i.p. bolus dose in the range of at least 100 mg/kg. Blood can be collected at defined time intervals (for example, 50 µL sample at 5, 15, 30 min., 1, 2, 4, 6, 8, and 24 hr. following compound administration) for HPLC analysis of kynurenine and tryptophan levels (pharmacodynamic analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective IC$_{50}$ for IDO inhibition in vivo can be roughly estimated. Compounds exhibiting efficacy can be evaluated to determine a maximum dose that achieves 100% IDO inhibition at the peak concentration.

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 µL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20 µL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Assessment of inhibitor activity in HeLa cell-based indoleamine 2,3-dioxygenase (IDO) assay:

HeLa (ATCC® CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100U/mL penicillin, 100 µg/mL streptomycin (#SV30010, HyClone) and 10% fetal bovine serum (#SH30071.03 HyClone). Cells were maintained in a humidified incubator at 37° C. in 5% $CO_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 µL of culture medium. After a further 48 hour incubation, 170 µL of supernatant was transferred from each well to a fresh 96-well plate. 12.1 µL of 6.1N trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 µL of the supernatant was transferred from each well to a fresh 96-well plate. 100 µl of 2% (w/v) p-dimethylaminobenzaldehyde (#15647-7, Sigma-Aldrich) in acetic acid (#A6283, Sigma-Aldrich) was added to each well mixed and incubated at room temperature for 20 mins. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Results of the IDO assays are shown in the table below.

| Ex. No. | IDO Hela $IC_{50}$ (µM) | IDO1 HEK Human $IC_{50}$ (µM) |
| --- | --- | --- |
| 1E | 0.0041 | 0.0031 |

What is claimed:

1. A compound of formula (I):

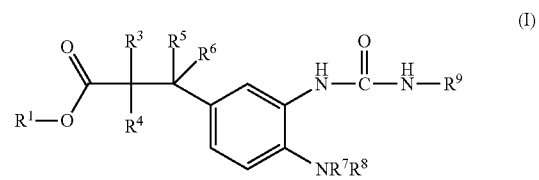

wherein:

$R^1$ is a straight or branched $C_1$-$C_8$ alkyl substituted with

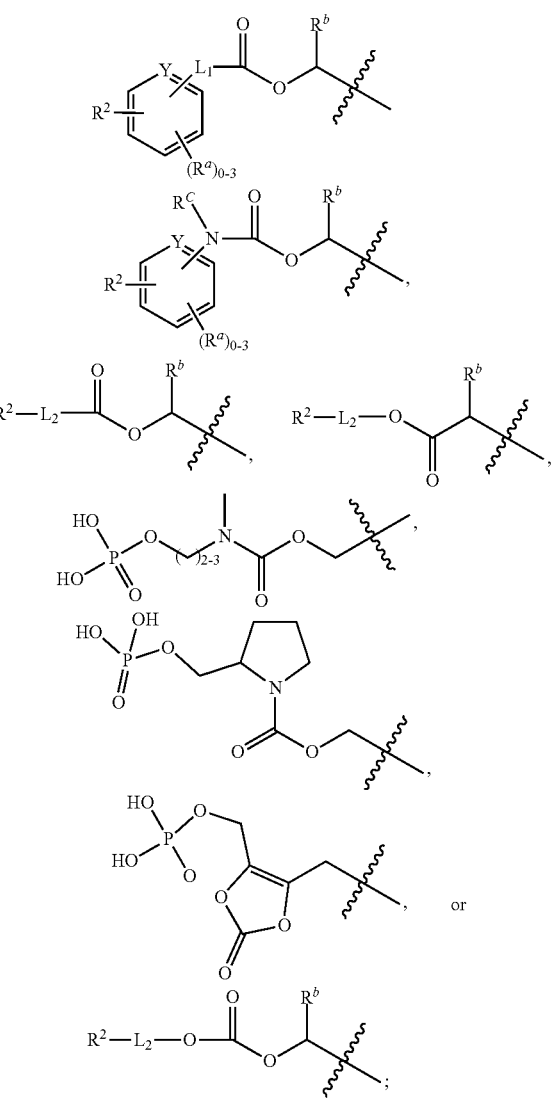

$R^2$,

Y is CH or N;

$L_1$ is independently a bond or a straight or branched $C_1$-$C_8$ alkylene;

$L_2$ is independently a bond, a straight or branched $C_1$-$C_8$ alkylene, —OC(O)N($R^c$)CH($R^b$)—, —C(O)N($R^c$)$L_3$-, $C_3$-$C_6$ cycloalkyl,

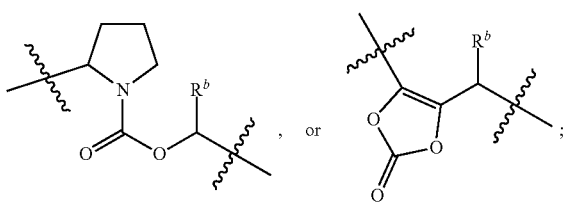

$R^2$ is independently $NH_2$,

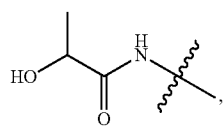

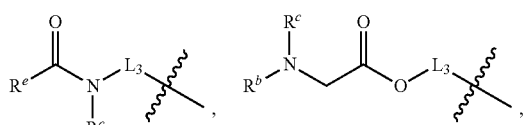

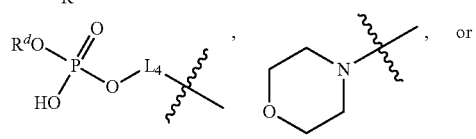

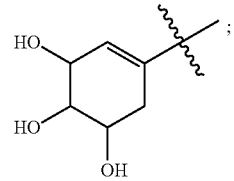

$L_3$ is independently a straight or branched $C_1$-$C_6$ alkylene;

$L_4$ is independently a bond, a straight or branched $C_1$-$C_6$ alkylene wherein two carbon atoms of said alkylene are optionally replaced by —C(O)N($R^c$)— or —N($R^c$)C(O)—;

$R^3$, $R^4$, $R^5$ and $R^6$ are independently H or $C_1$-$C_4$ alkyl;

$R^7$ and $R^8$ are independently H or $C_1$-$C_6$ alkyl;

$R^9$ is aryl optionally substituted with one to three substituents selected from: halo, OH, CN, $C_1$-$C_6$ alkyl, —O$C_1$-$C_6$ alkyl, $C_1$-$C_6$ haloalkyl, benzyl, and phenoxy;

$R^a$ is independently halo, OH, CN, $C_1$-$C_6$ alkyl, —O$C_1$-$C_6$ alkyl, or $C_1$-$C_6$ haloalkyl;

$R^b$ and $R^c$ are independently H, or $C_1$-$C_6$ alkyl;

$R^d$ is independently H, $C_1$-$C_6$ alkyl, —CH$_2$OC(O)($C_1$-$C_6$ alkyl), —CH$_2$OC(O)O($C_1$-$C_6$ alkyl), or Bn; and $R^e$ is independently $C_1$-$C_6$ alkyl optionally substituted with a substituent selected from halo, OH, CN, $C_1$-$C_4$ alkyl, —O$C_1$-$C_6$ alkyl, and $C_1$-$C_4$ haloalkyl;

or a salt, a stereoisomer, a tautomer, or a solvate thereof.

2. The compound according to claim 1, wherein:

$R^1$ is a straight or branched $C_1$-$C_6$ alkyls substituted with $R^2$,

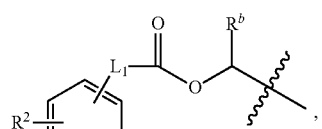

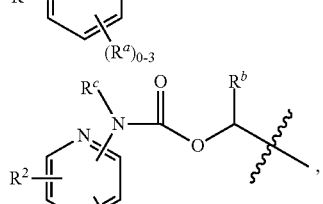

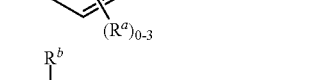

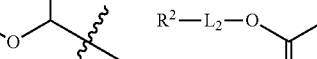

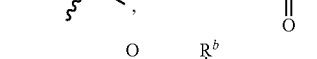

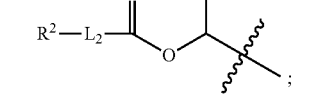

$L_1$ is independently a bond or a straight or branched $C_1$-$C_6$ alkylene;

$L_2$ is independently a bond, a straight or branched $C_1$-$C_6$ alkylene, —OC(O)N($R^c$)CH($R^b$)—, —C(O)N($R^c$)L$_3$-, $C_3$-$C_6$ cycloalkyl,

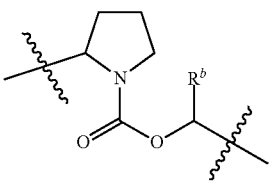

and $R^9$ is phenyl optionally substituted with one to three substituents selected from: halo, OH, CN, $C_1$-$C_6$ alkyl, —O$C_1$-$C_6$ alkyl, and $C_1$-$C_6$haloalkyl.

3. The compound according to claim 1, wherein:

$R^2$ is independently $NH_2$,

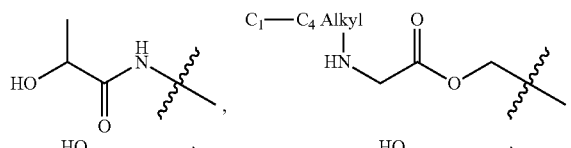

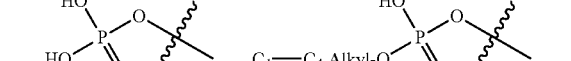

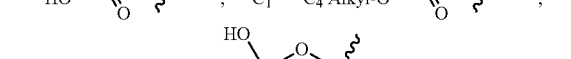

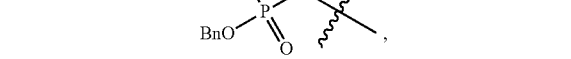

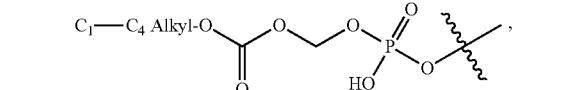

191
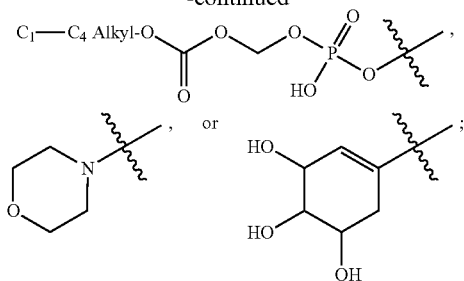
$R^a$ is independently $C_1$-$C_4$ alkyl or —$OC_1$-$C_4$ alkyl
$R^b$ is independently H or $C_1$-$C_4$ alkyl; and
$R^c$ is independently H or $C_1$-$C_2$ alkyl.
4. The compound according to claim 1, wherein:
$R^1$ is
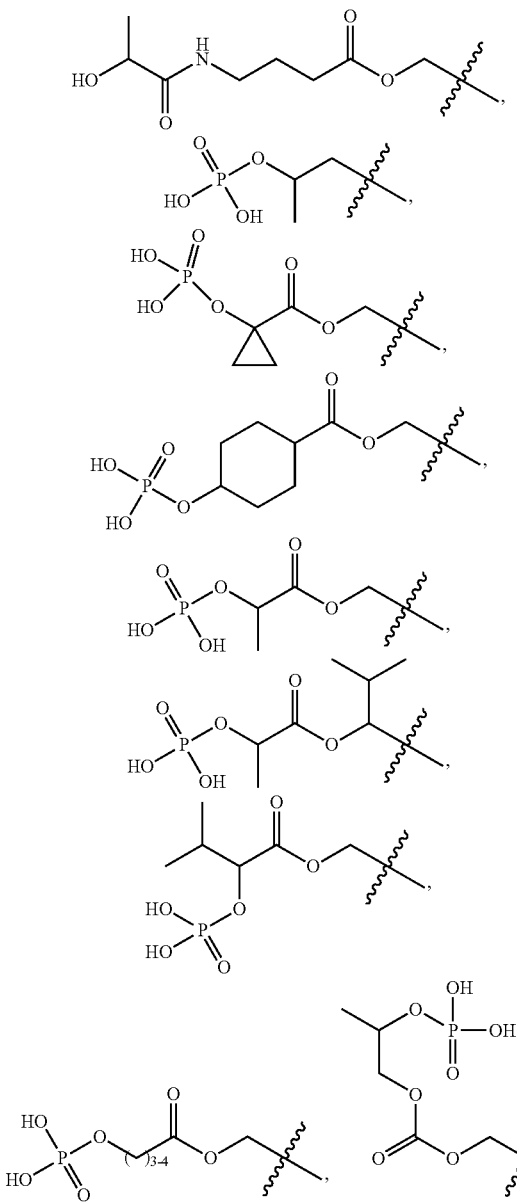
192
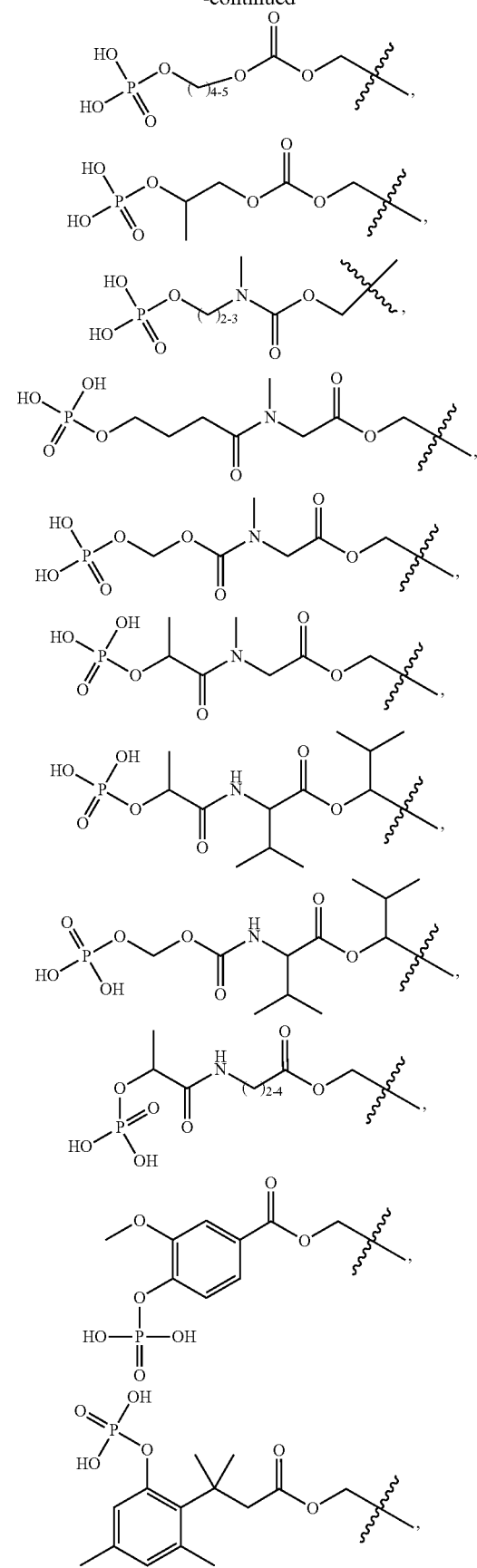

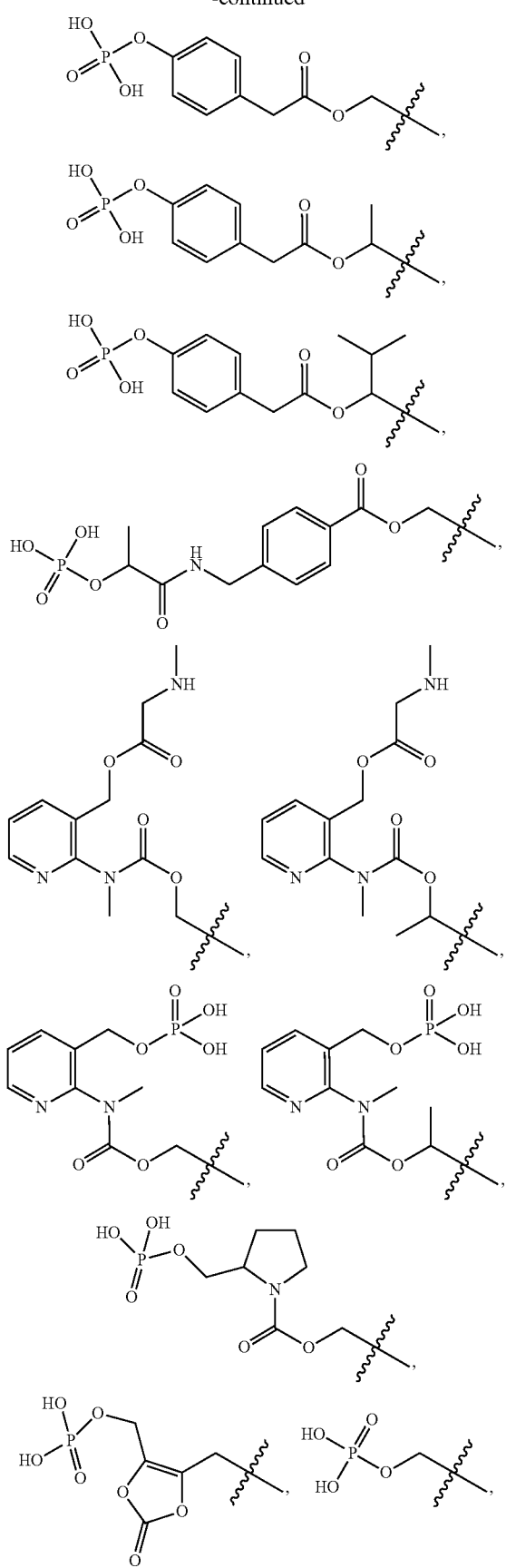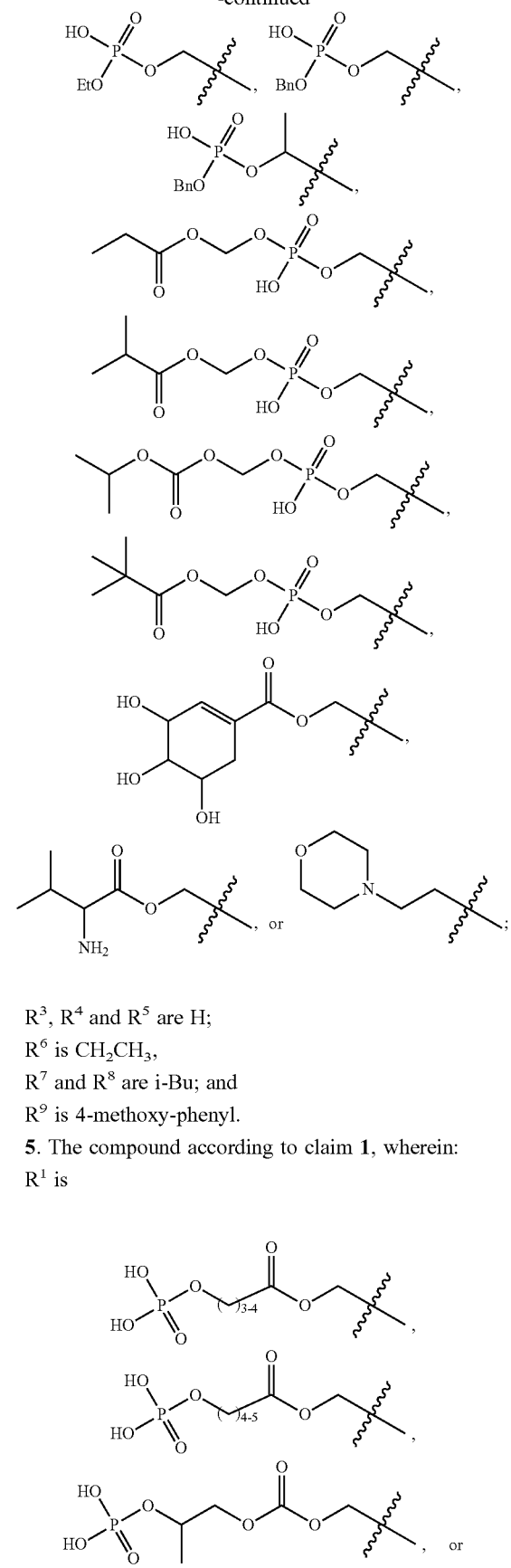
$R^3$, $R^4$ and $R^5$ are H;
$R^6$ is $CH_2CH_3$,
$R^7$ and $R^8$ are i-Bu; and
$R^9$ is 4-methoxy-phenyl.
5. The compound according to claim 1, wherein:
$R^1$ is -continued

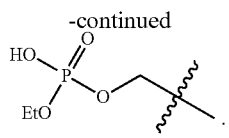

6. A pharmaceutical composition comprising a compound according to claim 1 and a pharmaceutically acceptable excipient.

7. The pharmaceutical composition of claim 1, further comprising ipilimumab, nivolumab, or pembrolizumab or a combination thereof.

8. A method of treating cancer in a patient in need of such treatment comprising administering to the patient a therapeutically effective amount of a compound according to claim 1; wherein the cancer is skin cancer, bladder cancer, ovarian cancer, breast cancer, pancreatic cancer, prostate cancer, colon cancer, blood cancer or lung cancer.

9. The compound according to claim 1, wherein the compound is selected from

3S)-1-(((Benzyloxy)(hydroxy)phosphoryl)oxy)ethyl-3-(4-(diisobutylamino)-3-(3-(p-tolyl)ureido)phenyl)pentanoate;

(S)-((3-(4-(Diisobutylamino)-3-(3 (p-tolyl)ureido)phenyl)pentanoyl)oxy)methyl 3-methoxy-4-(phosphonooxy) benzoate;

(S)-((3-(2,4-Dimethyl-6-(phosphonooxy)phenyl)-3-methylbutanoyl)oxy)methyl-3-(4-(diisobutylamino)-3-(3-(p-tolyl)ureido)phenyl)pentanoate;

(S)-((4-(Phosphonooxy)butanoyl)oxy)methyl3-(4-(diisobutylamino)-3-(3-(p-tolyl)ureido) phenyl)pentanoate;

(3S)-2-Methyl-1-(2-(4-(phosphonooxy)phenyl)acetoxy)propyl3-(4-(diisobutylamino)-3-(3-(p-tolyl)ureido) phenyl)pentanoate;

(3S)-1-(2-(4-(Phosphonooxy)phenyl)acetoxy)ethyl-3-(4-(diisobutylamino)-3-(3-(p-tolyl)ureido)phenyl)pentanoate;

(3S)-(Hydroxy((pivaloyloxy)methoxy)phosphoryl)oxy)methyl-3-(4-(diisobutylamino)-3-(3-(p-tolyl)ureido)phenyl)pentanoate;

(3S)-(((Benzyloxy(hydroxy)phosphoryl)oxy)methyl-3-(4-diisobutylamino)-3-(3-(p-tolyl)ureido)phenyl)pentanoate;

(3S)-((Ethoxy(hydroxy)phosphoryl)oxy)methyl 3-(4-(diisobutylamino)-3-(3-(p-tolyl)ureido)phenyl)pentanoate;

(3S)-((Hydroxy(((isopropoxycarbonyl)oxy)methoxy)phosphoryl)oxy)methyl 3-(4-(diisobutylamino)-3-(3-(p-tolyl)ureido)phenyl)pentanoate;

(S)-(2-(Methyl(((phosphonooxy)methoxy)carbonyl)amino)acetoxy)methyl 3-(4-(diisobutylamino)-3-(3-(p-tolyl)ureido)phenyl)pentanoate;

(3S)-2-Methyl-1-(S)-3-methyl-2-((((phosphonooxy)methoxy)carbonyl)amino) butanoyl)oxy)propyl 3-(4-(diisobutylamino)-3-(3-(p-tolyl(ureido)phenyl)pentanoate;

(3S,4S,5S)—(((S)-3-(4-(Diisobutylamino)-3-(3-(p-tolyl)ureido)phenyl)pentanoyl)oxy) methyl 3,4,5-trihydroxycyclohex-1-enecarboxylate;

(S)-(((4-(Phosphonooxy)butoxy)carbonyl)oxy)methyl 3-(4-(diisobutylamino)-3-(3-(p-tolyl)ureido)phenyl) pentanoate;

(S)-((((5-(Phosphonooxy)butoxy)carbonyl)oxy)methyl 3-(4-(diisobutylamino)-3-(3-(p-tolyl)ureido)phenyl) pentanoate;

(3S)-((Hydroxy((isobutyryloxy)methoxy)phosphoryl)oxy)methyl 3-(4-diisobutylamino)-3-(3-(p-tolyl)ureido)phenyl)pentanoate;

(3S)-(Hydroxy((propionyloxy)methoxy)phosphoryl)oxy)methyl 3-(4-(diisobutylamino)-3-(3-(p-tolyl)ureido)phenyl)pentanoate;

(S)-((Methyl(3-(phosphonooxy)propyl)carbamoyl)oxy)methyl 3-(4-(diisobutylamino)-3-(3-(p-tolyl)ureido)phenyl)pentanoate;

(S)-(((S)-3-(4-(Diisobutylamino)-3-(3-(p-tolyl)ureido)phenyl)pentanoyl)oxy)methyl 2-((phosphonooxy)methyl)pyrrolidine-1-carboxylate;

(3S)-1-(Methyl(3-((phosphonooxy)methyl)pyridin-2-yl)carbamoyl)oxy)ethyl 3-(4-(diisobutylamino)-3-(3-(p-tolyl)ureido)phenyl)pentanoate;

(S)-(((S)-3-Methyl-2-(phosphonooxy)butanoyl)oxy)methyl 3(4-(diisobutylamino)-3-(3-(p-tolyl)ureido)phenyl)pentanoate;

(3S)-(((2-(Phosphonooxy)propoxy)carbonyl)oxy)methyl 3-(4-(diisobutylamino)-3-(3-(p-tolyl)ureido)phenyl)pentanoate;

(S)-((Methyl(3-((phosphonooxy)methyl)pyridin-2-yl)carbamoyl)oxy)methyl 3-4-(diisobutylamino)-3-(3-(p-tolyl)ureido)phenyl)pentanoate;

(3S)-1-((Methyl(3-((2-(methylamino)acetoxy)methyl)pyridin-2-yl)carbamoyl)oxy)ethyl 3-(4-(diisobutylamino)-3-(3-(p-tolyl)ureido)phenyl)pentanoate dihydrochloride;

(S)-((Methyl(3-((2-(methylamino)acetoxy)methyl)pyridin-2-yl)carbamoyl)oxy)methyl 3-(4-(diisobutylamino)-3-(3-(p-tolyl)ureido)phenyl)pentanoate dihydrochloride;

(S)-((Methyl(2-(phosphonooxy)ethyl)carbamoyl)oxy)methyl 3-(4-(diisobutylamino)-3-(3-(p-tolyl)ureido)phenyl)pentanoate;

(S)-(((S)-2-(Phosphonooxy)propoxy)carbonyl)oxy)methyl 3-(4-(diisobutylamino)-3-(3-(p-tolyl)ureido)phenyl)pentanoate;

(S)-((4-((S)-2-(Phosphonooxy)propanamido)butanoyl)oxy)methyl 3-(4-(diisobutylamino)-3-(3-(p-tolyl)ureido)phenyl)pentanoate;

(S)-((4-((S)-2-Hydroxypropanamido)butanoyl)oxy)methyl 3-(4-(diisobutylamino)-3-(3-(p-tolyl)ureido)phenyl)pentanoate;

(S)-((3-((S)-2-(Phosphonooxy)propanamido)propanoyl)oxy)methyl 3-(4-(diisobutylamino)-3-(3-(p-tolyl)ureido)phenyl)pentanoate;

(3S)-2-Methyl-1-(((S)-3-methyl-2-((S)-2-(phosphonooxy)propanamido)butanoyl)oxy) propyl 3-(4-(diisobutylamino)-3-(3-(p-tolyl)ureido)phenyl)pentanoate;

(S)—(S)-2-(Phosphonooxy)propyl 3-(4-(diisobutylamino)-3-(3-(p-tolyl)ureido)phenyl) pentanoate;

(S)-((3-(4-(Diisobutylamino)-3-(3-(p-tolyl)ureido)phenyl)pentanoyl)oxy)methyl 1-(phosphonooxy)cyclopropanecarboxylate;

(3S)-2-(Methyl-1-(((S)-3-methyl-2-((S)-2-(phosphonooxy)propanamido)butanoyl) oxy)propyl 3-(4-(diisobutylamino)-3-(3-(p-tolyl)ureido)phenyl)pentanoate;

(3S)-2-Methyl-1-(((S)-2-(phosphonooxy)propanoyl)oxy) propyl 3-(4-(diisobutylamino)-3-(3-(p-tolyl)ureido)phenyl)pentanoate;

(S)-(2-((S)—N-Methyl-2-(phosphonooxy)propanamido)acetoxy)methyl 3-(4-(diisobutylamino)-3-(3-(p-tolyl)ureido)phenyl)pentanoate;

(((S)-3-(4-(Diisobutylamino)-3-(3-(p-tolyl)ureido)phenyl)pentanoyl)oxy)methyl trans-4-(phosphonooxy)cyclohexanecarboxylate;

(S)-(2-(N-Methyl-4-(phosphonooxy)butanamido)acetoxy)methyl 3-(4-(diisobutylamino)-3(3-(p-tolyl)ureido)phenyl)pentanoate;

(S)-(2-Oxo-5-((phosphonooxy)methyl)-1,3-dioxol-4-yl)methyl 3-(4-(diisobutylamino)-3-(3-(p-tolyl)ureido)phenyl)pentanoate;

(S)—(((S)-2-(Phosphonooxy)propanoyl)oxy)methyl 3-(4-(diisobutylamino)-3-(3-(p-tolyl) ureido)phenyl)pentanoate;

(((S)-3-(4-(Diisobutylamino)-3-(3-(p-tolyl)ureido)phenyl)pentanoyl)oxy)methyl 4-(((S)-2-(phosphonooxy)propanamido)methyl)benzoate;

(S)-((3-(4-(Diisobutylamino)-3-(3-(p-tolyl)ureido)phenyl)pentanoyl)oxy)methyl 5-(phosphonooxy)pentanoate;

(((S)-3-(4-(Diisobutylamino)-3-(3-(p-tolyl)ureido)phenyl)pentanoyl)oxy)methyl 5-((S)-2-(phosphonooxy)propanamido)pentanoate;

((S)-2-Morpholinoethyl 3-(4-(diisobutylamino)-3-(3-(p-tolyl)ureido)phenyl)pentanoate, HCl;

(S)—(((R)-2-Amino-3-methylbutanoyl)oxy)methyl 3-(4-(diisobutylamino)-3-(3-(p-tolyl)ureido)phenyl)pentanoate, HCl;

(S)-(Phosphonooxy)methyl 3-(4-(diisobutylamino)-3-(3-(p-tolyl)ureido)phenyl pentanoate;

or a salt, a stereoisomer, a tautomer, or a solvate thereof.

\* \* \* \* \*

UNITED STATES PATENT AND TRADEMARK OFFICE
CERTIFICATE OF CORRECTION

PATENT NO. : 11,447,449 B2  
APPLICATION NO. : 16/959487  
DATED : September 20, 2022  
INVENTOR(S) : James Aaron Balog et al.

Page 1 of 3

It is certified that error appears in the above-identified patent and that said Letters Patent is hereby corrected as shown below:

In the Claims

In Claim 1, Column 188, Line 13, "$R^1$ is a straight or branched $C_1$-$C_8$ alkyl substituted with" should be --$R^1$ is a straight or branched $C_1$-$C_8$ alkyl substituted with $R^2$,--.

In Claim 1, Column 188, Lines 16-22, " 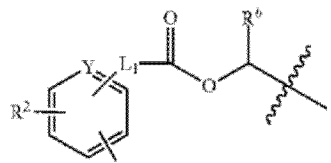 " should be -- 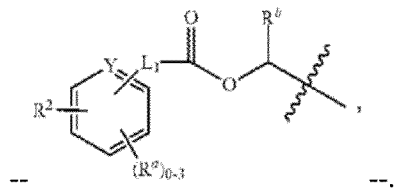 --.

In Claim 1, Column 188, Line 59, "$R^2$," should be deleted in its entirety.

In Claim 2, Column 190, Lines 21-25, " 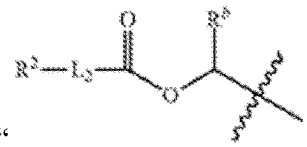 " should be -- 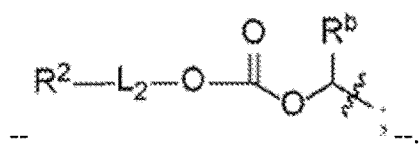 --.

In Claim 2, Column 190, Line 46, "$C_1$-$C_6$haloalkyl." should be --$C_1$-$C_6$ haloalkyl.--.

Signed and Sealed this  
Fourth Day of April, 2023

Katherine Kelly Vidal  
*Director of the United States Patent and Trademark Office*

In Claim 3, Column 190, Lines 63-67, delete "  " and insert
-- 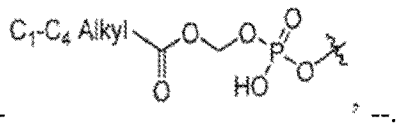 , --.

In Claim 4, Column 192, Lines 22-26, delete " 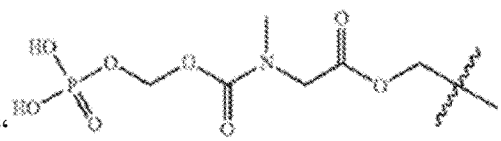 " and insert
-- 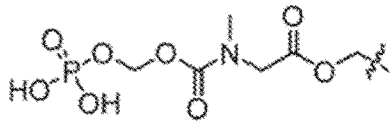 , --.

In Claim 4, Column 194, Line 45, "CH₂CH₃," should be --CH₂CH₃;--.

In Claim 5, Column 194, Lines 58-62, delete " 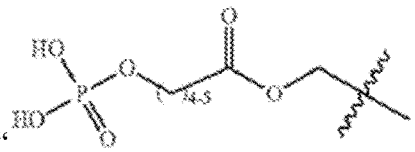 " and insert
-- 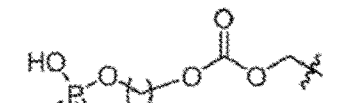 , --.

In Claim 9, Column 195, Line 22, delete "3S)" and insert --(3S)--.

In Claim 9, Column 195, Line 25, delete "(3 (p" and insert --(3-(p--.

In Claim 9, Column 195, Line 40, delete ""(Hydroxy" and insert --((Hydroxy--.

In Claim 9, Column 195, Line 43, delete "(((Benzyloxy" and insert --(((Benzyloxy)--.

In Claim 9, Column 195, Line 55, delete "(S)" and insert --(((S)--.

In Claim 9, Column 195, Line 57, delete "tolyl(" and insert --tolyl)--.

In Claim 9, Column 195, Line 65, delete "butoxy)" and insert --pentyl)oxy)--.

In Claim 9, Column 196, Line 4, delete "(Hydroxy" and insert --((Hydroxy--.

In Claim 9, Column 196, Line 13, delete "(Methyl" and insert --((Methyl--.

CERTIFICATE OF CORRECTION (continued)
U.S. Pat. No. 11,447,449 B2

In Claim 9, Column 196, Line 18, delete "3(4-" and insert --3-(4- --.

In Claim 9, Column 196, Line 24, delete "3-4-" and insert --3-(4- --.

In Claim 9, Column 196, Line 58, delete "(Methyl" and insert --Methyl--.

In Claim 9, Column 197, Line 5, delete "-3(3" and insert -- -3-(3--.